(12) United States Patent
Wallace

(10) Patent No.: US 11,464,815 B2
(45) Date of Patent: *Oct. 11, 2022

(54) DENGUE VACCINE UNIT DOSE AND ADMINISTRATION THEREOF

(71) Applicant: Takeda Vaccines, Inc., Cambridge, MA (US)

(72) Inventor: Derek Wallace, Walchwil (CH)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,611

(22) Filed: Mar. 7, 2019

(65) Prior Publication Data

US 2020/0069751 A1  Mar. 5, 2020

(30) Foreign Application Priority Data

Sep. 5, 2018  (EP) .................................. 18192701
Jan. 29, 2019  (EP) .................................. 19154334

(51) Int. Cl.
*A61K 39/12* (2006.01)
*A61K 35/76* (2015.01)

(52) U.S. Cl.
CPC .................................. *A61K 35/76* (2013.01)

(58) Field of Classification Search
None
See application file for complete search history.

(56) References Cited

U.S. PATENT DOCUMENTS

| | | |
|---|---|---|
| 4,810,092 A | 3/1989 | Auth |
| 5,021,347 A | 6/1991 | Yasui et al. |
| 5,229,293 A | 7/1993 | Matsuura et al. |
| 5,494,671 A | 2/1996 | Lai et al. |
| 5,514,375 A | 5/1996 | Paoletti et al. |
| 6,165,477 A | 12/2000 | Ivy et al. |
| 6,184,024 B1 | 2/2001 | Lai et al. |
| 6,660,273 B2 | 12/2003 | Pletnev et al. |
| 7,094,411 B2 | 8/2006 | Kinney et al. |

(Continued)

FOREIGN PATENT DOCUMENTS

| | | |
|---|---|---|
| EP | 2353609 A1 | 8/2011 |
| JP | H05276941 A | 10/1993 |

(Continued)

OTHER PUBLICATIONS

Huang et al., "Chimeric Dengue Type 2 (Vaccine Strain PDK-53)/Dengue Type 1 Virus as a Potential Candidate Dengue Type 1 Virus Vaccine," Journal of Virology, vol. 74, No. 7: 3020-3028 (Year: 2000).*

(Continued)

*Primary Examiner* — M Franco G Salvoza
(74) *Attorney, Agent, or Firm* — Honigman LLP; Fernando Alberdi; Jonathan P. O'Brien

(57) ABSTRACT

The invention relates to a unit dose of a dengue vaccine composition and methods and uses for preventing dengue disease and methods for stimulating an immune response to all four dengue virus serotypes in a subject or subject population. The unit dose of a dengue vaccine composition includes constructs of each dengue serotype, such as TDV-1, TDV-2, TDV-3 and TDV-4, at various concentrations in order to improve protection from dengue infection.

19 Claims, 12 Drawing Sheets

Specification includes a Sequence Listing.

(56) References Cited

U.S. PATENT DOCUMENTS

| | | |
|---|---|---|
| 8,673,316 B2 | 3/2014 | Kinney et al. |
| 2006/0062803 A1 | 3/2006 | Kinney et al. |
| 2010/0303860 A1 | 12/2010 | Stinchcomb et al. |
| 2011/0311579 A1 | 12/2011 | Mason et al. |
| 2014/0302088 A1 | 10/2014 | Stinchcomb et al. |
| 2015/0150961 A1 | 6/2015 | Stinchcomb et al. |
| 2015/0265695 A1* | 9/2015 | Yao .................. A61K 39/12 424/218.1 |
| 2017/0304426 A1* | 10/2017 | Tornieporth .......... A61K 39/12 |
| 2019/0381163 A1 | 12/2019 | Wallace et al. |

FOREIGN PATENT DOCUMENTS

| | | |
|---|---|---|
| JP | 2003-523189 A | 8/2003 |
| JP | 2016-513970 A | 5/2016 |
| KR | 20080018271 A | 2/2008 |
| WO | 1990001946 A1 | 3/1990 |
| WO | 1992003545 A1 | 3/1992 |
| WO | 1993006214 A1 | 4/1993 |
| WO | 1996040933 A1 | 12/1996 |
| WO | 1998037911 A1 | 9/1998 |
| WO | 1999063095 A1 | 12/1999 |
| WO | 2001060847 A2 | 8/2001 |
| WO | 2001060847 A3 | 4/2002 |
| WO | 2002072036 A2 | 9/2002 |
| WO | 2002072036 A3 | 5/2003 |
| WO | 2006134443 A1 | 12/2006 |
| WO | 2009048658 A9 | 6/2009 |
| WO | 2009139725 A1 | 11/2009 |
| WO | 2010141386 A1 | 5/2010 |
| WO | 2010/141386 A1 | 12/2010 |
| WO | 2011038473 A1 | 4/2011 |
| WO | 2013/188315 A1 | 12/2013 |
| WO | 2013188315 A1 | 12/2013 |
| WO | 2014016360 A1 | 1/2014 |
| WO | 2014016362 A1 | 1/2014 |
| WO | 2014074912 A1 | 5/2014 |
| WO | 2014/093182 A1 | 6/2014 |
| WO | 2014150939 A2 | 9/2014 |
| WO | 2016034629 A1 | 3/2016 |
| WO | 2017005652 A1 | 1/2017 |
| WO | 2017005654 A1 | 1/2017 |
| WO | 2017041156 A1 | 3/2017 |
| WO | 2017/179017 A1 | 10/2017 |
| WO | 2018052375 A1 | 3/2018 |

OTHER PUBLICATIONS

Bhamarapravati et al. (1987) Bulletin of the World Health Organization 65(2): 189-195.
Bhatt et al. (2013) Nature 496 (7446): 504-507.
Beatty et al. (2015) Sci. Transl. Med. 7(304): 304ra141.
Butrapet et al. (2000) J. Virol. 74(7): 3111-3119.
Capeding MR et al. Clinical efficacy and safety of a novel tetravalent dengue vaccine in healthy children in Asia: a phase 3, randomised, observer-masked, placebo-controlled trial. Lancet 2014, 384:1358-65.
Sentry et al. (1982) Am. J. Trop. Med. Hyg. 31, 548-555.
Glasner et al. (2017) PloS Pathog. 13(11): e1006673.
Henchal et al. (1985) Am. J. Trap. Med. Hyg. 34, 162-169.
Henchal et al. (1982) Am. J. Trap. Med. Hyg. 31(4):830-6).
Huang et al. (2003) J. Virology 77(21): 11436-11447.
Huang et al. (2013) PLOS Neglected Dis, 7(5):e2243.
Kinney et al. (1997) Virology 230(2): 300-308.
Puerta-Guardo et al. (2016) PloS Pathog. 12(7):e1005738.
Stanaway et al. (2016) Lancet Infect Dis. 16(6): 712-723.
Sridhar S et al. Effect of Dengue Serostatus on Dengue Vaccine Safety and Efficacy. N Engl J Med 2018, 379:327-40.
S.R. Hadinegoro et al. report in the New England Journal of Medicine, vol. 373, p. 1195, in "Efficacy and Long-Term Safety of a Dengue Vaccine in Regions of Endemic Disease".
Villar LA et al. Safety and immunogenicity of a recombinant tetravalent dengue vaccine in 9-16 year olds: a randomized, controlled, phase II trial in Latin America Pediatr Infect Dis J 2013, 32:1102-9.
World Health Organization Department of Immunization Vaccines Biologicals (2007) Guidelines for plaque reduction neutralization testing of human antibodies to dengue viruses, WHO/IVB/07.07.
World Health Organization. Dengue vaccine: WHO position paper—Sep. 2018. Wkly Epidemiol Rec 2018, 93:457-76.
Jorge E Osorio et al.: „Safety and immunogenicity of a recombinant live attenuated tetravalent dengue vaccine (DENVax) in flavivirus-naï6ve healthy adults in Colombia: a randomized, placebo-controlled, phase 1 study, Lancet Infectious Disease, vol. 14, No. 9, Sep. 1, 2014.
Sarah L. George et al.: „Safety and Immunogenicity of a live attenuated tetravalent dengue vaccine candidate in flavivirus-naïve adults: A randomized, double-blinded phase 1 Clinical trial Journal of Infectious Disease. JID, vol. 212, No. 7, Mar. 19, 2015.
Richard Rupp et al: „Safety and immunogenicity of different doses and schedules of a live attenuated tetravalent dengue vaccine (TDV) in healthy adults: A Phase 1b randomized study, Vaccine, vol. 33, No. 46, Nov. 1, 2015.
Saez-Llorens Xavier et al: „Safety and immunogenicity of one versus two doses of Takeda's tetravalent dengue vaccine in children in Asia and Latin America: interim results from a phase 2, randomized, placebo-controlled study, Lancet Infectious Diseases, Elsevier Ltd, US, vol. 17, No. 6, Mar. 30, 2017.
King Gail et al.: „Simultaneous administration of childhood vaccines: An important public health policy that is safe and efficacious Pedriatic Infectious Disease Jour. Lippincott Williams & Wilkins, US, vol. 13, No. 5, Jan. 1, 1994.
Chokephaibulkit Kulkanya: „Combination Vaccines, Chot Het-Thang Phaet—Journal of Medical Association of Thai, Medical association of Thailand, TH, vol. 85, No. Suupl. 2, Aug. 1, 2002.
Jorge E. Osorio et al: „A recombinant, chimeric tetravalent dengue vaccine candidate based on a dengue virus serotype 2 backbone, Expert Review of Vaccines, vol. 15, No. 4, Apr. 2, 2016.
Jorge E Osorio et al: "Development of DENVax: A chimeric dengue-2 PDK-53-based tetravalent vaccine for protection against dengue", Vaccine, vol. 29, No. 42.
Annelies Wilder-Smith et al.: "Age specific differences in efficacy and safety for the CYD-tetravalent dengue vaccine", Expert Review of Vaccines, vol. 15, No. 4, Apr. 2, 2016.
Anand Prakash Dubey et al: "Immunogenicity and safety of a tetravalent dengue vaccine in healthy adults in India: A randomized, observer-blind, placebo-controlled phase II trial", Human Vaccines and Immunotherapeutics, vol. 12, No. 2, Aug. 20, 2015.
Chukiat Sirivichayakul et al: "Safety and Immunogenicity of a Tetravalent Dengue Vaccine Candidate in healthy children and adults in dengue-endemic regions: A randomized, placebo-controlled Phase 2 Study", Journal of Infectious Diseases. JID, vol. 213, No. 10, Dec. 23, 2015.
Ole Wichmann et al.: "Live-attenuated tetravalent dengue vaccine: The needs and challenges of post-licensure avaluation of vaccine safety and effectiveness", vaccine, vol. 35, No. 42, Oct. 1, 2017.
Joseph N. Brewoo et al: "Immunogenicity and efficacy of chimeric dengue vaccine (DENVax) formulations in interferon-deficient AG129 mice", Vaccine, vol. 30, No. 8, Feb. 1 2A12 (Feb. 1, 2012), pp. 1513-1520.
John T. Roehrig et al: "Guidelines for Plaque-Reduction Neutralization Testing of Human Antibodies to Dengue Viruses", Viral Immunology., vol. 21, No. 2, Jun. 1, 2008 (Jun. 1, 2008), pp. 123-132.
Rafael De La Barrera et al.: "Comparative Evaluation of Three Assays for Measurement of Dengue Virus Neutralizing Antibodies", American Journal of Tropical Medicine & Hygiene., vol. 79, No. 1, Jul. 1, 2008 (Jul. 1, 2008), pp. 115-122.
Tatyana M. Timiryasova et al.: "Optimization and Validation of a Plaque Reduction Neutralization Test for the Detection of Neutralizing Antibodies to Four Serotypes of Dengue Virus Used in Support of Dengue Vaccine Development", American Journal of Tropical Medicine & Hygiene., vol. 88, No. 5, May 1, 2013 (May 1, 2013), pp. 962-970.

(56) References Cited

OTHER PUBLICATIONS

Anonymous: "Guidelines for plaque reduction neutralization testing of human antibodies to dengue viruses", immunization, Vaccines and Biologicals, Sep. 21, 2007 (Sep. 21, 2007), pp. 1-36, XP055519586.
Alape 2018. Takeda vacuna contra el dengue. McIntosh Sep. 5, 2018.
Haiyan Chu, et al., "CD8+ T-cell Responses in Flavivirus-Naive Individuals Following Immunization with a Live-Attenuated Tetravalent Dengue Vaccine Candidate"—Major Article JID 2015:212 (Nov. 15).
Lisa A. Jackson, et al., "A phase 1 study of safety and immunogenicity following intradermal administration of a tetravalent dengue vaccine candidate"—Vaccine 36 (2018) p. 3976-3983—May 19, 2018.
Medical Director Clinical Science Study Director Takeda: "Safety and Immunogenicity With Two Different Serotype 2 Potencies of Takeda's Tetravalent Dengue Vaccine Candidate (TDV) in Adults in Singapore"—Clinical Trials Jul. 16, 2019—DEN 205.
Jorge Osorio et al.: "Efficacy of a Tetravalent Chimeric Dengue Vaccine (DENVax) in Cynomolgus Macaques", Am J. Trop. Med. Hyg., 84(6), 2011, pp. 978-987—The American Society of Tropical Medicine and Hygiene.
Presentation Biswal Asia Dengue Summit (2016) DEN-204.
Presentation Lorenzato Medtrop (2018) DEN-204.
Presentation Wallace(2016) DEN-204 (p. 86).
Press Release: "Takeda's Dengue Vaccine Candidate Meets Primary Endpoint in Pivotal Phase 3 Efficacy Trial" -Jan. 29, 2019.
Takeda Press Release: "Takeda Completes Enrollment of More Than 20,000 Children and Adolescents in Global Phase 3 Trial of Dengue Vaccine Candidate"—Apr. 5, 2017—DEN-301.
Derek Wallace: "Persistence of neutralizing antibodies one year after two doses of a candidate recombinant tetravalent dengue vaccine in subjects aged from 1.5 to 45 years"—ASTMH Oct. 27, 2015 DEN-203.
Anonymous: "WHO Recommendations for all immunization programmes",! Aug. 2018, XP055519312.
Mmunogenicity and Safety of Tetravalent Dengue Vaccine (TDV) Co-administered with an Hepatitis A Virus Vaccine.
Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
López-Medina et al., "'Effcacy of a Dengue Vaccine Candidate (TAK-003) in Healthy Children and Adolescents 2 Tears after Vaccination,'" The Journal of Infectious Diseases, 2021, pp. 1-12.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.
Press Release: "Takeda's Pipeline Has Potential to Contribute Significantly to Revenue Growth Over Next Decade," Dec. 9, 2020, 4 pages.
Putnak, et al., "Comparative Evaluation of Three Assays for Measurement of Dengue Virus Neutralizing Antibodies," The American Journal of Tropical Medicine and Hygiene, 2008, vol. 79, No. 1, pp. 115-122.
Wallace Presentation: Abstract 5th Pan American Dengue Research Network Meeting, Apr. 20-23, 2016, DEN-204, p. 86.
Sabchareon, et al., "Protective effi cacy of the recombinant, live-attenuated, CYD tetravalent dengue vaccine in Thai schoolchildren: a randomised, controlled phase 2b trial," The Lancet, Nov. 3, 2021, vol. 380, pp. 1559-1567.
Biswal et al., "Efficacy of a Tetravalent Dengue Vaccine in Healthy Children and Adolescents," New England Journal of Medicine, Nov. 21, 2019, vol. 381, No. 21.
Biswal Presentation "Takeda Tetravalent Dengue Vaccine (TDV) Candidate: An Update (DEN-204)," Asia Dengue Summit, Jan. 13, 2016, 17 pages.
Brewoo et al., "Immunogenicity and efficacy of chimeric dengue vaccine (DENVax) formulations in interferon-deficient AG129 mice," Vaccine, Feb. 1, 2012, vol. 30, No. 8, pp. 1513-1520.
Chokephaibulkit K., "Combination Vaccines," Chot Mai Het Thang Phaet, Journal Of The Medical Association of Thai, Medical Association of Thailand, Aug. 1, 2002, vol. 85, No. Suppl. 2, pp. 5694-5699.
Chu et al., "CD8+ T-cell Responses in Flavivirus-Naïve Individuals Following Immunization with a Live-Attenuated Tetrava-lent Dengue Vaccine Candidate" Major Article, JID, Nov. 15, 2015, vol. 212, pp. 1618-1628.
Crevat et al., "First Experience of Concomitant Vaccination Against Dengue and MMR in Toddlers," Pediatric nfectious Disease Journal, Aug. 1, 2015, vol. 34, No. 8, pp. 884-892.
Dubey et al., "Immunogenicity and safety of a tetravalent dengue vaccine in healthy adults in India: A randomized, observer-blind, placebo-controlled phase II trial," Human Vaccines and Immunotherapeutics, Aug. 20, 2015, vol. 12, No. 2, pp. 512-518.
European Search Report dated Feb. 12, 2019 for corresponding EP application 18192701.3, 22 pages.
European Search Report dated May 3, 2019 for corresponding EP application 19161184.7, 16 pages.
European Search Report dated Nov. 13, 2018 for corresponding EP application 18192701.3, 20 pages.
European Search Report dated Nov. 13, 2018 for corresponding EP application 18192711.2, 16 pages.
European Search Report dated Nov. 13, 2018 for corresponding EP application 18192717.9, 16 pages.
European Search Report dated Nov. 13, 2018 for corresponding EP application 18192800.3, 18 pages.
European Search Report dated Nov. 13, 2018 for corresponding EP application 18192793.0, 16 pages.
European Search Report dated Nov. 13, 2018 for corresponding EP application 18192787.2, 18 pages.
European Search Report dated Nov. 13, 2018 for corresponding EP application 18192814.4, 16 pages.
European Search Report dated Nov. 29, 2018 for corresponding EP application 18192776.5, 17 pages.
George et al., "Safety and immunogenicity of a Live Attenuated Tetravalent Dengue Vaccine Candidate in Flavivirus-Nave Adults: A Randomized, Double-Blinded Phase 1 Clinical Trial," Journal Of Infectious Diseases, Mar. 19, 2015, vol. 21 2, No. 7, pp. 1032-1041.
Huang et al., "Concomitant administration of live attenuated Japanese encephalitis chimeric virus vaccine (JE-CV) and measles, mumps, rubella (MMR) vaccine: Randomized study in toddlers in Taiwan," Vaccine, Sep. 1, 2014, vol. 32, No. 41, pp. 5363-5369.
Jackson et al., "A phase 1 study of safety and immunogenicity following intradermal administration of a tetravalent dengue vaccine candidate," Vaccine, May 19, 2018, vol. 36, pp. 3976-3983.
King et al., "Simultaneous administration of childhood vaccines: An important public health policy that is safe and effica-cious," Pediatric Infectious Disease Jour, Lippincott Williams & Wilkins, US, Jan. 1, 1994, vol. 13, No. 5, pp. 394-407.
López et al., "Immunogenicity and Safety of Yellow Fever Vaccine (Stamaril) When Administered Concomitantly With a Tet-ravalent Dengue Vaccine Candidate in Healthy Toddlers at 12-13 Months of Age in Colombia and Peru A Randomized Trial," Pediatric Infectious Disease Journal, Oct. 1, 2016, vol. 35, No. 10, pp. 1140-1147.
Lorenzato Presentation "Update of Takeda's dengue candidate vaccine development programme (DEN-204)," Brazilian Tropical Medicine Congress (Medtrop) Sep. 5, 2018, 29 pages.
Mcintosh Presentation "Takeda vacuna contra el dengue," Alape Sep. 5-8, 2018, Luque Asuncion, Paraguy, 27 pages.
Melo et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico : A Randomized Trial," Pediatric Infec-tious Disease Journal, Jun. 1, 2017, vol. 36, No. 6, pp. 602-608.
NCT02425098 "Safety and Immunogenicity With Two Different Serotype 2 Potencies of Takeda's Tetravalent Dengue Vac-cine Candidate (TDV) in Adults in Singapore," Clinical Trials.gov, Jul. 16, 2019—DEN 205, Retrieved from internet Jul. 4, 2019, 12 pages.

(56) References Cited

OTHER PUBLICATIONS

NCT02993757 "Immunogenicjty and Safety of a Tetravalent Dengue Vaccine Administered Concomitantly or Sequentially With Gardasil," Clinicalirials gov, Apr. 5, 2018, Retrieved from the Internet Oct. 25, 2018, 10 pages.
Dsorio et al. "Efficacy of a Tetravalent Chimeric Dengue Vaccine (DENVax) in Cynomolgus Macaques," Am. J. Trop. Med. Hyg., 2011, vol. 84, No. 6, pp. 978-987.
Osorio et al., "A recombinant, chimeric tetravalent dengue vaccine candidate based on a dengue virus serotype 2 back-bone," Expert Review Of Vaccines, Apr. 2, 2016, vol. 15, No. 4, pp. 497-508.
Osorio et al., "Development of DENVax: A chimeric dengue-2 PDK-53-based tetravalent vaccine for protection against dengue fever," Vaccine, Jul. 11, 2011, vol. 29, No. 42, pp. 7251-7260.
Osorio et al., "Safety and immunogenicity of a recombinant live attenuated tetravalent dengue vaccine (DENVax) in fla-vivirus-naive healthy adults in Colombia: a randomised, placebo-controlled, phase 1 study," Lancet Infectious Diseases, Sep. 1, 2014, vol. 1 4, No. 9, pp. 830-838.
Pinheiro-Michelsen et al., "Anti-dengue Vaccines: From Development to Clinical Trials," Frontiers in Immunology, Jun. 18, 2020, vol. 11, Art 1252, pp. 1-18.
Press Release: "Takeda Completes Enrollment of More Than 20,000 Children and Adolescents in Global Phase 3 Trial of Dengue Vaccine Candidate" Apr. 5, 2017—DEN-301, 4 pages.
Press Release: "Takeda's Dengue Vaccine Candidate Meets Primary Endpoint in Pivotal Phase 3 Efficacy Trial" Jan. 29, 2019, 4 pages.
Rinderknecht et al., "Immunogenicity and Safety of an Inactivated Hepatitis A Vaccine When Coadministered With Mea-sles-mumps-rubella and Varicella Vaccines in Children Less Than 2 Years of Age," Pediatric Infectious Disease Journal, Oct. 1, 2011, vol. 30, No. 10, pp. e179-e185.
Roehrig et al., "Guidelines for Plague-Reduction Neutralization Testing of Human Antibodies to Dengue Viruses," Viral Immunology, Jun. 1, 2008, vol. 21, No. 2, pp. 123-132.
Rupp et al., "Safety and immunogenicity of different doses and schedules of a live attenuated tetravalent dengue vaccine (TDV) in healthy adults: A Phase 1b randomized study," Vaccine, Nov. 1, 2015, vol. 33, No. 46, pp. 3351-6359.
Saez-Llorens et al., "Immunogenicity and safety of one versus two doses of tetravalent dengue vaccine in healthy chil-dren aged 2-17 years in Asia and Latin America: 18-month interim data from a phase 2, randomised, placebo-controlled study," Lancet Infect Dis, Nov. 6, 2017, vol. 18, pp. 162-170.
Saez-Llorens et al., "Safety and immunogenicity of one versus two doses of Takeda's tetravalent dengue vaccine in chil-dren in Asia and Latin America: interim results from a phase 2, randomized, placebo-controlled study," vol. 17, No. 6, Ltd, US, Mar. 30, 2017, vol. 17, No. 6, pp. 615-625.
Schilling et al., "Coadministration of a 9-Valent Human Papillomavirus Vaccine With Meningococcal and Tdap Vaccines," Pediatrics, Sep. 1, 2015, vol. 136, No. 3, pp. e563-e572.
Sirivichayakul et al., "Safety and immunogenicity of a Tetravalent Dengue Vaccine Candidate in Healthy Children and Adults in Dengue-Endemic Regions: A Randomized, Placebo-Controlled Phase 2 Study," Journal of Infectious Diseases, Dec. 23, 2015, vol. 213, No. 10, pp. 1562-1572.
Timiryasova et al., "Optimization and Validation of a Plaque Reduction Neutralization Test for the Detection of Neutraliz-ing Antibodies to Four Serotypes of Dengue Virus Used in Support of Dengue Vaccine Development," American Journal Of Tropical Medicine & Hygiene, May 1, 2013, vol. 88, No. 5, pp. 962-970.
Vesikari et al., "Safety and Immunogenicity of a Booster Dose of the 10-Valent Pneumococcal Nontypeable Haemophilus influenza Protein D Conjugate Vaccine Coadministered With Measles-Mumps-Rubella-Varicella Vaccine in Children Aged 12to 16 Months," Pediatric Infectious Disease Journal, Jun. 1, 2010, vol. 29, No. 6, pp. e47-e56.
Wallace Presentation Session: Vaccines (Developpers),"Takeda's dengue vaccine candidate in children: one or two dos-es?," Apr. 20-23, 2016, p. 86.
Wallace Presentation: "Persistence of neutralizing antibodies one year after two doses of a candidate recombinant tetra-valent dengue vaccine in subjects aged from 1.5 to 45 years," ASTMH 64th Annual Meeting, Oct. 27, 2015, DEN-203, 2 pages.
Wichmann et al., "Live-attenuated tetravalent dengue vaccines: The needs and challenges of post-licensure evaluation of vaccine safety and effectiveness," Vaccine, Oct. 1, 2017, vol. 35, No. 42, pp. 5535-5542.
Wilder-Smith et al., "Age specific differences in efficacy and safety for the CYD-tetravalent dengue vaccine," Expert Re-view of Vaccines, Apr. 2, 2016, vol. 15, No. 4, pp. 437-441.
World Health Organization, "Table 3: Recommendations for Interrupted or Delayed Routine Immunization—Sum-mary of WHO position papers," Aug. 2018, 10 pages.
Endy, T.P., "Dengue Human Infection Model Performance Parameters," Journal Infectious Diseases, 2014, vol. 209 (Suppl. 2), pp. S56-S60.
Mullard, A., "Sanofi's dengue vaccine rounds final corner," Nature Reviews Drug Discovery, Nov. 2014, vol. 13, pp. 801-802.
Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.
Aberle et al., "A DNA Immunization Model Study with Constructs Expressing the Tick-Borne Encephalitis Virus Envelope Protein E in Different Physical Forms," Journal of Immunology, 199, vol. 163, pp. 6756-6761.
*AK Steel Corporation* v. *Sollac and Ugine*; United States Court of Appeals for the Federal Circuit; http://laws.lp.findlaw.com/fed/031074.html (Sep. 24, 2003), 8 pages.
Allison et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.
Alvarez et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.
Anderson et al., "Isolation of West Nile Virus from Mosquitoes, Crows, and a Cooper's Hawk in Connecticut", Ovid Anderson: Science, vol. Dec. 17, 1999, vol. 286(5448), pp. 2331-2333.
Arnon Ruth "Synthetic Vaccines vol. I" CRC Press, Inc. Boca Raton, Florida pp. 83-92.
Arroyo et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.
Azevedo et al., "Main features of DNA-based immunization vectors," Brazilian Journal of Medical and Biological Research 1999, vol. 32, No. 2, pp. 147-153.
Benjamin, Sarah, "Optimization and analysis of live attenuated denvax-4 constructs," Masters Thesis: Colorado State University, Summer 2013, 97 pages.
Bhamarapravati et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.
Bhamarapravati et al., "Live attenuated tetravalent dengue vaccine," Vaccine, 2000, vol. 18, pp. 44-47.
Bhatt et al., "Growth characteristics of the chimeric Japanese encephalitis virus vaccine candidate, chimeriVax-je (YF/JE SA14-14-2), in culex tritaeniorhynchus, aedes albopictus, and *Aedes aegypti* mosquitoes," Am. J. Trop. Med. Hyg., 2000, vol. 62, No. 4, pp. 480-484.
Blok et al., "Comparison of a Dengue-2 Virus and Its Candidate Vaccine Derivative: Sequence Relationships with the Flaviviruses and Other Viruses," Virology, 1992, vol. 187, pp. 573-590.

(56) References Cited

OTHER PUBLICATIONS

Bray et al., "Construction of intertypic chimeric dengue viruses by substitution of structural protein genes," Proc. Nat. Acad. Sci. USA, Medical Sciences, Nov. 1991, vol. 88, pp. 10342-10346.

Bray et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.

Bray et al., "Monkeys Immunized with Intertypic Chimeric Dengue Viruses Are Protected against Wild-Type Virus Challenge," Journal of Virology, Jun. 1998, vol. 70, No. 6, pp. 4162-4166.

Butrapet et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.

Butrapet et al., "Determining genetic stabilities of chimeric dengue vaccine candidates based on dengue 2 PDK-53 virus by sequencing and quantitative TaqMAMA," Journal of Virological Methods, 2006, vol. 131, No. 1, pp. 1-9.

Cahour et al., "Growth-Restricted Dengue Virus Mutants Containing Deletions in the 5' Noncoding Region of the RNA Genome," Virology, 1995, vol. 207, pp. 68-76.

Calvert et al., "Non-structural proteins of dengue 2 virus offer limited protection to interferon-deficient mice after dengue 2 virus challenge,", Journal of General Virology, vol. 87, 2006, pp. 339-346.

Caufour et al., "Construction, characterization and immunogenicity of recombinant yellow fever 17D-dengue type 2 viruses," Virus Research, 2011, vol. 79, pp. 1-14.

Chambers et al., "Flavivirus Genome Organization, Expression, and Replication," Annu. Rev. Microbiol. 1990, vol. 44, pp. 649-688.

Chambers et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. Vol. 77, No. 6, pp. 3655-3668.

Chambers et al., "Yellow Fever/Japanese Encephalitis Chimeric Viruses: Construction and Biological Properties," Journal of Virology, Apr. 1999, vol. 73, No. 4, pp. 3095-3101.

Chang et al., "A Single Intramuscular Injection of Recombinant Plasmid DNA Induces Protective Immunity and Prevents Japanese Encephalitis in Mice," Journal of Virology, May 2020, vol. 74, No. 9, pp. 4244-4252.

Chen et al., "Construction of Intertypic Chimeric Dengue Viruses Exhibiting Type 3 Antigenicity and Neurovirulence tor Mice," Journal of Virology, Aug. 1995, vol. 69, No. 8, pp. 5186-5190.

Clarke et al., "Techniques for Hemagglutination and Hemagglutination-Inhibition with Arthropod-Borne Viruses," The Rockefeller Foundation Virus Laboratories, New York, N.Y., Am. J. Trap. Med. Hyg., 1958, p. 561-573.

Cooper et al., "Update: Surveillance for West Nile Virus in Overwintering Mosquitoes —New York, 2000," 3 pages.

Database UniProt Accession No. Q9WLZ7, XP-002731515, http://ibis/exam/dbfetch.jsp?id=UNIPROT%3AQ9WLZ7, 2 pages.

Database UniProt accession No. D2KQW7 Database UniProt SubName: Full=Polyprotein (ECO:0000313 EMBL: ADA00411.1); XP002731516, retrieved from EBI accession No. UNIPROT:D2KQW7, http://ibis/exam/dbfetch.jsp?id=UNIPROT:D2KQW7 Feb. 9, 2010, 2 pages.

Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. Uniprot: P29991; Apr. 1, 1993 http://ibis/exam/dbfetch.jsp?id=UNIPROT%3AP29991 .6 pages.

Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.

Deubel et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.

Deubel et al., "Nucleotide Sequence and Deduced Amino Acid Sequence of the Structural Proteins of Dengue Type 2 Virus, Jamaica Genotype," Virology, 1986, vol. 155, pp. 365-377.

Dharakul et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.

Dmitriev et al., "Immunization with recombinant vaccinia viruses expressing structural and part of the nonstructural region of tick-borne encephalitis virus eDNA protect mice against lethal encephalitis," Journal of Biotechnology, 1996, vol. 44, pp. 97-103.

Duarte Dos Santos et al., "Complete nucleotide sequence of yellow fever virus vaccine strains 17DD and 17D-213," Virus Research 1995, vol. 35, pp. 35-41.

Durbin et al., "Attenuation and Immunogenicity in Humans of a Live Dengue Virus Type-4 Vaccine Candidate with a 30 Nucleotide Deletion in its 3'-Untranslated Region," Am. J Trap. Med Hyg 2001, vol. 65(5), pp. 405-413.

Falgout et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 34, No. 9, pp. 4356-4363.

Falgout et al., "Proper Processing of Dengue Virus Nonstructural Glycoprotein NS1 Requires the N-Terminal Hydrophobic Signal Sequence and the Downstream Nonstructural Protein NS2a," Journal of Virology, May 1989, vol. 33, No. 5, pp. 1852-1860.

Garmendia et al., "Recovery and Identification of West Nile Virus from a Hawk in Winter," Journal of Clinical Microbiology, Aug. 2000, vol. 38, No. 8, pp. 3110-3111.

Gruenberg et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-198.

Guirakhoo et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.

Guirakhoo et al., "Immunogenicity, Genetic Stability, and Protective Efficacy of a Recombinant, Chimeric Yellow Fever-Japanese Encephalitis Virus (ChimerVax-JE) as a Live, Attenuated Vaccine Candidate against Japanese Encephalitis," Virology, 1999, vol. 257, pp. 363-372.

Guirakhoo et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.

Guirakhoo et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Mirus Isolates" Virology, 2002, vol. 298, pp. 146-159.

Hahn et al., "Nucleotide Sequence of Dengue 2 RNA and Comparison of the Encoded Proteins with Those of Other Flaviviruses," Virology, 1988, vol. 162, pp. 167-180.

Halstead et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.

Hashimoto et al., "Molecular Cloning and Complete Nucleotide Sequence of the Genome of Japanese Encephalitis Virus Beijing-1 Strain," Virus Genes, 1988, vol. 1, No. 3, pp. 305-317.

Heinz et al., "Flaviviruses" Immunochemistry of viruses II, The basis for serodiagnosis and vaccines, (edited by von Regenmortel and Neurath), Elsevier Science Publishers B.V, Chapter 14, 1990 pp. 289-305.

Henchal et al., "Dengue Virus-Specific and Flavivirus Group Determinants Identified with Monoclonal Antibodies by ndirect Immunofluorescence," Flavivirus-Specific and Group Determinants, Am. J. Trop Med. Hyg., 1982, vol. 31, No. 4, pp. 830-836.

(56) References Cited

OTHER PUBLICATIONS

Hennessy et al., "Effectiv ness of live-attenuated Japanese encephalitis vaccine (SA14-14-2): a case-control study" The Lancet, vol. 347, Jun. 8, 1996, pp. 1583-1586.

Ho et al., "DNA vaccination induces a long-term antibody response and protective immunity against pseudorabies virus in mice" Archives of Virology, 1998, vol. 143, pp. 115-125.

Hsiang-Chi et al., "Dengue Type 4 Live-Attenuated Vaccine Viruses Passaged in Vero Cells Affect Genetic Stability and Dengue-Induced Hemorrhaging in Mice," PLOS ONE, Oct. 28, 2011 (Oct. 28, 2011), vol. 6, No. 10, p. E25800.

Hubálek et al., "West Nile Fever—a Reemerging Mosquito-Borne Viral Disease in Europe". Emerg. Infect. Dis., Oct. 1988, vol. 5, No. 5, pp. 643-650.

Hunt et al., "Relationships of Bunyamwera Group Viruses by Neutralization" Am. J. Trop. Med. Hyg. 1979, vol. 28, No. 4, pp. 740-749.

Jia et al., "Genetic analysis of West Nile New York 1999 encephalitis virus" The Lancet, Dec. 4, 1999, vol. 354, pp. 1971-1972.

Jirakanjanakit et al., "Dynamics of Susceptibility and Transmissibility of The Live Attenuated, Candidate Vaccines Dengue-1 PDK-13, Dengue-3 PGMK30F3, and Dengue-4 PDK-48 after Oral Infection in Aedes Aegypti," Am. J. Trap. Med. Hyg. 1999, vol. 61, No. 4, pp. 672-676.

Johnson et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.

Johnson et al., "Growth Characteristics of ChimeriVax-DEN2 Vaccine Virus in Aedes Aegypti and Aedes Albopictus Mosquitoes," Am J. Trap Med Hyg , 2002, vol. 67, No. 3, pp. 260-265.

Kanesa-Thasan et al., "Safety and immunogenicity of attenuated dengue virus vaccines (Aventis Pasteur) in human volunteers," Vaccine, 2001 vol. 19 pp. 3179-3188.

Kawano et al., "Genetic Determinants of Dengue Type 4 Virus Neurovirulence for Mice," Journal of Virology, Nov. 1993, vol. 67, No. 11, pp. 6567-6575.

Kelly et al., "Evolution of attenuating mutations in dengue-2 strain S16803 PDK50 vaccine and comparison of growth kinetics with parent virus," Virus Genes, 2011, vol. 43, pp. 18-26.

Khin et al., "Infection, Dissemination, Transmission, and Biological Attributes of Dengue-2 PDK53 Candidate Vaccine Mirus after Oral Infection in Aedes Aegypti," Am. J. Trop Med. Hyg., 1994, vol. 51, No. 6, pp. 864-869.

Kimura-Kuroda et al., "Antigenic Comparison of Envelope Protein E between Japanese Encephalitis Virus and Some Other Flaviviruses Using Monoclonal Antibodies," J Gen Virol, 1986, vol. 67, pp. 2663-1672.

Kimura-Kuroda et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.

Kinney et al., "Development of New Vaccines against Dengue Fever and Japanese Encephalitis," Intervirology, 2001, vol. 44, pp. 176-197.

Klinman et al., "CpG motifs as immune adjuvants," Vaccine, 1999, vol. 17, pp. 19-25.

Kochel Tadeusz et al., "Inoculation of plasmids expressing the dengue-2 envelope gene elicit neutralizing antibodies in mice," Vaccine. 1997, vol. 15, No. 5, pp. 547-552.

Kohler et al., "Continuous cultures of fused cells secreting antibody of predefined specificity," Nature, Aug. 7, 1975, vol. 256, pp. 495-497.

Konishi et al., "Avipox virus-vectored Japanese encephalitis virus vaccines: use as vaccine candidates in combination with purified subunit immunogens," Vaccine, 1994, vol. 12, No. 7, pp. 633-638.

Konishi et al., "Comparison of Protective Immunity Elicited by Recombinant Vaccinia Viruses That Synthesize E or NS1 of Japanese Encephalitis Virus," Virology, 1991, vol. 185, pp. 401-410.

Konishi et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.

Konishi et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.

Konishi et al., "Mice Immunized with a Subviral Particle Containing the Japanese Encephalitis Virus prM/M and E Proteins Are Protected from Lethal JEV Infection," Virology, 1992, vol. 188, pp. 714-720.

Kozak "Circumstances and Mechanisms of Inhibition of Translation by Secondary Structure in Eucaryotic mRNAs," Molecular and Cellular Biology, Nov. 1989, vol. 9, No. 11, pp. 5134-5142.

Kuno et al., "Phylogeny of the Genus Flavivirus," Journal of Virology, Jan. 1998, vol. 72, No. 1, pp. 73-83.

Laemmli U.K. "Cleavage of Structural Proteins during the Assembly of the Head of Bacteriophage T4," Nature, Aug. 15, 1970, vol. 227, pp. 680-685.

Lai et al., "Evaluation of molecular strategies to develop a live dengue vaccine," Clinical and Diagnostic Virology, 1998, vol. 10, pp. 173-179.

Lai et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY, 1990, pp. 119-124.

Lanicotti R. et al., "Origin of the West Nile Virus Responsible for an Outbreak of Encephalitis in the Northeastern United States," Science, Dec. 17, 1999, vol. 286, pp. 2333-2337.

Liljeström et al., "In Vitro Mutagenesis of a Full-Length eDNA Clone of Semliki Forest Virus: the Small 6,000-Molecular-Weight Membrane Protein Modulates Virus Release," Journal of Virology, Aug. 1991, vol. 65, No. 8, pp. 4107-4113.

Lin et al., "DNA Immunization with Japanese Encephalitis Virus Nonstructural Protein NS1 Elicits Protective Immunity in Mice," Journal of Virology, Jan. 1998, vol. 72, No. 1, pp. 191-200.

Mackow et al., "The Nucleotide Sequence of Dengue Type 4 Virus: Analysis of Genes Coding for Nonstructural Proteins," Virology, 1987, vol. 159, pp. 217-228.

Mandl et al., "Complete Genomic Sequence of Powassan Virus: Evaluation of Genetic Elements in Tick-Borne versus Mosquito-Borne Flaviviruses," Virology, 1993, vol. 194, pp. 173-184.

Martin et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.

Mason et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.

Mason et al., "Sequence of the Dengue-1 Virus Genome in the Region Encoding the Three Structural Proteins and the Major Nonstructural Protein NS1," Virology,1987, vol. 161, pp. 262-267.

Men et al., "Dengue Type 4 Virus Mutants Containing Deletions in the 3' Noncoding Region of the RNA Genome Analysis of Growth Restriction in Cell Culture and Altered Viremia Pattern and Immunogenicity in Rhesus Monkeys," Journal of Virology, Jun. 1996, vol. 70, No. 6, pp. 3930-3937.

Mir et al., "High-efficiency gene transfer into skeletal muscle mediated by electric pulses," Applied Biological Sciences, Proc. Natl. Acad. Sci. USA, Apr. 1999, vol. 96, pp. 4262-4267.

Nitayaphan et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.

Novello et al., "Update: West Nile Virus Activity—Northeastern United States, 2000," http://www.cdc.gov/mmwr/?review/mmwrhtml/mm4936a4.htm MMWR Weekly Sep. 15, 2000 / vol. 49, No. 36, pp. 820-822.

Nowak et al., "Analysis of the Terminal 4 Sequences of West Nile Virus Structural Proteins and of the in Vitro Translation of these Proteins Allow the Proposal of a Complete Scheme of the Proteolytic

(56) References Cited

OTHER PUBLICATIONS

Cleavages Involved in Their Synthesis," Virology, Academic Press. Orlando, Apr. 1, 1989, vol. 169, No. 2, pp. 365-376.
Osatomi et al., "Complete Nucleotide Sequence of Dengue Type 3 Virus Genome RNA," Virology, 1990, vol. 176, pp. 643-647.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Phillpotts et al., "Immunisation with DNA polynucleotides protects mice against lethal challenge with St. Louis encephalitis virus" Arch Virol., 1996, vol. 141, pp. 743-749.
Pletnev et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.
Pletnev, et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.
Puri et al., "Molecular analysis of dengue virus attenuation after serial passage in primary in dog kidney cells." J. Gen Virol., 1997, vol. 78, pp. 2287-2291.
Rice et al., "Nucleotide Sequence of Yellow Fever Virus: Implications for Flavivirus Gene Expression and Evolution," Science, 1985, vol. 229, pp. 726-733.
Rice et al., "Transcription of Infectious Yellow Fever RNA From Full-Length cDNA Templates Produced by In Vitro Ligation," The New Biologist, Dec. 1989, vol. 1, No. 3, pp. 285-296.
Roehrig et al., "Identification of Epitopes on the E Glycoprotein of Saint Louis Encephalitis Virus Using Monoclonal Antibodies." Virology, 1986, vol. 128, pp. 118-126.
Roehrig et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.
Sabchareon et al., "Safety and Immunogenicity of Tetravalent Live-Attenuated Dengue Vaccines in Thai Adult Volunteers: Role of Serotype Concentration, Ratio, and Multiple Doses," Am. J. Trop. Med. Hyg., 2002, vol. 66, No. 3, pp. 264-272.
Sato et al., "Immunostimulatory DNA Sequences Necessary for Effective Intradermal Gene Immunization," Science, Jul. 19, 1996, vol. 273, No. 5273, pp. 352-354.
Seeger et al., "The cloned genome of ground squirrel hepatitis virus is infectious in the animal," Proc. Nat. Acad. Sci. USA, Medical Sciences, Sep. 1984, vol. 81, pp. 5849-5852.
Sela, Michael, "The Choice of Carrier." In Synthetic Vaccines vol. I, R. Amon, (ed) CRC Press Inc., Boca Raton, FL. Chapter 6, 1987, pp. 83-92.
Smithburn et al., "A Neurotropic Virus Isolated From The Blood Of a Native Of Uganda," Am. J. Trop. Med. Hyg., 1940, vol. 20, pp. 471-492.
Stocks et al.: "Signal Peptidase Cleavage at the Flavivirus C-prM Junction: Dependence on the Viral NS2B-3 Protease for Efficient Processing Requires Determinants in C, the Signal Peptide, and prM," Journal Of Virology, LNKDPUBMED: 9499070, Mar. 1998, Mar. 1998 (Mar. 1998), vol. 72, No. 3, pp. 2141-2149.
Tardei et al., "Evaluation of Immunoglobulin M (IgM) and IgG Enzyme Immunoassays in Serologic Diagnosis of West Nile Virus Infection," J Clin. Microbiol. Jun. 2000, vol. 38, No. 6, pp. 2232-2239.
Tsai et al. "Japanese Encephalitis Vaccines," In Vaccines, (3rd edition) Plotkin and Orenstein (eds), W.B. Saunders Company, Philadelphia, PA. Chapter 27, 199, pp. 672-710.
Tsai et al., "Japanese Encephalitis Vaccines," In Vaccines, (2nd edition), Plotkin and Mortimer (eds.), W.B. Saunders Do , Philadelphia, PA Chapter 24, 1994, pp. 671-713.
Update: "Surveillance for Weste Nile Virus in Overwintering Mosquitoes—New York, 2000," Morb. Mortal. Wkly. Rep., Mar. 10, 2000, vol. 49, No. 09, pp. 178-179.
Update: "West Nile Virus Activity—Northeastern United States, 2000," Morb. Mortal. Wkly. Rep., Sep. 15, 2000, vol. 49, No. 36, pp. 820-822.

Van Der Most et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.
Vaughn et al., "Testing of dengue 2 live-attenuated vaccine (strain 16681 PDK 53) in ten American volunteers," Vaccine 1996, vol. 14 No. 4, pp. 329-336.
Venugopal et al., "Immunity to St. Louis encephalitis virus by sequential immunization with recombinant vaccinia and baculovirus derived PrM/E proteins," Vaccine, 1995, vol. 13, No. 11, pp. 1000-1005.
Wang et al., "Immune Response to Neonatal Genetic Immunization," Virology, 1997, vol. 228, pp. 278-284.
Wolff et al., "Long-term persistence of plasmid DNA and foreign gene expression in mouse muscle," Hum. Mol. Genet., 1992, vol. 1, No. 6, pp. 363-369.
World Health Organization, "Dengue vaccine research: Immunization, Vaccines and Biologicals" www.who.int/immunization/research/development/dengue_vaccines/en/, Sep. 12, 2018, 3 pages.
World Health Organization, Dengue Vaccine Research, website page at www.who.int/immunuzation/research/development/dengue_vaccines/en, last updated Dec. 5, 2017, 3 pages.
World Health Organization, Updated Questions and Answers related to the dengue vaccine Dengvaxia and its use, website page at www.who.int/immunization/diseases/dengue/q_and_a_dengue_vaccine_dengvaxia_use/en/published Dec. 22, 2017, 7 pages.
Yamshchikov et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.
Yang et al., "A p300/CBP-associated factor that competes with the adenoviral oncoprotein E1A," Nature, Jul. 25, 1996, vol. 382.
Zhang et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.
Zhang et al., "Passive Protection of Mice, Goats, and Monkeys Against Japanese Encephalitis With Monoclonal Antibodies," 1989, J. Med. Virol., vol. 29, pp. 133-138.
Zhao et al., "Cloning Full-Length Dengue Type 4 Viral DNA Sequences: Analysis of Genes Coding for Structural Proteins," Virology, 1986, vol. 155, pp. 77-88.
Zhao et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.
Asnis et al., "The West Nile Virus Outbreak of 1999 in New York: The Flushing Hospital Experience," Clinical Infectious Diseases, 2000, vol. 30, pp. 413-418.
Monath et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, mmunogenic and protective in non-human primates," Vaccine, 1999, vol. 17pp. 1869-1882.
Subchareon et al., "Safety and Immunogenictiy of Tetra Live-Attenuated Dengue Vaccines in Thai Adult Volunteers: Role of Serotype Concentration, Ratio, and Multiple Doses," Am. J. Trap. Med. Hyg., 2002, vol. 66, No. 3, pp. 264-272.
Sumiyoshi et al., "Complete Nucleotide Sequence of Japanese Encephalitis Virus Genome RNA," Virology, 1987, vol. 161, pp. 497-510.
Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.
Trent Dennis W. et al., "Recombinant dengue virus vaccines." In: Dengue and Dengue Hemorrhagic Fever. D.J. Gubler and G. Kuno (eds ). CAB International, New York, NY Chapter 18, 1997, pp. 379-403.
Troyer et al., "A Live Attenuated Recombinant Dengue-4 Virus Vaccine Candidate With Restricted Capacity For Dissemination In Mosquitoes And Lack Of Transmission From Vaccinees To Mosquitoes," Am. J. Trap. Med. Hyg., 2001, vol. 65, No. 5, pp. 414-419.

(56) References Cited

OTHER PUBLICATIONS

Xie et al., "Membrane Topology and Function of Dengue Virus NS2A Protein," Journal of Virology, Apr. 2013, vol. 87, No. 8, pp. 4609-4622.

Yoksan et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.

Bray, M. et al., "Monkeys Immunized with Intertypic Chimeric Dengue Viruses Are Protected against Wild-Type Virus Challenge," Journal of Virology, Jun. 1996, vol. 70, No. 6, pp. 4162-4166.

Caufour, P. S. et al., "Construction, characterization and immunogenicity of recombinant yellow fever 17D-dengue type 2 viruses," Virus Research, 2001, vol. 79, pp. 1-14.

Chang, G et al., "A Single Intramuscular Injection of Recombinant Plasmid DNA Induces Protective Immunity and Prevents Japanese Encephalitis in Mice," Journal of Virology, May 2000, vol. 74, No. 9, pp. 4244-4252.

Huang, C. et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus" Journal of Virology, vol. 79, No. 12, Jun. 2005, pp. 7300-7310.

Hubálek et al., "West Nile Fever—a Reemerging Mosquito-Borne Viral Disease in Europe" Emerging Infectious Diseases, Sep.-Oct. 1999, vol. 5, No. 5, pp. 643-650.

JP 19920043682 Feb. 28, 1992 "Non-infective structure particle prepn., useful as vaccine—by infecting preliminarily flavivirus infected cell with cDNA integrated recombinant vaccinia virus, and then sepg. non-infective structure particles contg. E-protein of flavivirus" XP-00211903; Abtract Only.

Köhler, G. et al., "Continuous cultures of fused cells secreting antibody of predefined specificity," Nature, Aug. 7, 1975, vol. 256, pp. 495-497.

Roehrig, J. T. et al., "Identification of Epitopes on the E Glycoprotein of Saint Louis Encephalitis Virus Using Monoclonal Antibodies." Virology, 1983, vol. 128, pp. 118-126.

Villar, L. et al., "Efficacy of a Tetravalent Dengue Vaccine in Children in Latin America," New England Journal of Medicine, Jan. 8, 2015, vol. 372, No. 2, pp. 113-123.

* cited by examiner

FIG. 1

DENGUE VACCINE UNIT DOSE AND ADMINISTRATION THEREOF

The Sequence Listing submitted in text format (.txt) filed herewith on Mar. 7, 2019, named "T08269US Sequence Listing" (created on Sep. 5, 2018, 173 KB), is incorporated herein by reference.

FIELD OF THE INVENTION

The present invention relates to unit doses of a dengue vaccine composition and methods for administering a unit dose of a dengue vaccine composition to a subject or a subject population. The unit dose according to this invention provides immune responses against all serotypes of dengue virus, i.e. DENV-1, DENV-2, DENV-3 and DENV-4.

BACKGROUND OF THE INVENTION

Vaccines for protection against viral infections have been effectively used to reduce the incidence of human disease. One of the most successful technologies for viral vaccines is to immunize animals or humans with a weakened or attenuated virus strain (a "live attenuated virus"). Due to limited replication after immunization, the attenuated virus strain does not cause disease. However, the limited viral replication is sufficient to express the full repertoire of viral antigens and can generate potent and long-lasting immune responses to the virus. Thus, upon subsequent exposure to a pathogenic virus strain, the immunized individual is protected from the disease. These live attenuated viral vaccines are among the most successful vaccines used in public health.

Dengue disease is a mosquito-borne disease caused by infection with a dengue virus. Dengue virus infections can lead to debilitating and painful symptoms, including a sudden high fever, headaches, joint and muscle pain, nausea, vomiting and skin rashes. To date, four serotypes of dengue virus have been identified: dengue-1 (DENV-1), dengue-2 (DENV-2), dengue-3 (DENV-3) and dengue-4 (DENV-4). Dengue virus serotypes 1-4 can also cause dengue hemorrhagic fever (DHF) and dengue shock syndrome (DSS). In the most severe cases, DHF and DSS can be life threatening. Dengue viruses cause 50-100 million cases of debilitating dengue fever, 500,000 cases of DHF/DSS, and more than 20,000 deaths each year, a large portion of which are children. All four dengue virus serotypes are endemic throughout the tropical regions of the world and constitute the most significant mosquito-borne viral threat to humans there. Dengue viruses are transmitted to humans primarily by *Aedes aegypti* mosquitoes, but also by *Aedes albopictus* mosquitoes. Infection with one dengue virus serotype results in life-long protection from re-infection by that serotype, but does not prevent secondary infection by one of the other three dengue virus serotypes. In fact, previous infection with one dengue virus serotype may lead to an increased risk of severe disease (DHF/DSS) upon secondary infection with a different serotype.

To date, only one vaccine, a tetravalent dengue vaccine based on a yellow fever backbone, CYD-TDV (Dengvaxia®, Sanofi Pasteur, Lyon, France), has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). However, clinical trials have shown that Dengvaxia® can enhance, rather than reduce, the risk of severe disease due to dengue infection in individuals who had not been previously infected by a dengue virus (seronegative populations). Therefore, Dengvaxia® is only recommended for use in individuals who had been previously infected with at least one dengue virus serotype (seropositive populations). More specifically, according to the European Medicine Agencys European Public Assessment report (EPAR) for the product, Dengvaxia® is only for use in people from 9 to 45 years of age who have been infected with dengue virus before and who live in areas where this infection is endemic. Endemic areas are areas where the disease occurs regularly throughout the year. See also Sridhar S et al. Effect of Dengue Serostatus on Dengue Vaccine Safety and Efficacy. N Engl J Med 2018, 379:327-40; and World Health Organization. Dengue vaccine: WHO position paper—September 2018. Wkly Epidemiol Rec 2018, 93:457-76. S. R. Hadinegoro et al. report in the New England Journal of Medicine, Vol. 373, page 1195, in "Efficacy and Long-Term Safety of a Dengue Vaccine in Regions of Endemic Disease" a pooled risk of hospitalization for virologically-confirmed dengue disease among those under the age of 9 years of 1.58 indicating an increased risk for the vaccinated group with respect to severe dengue. This leaves a substantial unmet need for an effective vaccine with a good safety profile in both dengue-naïve and seropositive individuals, including those dengue-naïve populations living in endemic areas, younger individuals who may not have developed any seropositive response to dengue or been exposed to dengue, and travelers and individuals from non-endemic regions. There is also a need for outbreak control or travel vaccination, offering a reduction in the risk of dengue after only one dose.

One further disadvantage of the only currently approved dengue vaccine, Dengvaxia®, is that it must only be given to people who have had a positive test result showing a previous infection with dengue virus (EPAR), i.e. individuals with known serostatus for dengue. Thus, individuals with unknown serostatus for dengue cannot be vaccinated with Dengvaxia®. There is thus a medical need for a dengue vaccine which, as well as being safe and efficacious for seropositive individuals, can also be administered to individuals with unknown dengue serostatus, children under 9 years old and seronegative individuals.

There is also a need for a vaccine that is administered in fewer doses than the current Dengvaxia® dosing schedule of 3 doses, 6 months apart, such as a vaccine that can be administered in only two doses or one dose to be efficacious.

Also, there is a need for a dengue vaccine that stimulates an immune response to all dengue serotypes, preferably a balanced immune response to all serotypes, and protects against dengue disease of any severity (including DSS, DHF), preferably both in seronegative and seropositive populations, which is safe for a larger group of ages, in particular for subjects of 9 years and younger. The development of a safe and effective vaccine capable of protecting all populations, including both seronegative and seropositive populations, and in particular children and young adults in endemic settings, represents an important approach to the prevention and control of this global disease.

OBJECTS AND SUMMARY

It is an object of the present invention to provide a safe and effective vaccine against all serotypes of dengue virus for dengue-endemic and dengue non-endemic populations and for a broad range of ages, in particular for subjects between 2 months and 60 years of age, and independent of previous exposure to dengue virus and corresponding seropositive or seronegative status before vaccination.

It is an object of the present invention to minimize the risk of DHF and DSS caused by infection with DENV-1, DENV-2, DENV-3 or DENV-4, in particular following vaccination in children of young age and individuals of any age who have never been previously exposed to dengue, or who are seronegative to dengue before vaccination.

It is an object of the present invention to provide a vaccine which stimulates a balanced immune response to all four dengue serotypes in a subject.

The present invention is therefore directed in part to a reconstituted dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent
  (i) dengue serotype 1 has a concentration of at least 3.3 log 10 pfu/0.5 mL and optionally to 5.0 log 10 pfu/0.5 mL,
  (ii) dengue serotype 2 has a concentration of at least 2.7 log 10 pfu/0.5 mL and optionally to 4.9 log 10 pfu/0.5 mL,
  (iii) dengue serotype 3 has a concentration of at least 4.0 log 10 pfu/0.5 mL and optionally to 5.7 log 10 pfu/0.5 mL, and
  (iv) dengue serotype 4 has a concentration of at least 4.5 log 10 pfu/0.5 mL and optionally to 6.2 log 10 pfu/0.5 mL.

The present invention is therefore directed in part to a dengue vaccine composition for use in a method of preventing virologically confirmable dengue disease (VCD) in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and preferably at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL, in particular wherein the dengue serotype 3 is at least about 10% of the total concentration in pfu/0.5 mL and in particular wherein the dengue serotype 4 is at least about 70% of the total concentration in pfu/0.5 mL.

The present invention is therefore directed in part to a unit dose of a dengue vaccine composition and use thereof, the unit dose comprising: a tetravalent dengue virus composition including four live attenuated dengue serotypes (e.g. virus strains):
  (i) a dengue serotype 1 (e.g. chimeric dengue serotype 2/1 strain),
  (ii) a dengue serotype 2 (e.g. dengue serotype 2 strain),
  (iii) a dengue serotype 3 (e.g. chimeric dengue serotype 2/3 strain),
  (iv) a dengue serotype 4 (e.g. chimeric dengue serotype 2/4 strain),
and one or more pharmaceutically acceptable excipients thereof.

The present invention is further directed in part to a unit dose of a dengue vaccine composition and use thereof, the unit dose comprising:
a tetravalent virus composition including four live attenuated dengue virus strains:
  (i) a dengue serotype 1 (e.g. chimeric dengue serotype 2/1 strain) in a concentration of at least 3.3 log 10 pfu/0.5 ml,
  (ii) a dengue serotype 2 (e.g. dengue serotype 2 strain) in a concentration of at least 2.7 log 10 pfu/0.5 ml,
  (iii) a dengue serotype 3 (e.g. chimeric dengue serotype 2/3 strain) in a concentration of at least 4.0 log 10 pfu/0.5 ml, and
  (iv) a dengue serotype 4 (e.g. chimeric dengue serotype 2/4 strain) in a concentration of at least 4.5 log 10 pfu/0.5 ml,
and one or more pharmaceutically acceptable excipients.

The present invention is further directed in part to a unit dose of a dengue vaccine composition and use thereof, the unit dose comprising:
a tetravalent virus composition including four live attenuated dengue virus strains, wherein the unit dose is lyophilized and upon reconstitution with 0.5 mL of a pharmaceutically acceptable diluent comprises:
  (i) a dengue serotype 1 (e.g. chimeric dengue serotype 2/1 strain) in a concentration of at least 3.3 log 10 pfu/0.5 ml,
  (ii) a dengue serotype 2 (e.g. dengue serotype 2 strain) in a concentration of at least 2.7 log 10 pfu/0.5 ml,
  (iii) a dengue serotype 3 (e.g. chimeric dengue serotype 2/3 strain) in a concentration of at least 4.0 log 10 pfu/0.5 ml, and
  (iv) a dengue serotype 4 (e.g. chimeric dengue serotype 2/4 strain) in a concentration of at least 4.5 log 10 pfu/0.5 ml.

The present invention is further directed in part to a unit dose of a dengue vaccine composition and use thereof, wherein said unit dose is lyophilized and obtained by lyophilizing 0.5 mL of a solution comprising:
a tetravalent virus composition including four live attenuated dengue virus strains:
  (i) a dengue serotype 1 (e.g. chimeric dengue serotype 2/1 strain) in a concentration of at least 3.3 log 10 pfu/0.5 ml,
  (ii) a dengue serotype 2 (e.g. dengue serotype 2 strain) in a concentration of at least 2.7 log 10 pfu/0.5 ml,
  (iii) a dengue serotype 3 (e.g. chimeric dengue serotype 2/3 strain) in a concentration of at least 4.0 log 10 pfu/0.5 ml, and
  (iv) a dengue serotype 4 (e.g. chimeric dengue serotype 2/4 strain) in a concentration of at least 4.5 log 10 pfu/0.5 ml,
and one or more pharmaceutically acceptable excipients.

The present invention is further directed in part to a kit for preparing a reconstituted unit dose and use thereof, the kit comprising the following components:
a) a lyophilized unit dose of the present invention as described herein, and
b) a pharmaceutically acceptable diluent for reconstitution.

The present invention is further directed in part to a container, such as a vial, comprising one to ten unit doses of the present invention as described herein.

The present invention is further directed to a method of preventing dengue disease in a subject comprising administering to the subject a reconstituted unit dose of a dengue vaccine composition as described herein, for example by subcutaneous injection.

The present invention is further directed in part to a method of preventing virologically confirmable dengue disease in a subject comprising administering to the subject a tetravalent dengue virus composition including four live, attenuated dengue virus strains representing serotype 1, serotype 2, serotype 3 and serotype 4, in particular without determining the serostatus of the subject at baseline, said method being safe and effective.

The present invention is further directed in part directed to such a method having a combined vaccine efficacy against all four dengue serotypes with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein preferably said unit dose or said placebo is administered at least twice within less than 6 months, such as within 3 months, and optionally at least 4 weeks apart, about 30 days after the second administration of the administration schedule until at least 12 months after the second administration of the administration schedule.

The present invention is further directed in part to such a method having a combined vaccine efficacy against all four dengue serotypes of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, and optionally at least 4 weeks apart, 30 days after the second administration until at least 12 months after the second administration.

The present invention is further directed to a method of preventing dengue disease in a subject population, comprising administering to the subject population a reconstituted unit dose of a vaccine composition as described herein, wherein the subject population is seronegative to all dengue serotypes. In said method the geometric mean neutralizing antibody titers (GMTs) when tested in at least 40, or at least 50, or at least 60 subjects at day 180 or day 365 after at least a first administration of said unit dose, and optionally a second administration of said unit dose 90 days after said first administration, may provide a ratio of not more than 50, or not more than 40, or nor more than 30, or not more than 20 for the GMT of dengue serotype 2 to the GMT of dengue serotype 4 (GMT DENV-2:GMT DENV-4), and optionally a ratio of not more than 20 for the GMT of dengue serotype 2 to the GMT of dengue serotype 1 (GMT DENV-2:GMT DENV-1), and optionally a ratio of not more than 20 for the GMT of dengue serotype 2 to the GMT of dengue serotype 3 (GMT DENV-2:GMT DENV-3).

The present invention is further directed to a method of preventing dengue disease in a subject, comprising administering to the subject a reconstituted unit dose of a vaccine composition as described herein, wherein the subject is seronegative to all dengue serotypes. In said method the neutralizing antibody titers when tested in the subject at day 180 or day 365 after at least a first administration of said unit dose, and optionally a second administration of said unit dose 90 days after said first administration, may provide a ratio of not more than 50, or not more than 40, or nor more than 30, or not more than 20 for the neutralizing antibody titer of dengue serotype 2 to the neutralizing antibody titer of dengue serotype 4, and optionally a ratio of not more than 20 for the neutralizing antibody titer of dengue serotype 2 to the neutralizing antibody titer of dengue serotype 1, and optionally a ratio of not more than 20 for the neutralizing antibody titer of dengue serotype 2 to the neutralizing antibody titer of dengue serotype 3.

In one preferred embodiment, the methods of preventing dengue disease of the present invention are not associated with an increased likelihood of solicited systemic adverse events, such as in children under 9 or seronegative individuals.

The present invention is further directed in part to the use of the reconstituted unit dose of a dengue vaccine composition as described herein for the manufacture of a medicament for preventing dengue disease in a subject.

The present invention is further directed in part to the reconstituted unit dose of a dengue vaccine composition as described herein for use in a method of preventing dengue disease in a subject as described herein.

DEFINITIONS

In describing the present invention, the following terms are to be used as indicated below. As used herein, the singular forms "a," "an," and "the" include plural references unless the context clearly indicates otherwise.

As used herein, the terms "unit dose of a dengue vaccine composition", "unit dose" and "unit dose of the invention as described herein" refer to the amount of a dengue vaccine which is administered to a subject in a single dose. In one embodiment, one unit dose is present in a vial and this unit dose is administered to a subject, optionally after reconstitution. In one embodiment, more than one unit dose of the dengue vaccine composition may be present in a vial so that with the content of one vial more than one subject can be vaccinated.

A "lyophilized unit dose" or "unit dose in lyophilized form" refers to the unit dose that is obtained by subjecting a given volume of the liquid dengue vaccine composition, such as 0.5 mL, to lyophilization. Thus, the aqueous formulations of the dengue vaccine composition being produced by combining the pharmaceutically acceptable excipients and the dengue virus composition comprising the four dengue virus strains, preferably TDV-1 to TDV-4, is subjected to lyophilization to obtain the lyophilized unit dose.

A "reconstituted unit dose" or "unit dose in reconstituted form" is obtained from the lyophilized dose by reconstitution with a pharmaceutically acceptable diluent. The diluent does not contain dengue virus. The reconstituted unit dose is a liquid which can be administered to a subject, for example by injection, such as subcutaneous injection.

As used herein, the term "upon reconstitution with 0.5 mL" is not limiting the reconstitution to be performed using 0.5 mL of the diluent, but refers to the concentration of the dengue viruses that will be present in the reconstituted unit dose when 0.5 mL diluent are used for reconstitution. While using a different volume for reconstitution (e.g. 0.8 mL) will result in a different concentration of dengue viruses in the reconstituted unit dose, the administration of the total volume of the unit dose (e.g. 0.8 mL) will result in the same total amount of dengue virus being administered.

As used herein, a "concentration of at least X log 10 pfu/0.5 mL" refers to the concentration of a dengue serotype in 0.5 mL, but is not limiting the unit dose to be 0.5 mL. If the unit dose has a volume different than 0.5 mL, or is lyophilized from a volume different than 0.5 mL, or is reconstituted with a volume different than 0.5 mL, said concentration will differ from the "concentration of at least X log 10 pfu/0.5 mL". However, if the unit dose has a volume of 0.5 mL, or is lyophilized from a volume of 0.5 mL, or is reconstituted with a volume of 0.5 mL, said concentration will be the "concentration of at least X log 10 pfu/0.5 mL". Thus, while the concentration may differ, the total amount of virus in the unit dose remains the same.

As used herein, the term "dengue serotype" refers to a species of dengue virus which is defined by its cell surface antigens and therefore can be distinguished by serological methods known in the art. At present, four serotypes of dengue virus are known, i.e. dengue serotype 1 (DENV-1), dengue serotype 2 (DENV-2), dengue serotype 3 (DENV-3) and dengue serotype 4 (DENV-4).

As used herein, the term "tetravalent dengue virus composition" refers to a dengue virus composition comprising four different immunogenic components from the four different dengue serotypes DENV-1, DENV-2, DENV-3 and DENV-4, preferably comprising four different live, attenuated dengue viruses, each representing one dengue serotype, and which aims to stimulate immune responses to all four dengue serotypes.

As used herein, the term "live attenuated dengue virus" refers to a viable dengue virus which is mutated to provide reduced virulence. The live attenuated dengue virus can be a dengue virus in which all components are derived from the same dengue serotype or it can be a chimeric dengue virus having parts from two or more dengue serotypes.

A "virus strain" and in particular a "dengue virus strain" is a genetic subtype of a virus, in particular of a dengue virus, which is characterized by a specific nucleic acid sequence. A dengue serotype may comprise different strains with different nucleic acid sequences which have the same cell surface antigens. A dengue virus strain can be a dengue virus in which all components are derived from the same dengue serotype or it can be a chimeric dengue virus having parts from two or more dengue serotypes.

As used herein, "TDV-2" refers to a molecularly characterized and cloned dengue serotype 2 strain derived from the live attenuated DEN-2 PDK-53 virus strain. The PDK-53 strain is described for example in Bhamarapravati et al. (1987) Bulletin of the World Health Organization 65(2): 189-195. In one embodiment, the TDV-2 strain served as a backbone for the chimeric TDV-1, TDV-3 and TDV-4 strains into which parts from the TDV-1, TDV-3 and TDV-4 strains were introduced.

A "non-chimeric dengue virus" or "non-chimeric dengue serotype strain" or "non-chimeric dengue strain" comprises only parts from one dengue serotype. In particular, a non-chimeric dengue virus does not include parts from a different flavivirus such as yellow fever virus, Zika virus, West Nile virus, Japanese encephalitis virus, St. Louis encephalitis virus, tick-borne encephalitis virus. TDV-2 is an example of a non-chimeric dengue virus.

A "chimeric dengue virus" or "chimeric dengue serotype strain" or "chimeric dengue strain" comprises parts from at least two different dengue serotypes. As used herein, the chimeric dengue virus does not include parts from a different flavivirus such as yellow fever virus, Zika virus, West Nile virus, Japanese encephalitis virus, St. Louis encephalitis virus, tick-borne encephalitis virus. In particular, the chimeric dengue virus described herein does not include parts from the yellow fever virus. As used herein, a "chimeric dengue serotype 2/1 strain" or "DENV-2/1 chimera" or "TDV-1" refers to a dengue virus chimeric construct which comprises parts from both DENV-2 and DENV-1. In particular, in the chimeric dengue serotype 2/1 strain the prM and E proteins from DENV-1 replace the prM and E proteins from DENV-2 as detailed below. As used herein, a "chimeric dengue serotype 2/3 strain" or "DENV-2/3 chimera" or "TDV-3" refers to a dengue virus chimeric construct which comprises parts from both DENV-2 and DENV-3. In particular, in the chimeric dengue serotype 2/3 strain the prM and E proteins from DENV-3 replace the prM and E proteins from DENV-2 as detailed below. As used herein, a "chimeric dengue serotype 2/4 strain" or "DENV-2/4 chimera" or "TDV-4" refers to a dengue virus chimeric construct which comprises parts from both DENV-2 and DENV-4. In particular, in the chimeric dengue serotype 2/4 strain the prM and E proteins from DENV-4 replace the prM and E proteins from DENV-2 as detailed below.

As used herein, "TDV" refers to a tetravalent live attenuated dengue vaccine that comprises a mixture of the four live attenuated dengue virus strains TDV-1, TDV-2, TDV-3 and TDV-4 expressing surface antigens from the four dengue serotypes DENV-1, DENV-2, DENV-3 and DENV-4, respectively. In one embodiment, TDV-1 has the nucleotide sequence according to SEQ ID No. 1 and/or the amino acid sequence according to SEQ ID No. 2. In one embodiment, TDV-2 has the nucleotide sequence according to SEQ ID No. 3 and/or the amino acid sequence according to SEQ ID No. 4. In one embodiment, TDV-3 has the nucleotide sequence according to SEQ ID No. 5 and/or the amino acid sequence according to SEQ ID No. 6. In one embodiment, TDV-4 has the nucleotide sequence according to SEQ ID No. 7 and/or the amino acid sequence according to SEQ ID No. 8.

As used herein, the term "dengue disease" refers to the disease which is caused by infection with dengue virus. Symptoms of dengue disease include sudden high fever, headaches, joint and muscle pain, nausea, vomiting and skin rashes. The term dengue disease also includes the more severe forms of dengue hemorrhagic fever (DHF) and dengue shock syndrome (DSS). Symptoms of DHF include increased vascular permeability, hypovolemia and abnormal blood clotting mechanisms. Subjects with DHF may present with severe manifestations of plasma leakage and hemorrhage. When a subject with DHF experiences shock he or she will be categorized as having DSS. Symptoms of DSS include bleeding that may appear as tiny spots of blood on the skin and larger patches of blood under the skin. Prolonged shock is the main factor associated with complications including massive gastrointestinal hemorrhage that can lead to death. As used herein, DHF cases are defined as VCD cases meeting WHO 1997 DHF criteria.

As used herein, "preventing dengue disease" refers to preventing a subject from developing one or more symptoms of dengue disease because of an infection with a dengue virus. In particular, preventing dengue disease is achieved by vaccinating or inoculating a subject with a dengue vaccine composition, such as the reconstituted unit dose described herein. As used herein, the term "prophylactically treating dengue disease" is equivalent to "preventing dengue disease". In a particular embodiment, preventing dengue disease includes preventing DHS and/or DSS.

As used herein, the terms "virologically-confirmed dengue disease", "VCD case", or "VCD fever" refer to febrile illness or illness clinically suspected to be dengue disease with a positive serotype-specific reverse transcriptase polymerase chain reaction (RT-PCR). The term "virologically confirmable dengue" disease refers to a subject having febrile illness or illness clinically suspected to be dengue disease, wherein testing the subject, e.g. using RT-PCR, would confirm the presence of at least one dengue serotype. Severe forms of VCD fever will be identified as follows: Dengue Hemorrhagic Fever (DHF) was defined according to the WHO 1997 criteria. Severe dengue was defined through an assessment of an independent Dengue Case Adjudication Committee which will assess all hospitalized VCD cases (severe/non-severe) based on criteria redefined in a charter. All non-hospitalized cases are considered non-severe.

As used herein, the term "febrile illness" is defined as temperature ≥38° C. on any 2 of 3 consecutive days.

As used herein, the terms "virologically-confirmed dengue disease with hospitalization", is considered to be a surrogate for severe dengue and the "incidence of virologically-confirmed dengue disease with hospitalization" is used as a safety parameter. As used herein, the "relative risk with respect to virologically-confirmed dengue disease with hospitalization" means the number of events of virologically confirmed dengue disease with hospitalization divided by the number of subjects treated with the unit dose as disclosed herein over the number of events of virologically confirmed dengue disease with hospitalization divided by the number of subjects treated with placebo. If the "relative risk with respect to virologically-confirmed dengue disease with hospitalization" is 1 or lower the vaccine provides for the same or less risk for virologically-confirmed dengue disease with hospitalization as placebo and is considered "safe". In this context the risk of virologically-confirmed dengue disease with hospitalization may be also 0.9 or less, 0.8 or less, 0.7 or less, 0.6 or less, 0.5 or less, 0.4 or less, 0.3 or less, 0.2 or less, or 0.1 or less, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects.

As used herein, alternatively a vaccine is considered "safe" when the vaccine efficacy (VE) with respect to virologically-confirmed dengue disease with hospitalization is 0% or higher. This means that the vaccine provides for the same likelihood or less for virologically-confirmed dengue disease with hospitalization as placebo. In particular considered "safe" is the combined vaccine efficacy against virologically-confirmed dengue with hospitalization against all four serotypes with a 2-sided 95% confidence interval, wherein the lower bound is more than 25%, in particular when measured against placebo in a subject population of at least 2,000 healthy subjects (in particular when measured in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects) being seronegative against all serotypes at baseline or being seropositive against at least one serotype at baseline, in particular when said unit dose or said placebo is administered at least twice within less than 6 months, such as within 3 months, about 30 days after the second administration of the administration schedule until at least 12 months after the second administration of the administration schedule. In particular, the lower bound may be more than 30%, more than 40%, more than 50%, more than 60%, more than 70%, or more than 75%. In particular, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points.

If one of the criteria as defined above for the term "safe" is fulfilled, the vaccine is considered safe within the meaning of this invention. In this context, safe in particular refers to a vaccine that is safe for all subjects irrespective of their serostatus at baseline. This means that the vaccine can be administered without the need to determine the occurrence of a previous dengue infection in the subject before administration. Preferably, the vaccine is safe as defined above with respect to all age groups starting from 4 years of age and preferably irrespective of the serostatus, in particular from 4 years of age to 60 years of age, or 4 years of age to 16 years of age. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age.

As used herein, "vaccine efficacy" or "VE" measure the proportionate reduction in cases among vaccinated persons. Vaccine efficacy (VE) is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy. For example, a VE of 90% indicates a 90% reduction in disease occurrence among the vaccinated group, or a 90% reduction from the number of cases you would expect if they have not been vaccinated. The vaccine efficiency is calculated by the formula: 100*(1−HR), wherein HR is the Hazard Ratio which is defined as the Hazard rate of vaccine ($\lambda v$) divided by the Hazard rate of placebo ($\lambda c$), i.e. HR=$\lambda v/\lambda c$. $\lambda v$ denote the hazard rate for the subjects vaccinated with a tetravalent dengue vaccine composition as disclosed herein and $\lambda c$ denote the hazard rate for unvaccinated subjects, i.e. subjects receiving placebo. The hazard rate ratio HR is estimated from a Cox proportional hazard model with study vaccine as a factor, adjusted for age, and stratified by region. As used herein the term"combined vaccine efficacy against all four serotypes" is defined as the vaccine efficacy in relation to the risk of dengue disease irrespective of the serotype being responsible for the virologically-confirmed dengue disease and the subject baseline serostatus. A vaccine is considered "effective" in case the combined vaccine efficacy is above 30%. In this context the combined vaccine efficacy may be also 40% or more, 50% or more, 60% or more, 70% or more, or 80% or more, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects. In this context, effective in particular refers to a vaccine that is effective for all subjects irrespective of their serostatus at baseline. Preferably, the vaccine is effective with respect to all age groups starting from 4 years of age and preferably irrespective of the serostatus, in particular from 4 years of age to 60 years of age or from 4 years of age to 16 years of age and irrespective of the serostatus. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. Further specific efficacies can be defined. As used herein, "combined vaccine efficacy against all four serotypes in seronegative subjects" refers to the efficacy measured in subjects which are seronegative at baseline. As used herein, "vaccine efficacy against a specific serotype, e.g. serotype 1" refers to the efficacy in relation to a specific serotype being responsible for the virologically-confirmed dengue disease. As used herein, "combined vaccine efficacy against all four serotypes against virologically-confirmed dengue with hospitalization" refers to the efficacy wherein only virologically-confirmed dengue cases with hospitalization are considered. Such vaccine efficacies can be determined with respect to subjects being seronegative or seropositive at baseline and for different age groups.

As used herein, the "relative risk" means the number of events of virologically confirmed dengue disease divided by the number of subjects treated with the unit dose as disclosed herein over the number of events of virologically confirmed dengue disease divided by the number of subjects treated with placebo. As used herein the term"combined relative risk against all four serotypes" is defined as the relative risk in relation to the risk of dengue disease irrespective of the serotype being responsible for the virologically-confirmed dengue disease and the subject baseline serostatus.

As used herein, "vaccinating" or "inoculating" refers to the administration of a vaccine to a subject with the aim to prevent the subject from developing one or more symptoms of a disease. As used herein, "vaccinating against dengue disease" or "inoculating against dengue disease" refers to the administration of a dengue vaccine composition to a subject with the aim to prevent the subject from developing one or more symptoms of dengue disease.

As used herein, the terms "subject" or "subjects" are limited to human subjects (e.g. infants, children or adults).

As used herein, "subject population" refers to a group of subjects. The subject population may refer to least 40 subjects, at least 50 subjects, at least 60 subjects, at least 100 subjects or at least 1000 subjects and is defined by certain parameters. The parameters that may be used to define a subject population include, but are not limited to, the age of the subjects, whether the subjects are from a dengue endemic region or from a dengue non-endemic region and the serostatus of the subjects.

As used herein, "endemic region" refers to a region where a disease or infectious agent is constantly present and/or usually prevalent in a population within this region. As used herein, "non-endemic region" refers to a region from which the disease is absent or in which it is usually not prevalent. Accordingly, a "dengue endemic region" refers to geographic areas in which an infection with dengue virus is constantly maintained at a baseline level. A "dengue non-endemic region" is a geographic area in which an infection with dengue virus is not constantly maintained at a baseline level. Accordingly, subject populations or subjects "from a dengue endemic region" or "from a dengue non-endemic region" refer to subject populations or subjects living in geographic areas as defined above. Whether a geographic area or a subject population is dengue-endemic or not can be determined by different calculatory methods such as the ones described in Bhatt et al. (2013) Nature 496 (7446): 504-507 and supplementary material and in Stanaway et al. (2016) Lancet Infect Dis. 16(6): 712-723 and supplementary material. Overviews of dengue endemic regions and dengue epidemiology are regularly published, for example, by the WHO or CDC. Typical dengue-endemic regions are in Latin America, Southeast Asia and the Pacific islands and dengue endemic countries include, but are not limited to, Australia, Brazil, Bangladesh, Colombia, China, Dominican Republic, Indonesia, India, Mexico, Malaysia, Nicaragua, Nigeria, Pakistan, Panama, Philippines, Puerto Rico, Singapore, Sri Lanka, Thailand and Vietnam.

As used herein, "serostatus" refers to the amount of antibodies a subject has with respect to a certain infectious agent, in particular dengue virus. As used herein, "seronegative" or "seronaïve" means that the subject does not have neutralizing antibodies against any one of dengue serotypes DENV-1, DENV-2, DENV-3 and DENV-4 in the serum. A seronegative or seronaïve subject or subject population is defined by a neutralizing antibody titer of less than 10 for each one of the four dengue serotypes. A subject or subject population having a neutralizing antibody titer of equal to or more than 10 for at least one dengue serotype is defined as being "seropositive" with respect to said dengue serotype. Serostatus at baseline refers to the serostatus before the administration of a dengue vaccine composition as described herein.

As used herein, a "neutralizing antibody titer" refers to the amount of antibodies in the serum of a subject that neutralize the respective dengue serotype. The neutralizing antibody titer against DENV-1, DENV-2, DENV-3 and DENV-4 is determined in a serum sample of the subject using known methods such as the plaque reduction neutralization test (PRNT) as described in the WHO Guidelines (World Health Organization Department of Immunization Vaccines Biologicals (2007) Guidelines for plaque reduction neutralization testing of human antibodies to dengue viruses, WHO/IVB/07.07) or a microneutralization (MNT50) assay as described herein. As used herein, the "ratio of not more than 20 for the neutralizing antibody titer of dengue serotype 2 to the neutralizing antibody titer of dengue serotype 4" means that the neutralizing antibody titer of dengue serotype 2 is divided by the neutralizing antibody titer of dengue serotype 4 and that the ratio obtained hereby is no more than 20. In other words, the neutralizing antibody titer of dengue serotype 2 is not more than 20-times higher than the neutralizing antibody titer of dengue serotype 4 in the subject.

As used herein, the terms "geometric mean neutralizing antibody titer" and "GMT" refer to the geometric mean value of the titer of neutralizing antibodies against the corresponding dengue serotype in the serum of subjects in a subject population. The geometric mean value is calculated by a well-known formula. As used herein, the "ratio of not more than 20 for the GMT of dengue serotype 2 to the GMT of dengue serotype 4" means that the geometric mean neutralizing antibody titer of dengue serotype 2 (GMT DENV-2) is divided by the geometric mean neutralizing antibody titer of dengue serotype 4 (GMT DENV-4) and that the ratio obtained hereby is no more than 20. In other words, the geometric mean neutralizing antibody titer of dengue serotype 2 is not more than 20-times higher than the geometric mean neutralizing antibody titer of dengue serotype 4 in the subject population.

As used herein, an "immune response" refers to a subjects response to the administration of the dengue vaccine. In particular, the immune response includes the formation of neutralizing antibodies to one or more dengue serotypes. It may also include the stimulation of a cell-mediated response or the formation of antibodies to non-structural proteins such as NS1. An immune response is stimulated by the administration of a unit dose of the invention as described herein, if the titer of neutralizing antibodies against at least one dengue virus serotype and preferably against all four dengue virus serotypes is increased after said administration of said unit dose. An immune response is stimulated by the administration of a unit dose of the invention as described herein, if the secretion of interferon gamma by peripheral blood mononuclear cells stimulated with peptides from dengue virus proteins is increased after said administration of said unit dose. An immune response is stimulated by the administration of a unit dose of the invention as described herein, if the titer of antibodies to non-structural proteins such as NS1 is increased after said administration of said unit dose. In a particular embodiment, the administration of a reconstituted unit dose of the present invention as described herein stimulates the formation of neutralizing antibodies to one or more dengue serotypes, a cell-mediated response and the formation of antibodies to non-structural proteins such as NS1.

As used herein, a "balanced immune response" means that the immune response to the four dengue serotypes is sufficient to provide protection against infection by all four dengue serotypes and preferably the immune response to the four dengue serotypes has a similar strength. In particular, the neutralizing antibody titer against the four dengue serotypes at day 180 or day 365 after administration of a first reconstituted unit dose of the invention as described herein is similar, i.e. it differs by less than factor 30, by less than factor 25 or by less than factor 20.

As used herein, "solicited systemic adverse events" in children under 6 years are defined as fever, irritability/fussiness, drowsiness and loss of appetite that occurred within 14 days after each vaccination, and in children of 6 years or more are defined as fever, headache, asthenia, malaise and myalgia that occurred within 14 days after each vaccination.

As used herein, "solicited local adverse events" are injection site pain, injection site erythema and injection site swelling that occurred within 7 days after each vaccination.

As used herein, "unsolicited adverse events" are any adverse events (AEs) that are not solicited local or systemic AEs, as defined above.

As used herein, a "serious adverse event" or "SAE" is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

The relationship of each AE, including solicited systemic AEs (solicited local AEs are considered as related) to trial vaccine(s) will be assessed using the following categories: As used herein, "IP-Related AE" or "vaccine related AE" means that there is suspicion that there is a relationship between the vaccine and the AE (without determining the extent of probability); there is a reasonable possibility that the vaccine contributed to the AE. As used herein, "Non-IP Related" or "non-vaccine related" means that there is no suspicion that there is a relationship between the vaccine and the AE; there are other more likely causes and administration of the vaccine is not suspected to have contributed to the AE.

As used herein, a subject or subject population being "2 to 17 years of age" refers to a subject or subject population being 2 to 17 years of age on the first day of the administration of the dengue vaccine composition as described herein.

As used herein "%-points" refers to the difference of two %-values in a %-value. For example two values in % which are within 5%-points refers to e.g. one value at 1% and a second value at 6%.

As used herein, the term "determination of the previous dengue infection in the subject before administration" means that a previous dengue infection has to be assessed before vaccination in that there is a laboratory confirmed history of dengue or through an appropriately validated serological test e.g. by the method as disclosed herein such as the MNT50 test described in Example 2 or any serotesting with adequate performance in terms of specificity and cross reactivity based on the locale disease epidemiology.

BRIEF DESCRIPTION OF THE DRAWINGS

Figure 1:
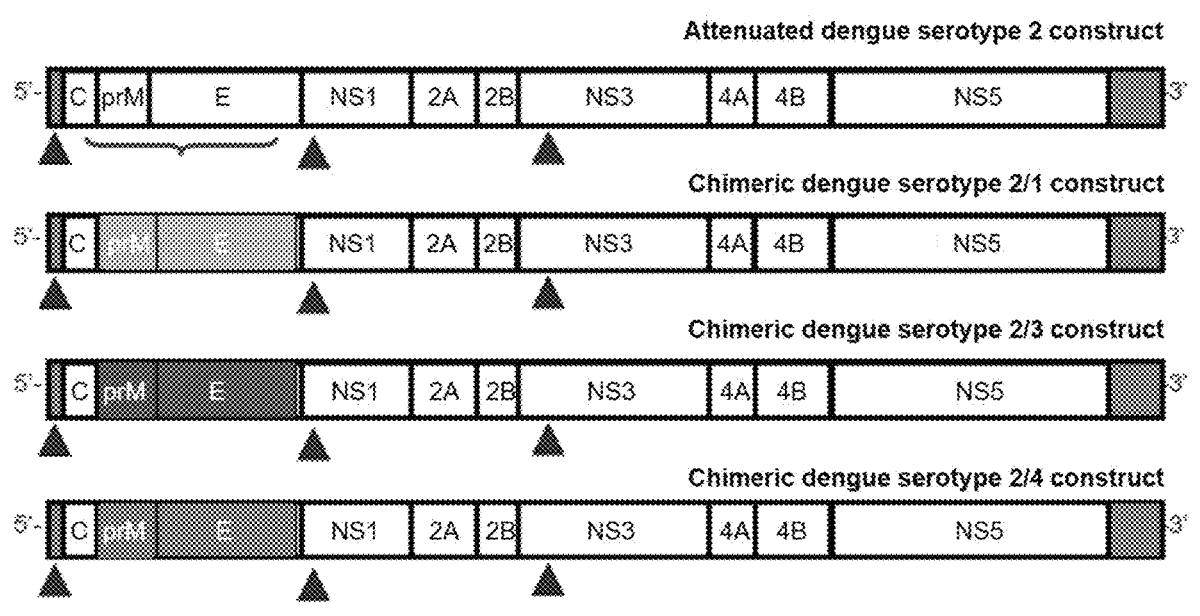

FIG. 1: Genetic structure of the four dengue strains contained in TDV. The solid red triangles indicate the three attenuating mutations present in the 5'NCR, NS1 and NS3 proteins. The TDV-1, TDV-3 and TDV-4 strains are chimeric viruses where the prM and E genes from dengue serotype 1, 3 and 4, respectively, are inserted into the TDV-2 backbone.

FIG. 3A shows the results for participants seropositive (set of graphs on the left) and seronegative (set of graphs on the right) at baseline, per-protocol set. FIG. 3B shows the results for the entire trial population (all) per-protocol set

DETAILED DESCRIPTION

Dengue Virus Strains

Figure 2:
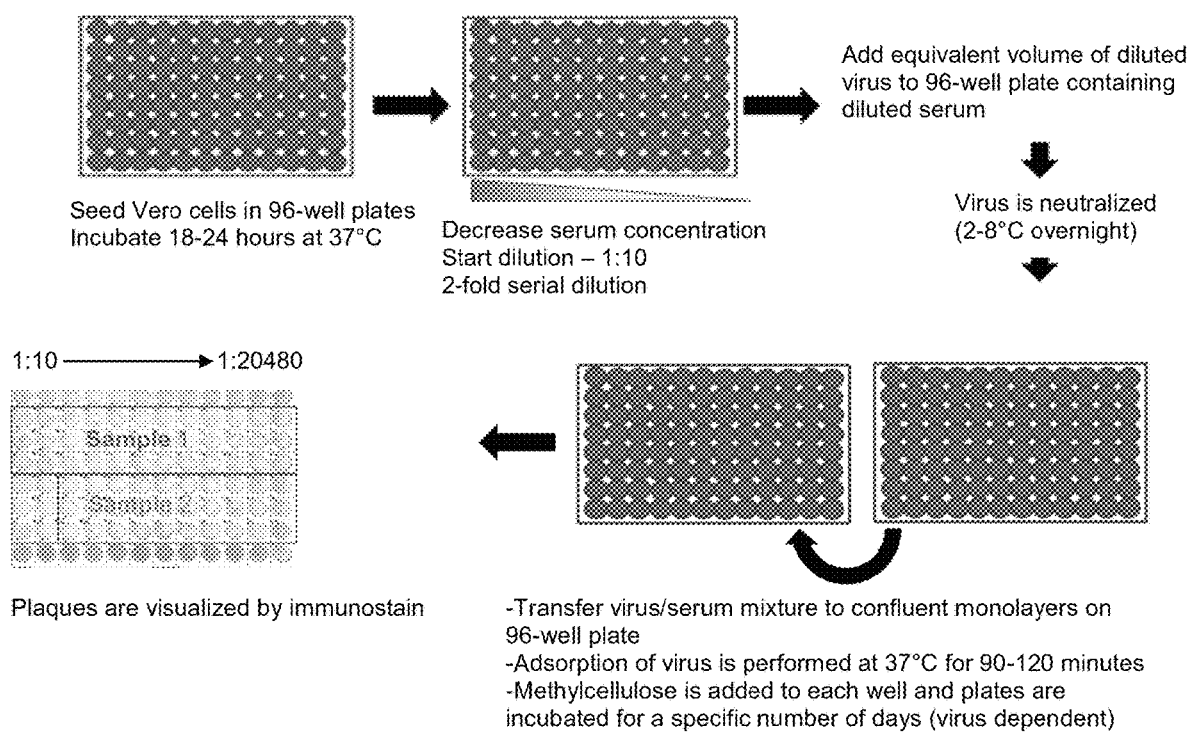
FIG. 2: Schematic drawing illustrating the microneutralization test (MNT) used to determine the titer of neutralizing antibodies.

The dengue virus is a single stranded, positive sense RNA virus of the family flaviviridae. The taxonomy is outlined in Table 1. The family flaviviridae includes three genera, flavivirus, hepacivirus and pestivirus. The genus flavivirus contains highly pathogenic and potentially hemorrhagic fever viruses, such as yellow fever virus and dengue virus, encephalitic viruses, such as Japanese encephalitis virus, Murray Valley encephalitis virus and West Nile virus, and a number of less pathogenic viruses.

TABLE 1

| Dengue Virus Taxonomy of the GMO Parental Strain | |
|---|---|
| Family | Flaviviridae |
| Genus | Flavivirus |
| Species | Dengue virus |
| Strains | Dengue Serotype 2 (Strain 16681), Strain DEN-2 PDK-53 |
| GMO parent | TDV-2 |

The flavivirus genome comprises in 5' to 3' direction (see FIG. 1):
- a 5'-noncoding region (5'-NCR),
- a capsid protein (C) encoding region,
- a pre-membrane protein (prM) encoding region,
- an envelope protein (E) encoding region,
- a region encoding nonstructural proteins (NSI, NS2A, NS2B, NS3, NS4A, NS4B, NS5) and
- a 3' noncoding region (3'-NCR).

The viral structural proteins are C, prM and E, and the nonstructural proteins are NSI to NS5. The structural and nonstructural proteins are translated as a single polyprotein and processed by cellular and viral proteases.

The unit dose of the invention as described herein comprises a dengue virus composition that comprises four live attenuated dengue virus strains (tetravalent dengue virus composition) representing dengue serotype 1, dengue serotype 2, dengue serotype 3 and dengue serotype 4. Preferably the composition comprises chimeric dengue viruses and optionally at least one non-chimeric dengue virus, in particular a molecularly characterized and cloned dengue serotype 2 strain derived from the live attenuated DEN-2 PDK-53 virus strain (TDV-2), and three chimeric dengue strains derived from the TDV-2 strain by replacing the structural proteins prM and E from TDV-2 with the corresponding structural proteins from the other dengue serotypes, resulting in the following chimeric dengue strains:
- a DENV-2/1 chimera (TDV-1),
- a DENV-2/3 chimera (TDV-3) and
- a DENV-2/4 chimera (TDV-4).

The genetically modified tetravalent dengue vaccine TDV is based on a molecularly characterized and cloned dengue-2 virus strain (TDV-2). This attenuated TDV-2 strain was generated by cDNA cloning of the attenuated laboratory-derived DEN-2 PDK-53 virus strain that was originally isolated at Mahidol University, Bangkok, Thailand (Kinney et al. (1997) Virology 230(2): 300-308). DEN-2 PDK-53 was generated by 53 serial passages in primary dog kidney (PDK) cells at 32° C. (Bhamarapravati et al. (1987) Bull. World Health Organ. 65(2): 189-195).

The attenuated DEN-2 PDK-53 strain (the precursor of TDV-2) was derived from the wild type virus strain DEN-2 16681 and differs in nine nucleotides from the wild type as follows (Kinney et al. (1997) Virology 230(2): 300-308):

(i) 5'-noncoding region (NCR)-57 (nt-57 C-to-T): major attenuation locus (ii) prM-29 Asp-to-Val (nt-524 A-to-T)

(iii) nt-2055 C-to-T (E gene) silent mutation (iv) NS1-53 Gly-to-Asp (nt-2579 G-to-A): major attenuation locus (v) NS2A-181 Leu-to-Phe (nt-4018 C-to-T)

(vi) NS3-250 Glu-to-Val (nt-5270 A-to-T): major attenuation locus (vii) nt-5547 (NS3 gene) T-to-C silent mutation (viii) NS4A-75 Gly-to-Ala (nt-6599 G-to-C)

* nt-8571 C-to-T (NS5 gene) silent mutation

The three nucleotide changes located in the 5' noncoding region (NCR) (nucleotide 57) (mutation (i)), the NS-1 (amino acid 828 of SEQ ID NO. 4) (mutation (iv)) and NS-3 genes (amino acid 1725 of SEQ ID NO. 4) (mutation (vi)) form the basis for the attenuation phenotype of the DEN-2 PDK-53 strain (Butrapet et al. (2000) J. Virol. 74(7): 3111-3119) (Table 2). These three mutations are referred to herein as the "attenuating mutations" and are comprised in TDV-1, TDV-2, TDV-3 and TDV-4.

TABLE 2

Attenuating mutations in the common genetic backbone of all TDV strains

| Location of Mutation | Nucleotide Change in TDV-2 | Amino Acid Change in TDV-2 |
|---|---|---|
| 5' Noncoding Region (5'NCR) | 57 C to T | Not applicable (silent) |
| Nonstructural Protein 1 (NS1) | 2579 G to A | 828 Gly to Asp |
| Nonstructural Protein 3 (NS3) | 5270 A to T | 1725 Glu to Val |

In one embodiment, TDV-2 comprises in addition to the three attenuating mutations one or more mutations selected from:

a) a mutation in the prM gene at nucleotide 524 from adenine to thymidine resulting in an amino acid change at position 143 from asparagine to valine, and/or b) a silent mutation in the E gene at nucleotide 2055 from cytosine to thymidine, and/or c) a mutation in the NS2A gene at nucleotide 4018 from cytosine to thymidine resulting in an amino acid change at position 1308 from leucine to phenylalanine, and/or d) a silent mutation in the NS3 gene at nucleotide 5547 from thymidine to cytosine, and/or e) a mutation in the NS4A gene at nucleotide 6599 from guanine to cytosine resulting in an amino acid change at position 2168 from glycine to alanine, and/or f) a silent mutation in the prM gene at nucleotide 900 from thymidine to cytosine.

The silent mutation in the NS5 gene at nucleotide 8571 from cytosine to thymidine of DEN-2 PDK-53 is not present in the TDV-2 strain.

In another embodiment, TDV-2 comprises in addition to the three attenuating mutations one or more mutations selected from:

g) a mutation in the prM gene at nucleotide 592 from adenine to guanine resulting in an amino acid change at position 166 from lysine to glutamine, and/or h) a mutation in the NS5 gene at nucleotide 8803 from adenine to guanine resulting in an amino acid change at position 2903 from isoleucine to valine.

In another embodiment, TDV-2 comprises in addition to the three attenuating mutations the mutations a) and g), preferably the mutations a), g), c), e) and h), more preferably the mutations a), g), c), e), h) and b), even more preferably the mutations a), g), c), e), h), b) and d), and most preferably the mutations a) to h). The nucleotide positions and amino acids positions of TDV-2 refer to the nucleotide sequence as shown in SEQ ID NO. 3 and amino acid sequence as shown in SEQ ID NO. 4.

The dengue virus structural envelope (E) protein and pre-membrane (prM) protein have been identified as the primary antigens that elicit a neutralizing protective antibody response (Plotkin 2001). For creation of the tetravalent dengue vaccine (TDV), TDV-2 was modified by replacing the nucleic acid sequence encoding the DENV-2 prM and E glycoproteins with the nucleic acid sequence encoding the corresponding wild type prM and E glycoproteins from the DENV-1, DENV-3, and DENV-4 wild type strains DENV-1 16007, DENV-3 16562 or DENV-4 1036 virus, respectively, (see Table 3) using standard molecular genetic engineering methods (Huang et al. (2003) J. Virol. 77(21): 11436-11447).

TABLE 3

Viral origin of prM/E gene regions of the TDV virus strains

| Virus | Strain | Origin | Source | Reference |
|---|---|---|---|---|
| DENV-1 | 16007 | Thailand, 1964 | DHF/DSS patient | Halstead and Simasthien, 1970 |
| DENV-2 | 16681 | Thailand, 1964 | DHF/DSS patient | Halstead and Simasthien, 1970 |
| DENV-3 | 16562 | Philippines, 1964 | DHF patient | Halstead and Simasthien, 1970 |
| DENV-4 | 1036 | Indonesia, 1976 | DF patient | Gubler et al., 1979 |

A diagram of the four TDV strains comprised in the dengue vaccine composition is shown in FIG. 1.

The chimeric dengue strains TDV-1, TDV-3 and TDV-4 express the surface antigens prM and E of the DENV-1, DENV-3 or DENV-4 viruses, as depicted in Table 3 respectively, and retain the genetic alterations responsible for the attenuation of TDV-2. Thus, each of the TDV-1, TDV-3 and TDV-4 strains comprises the attenuating mutations described in Table 2.

In one embodiment, TDV-1 comprises in addition to the three attenuating mutations one or more mutations selected from:

c) a mutation in the NS2A gene at nucleotide 4018 from cytosine to thymidine resulting in an amino acid change at position 1308 from leucine to phenylalanine, and/or d) a silent mutation in the NS3 gene at nucleotide 5547 from thymidine to cytosine, and/or e) a mutation in the NS4A gene at nucleotide 6599 from guanine to cytosine resulting in an amino acid change at position 2168 from glycine to alanine, and/or i) a silent mutation in the E gene at nucleotide 1575 from thymidine to cytosine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymidine-guanine to cytosine-cytosine resulting in an amino acid change at position 762 from valine to alanine.

In another embodiment, TDV-1 comprises in addition to the three attenuating mutations one or more mutations selected from:

l) a mutation in the NS2A gene at nucleotide 3823 from adenine to cytosine resulting in an amino acid change at position 1243 from isoleucine to leucine, and/or m) a mutation in the NS2B gene at nucleotide 4407 from adenine to thymidine resulting in an amino acid change at position 1437 from glutamine to asparagine, and/or n) a silent mutation in the NS4B gene at nucleotide 7311 from adenine to guanine.

In another embodiment, the TDV-1 strain comprises in addition to the three attenuating mutations the mutations l) and m), preferably the mutations l), m), c) and e), even more preferably the mutations l), m), c), e), d) and n), and most preferably the mutations l), m), c), e), d), n), i), j) and k). The nucleotide positions and amino acids positions of TDV-1 refer to the nucleotide sequence as shown in SEQ ID NO. 1 and amino acid sequence as shown in SEQ ID NO. 2.

In one embodiment, TDV-3 comprises in addition to the three attenuating mutations one or more mutations selected from:

c) a mutation in the NS2A gene at nucleotide 4012 from cytosine to thymidine resulting in an amino acid change at position 1306 from leucine to phenylalanine, and/or d) a silent mutation in the NS3 gene at nucleotide 5541 from thymidine to cytosine, and/or
e) a mutation in the NS4A gene at nucleotide 6593 from guanine to cytosine resulting in an amino acid change at position 2166 from glycine to alanine, and/or
j) a silent mutation in the junction site between the prM-E gene and the DEN-2 PDK-53 backbone at nucleotide 453 from adenine to guanine, and/or
k) a mutation in the junction site between the prM-E gene and the DEN-2 PDK-53 backbone at nucleotides 2375/2376 from thymidine-guanine to cytosine-cytosine resulting in an amino acid change at position 760 from valine to alanine, and/or
o) a silent mutation in the prM gene at nucleotide 552 from cytosine to thymidine, and/or
p) a mutation in the E gene at nucleotide 1970 from adenine to thymidine resulting in an amino acid change at position 625 from histidine to leucine.

In another embodiment, TDV-3 comprises in addition to the three attenuating mutations one or more mutations selected from:
q) a mutation in the E gene at nucleotide 1603 from adenine to thymidine resulting in an amino acid change at position 503 from threonine to serine, and/or
r) a silent mutation in the NS5 gene at nucleotide 7620 from adenine to guanine.

In another embodiments, TDV-3 comprises in addition to the three attenuating mutations the mutations p) and q), preferably the mutations p), q), c) and e), even more preferably the mutations p), q), c), e), d) and r), and most preferably the mutations p), q), c), e), d), r), j), k) and o). The nucleotide positions and amino acids positions of TDV-3 refer to the nucleotide sequence as shown in SEQ ID NO. 5 and amino acid sequence as shown in SEQ ID NO. 6.

In one embodiment, TDV-4 comprises in addition to the three attenuating mutations one or more mutations selected from:
c) a mutation in the NS2A gene at nucleotide 4018 from cytosine to thymidine resulting in an amino acid change at position 1308 from leucine to phenylalanine, and/or
d) a silent mutation in the NS3 gene at nucleotide 5547 from thymidine to cytosine, and/or
e) a mutation in the NS4A gene at nucleotide 6599 from guanine to cytosine resulting in an amino acid change at position 2168 from glycine to alanine, and/or
j) a silent mutation in the junction site between the prM-E gene and the DEN-2 PDK-53 backbone at nucleotide 453 from adenine to guanine, and/or
k) a mutation in the junction site between the prM-E gene and the DEN-2 PDK-53 backbone at nucleotides 2381/2382 from thymidine-guanine to cytosine-cytosine resulting in an amino acid change at position 762 from valine to alanine, and/or
s) a mutation in the C gene at nucleotide 396 from adenine to cytosine resulting in an amino acid change at position 100 from arginine to serine, and/or
t) a silent mutation in the E gene at nucleotide 1401 from adenine to guanine, and/or
u) a mutation in the E gene at nucleotide 2027 from cytosine to thymidine resulting in an amino acid change at position 644 from alanine to valine, and/or
v) a mutation in the E gene at nucleotide 2275 from adenine to cytosine resulting in an amino acid change at position 727 from methionine to leucine.

In another embodiment, TDV-4 comprises in addition to the three attenuating mutations one or more mutations selected from:
w) a silent mutation in the C gene at nucleotide 225 from adenine to thymidine, and/or
x) a mutation in the NS2A gene at nucleotide 3674 from adenine to guanine resulting in an amino acid change at position 1193 from asparagine to glycine, and/or
y) a mutation in the NS2A gene at nucleotide 3773 from adenine to an adenine/guanine mix resulting in an amino acid change at position 1226 from lysine to a lysine/asparagine mix, and/or
z) a silent mutation in the NS3 gene at nucleotide 5391 from cytosine to thymidine, and/or
aa) a mutation in the NS4A gene at nucleotide 6437 from cytosine to thymidine resulting in an amino acid change at position 2114 from alanine to valine, and/or
bb) a silent mutation in the NS4B gene at nucleotide 7026 from thymidine to a thymidine/cytosine mix, and/or
cc) a silent mutation in the NS5 gene at nucleotide 9750 from adenine to cytosine.

In another embodiments, TDV-4 comprises in addition to the three attenuating mutations the mutation s), u) and v), preferably the mutations s), u), v), c), e), x), y) and aa), even more preferably the mutations s), u), v), c), e), x), y), aa) and w), even more preferably the mutations s), u), v), c), e), x), y), aa), w), d), z), bb) and cc), and most preferably the mutations s), u), v), c), e), x), y), aa), w), d), z), bb), cc), j), k) and t). The nucleotide positions and amino acids positions of TDV-4 refer to the nucleotide sequence as shown in SEQ ID NO. 7 and amino acid sequence as shown in SEQ ID NO. 8.

In a preferred embodiment, TDV-1 has the nucleotide sequence of SEQ ID NO. 1, TDV-2 has the nucleotide sequence of SEQ ID NO. 3, TDV-3 has the nucleotide sequence of SEQ ID NO. 5, and/or TDV-4 has the nucleotide sequence of SEQ ID NO. 7. In a further preferred embodiment, TDV-1 has the amino acid sequence of SEQ ID NO. 2, TDV-2 has the amino acid sequence of SEQ ID NO. 4, TDV-3 has the amino acid sequence of SEQ ID NO. 6, and TDV-4 has the amino acid sequence of SEQ ID NO. 8. In a further preferred embodiment, TDV-1 has a nucleotide sequence encoding the amino acid sequence of SEQ ID NO. 2, TDV-2 has a nucleotide sequence encoding the amino acid sequence of SEQ ID NO. 4, TDV-3 has a nucleotide sequence encoding the amino acid sequence of SEQ ID NO. 6, and TDV-4 has a nucleotide sequence encoding the amino acid sequence of SEQ ID NO. 8.

TABLE 4

Sequences of the TDV virus strains

| SEQ ID NO. | dengue virus strain | sequence type |
| --- | --- | --- |
| SEQ ID NO. 1 | TDV-1 | nucleotide sequence |
| SEQ ID NO. 2 | TDV-1 | amino acid sequence |
| SEQ ID NO. 3 | TDV-2 | nucleotide sequence |
| SEQ ID NO. 4 | TDV-2 | amino acid sequence |
| SEQ ID NO. 5 | TDV-3 | nucleotide sequence |
| SEQ ID NO. 6 | TDV-3 | amino acid sequence |
| SEQ ID NO. 7 | TDV-4 | nucleotide sequence |
| SEQ ID NO. 8 | TDV-4 | amino acid sequence |

Thus, in a particularly preferred embodiment, the unit dose of the invention as described herein comprises the live attenuated dengue virus strains TDV-1, TDV-2, TDV-3 and TDV-4, wherein TDV-1, TDV-3 and TDV-4 are based on TDV-2 and comprise the prM and E regions of DENV-1, -3 and -4, respectively. In another particularly preferred embodiment, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The E protein of DENV-3 has two fewer amino acids than the E protein of DENV-2. Therefore, the nucleotides and encoded amino acid backbone of TDV-2 starting after the E region of DENV-3 at nucleotide 2374 of SEQ ID NO. 5 and amino acid 760 of SEQ ID NO. 6 are 6 nucleotides less and 2 amino acids less than the original TDV-2 nucleotide and amino acid positions, respectively.

Dengue Vaccine Composition

The present invention is in part directed to a unit dose of a dengue vaccine composition as described. The dengue vaccine composition comprises a tetravalent dengue virus composition, also referred to as dengue virus composition, and pharmaceutically acceptable excipients.

Dengue Virus Composition, Virus Concentrations and %-Concentrations

The present invention is in part directed to a unit dose of a dengue vaccine composition, wherein the dengue vaccine composition comprises a tetravalent dengue virus composition including four live attenuated dengue virus strains:
(i) a dengue serotype 1 preferably in a concentration of at least 3.3 log 10 pfu/0.5 mL,
(ii) a dengue serotype 2 preferably in a concentration of at least 2.7 log 10 pfu/0.5 mL,
(iii) a dengue serotype3 preferably in a concentration of at least 4.0 log 10 pfu/0.5 mL, and
(iv) a dengue serotype 4 preferably strain in a concentration of at least 4.5 log 10 pfu/0.5 mL.

The present invention is further in part directed to a unit dose of a dengue vaccine composition, wherein the dengue vaccine composition comprises a tetravalent dengue virus composition including four live attenuated dengue virus strains:
(i) a chimeric dengue serotype 2/1 strain in a concentration of at least 3.3 log 10 pfu/0.5 mL,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and
(iv) a chimeric dengue serotype 2/4 strain in a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/0.5 mL to 5.3 log 10 pfu/0.5 mL,
(ii) the dengue serotype 2 (e.g. dengue serotype 2 strain) has a concentration of 2.7 log 10 pfu/0.5 mL to 5.0 log 10 pfu/0.5 mL,
(iii) the dengue serotype 3 (e.g. chimeric dengue serotype 2/3 strain) has a concentration of 4.0 log 10 pfu/0.5 mL to 6.0 log 10 pfu/0.5 mL, and
(iv) the dengue serotype 4 (e.g. chimeric dengue serotype 2/4 strain) has a concentration of 4.5 log 10 pfu/0.5 mL to 6.5 log 10 pfu/0.5 mL.

In one such embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/0.5 mL to 5.0 log 10 pfu/0.5 mL,
(ii) the dengue serotype 2 (e.g. dengue serotype 2 strain) has a concentration of 2.7 log 10 pfu/0.5 mL to 4.9 log 10 pfu/0.5 mL,
(iii) the dengue serotype 3 (e.g. chimeric dengue serotype 2/3 strain) has a concentration of 4.0 log 10 pfu/0.5 mL to 5.7 log 10 pfu/0.5 mL, and
(iv) the dengue serotype 4 (e.g. chimeric dengue serotype 2/4 strain) has a concentration of 4.5 log 10 pfu/0.5 mL to 6.2 log 10 pfu/0.5 mL.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/0.5 mL to 5.0 log 10 pfu/0.5 mL,
(ii) a dengue serotype 2 (e.g. dengue serotype 2 strain) has a concentration of 2.7 log 10 pfu/0.5 mL to 4.9 log 10 pfu/0.5 mL,
(iii) a dengue serotype 3 (e.g. chimeric dengue serotype 2/3 strain) has a concentration of 4.0 log 10 pfu/0.5 mL to 5.7 log 10 pfu/0.5 mL, and
(iv) a dengue serotype 4 (e.g. chimeric dengue serotype 2/4 strain) has a concentration of 4.5 log 10 pfu/0.5 mL to 5.5 log 10 pfu/0.5 mL.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/0.5 mL to 4.1 log 10 pfu/0.5 mL,
(ii) a dengue serotype 2 (e.g. dengue serotype 2 strain) has a concentration of 2.7 log 10 pfu/0.5 mL to 3.6 log 10 pfu/0.5 mL,
(iii) a dengue serotype 3 (e.g. chimeric dengue serotype 2/3 strain) has a concentration of 4.0 log 10 pfu/0.5 mL to 4.7 log 10 pfu/0.5 mL, and
(iv) a dengue serotype 4 (e.g. chimeric dengue serotype 2/4 strain) has a concentration of 4.5 log 10 pfu/0.5 mL to 5.3 log 10 pfu/0.5 mL.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/0.5 mL to 3.6 log 10 pfu/0.5 mL,
(ii) a dengue serotype 2 (e.g. dengue serotype 2 strain) has a concentration of 2.7 log 10 pfu/0.5 mL to 4.0 log 10 pfu/0.5 mL,
(iii) a dengue serotype 3 (e.g. chimeric dengue serotype 2/3 strain) has a concentration of 4.0 log 10 pfu/0.5 mL to 4.6 log 10 pfu/0.5 mL, and
(iv) a dengue serotype 4 (e.g. chimeric dengue serotype 2/4 strain) has a concentration of 4.5 log 10 pfu/0.5 mL to 5.1 log 10 pfu/0.5 mL.

In another embodiment, the dengue vaccine composition comprises a tetravalent dengue virus composition including four live attenuated dengue virus strains wherein:
  (i) the dengue serotype 1 (e.g. chimeric dengue serotype 2/1 strain) has a concentration of 4.3 log 10 pfu/0.5 mL to 4.4 log 10 pfu/0.5 mL,
  (ii) the dengue serotype 2 (e.g. dengue serotype 2 strain) has a concentration of 3.7 log 10 pfu/0.5 mL to 3.8 log 10 pfu/0.5 mL,
  (iii) the dengue serotype 3 (e.g. chimeric dengue serotype 2/3 strain) has a concentration of 4.5 log 10 pfu/0.5 mL to 5.0 log 10 pfu/0.5 mL, and
  (iv) the dengue serotype 4 (e.g. chimeric dengue serotype 2/4 strain) has a concentration of 5.5 log 10 pfu/0.5 mL to 5.6 log 10 pfu/0.5 mL.

In a particularly preferred embodiment, the dengue vaccine composition comprises a tetravalent dengue virus composition including four live attenuated dengue virus strains wherein:
  (i) the dengue serotype 1 (e.g. chimeric dengue serotype 2/1 strain) has a concentration of 4.4 log 10 pfu/0.5 mL,
  (ii) the dengue serotype 2 (e.g. dengue serotype 2 strain) has a concentration of 3.8 log 10 pfu/0.5 mL,
  (iii) the dengue serotype 3 (e.g. chimeric dengue serotype 2/3 strain) has a concentration of 4.5 log 10 pfu/0.5 mL, and
  (iv) the dengue serotype 4 (e.g. chimeric dengue serotype 2/4 strain) has a concentration of 5.6 log 10 pfu/0.5 mL.

In another particularly preferred embodiment, the dengue vaccine composition comprises a tetravalent dengue virus composition including four live attenuated dengue virus strains wherein:
  (i) the dengue serotype 1 (e.g. chimeric dengue serotype 2/1 strain) has a concentration of 3.6 log 10 pfu/0.5 mL,
  (ii) the dengue serotype 2 (e.g. dengue serotype 2 strain) has a concentration of 4.0 log 10 pfu/0.5 mL,
  (iii) the dengue serotype 3 (e.g. chimeric dengue serotype 2/3 strain) has a concentration of 4.6 log 10 pfu/0.5 mL, and
  (iv) the dengue serotype 4 (e.g. chimeric dengue serotype 2/4 strain) has a concentration of 5.1 log 10 pfu/0.5 mL.

In another preferred embodiment, the dengue vaccine composition comprises a tetravalent dengue virus composition including four live attenuated dengue virus strains wherein the arithmetic sum of all four serotypes is less than 6.7 log 10 pfu/0.5 mL, preferably less than 5.5 log 10 pfu/0.5 mL. In certain such embodiments, the arithmetic sum of all four serotypes is at least 4.6 log 10 pfu/0.5 mL. In a preferred embodiment, the dengue vaccine composition comprises a tetravalent dengue virus composition including four live attenuated dengue virus strains wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The present invention is in part directed to a unit dose of a dengue vaccine composition, wherein the dengue vaccine composition comprises a tetravalent dengue virus composition including four live attenuated dengue virus strains:
  (i) a dengue serotype 1 (e.g. chimeric dengue serotype 2/1 strain) in a concentration of at least 3.3 log 10 pfu/dose,
  (ii) a dengue serotype 2 (e.g. dengue serotype 2 strain) in a concentration of at least 2.7 log 10 pfu/dose,
  (iii) a dengue serotype 3 (e.g. chimeric dengue serotype 2/3 strain) in a concentration of at least 4.0 log 10 pfu/dose, and
  (iv) a dengue serotype 4 (e.g. chimeric dengue serotype 2/4 strain) in a concentration of at least 4.5 log 10 pfu/dose.

In one embodiment, the dengue vaccine composition comprises a tetravalent dengue virus composition including four live attenuated dengue virus strains wherein:
  (i) the dengue serotype 1 (e.g. chimeric dengue serotype 2/1 strain) has a concentration of 3.3 log 10 pfu/dose to 5.3 log 10 pfu/dose,
  (ii) the dengue serotype 2 (e.g. dengue serotype 2 strain) has a concentration of 2.7 log 10 pfu/dose to 5.0 log 10 pfu/dose,
  (iii) the dengue serotype 3 (e.g. chimeric dengue serotype 2/3 strain) has a concentration of 4.0 log 10 pfu/dose to 6.0 log 10 pfu/dose, and
  (iv) the dengue serotype 4 (e.g. chimeric dengue serotype 2/4 strain) has a concentration of 4.5 log 10 pfu/dose to 6.5 log 10 pfu/dose.

In one such embodiment, the dengue vaccine composition comprises a tetravalent dengue virus composition including four live attenuated dengue virus strains wherein:
  (i) the dengue serotype 1 (e.g. chimeric dengue serotype 2/1 strain) has a concentration of 3.3 log 10 pfu/dose to 5.0 log 10 pfu/dose,
  (ii) the dengue serotype 2 (e.g. dengue serotype 2 strain) has a concentration of 2.7 log 10 pfu/dose to 4.9 log 10 pfu/dose,
  (iii) the dengue serotype 3 (e.g. chimeric dengue serotype 2/3 strain) has a concentration of 4.0 log 10 pfu/dose to 5.7 log 10 pfu/dose, and
  (iv) the dengue serotype 4 (e.g. chimeric dengue serotype 2/4 strain) has a concentration of 4.5 log 10 pfu/dose to 6.2 log 10 pfu/dose.

In a further such embodiment, the dengue vaccine composition comprises a tetravalent dengue virus composition including four live attenuated dengue virus strains wherein:
  (i) a dengue serotype 1 (e.g. chimeric dengue serotype 2/1 strain) has a concentration of 3.3 log 10 pfu/dose to 5.0 log 10 pfu/dose,
  (ii) a dengue serotype 2 (e.g. dengue serotype 2 strain) has a concentration of 2.7 log 10 pfu/dose to 4.9 log 10 pfu/dose,
  (iii) a dengue serotype 3 (e.g. chimeric dengue serotype 2/3 strain) has a concentration of 4.0 log 10 pfu/dose to 5.7 log 10 pfu/dose, and
  (iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:
  (i) a dengue serotype 1 (e.g. chimeric dengue serotype 2/1 strain) has a concentration of 3.3 log 10 pfu/dose to 4.1 log 10 pfu/dose, (ii) a dengue serotype 2 (e.g. dengue serotype 2 strain) has a concentration of 2.7 log 10 pfu/dose to 3.6 log 10 pfu/dose,
(iii) a dengue serotype 3 (e.g. chimeric dengue serotype 2/3 strain) has a concentration of 4.0 log 10 pfu/dose to 4.7 log 10 pfu/dose, and
(iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 3.6 log 10 pfu/dose,
(ii) a dengue serotype 2 (e.g. dengue serotype 2 strain) has a concentration of 2.7 log 10 pfu/dose to 4.0 log 10 pfu/dose,
(iii) a dengue serotype 3 (e.g. chimeric dengue serotype 2/3 strain) has a concentration of 4.0 log 10 pfu/dose to 4.6 log 10 pfu/dose, and
(iv) a dengue serotype 4 (e.g. chimeric dengue serotype 2/4 strain) has a concentration of 4.5 log 10 pfu/dose to 5.1 log 10 pfu/dose.

In another embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.3 log 10 pfu/dose to 4.4 log 10 pfu/dose,
(ii) the dengue serotype 2 (e.g. dengue serotype 2 strain) has a concentration of 3.7 log 10 pfu/dose to 3.8 log 10 pfu/dose,
(iii) the dengue serotype 3 (e.g. chimeric dengue serotype 2/3 strain) has a concentration of 4.5 log 10 pfu/dose to 5.0 log 10 pfu/dose, and
(iv) the dengue serotype 4 (e.g. chimeric dengue serotype 2/4 strain) has a concentration of 5.5 log 10 pfu/dose to 5.6 log 10 pfu/dose.

In a particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.4 log 10 pfu/dose,
(ii) the dengue serotype 2 (e.g. dengue serotype 2 strain) has a concentration of 3.8 log 10 pfu/dose,
(iii) the dengue serotype 3 (e.g. chimeric dengue serotype 2/3 strain) has a concentration of 4.5 log 10 pfu/dose, and
(iv) the dengue serotype 4 (e.g. chimeric dengue serotype 2/4 strain) has a concentration of 5.6 log 10 pfu/dose.

In another particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.6 log 10 pfu/dose,
(ii) the dengue serotype 2 (e.g. dengue serotype 2 strain) has a concentration of 4.0 log 10 pfu/dose,
(iii) the dengue serotype 3 (e.g. chimeric dengue serotype 2/3 strain) has a concentration of 4.6 log 10 pfu/dose, and
(iv) the dengue serotype 4 (e.g. chimeric dengue serotype 2/4 strain) has a concentration of 5.1 log 10 pfu/dose.

In another preferred embodiment, the dengue vaccine composition comprises a tetravalent dengue virus composition including four live attenuated dengue virus strains wherein the arithmetic sum of all four serotypes is less than 6.7 log 10 pfu/dose, preferably less than 5.5 log 10 pfu/dose. In certain such embodiments, the arithmetic sum of all four serotypes is at least 4.6 log 10 pfu/dose. in a preferred embodiment, the dengue vaccine composition comprises a tetravalent dengue virus composition including four live attenuated dengue virus strains wherein the arithmetic sum of all four serotypes is in the range of 4.6 log 10 pfu/dose to 6.7 log 10 pfu/dose, preferably in the range of 4.6 log 10 pfu/dose to 5.5 log 10 pfu/dose.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The concentration of the different dengue viruses is preferably determined by an immuno-focus assay known in the art. For example, the concentration may be determined by an immuno-focus assay wherein serial dilutions of dengue virus are applied to monolayers of adherent cells, such as Vero cells. After a period of time which allows infectious viruses to bind to the cells and to be taken up by the cells, an overlay containing thickening agents, such as agarose or carboxymethylcellulose, is added to prevent diffusion of viruses so that progeny viruses can only infect cells adjacent to the original infected cells. After a period of incubation to allow viral replication, cells are fixed and stained using serotype-specific anti-dengue monoclonal antibodies and a secondary antibody such as an antibody labeled with alkaline phosphatase. The foci are stained by adding a suitable substrate for the enzyme attached to the secondary antibody, such as 5-bromo-4-chloro-3-indolyl-phosphate/nitro blue tetrazolium phosphatase substrate. The number of plaques on the plate corresponds to the plaque forming units of the virus in the solutions applied to the cells. For example, a concentration of 1.000 pfu/µl indicates that 1 µl of the solution applied to the cells contains enough viruses to produce 1.000 plaques in a cell monolayer.

The dengue vaccine composition comprises a tetravalent dengue virus composition including four live attenuated dengue virus strains, wherein a chimeric dengue serotype 2/1 strain, a dengue serotype 2 strain, a chimeric dengue serotype 2/3 strain, and a chimeric dengue serotype 2/4 strain provide a total concentration in pfu/0.5 mL. The term "total concentration in pfu/0.5 mL" or "total concentration in pfu/dose" is the sum of the concentrations of the dengue serotype 1 (e.g. chimeric dengue serotype 2/1 strain), dengue serotype 2 (e.g. the dengue serotype 2 strain), the dengue serotype 3 (e.g. chimeric dengue serotype 2/3 strain) and the dengue serotype 4 (e.g. chimeric dengue serotype 2/4 strain), preferably the sum of the concentrations of TDV-1, TDV-2, TDV-3 and TDV-4, and is defined as 100% of the dengue virus concentration as determined by pfu (plaque forming units) in 0.5 mL or in a dose.

In one embodiment, the dengue vaccine composition comprises a tetravalent dengue virus composition including four live attenuated dengue virus strains, wherein a dengue serotype 1 (e.g. chimeric dengue serotype 2/1 strain), a dengue serotype 2 (e.g. dengue serotype 2 strain), a dengue serotype 3 (e.g. chimeric dengue serotype 2/3 strain), and a dengue serotype 4 (e.g. chimeric dengue serotype 2/4 strain) provide a total concentration in pfu/0.5 mL, wherein based on said total concentration the concentration of a dengue serotype 2 (e.g. dengue serotype 2 strain) measured in pfu/0.5 mL is less than 10% of the total concentration, or less than 8%, or less than 6% of the total concentration, and wherein the concentration of a dengue serotype 4 (e.g. chimeric dengue serotype 2/4 strain) measured in pfu/0.5 mL is at least 50% or at least 60% or at least 65% of the total concentration. In one embodiment, based on said total concentration the concentration of a dengue serotype 2 (e.g. dengue serotype 2 strain) measured in pfu/0.5 mL is 0.3 to 10% or 0.5 to 8% of the total concentration and the concentration of a dengue serotype 4 (e.g. chimeric dengue serotype 2/4 strain) measured in pfu/0.5 mL is 50% to 90% or 60% to 88% of the total concentration. This means that the concentration of the dengue serotype 2 (e.g. dengue serotype 2 strain) is lower than the concentration of the dengue serotype 4 (e.g. chimeric dengue serotype 2/4 strain).

In one such embodiment, the concentration of a dengue serotype 1 (e.g. chimeric dengue serotype 2/1 strain) measured in pfu/0.5 mL is at least 1% of the total concentration, and/or the concentration of a dengue serotype 3 (e.g. chimeric dengue serotype 2/3 strain) measured in pfu/0.5 mL is at least 6% of the total concentration, or at least 7% or 8%, 10%, 12%, 14%, 16% or 18% of the total concentration. In one such embodiment, the concentration of a dengue serotype 2 (e.g. chimeric dengue serotype 2/1 strain) measured in pfu/0.5 mL is 1% to 7% or 2% to 6% or 2.0% to 5.0% of the total concentration, and/or the concentration of a dengue serotype 3 (e.g. chimeric dengue serotype 2/3 strain) measured in pfu/0.5 mL is 6% to 25% or 7% to 25% or 10% to 25% or 18% to 25% of the total concentration. This means that the concentration of the dengue serotype 1 (e.g. chimeric dengue serotype 2/1 strain) is lower than the concentration of the dengue serotype 3 (e.g. chimeric dengue serotype 2/3 strain).

In a preferred embodiment, the concentration of a dengue serotype 2 strain, such as TDV-2, measured in pfu/0.5 mL is less than 10% of the total concentration, preferably less than 6% or less than 2%, the concentration of a dengue serotype 4 (e.g. chimeric dengue serotype 2/4 strain), such as TDV-4, measured in pfu/0.5 mL is at least 50% of the total concentration, preferably at least 65%, the concentration of a dengue serotype 1 (e.g. chimeric dengue serotype 2/1 strain), such as TDV-1, measured in pfu/0.5 mL is at least 1% of the total concentration, preferably between 1% and 7% or 2.0% to 5.0%, and the concentration of a dengue serotype 3 (e.g. chimeric dengue serotype 2/3 strain), such as TDV-3, measured in pfu/0.5 mL is at least 6% of the total concentration, preferably between 6% and 25% or 10% to 25% or 18% to 25%.

In a further preferred embodiment, a dengue virus composition comprising a dengue serotype 1 (e.g. chimeric dengue serotype 2/1 strain), a dengue serotype 2 (e.g. dengue serotype 2 strain), a dengue serotype 1 (e.g. chimeric dengue serotype 2/3 strain), and a dengue serotype 4 (e.g. chimeric dengue serotype 2/4 strain), such as TDV-1, TDV-2, TDV-3 and TDV-4, is provided, wherein the concentration of the dengue serotype 1 (e.g. chimeric dengue serotype 2/1 strain) measured in pfu/0.5 mL is at least 1% of the total concentration, preferably between 1% and 7% or 2.0% and 5.0%, the concentration of the dengue serotype 2 (e.g. dengue serotype 2 strain) measured in pfu/0.5 mL is less than 10% of the total concentration, preferably less than 6% or less than 2% and the concentration of the dengue serotype 3 (e.g. chimeric dengue serotype 2/3 strain) measured in pfu/0.5 mL is at least 6% of the total concentration, preferably between 6% and 25% or 10% to 25% or 18% to 25%. It is particularly preferred that the dengue serotype 4 (e.g. chimeric dengue serotype 2/4 strain) has the highest concentration of all four dengue serotypes.

In a further preferred embodiment, the dengue vaccine composition comprises a tetravalent dengue virus composition including four live attenuated dengue virus strains, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

According to a further embodiment, the chimeric dengue serotype 2/4 strain, preferably TDV-4, has the highest concentration in the dengue vaccine composition, followed by the chimeric dengue serotype 2/3 strain, preferably TDV-3, followed by the chimeric dengue serotype 2/1 strain, preferably TDV-1, followed by the dengue serotype 2 strain, preferably TDV-2. It is particularly preferred that the dengue serotype 2 strain has the lowest concentration of the four strains present in the dengue vaccine composition.

Pharmaceutically Acceptable Excipients

The present invention is in part directed to a unit dose of a dengue vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

In one embodiment, the unit dose of a dengue vaccine composition comprises the following pharmaceutically acceptable excipients:
from about 10% w/v to about 20% w/v α,α-trehalose dihydrate or an equimolar amount of other forms of α,α-trehalose,
from about 0.5% w/v to about 1.5% w/v poloxamer 407,
from about 0.05% w/v to about 2% w/v human serum albumin, and
from about 70 mM to 140 mM sodium chloride.

In a preferred embodiment, the lyophilized unit dose of the invention as described herein comprises the following pharmaceutically acceptable excipients:
about 15% w/v α,α-trehalose dihydrate,
about 1% w/v poloxamer 407,
about 0.1% w/v human serum albumin, and
about 100 mM sodium chloride.

In a preferred embodiment, the reconstituted unit dose of the invention as described herein comprises the following pharmaceutically acceptable excipients:
about 15% w/v α,α-trehalose dihydrate,
about 1% w/v poloxamer 407,
about 0.1% w/v human serum albumin, and
about 137 mM sodium chloride.

The human serum albumin may be a native or recombinant human serum albumin (rHSA). The poloxamer 407 may be e.g. Pluronic F127.

In one embodiment, the unit dose further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of 7.0 to 8.5 at 25° C.

Unit Dose

The present invention is directed in part to a unit dose of a dengue vaccine composition comprising a tetravalent dengue virus composition as described herein and pharmaceutically acceptable excipients as described herein.

The present invention is directed in part to a unit dose of a dengue vaccine composition as described above e.g. of
(i) a dengue serotype 1 (e.g. chimeric dengue serotype 2/1 strain) with a concentration of at least 3.3 log 10 pfu/0.5 mL,
(ii) a dengue serotype 2 (e.g. dengue serotype 2 strain) with a concentration of at least 2.7 log 10 pfu/0.5 mL,
(iii) a dengue serotype 3 (e.g chimeric dengue serotype 2/3 strain) with a concentration of at least 4.0 log 10 pfu/0.5 mL, and
(iv) a dengue serotype 4 (e.g. chimeric dengue serotype 2/4 strain) with a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3, and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one embodiment, the unit dose is lyophilized. In one such embodiment, the lyophilized unit dose is obtained by subjecting a volume of 0.5 mL of the aqueous dengue vaccine composition produced by combining pharmaceutically acceptable excipients as described herein and the dengue vaccine composition as described herein comprising the four dengue virus strains, in particular TDV-1 to TDV-4, to lyophilization. In a preferred embodiment the residual moisture content as determined by Karl Fischer Determination is equal to or less than 5.0%, preferably equal to or less than 3%.

In another embodiment, the unit dose is reconstituted. The reconstituted unit dose is obtained by subjecting the lyophilized unit dose to reconstitution with a pharmaceutically acceptable diluent, preferably before administration of the dengue vaccine. In one such embodiment, reconstitution will be accomplished by adding a pharmaceutically acceptable diluent, such as water for injection, phosphate buffered saline or an aqueous sodium chloride solution, to the lyophilized unit dose. In one embodiment, an aqueous sodium chloride solution, such as a 37 mM aqueous sodium chloride solution, is added to the lyophilized unit dose for reconstitution. In one such embodiment, the lyophilized unit dose will be reconstituted with 0.3 to 0.8 mL, or 0.4 to 0.7 mL, or 0.5 mL of diluent. In a preferred embodiment, the lyophilized unit dose is reconstituted with 0.3 to 0.8 mL, 0.4 to 0.7 mL or 0.5 mL of 37 mM aqueous sodium chloride solution. In a more preferred embodiment, the lyophilized unit dose is reconstituted with 0.5 mL of 37 mM aqueous sodium chloride solution. The reconstituted unit dose can subsequently be administered subcutaneously.

It is preferred that the unit dose in lyophilized form is the final product after manufacture of the unit dose and the storage form of the unit dose, wherein the unit dose in reconstituted form is prepared before administration of the unit dose to a subject.

In one embodiment, the present invention is directed to a lyophilized unit dose of a dengue vaccine composition comprising upon reconstitution with 0.5 mL of a pharmaceutically acceptable diluent a dengue serotype 1 (e.g. chimeric dengue serotype 2/1 strain) with a concentration of at least 3.3 log 10 pfu/0.5 mL, a dengue serotype 2 (e.g. dengue serotype 2 strain) with a concentration of at least 2.7 log 10 pfu/0.5 mL, a dengue serotype 3 (e.g. chimeric dengue serotype 2/3 strain) with a concentration of at least 4.0 log 10 pfu/0.5 mL, and a dengue serotype 4 (e.g. chimeric dengue serotype 2/4 strain) with a concentration of at least 4.5 log 10 pfu/0.5 mL and pharmaceutically acceptable excipients as described herein, wherein the unit dose is preferably formulated in 0.5 mL before lyophilization. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/dose to 5.0 log 10 pfu/0.5 mL, a dengue serotype 2 (e.g. dengue serotype 2 strain) in a concentration of 2.7 log 10 pfu/dose to 4.9 log 10 pfu/0.5 mL, a dengue serotype 3 (e.g. chimeric dengue serotype 2/3 strain) in a concentration of 4.0 log 10 pfu/dose to 5.7 log 10 pfu/0.5 mL, and a dengue serotype 4 (e.g. chimeric dengue serotype 2/4 strain) in a concentration of 4.5 log 10 pfu/dose to 5.5 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/0.5 mL to 3.6 log 10 pfu/0.5 mL, a dengue serotype 2 (e.g. dengue serotype 2 strain) in a concentration of 2.7 log 10 pfu/0.5 mL to 4.0 log 10 pfu/0.5 mL, a dengue serotype 3 (e.g. chimeric dengue serotype 2/3 strain) in a concentration of 4.0 log 10 pfu/0.5 mL to 4.6 log 10 pfu/0.5 mL, and a dengue serotype 4 (e.g. chimeric dengue serotype 2/4 strain) in a concentration of 4.5 log 10 pfu/0.5 mL to 5.1 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In certain embodiments, the lyophilized unit dose refers to 0.5 mL before lyophilization, wherein TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In certain embodiments, the reconstituted unit dose has a volume of 0.5 mL and TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In a further preferred embodiment, the reconstituted unit dose has a volume of 0.5 mL and comprises a tetravalent dengue virus composition including four live attenuated dengue virus strains, wherein the concentration of the dengue serotype 1 (e.g. dengue serotype 2/1 strain) measured in pfu/0.5 mL is 1% to 7% of the total concentration, the concentration of the dengue serotype 2 (e.g dengue serotype 2 strain) measured in pfu/0.5 mL is less than 8% of the total concentration, such as in the range of 1% to 8% of the total concentration, the concentration of the dengue serotype 3 (e.g. dengue serotype 2/3 strain) measured in pfu/0.5 mL is at least 10% of the total concentration, and the concentration of the dengue serotype 4 (e.g. dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment, the reconstituted unit dose has a volume of 0.5 mL and comprises a tetravalent dengue virus composition including four live attenuated dengue virus strains, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

The lyophilized unit dose reconstituted in 0.5 mL will provide the above concentrations for the four dengue serotypes. While the unit dose of a dengue vaccine composition as described herein refers to the concentrations of the dengue serotypes in 0.5 mL, the lyophilized unit dose can be reconstituted with other volumes of a pharmaceutically acceptable diluent, such as an aqueous sodium chloride solution, without changing the absolute virus amount administered or the ratios of the viruses to one another.

In certain embodiments, the lyophilized unit dose of the invention is prepared from a solution comprising a non-reducing sugar, a surfactant, a protein and an inorganic salt.

In certain embodiments, the lyophilized unit dose of the invention is prepared from a solution comprising trehalose, poloxamer 407, human serum albumin and sodium chloride.

In certain embodiments, the lyophilized unit dose of the invention is prepared from a solution comprising about 10% w/v to about 20% w/v $\alpha,\alpha$-trehalose dihydrate or an equimolar amount of other forms of $\alpha,\alpha$-trehalose, from about 0.5% w/v to about 1.5% w/v poloxamer 407, from about 0.05% w/v to about 2% w/v human serum albumin, and about 70 mM to about 120 mM sodium chloride.

In preferred embodiments, the lyophilized unit dose of the invention as described herein is prepared from a solution comprising about 15% w/v $\alpha,\alpha$-trehalose dihydrate, about 1% w/v poloxamer 407, about 0.1% w/v human serum albumin and about 100 mM sodium chloride.

In one embodiment, the solution from which the lyophilized unit dose is prepared further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of about 7.0 to about 8.5 at 25° C. or a pH of about 6.8 to about 7.6 at 25° C., preferably a pH of about 7.2 at 25° C.

In preferred embodiments, the reconstituted unit dose of the invention as described herein comprising about 15% w/v $\alpha,\alpha$-trehalose dihydrate, about 1% w/v poloxamer 407, about 0.1% w/v human serum albumin and about 137 mM sodium chloride. The reconstituted unit dose may have a pH of about 7.0 to about 8.5 at 25° C., preferably a pH of about 7.2 at 25° C.

The unit dose of the invention as described herein activates multiple arms of the immune system—neutralizing antibodies, cellular immunity and anti-NS1 antibodies—in both seronegative and seropositive subject populations or in both seronegative and seropositive subjects. Thus, the unit dose of the invention as described herein protects both dengue seronegative and dengue seropositive subject populations or subjects against dengue disease.

In one embodiment, one unit dose is present in a container, preferably a vial, and said unit dose is administered to a subject after reconstitution. In one embodiment, more than one unit dose of the dengue vaccine composition may be present in a container, preferably a vial, so that with the content of one container, preferably a vial, more than one subject can be vaccinated. In one embodiment, the container comprising more than one unit doses of the invention as described herein is used for providing the reconstituted unit dose to be used in the methods of the invention as described herein.

The certain embodiments, the container comprising the unit dose of the invention is part of a kit. Thus, the invention is directed in part to a kit for preparing a reconstituted unit dose comprising a lyophilized unit dose of the present invention as described herein, and a pharmaceutically acceptable diluent for reconstitution.

In certain embodiments, the diluent for reconstitution provided in a container, preferably a vial, or a pre-filled syringe. In some embodiments, the diluent for reconstitution is selected from water for injection, phosphate buffered saline or an aqueous sodium chloride solution. In a preferred embodiment, the diluent for reconstitution is 30 to 40 mM sodium chloride, such as 37 mM sodium chloride.

Method of Preventing and Uses

Method of Preventing

The present invention is directed in part to a method of preventing dengue disease (in particular virologically confirmable dengue, VCD) in a subject. Thus, in certain embodiments the invention is directed to a method of preventing dengue disease in a subject, comprising administering to the subject a unit dose, in particular a reconstituted unit dose of the invention as described herein.

The present invention is directed in part to a method of preventing dengue disease (in particular virologically confirmable dengue, VCD) in a subject population. Thus, in certain embodiments the invention is directed to a method of preventing dengue disease in a subject population, comprising administering to the subject population a unit dose, in particular a reconstituted unit dose of the invention as described herein.

The present invention is in part directed to said method for preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2. Without wishing to be bound to any theory, it is presently understood that a method inducing a more balanced immune response due to the administration of the reconstituted unit dose of the invention as described herein, in terms of less differences between the geometric mean neutralizing antibody titers (GMTs) against the four dengue serotypes or the neutralizing antibody titers against the four dengue serotypes, is beneficial to the subject or subject population to be vaccinated. In particular, it is understood that a much greater response to any one of the four serotypes, such as to DENV-2 in comparison to the other serotypes, is less beneficial.

The present invention is in part directed to said method for preventing dengue disease (in particular virologically confirmable dengue, VCD) in a subject or subject population wherein the method provides a seropositivity rate in a subject population of at least 50 subjects including the administration of two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85%, or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

The present invention is in part directed to said method for preventing dengue disease (in particular virologically confirmable dengue, VCD) in a subject or subject population wherein the method provides a seropositivity rate in a subject population of at least 100 subjects including administration of two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to a method of preventing virologically confirmable dengue disease in a subject or subject population comprising administering to the subject or subject population a reconstituted unit dose of a tetravalent dengue virus composition including four live, attenuated dengue serotypes, in particular the virus strains as described herein.

The present invention is in part directed to a method of preventing virologically confirmable dengue disease with hospitalization in a subject or subject population comprising administering to the subject or subject population a reconstituted unit dose of a tetravalent dengue virus composition including four live, attenuated dengue serotypes, in particular the virus strains as described herein.

In certain embodiments, the invention is directed to said methods, wherein said dose unit comprises a tetravalent dengue virus composition including four live attenuated dengue serotypes, in particular the virus strains described herein wherein the serotypes have certain concentrations as described herein with respect to the virus composition and unit dose such as:
 (i) a dengue serotype 1 (e.g. chimeric dengue serotype 2/1 strain) has a concentration of 3.3 log 10 pfu/0.5 mL to 5.0 log 10 pfu/0.5 mL,
 (ii) a dengue serotype 2 (e.g. dengue serotype 2 strain) has a concentration of 2.7 log 10 pfu/0.5 mL to 4.9 log 10 pfu/0.5 mL,
 (iii) a dengue serotype 3 (e.g. chimeric dengue serotype 2/3 strain) has a concentration of 4.0 log 10 pfu/0.5 mL to 5.7 log 10 pfu/0.5 mL, and
 (iv) a dengue serotype 4 (e.g. chimeric dengue serotype 2/4 strain) has a concentration of 4.5 log 10 pfu/0.5 mL to 5.5 log 10 pfu/0.5 mL.

In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein said unit dose upon reconstitution with 0.5 mL of a pharmaceutically acceptable diluent has a concentration of 3.3 log 10 pfu/0.5 mL to 3.6 log 10 pfu/0.5 mL for dengue serotype 1 (e.g. chimeric dengue serotype 2/1 strain), has a concentration of 2.7 log 10 pfu/0.5 mL to 4.0 log 10 pfu/0.5 mL for dengue serotype 2 (e.g. dengue serotype 2 strain), has a concentration of 4.0 log 10 pfu/0.5 mL to 4.6 log 10 pfu/0.5 mL for dengue serotype 3 (e.g. chimeric dengue serotype 2/3 strain) and has a concentration of 4.5 log 10 pfu/0.5 mL to 5.1 log 10 pfu/0.5 mL for dengue serotype 4 (e.g. chimeric dengue serotype 2/4 strain). In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL Preferably, in said embodiments the subject or subject population is of 2 to 17 years of age, such as 4 to 16 years of age, and even more preferably less than 9 years of age. In other preferred embodiments, the subject or subject population is 4-5 years of age, 6-11 years of age or 12-16 years of age.

In a further preferred embodiment, the invention is directed to said methods, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to said methods, wherein the reconstituted unit dose of the invention as described herein is administered by subcutaneous injection. According to some of these embodiments, the subcutaneous injection is administered to the arm, preferably to the deltoid region of the arm.

In certain embodiments, the invention is directed to said methods, wherein the reconstituted unit dose is administered to a subject of unknown serostatus and/or wherein no test has been carried out to determine whether the subject is seropositive or seronegative before the unit dose as described herein is administered.

In certain embodiments, the invention is directed to said methods, wherein the subject or subject population is seronegative to all dengue serotypes.

In certain embodiments, the invention is directed to said methods, wherein two unit doses of the invention as described herein are administered. In some embodiments the two unit doses are administered within 12 months or more, or within six months, or within three months, and optionally at least 4 weeks apart such as at day 0 and day 90 or at day 1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months after the second administration.

In certain embodiments, the method of the invention comprises or consists of a single unit dose of the invention being administered.

In certain embodiments, the invention is directed to said methods, wherein the reconstituted unit dose of the invention as described herein is administered subcutaneously to a subject or subject population that is seronegative with respect to all dengue serotypes. In other embodiments, the subject or subject population is seropositive with respect to at least one dengue serotype.

In certain embodiments, the invention is directed to said methods, wherein the unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In a preferred embodiment, the subject or subject population is from Asia Pacific or from Latin America. In some other of these embodiments, the subject or subject population is from Thailand, Sri Lanka, Philippines, Panama, Nicaragua, Dominican Republic, Colombia or Brazil. In other embodiments, the subject or subject population is from a dengue non-endemic region. Such a subject population or such a subject may be vaccinated according to the present invention in the context of traveling to a dengue endemic region. In certain embodiments, the reconstituted unit dose of the invention as described herein is administered subcutaneously to a subject or subject population that is from a dengue endemic region or a dengue non-endemic region.

In certain embodiments, the invention is directed to said methods, wherein the reconstituted unit dose of the invention as described herein is administered subcutaneously to a subject or subject population of 2 to 60 years of age. In some embodiments, the subjects or subject population are adults of 18 to 60 years.

In certain embodiments, the invention is directed to said methods, wherein the reconstituted unit dose of the invention as described herein is administered subcutaneously to children and adolescents of 2 to 17 years of age. In some embodiments, the subjects or subject population are less than 9 years of age, or less than 4 years of age. In some embodiments, the subjects or subject population are from 2 to 9 years of age, or from 2 to 5 years of age, or from 4 to 9 years of age or from 6 to 9 years of age. In other embodiment, the subject or subject population is 4 to 16 years of age. In some such embodiments, the subject or subject population is 4-5 years of age, 6-11 years of age or 12-16 years of age. Optionally, the subject or subject population is seronegative with respect to all dengue serotypes.

In certain embodiments, the invention is directed to said methods, wherein the unit dose of the invention as described herein is administered to a pediatric subject or pediatric subject population of less than 2 years of age, preferably of 2 months to 2 years or 2 months to 1.5 years or 2 months to 1 year. According to some of these embodiments, the pediatric subject or pediatric subject population is seronegative and from a dengue endemic region.

In certain embodiments, the invention is directed to said methods, wherein the reconstituted unit dose of the invention as described herein is administered to a pediatric subject or pediatric subject population of less than 2 years of age, preferably of 2 months to 2 years or 2 months to 1.5 years or 2 months to 1 year, preferably by subcutaneous injection. According to some of these embodiments, the pediatric subject or pediatric subject population is seronegative and from a dengue endemic region.

In a certain embodiments, the invention is directed to said methods, wherein the subject or subject population is 4-5 years of age and from Asia Pacific, 6-11 years of age and from Asia Pacific, or 12-16 years of age and from Asia Pacific. In other embodiments, the subject or subject population is 4-5 years of age and from Latin America, 6-11 years of age and from Latin America, or 12-16 years of age and from Latin America.

In a certain embodiments, the invention is directed to said methods, wherein the subject or subject population is 4-5 years of age and seropositive for at least 1 dengue serotype, 6-11 years of age and seropositive for at least 1 dengue serotype, or 12-16 years of age and seropositive for at least 1 dengue serotype. In other embodiments, the subject or subject population is 4-5 years of age and seronegative for all dengue serotypes, 6-11 years of age and seronegative for all dengue serotypes, or 12-16 years of age and seronegative for all dengue serotypes.

In a certain embodiments, the invention is directed to said methods, wherein the subject or subject population is from Asia Pacific or Latin America and seropositive for at least one dengue serotype at baseline. In other embodiments, the subject or subject population is from Asia Pacific or Latin America and seronegative for at all dengue serotype at baseline.

In certain embodiments, the invention is directed to said methods, wherein the subject or subject population is from Asia Pacific, seropositive for at least one dengue serotype at baseline and 4-5 years of age, 6-11 years of age, or 12-16 years of age. In other embodiments, the subject or subject population is from Asia Pacific, seronegative for all dengue serotypes at baseline and 4-5 years of age, 6-11 years of age, or 12-16 years of age. In yet other embodiments, the subject or subject population is from Latin America, seropositive for at least one dengue serotype at baseline and 4-5 years of age, 6-11 years of age, or 12-16 years of age. In other embodiments, the subject or subject population is from America, seronegative for all dengue serotypes at baseline and 4-5 years of age, 6-11 years of age, or 12-16 years of age.

In certain embodiments, the invention is directed to said methods, wherein the subject or subject population had prior vaccination against Yellow Fever. In other embodiments, the subject or subject population had prior vaccination against Japanese Encephalitis. In yet other embodiments, the subject or subject population had no prior vaccination against Yellow Fever. In other embodiments, the subject or subject population had no prior vaccination against Japanese Encephalitis. Prior vaccination indicates a vaccination prior to 30 days after a second administration, such as within 4 months after the first administration, with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination. In certain embodiments, the subject or subject population received Denvaxia within the administration regimen as described herein or within 4.5 years after administration of the first dose.

Particularly unbalanced titers of neutralizing antibodies against the four dengue serotypes are observed in seronegative populations or subjects after administration of the commercially available dengue vaccine. The present invention shows that in particular seronegative subjects show a more balanced immune response to the four dengue serotypes after administration of the reconstituted unit dose of the invention as described herein. It is therefore contemplated that the unit dose of the invention as described herein and methods of the present invention as described herein may provide a more robust immune response in a subject population including both seropositive and seronegative subjects.

The present invention is directed in part to a method of preventing virologically confirmable dengue disease in a subject comprising administering to the subject a tetravalent dengue virus composition including four dengue virus strains representing serotype 1, serotype 2, serotype 3 and serotype 4, wherein the virus strains are optionally live, attenuated dengue virus strains.

The present invention is directed in part to a method of preventing virologically confirmable dengue disease in a subject consisting of administering to the subject a tetravalent dengue virus composition including four dengue virus strains representing serotype 1, serotype 2, serotype 3 and serotype 4, wherein the virus strains are optionally live, attenuated dengue virus strains.

In certain embodiments, the invention is directed to said methods, wherein there is no step of determining the serostatus of the subject at baseline, in other words, said methods do not comprise a determination of a previous dengue infection of the subject at baseline before the administration of the tetravalent dengue virus composition. In particular, such methods are safe and effective. Thus, in certain such embodiments, the subject has not been tested for the presence a previous dengue infection.

In certain embodiments, the invention is directed to said methods, wherein the vaccine administration is safe irrespective of whether there is a determination that the subject had a previous dengue infection before the administration of the tetravalent dengue virus composition. In particular, such methods are also effective.

In certain embodiments, the invention is directed to said methods, wherein the method is safe and/or effective.

In certain embodiments, the invention is directed to said methods, wherein the composition includes at least one chimeric dengue virus. In certain such embodiments, the invention is directed to said methods, wherein the composition includes at least one non-chimeric dengue virus and at least one chimeric dengue virus, in particular a chimeric dengue serotype 2/1 strain and a dengue serotype 2 strain and a chimeric dengue serotype 2/3 strain and a chimeric dengue serotype 2/4 strain. The details of the composition are described above.

Therefore, in certain embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 12 months after the second administration. In embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least once, until 15 months after the first administration of the administration schedule. In certain such embodiments, the lower bound is more than 30%, more than 40%, more than 50%, more than 55%, more than 60%, more than 65%, more than 70% or more than 72%. Preferably said reconstituted unit dose or placebo is administered subcutaneously within about 3 month, such as on days 0 and 90.

In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 12 months after the second administration. In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least once, until 15 months after the first administration of the administration schedule. In certain such embodiments, the vaccine efficacy is more than 40%, more than 50%, more than 55%, more than 60%, more than 65%, more than 70%, more than 75%, more than 78%, more than 79% or about 80%. Preferably said reconstituted unit dose or placebo is administered subcutaneously within about 3 month, such as on days 0 and 90.

In certain embodiments, the invention is directed to said methods having a vaccine efficacy, preferably a combined vaccine efficacy against all four serotypes, in preventing virologically confirmable dengue disease with hospitalization with a 2-sided 95% confidence interval, wherein the lower bound is more than 0%, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 18 months after the second administration. In certain such embodiments, the lower bound is more than 10%, is more than 20%, is more than 30%, is more than 40%, is more than 50%, is more than 55%, is more than 60%, is more than 65%, is more than 70% or is more than 80%, or more than 90%.

In certain embodiments, the invention is directed to said methods having a combined vaccine efficacy against all four dengue serotypes in seronegative subjects with a 2-sided 95% confidence interval, wherein the lower bound is more than 25%, when measured against placebo in a subject population of at least 2,000 healthy subjects being seronegative against all serotypes at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50%, or is more than 55%.

In certain embodiments, the invention is directed to said methods having a combined vaccine efficacy against all four dengue serotypes in seronegative subjects of more than 30%, when measured against placebo in a subject population of at least 2,000 healthy subjects being seronegative against all serotypes at baseline, wherein said unit dose or said placebo is administered at least twice within less than 6 months, such as within 3 months, 30 days after the second administration until at least 12 months after the second administration. In certain such embodiments, the combined vaccine efficacy against all four dengue serotypes in seronegative subjects is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 45%.

In certain embodiments, the invention is directed to said methods having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose or said placebo is administered at least twice within less than 6 months, such as within 3 months, 30 days after the second administration until at least 12 months after the second administration. In certain such embodiments, the combined vaccine efficacy against all four dengue serotypes is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50%, is more than 60%, or is more than 70%.

In certain embodiments, the invention is directed to said methods having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose or said placebo is administered at least twice within less than 6 months, such as within 3 months, 30 days after the second administration until at least 12 months after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50%, is more than 60%, is more than 65%, or is more than 68%.

In certain embodiments, the invention is directed to said methods having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose or said placebo is administered at least twice within less than 6 months, such as within 3 months, 30 days after the second administration until at least 12 months after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, or is more than 50%.

In certain embodiments, the invention is directed to said methods having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration. In certain such embodiments, the vaccine efficacy against dengue serotype 1 is more than 40%, is more than 50%, is more than 60%, is more than 65%, or is more than 70%.

In certain embodiments, the invention is directed to said methods having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50, is more than 60, is more than 70, is more than 80, or is more than 90%.

In certain embodiments, the invention is directed to said methods having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration. In certain such embodiments, the vaccine efficacy against dengue serotype 2 is more than 40%, is more than 50%, is more than 60%, is more than 70%, is more than 80, or is more than 90%.

In certain embodiments, the invention is directed to said methods having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%.

In certain embodiments, the invention is directed to said methods having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration. In certain such embodiments, the vaccine efficacy against dengue serotype 3 is more than 40%, is more than 50%, is more than 55%, or is more than 60%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 2,000 healthy subjects being seronegative against all serotypes at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50%, is more than 60%, is more than 70%, or is more than 75%.

In certain embodiments, the invention is directed to said methods having a combined vaccine efficacy against virologically-confirmed dengue with hospitalization against all four serotypes of more than 30%, when measured against placebo in a subject population of at least 2,000 healthy subjects, healthy subjects being seronegative against all serotypes at baseline, wherein said unit dose or said placebo is administered at least twice within less than 6 months, such as within 3 months, 30 days after the second administration until at least 12 months after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 2,000 healthy subjects being seropositive at baseline, wherein said unit dose or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%, is more than 50%, is more than 60%, is more than 70%, or is more than 80%.

In certain embodiments, the invention is directed to said methods having a combined vaccine efficacy against virologically-confirmed dengue with hospitalization against all four serotypes of more than 30%, when measured against placebo in a subject population of at least 2,000 healthy subjects, healthy subjects being seropositive at baseline, wherein said unit dose or said placebo is administered at least twice within less than 6 months, such as within 3 months, 30 days after the second administration until at least 12 months after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a relative risk, preferably a combined relative risk against all four serotypes, with a 2-sided 95% confidence interval, wherein the upper bound is less than 0.75, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 12 months after the second administration. In certain such embodiments, the upper bound is less than 0.70, less than 0.65, less than 0.60, less than 0.55, less than 0.50, less than 0.45, less than 0.40, less than 0.35, less than 0.30 or less than 0.28. Preferably said reconstituted unit dose or placebo is administered subcutaneously within about 3 month, such as on days 0 and 90.

In certain embodiments, the invention is directed to said methods having a relative risk, preferably a combined relative risk against all four serotypes, of less than 0.70, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 12 months after the second administration. In certain such embodiments, the relative risk is less than 0.65, less than 0.60, less than 0.55, less than 0.50, less than 0.45, less than 0.40, less than 0.35, less than 0.30, less than 0.25 or less than 0.23. Preferably said reconstituted unit dose or placebo is administered subcutaneously within about 3 month, such as on days 0 and 90.

In certain embodiments, the invention is directed to said methods, wherein virologically confirmable dengue disease occurs in less than 2.5% of the subjects, when measured against placebo in a subject population of at least 5,000 healthy subjects (or at least 10,000, or at least 15,000 healthy subjects) irrespective of serostatus at baseline, wherein a reconstituted unit dose as described herein or placebo is administered at least twice within less than 6 months, such as within 3 months, 30 days after the second administration until at least 12 months or at least 18 months after the second administration. In certain such embodiments, virologically confirmable dengue disease occurs in less than 2.0% of the subjects, less than 1.5% of the subjects, less than 1.0% of the subjects, less than 0.8% of the subjects, or less than 0.6% of the subjects. Preferably said reconstituted unit dose or placebo is administered subcutaneously within about 3 month, such as on days 0 and 90.

In certain embodiments, the invention is directed to said methods having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects (or at least 10,000, or at least 15,000 healthy subjects) from endemic irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 or 13 months after the last administration of the administration schedule.

In certain embodiments, the invention is directed to said methods having a combined vaccine efficacy against all four serotypes of more than 66%, or of more than 70%, or of more than 75%, or of more than 77%, or of more than 80.0%, when measured against placebo in a subject population of at least 5,000 healthy subjects (or at least 10,000, or at least 15,000 healthy subjects) from endemic areas irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 months or 13 month after the last administration of the administration schedule.

In certain embodiments, the invention is directed to said methods, wherein the combined vaccine efficacy against all four serotypes is measured about 30 days after the last administration of the administration schedule until 12 or 13 months after the last administration of the administration schedule.

In certain embodiments, the invention is directed to said methods, wherein said unit dose or said placebo is administered at twice within three months, in particular at about day 1 and about day 90, and wherein the combined vaccine efficacy against all four serotypes is measured 30 days after the second administration until 12 or 13 months after the second administration of the administration schedule.

In certain embodiments, the invention is directed to said methods, wherein said methods are effective and safe. In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein said methods having a relative risk for virologically confirmed dengue with hospitalization of 1 or less, or 0.8 or less, or 0.6 or less, when measured against placebo in a subject population of at least 5,000 healthy subjects (or at least 10,000, or at least 15,000 healthy subjects). In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein the healthy subjects of the subject population are 4 to 16 years of age. In some of such embodiments, the healthy subjects of the subject population are 4 to 5 years of age, 6 to 11 years of age, or 12 to 16 years of age.

In certain embodiments, the invention is directed to said methods, wherein the healthy subjects of the subject population are defined as being healthy in view of the exclusion criteria specified in Example 6.

In certain embodiments, the invention is directed to said methods, wherein the healthy subjects of the subject population are from Asia Pacific or Latin America.

In certain embodiments, the invention is directed to said methods, wherein the healthy subjects of the subject population are seropositive with respect to at least one serotype. In other embodiments, the healthy subjects of the subject population are seronegative with respect to all serotypes.

In certain embodiments, the invention is directed to said methods, wherein the healthy subjects of the subject population are 4-5 years of age and from Asia Pacific, 6-11 years of age and from Asia Pacific, or 12-16 years of age and from Asia Pacific. In other embodiments, the healthy subjects of the subject population are 4-5 years of age and from Latin America, 6-11 years of age and from Latin America, or 12-16 years of age and from Latin America.

In certain embodiments, the invention is directed to said methods, wherein the healthy subjects of the subject population are 4-5 years of age and seropositive for at least 1 dengue serotype, 6-11 years of age and seropositive for at least 1 dengue serotype, or 12-16 years of age and seropositive for at least 1 dengue serotype. In other embodiments, the healthy subjects of the subject population are 4-5 years of age and seronegative for all dengue serotypes, 6-11 years of age and seronegative for all dengue serotypes, or 12-16 years of age and seronegative for all dengue serotypes.

In certain embodiments, the invention is directed to said methods, wherein the healthy subjects of the subject population are from Asia Pacific or Latin America and seropositive for at least one dengue serotype at baseline. In other embodiments, the healthy subjects of the subject population are from Asia Pacific or Latin America and seronegative for at all dengue serotype at baseline.

In certain embodiments, the invention is directed to said methods, wherein the healthy subjects of the subject population are from Asia Pacific, seropositive for at least one dengue serotype at baseline and 4-5 years of age, 6-11 years of age, or 12-16 years of age. In other embodiments, the healthy subjects of the subject population are from Asia Pacific, seronegative for all dengue serotypes at baseline and 4-5 years of age, 6-11 years of age, or 12-16 years of age. In yet other embodiments, the healthy subjects of the subject population are from Latin America, seropositive for at least one dengue serotype at baseline and 4-5 years of age, 6-11 years of age, or 12-16 years of age. In other embodiments, the healthy subjects of the subject population are from America, seronegative for all dengue serotypes at baseline and 4-5 years of age, 6-11 years of age, or 12-16 years of age.

In certain embodiments, the invention is directed to said methods, wherein the healthy subjects of the subject population had prior vaccination against Yellow Fever. In other embodiments, the healthy subjects of the subject population had no prior vaccination against Yellow Fever. Prior vaccination indicates a vaccination prior to the first vaccination with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination.

In certain embodiments, the invention is directed to said methods, wherein the healthy subjects of the subject population had prior vaccination against Japanese Encephalitis. In other embodiments, the healthy subjects of the subject population had no prior vaccination against Japanese Encephalitis.

In certain embodiments, the invention is directed to said methods, wherein the healthy subjects of the subject population received Denvaxia within the administration regimen as described herein or within 4.5 years after administration of the first dose. In certain embodiments, the invention is directed to said methods, wherein the occurrence of vaccine related serious adverse events is less than 0.1%.

In certain embodiments, the invention is directed to said methods, wherein the occurrence of vaccine related unsolicited adverse events occurring within 4 weeks of administration is less than 2%.

In certain embodiments, the invention is directed to said methods, wherein the occurrence of vaccine related solicited adverse events occurring within 2 weeks of administration is less than 35%.

In certain embodiments, the invention is directed to said methods, wherein the occurrence of vaccine related solicited local reactions occurring within 1 weeks of administration is less than 40%.

In certain embodiments, the invention is directed to said methods, wherein the method does not increase the risk of virologically-confirmed dengue with hospitalization in the individual, such as in a seronegative individual.

Unit Dose for Use in a Method of Preventing Dengue Disease

The present invention is directed in part to the composition or unit dose of the invention as described herein for use in a method of preventing dengue disease (in particular virologically confirmable dengue, VCD) in a subject.

The present invention is directed in part to the composition or unit dose of the invention as described herein for use in a method of preventing dengue disease (in particular virologically confirmable dengue, VCD) in a subject population.

Any method described herein above under the heading "Method of preventing" is to be understood to be also disclosed as unit dose for use in such a method of preventing dengue disease in a subject or subject population irrespective of being expressly stated below.

The present invention is directed in part to a reconstituted unit dose of a dengue vaccine composition as described herein for use in a method of preventing virologically confirmable dengue disease in a subject comprising administering at least a first unit dose of the dengue vaccine composition to the subject, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated dengue virus strains and/or comprise chimeric dengue viruses and/or at least one non-chimeric dengue virus, and wherein upon reconstitution with 0.5 mL of a pharmaceutically acceptable diluent
  (i) dengue serotype 1 has a concentration of at least 3.3 log 10 pfu/0.5 mL and optionally to 5.0 log 10 pfu/0.5 mL,
  (ii) dengue serotype 2 has a concentration of at least 2.7 log 10 pfu/0.5 mL and optionally to 4.9 log 10 pfu/0.5 mL,
  (iii) dengue serotype 3 has a concentration of at least 4.0 log 10 pfu/0.5 mL and optionally to 5.7 log 10 pfu/0.5 mL, and
  (iv) dengue serotype 4 has a concentration of at least 4.5 log 10 pfu/0.5 mL and optionally to 6.2 log 10 pfu/0.5 mL.

The present invention is directed in part to a reconstituted unit dose of a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent
  (v) dengue serotype 1 has a concentration of at least 3.3 log 10 pfu/0.5 mL and optionally to 5.0 log 10 pfu/0.5 mL,
  (vi) dengue serotype 2 has a concentration of at least 2.7 log 10 pfu/0.5 mL and optionally to 4.9 log 10 pfu/0.5 mL,
  (vii) dengue serotype 3 has a concentration of at least 4.0 log 10 pfu/0.5 mL and optionally to 5.7 log 10 pfu/0.5 mL, and
  (viii) dengue serotype 4 has a concentration of at least 4.5 log 10 pfu/0.5 mL and optionally to 6.2 log 10 pfu/0.5 mL.

In certain embodiments, the invention is directed to a reconstituted unit dose of a dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, wherein the subject is under 9 years of age and/or when the serostatus of the subject is unknown or seronegative and wherein upon reconstitution with 0.5 mL of a pharmaceutically acceptable diluent
  (i) dengue serotype 1 has a concentration of at least 3.3 log 10 pfu/0.5 mL and optionally to 5.0 log 10 pfu/0.5 mL,
  (ii) dengue serotype 2 has a concentration of at least 2.7 log 10 pfu/0.5 mL and optionally to 4.9 log 10 pfu/0.5 mL,
  (iii) dengue serotype 3 has a concentration of at least 4.0 log 10 pfu/0.5 mL and optionally to 5.7 log 10 pfu/0.5 mL, and
  (iv) dengue serotype 4 has a concentration of at least 4.5 log 10 pfu/0.5 mL and optionally to 6.2 log 10 pfu/0.5 mL.

In certain embodiments, the reconstituted unit dose is administered to a subject of unknown serostatus and/or wherein no test has been carried out to determine whether the subject is seropositive or seronegative before the unit dose as described herein is administered.

In certain embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the method is safe. In certain such embodiments, the subject is under 9 years of age or from 4 years of age and/or the serostatus of the subject is unknown or seronegative. In certain such embodiments, the subject is from 4 years of age and the serostatus of the subject is unknown or seronegative, preferably seronegative.

In certain embodiments, the method is effective. In certain such embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the dengue serotype 1 and the dengue serotype 2 are present each in a concentration based on the total concentration in pfu/0.5 mL which is within 5%-points of each other and/or are together less than about 10% of the total concentration in pfu/0.5 mL. In certain such embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the composition includes at least one chimeric dengue virus. In certain such embodiments, the composition includes at least one non-chimeric dengue virus and at least one chimeric dengue virus.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age.

In certain embodiments, the method does not comprise a determination of a previous dengue infection in the subject before the administration of the first unit dose of the tetravalent dengue virus composition. Thus, in certain embodiments, the subject has not been tested for the presence a previous dengue infection.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, the unit dose further comprises from about 10% w/v to about 20% w/v trehalose dihydrate or an equimolar amount of other forms of α,α-trehalose, from about 0.5% w/v to about 1.5 w/v poloxamer 407, from about 0.05% w/v to about 2% w/v human serum albumin, and from about 70 mM to 140 mM sodium chloride when measured in 0.5 mL. In certain such embodiments, the unit dose comprises about 15 (w/v) α,α-trehalose dihydrate, about 1% (w/v) poloxamer 407, about 0.1% (w/v) human serum albumin, and about 100 mM sodium chloride when measured in 0.5 mL.

In certain embodiments, the method is for preventing dengue hemorrhagic fever (DHF) or dengue shock syndrome (DSS).

In certain embodiments, the subject is from a dengue endemic region. In other embodiments, the subject is from a dengue non-endemic region.

In certain embodiments, the subject is from Asia Pacific or Latin America.

In certain embodiments, the reconstituted unit dose provides a seropositivity rate when it is administered to a subject population of at least 50 subjects in two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270. In certain such embodiments, at least 80% of the subject population are seropositive for all four dengue serotypes at least one month after administration of the first unit dose, such as at day 30, and before or at the time of the administration of the second unit dose, such as at day 90, and after the administration of the second unit dose, such as at day 120 and at day 270.

In certain embodiments, the reconstituted unit dose provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

In certain particular embodiments, the invention is directed to a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4 wherein the attenuated dengue virus strains comprise chimeric dengue viruses and at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL.

In certain embodiments, the method does not comprise a determination of a previous dengue infection of the subject before the administration of the first unit dose of the tetravalent dengue virus composition and wherein the method is safe and effective. Thus, in certain embodiments, the subject has not been tested for the presence a previous dengue infection.

In certain embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, in the unit dose upon reconstitution with 0.5 mL of a pharmaceutically acceptable diluent
  (i) dengue serotype 1 has a concentration of 3.3 log 10 pfu/0.5 mL to 5.0 log 10 pfu/0.5 mL,
  (ii) dengue serotype 2 has a concentration of 2.7 log 10 pfu/0.5 mL to 4.9 log 10 pfu/0.5 mL,
  (iii) dengue serotype 3 has a concentration of 4.0 log 10 pfu/0.5 mL to 5.7 log 10 pfu/0.5 mL, and
  (iv) dengue serotype 4 has a concentration of 4.5 log 10 pfu/0.5 mL to 6.2 log 10 pfu/0.5 mL, and optionally the composition further comprises about 15% (w/v) α,α-trehalose dihydrate, about 1% (w/v) poloxamer 407, about 0.1% (w/v) human serum albumin, and about 100 mM sodium chloride when measured in 0.5 mL.

In certain embodiments, the unit doses are administered to the deltoid region of the arm.

In certain embodiments, the composition is administered without determining the serostatus of the subject at baseline and wherein the administration is safe and effective regardless of the serostatus at base line.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seronegative to all four dengue serotypes at baseline. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seropositive to at least one dengue serotypes at baseline. In certain preferred embodiments, the subject is 4 to 5 years of age, 6 to 11 years of age or 12 to 16 years of age.

In certain embodiments, the method is for preventing dengue hemorrhagic fever (DHF) or dengue shock syndrome (DSS).

In certain embodiments, the subject is from a dengue endemic region or from a dengue non-endemic region.

In certain embodiments, the subject is from Asia Pacific or Latin America.

In certain embodiments, the composition provides a seropositivity rate when it is administered to a subject population of at least 50 subjects in two unit doses subcutaneously at day 1 and at day 90, wherein the subjects of the subject population are seronegative to all dengue serotypes at baseline, in particular wherein at least one month after administration of the first unit dose, such as at day 30, at least 80% of the subject population are seropositive for all four dengue serotypes, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

In certain embodiments, the composition provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to the unit dose of the invention as described herein for use in a method of preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of the invention as described herein for use in a method of preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to the reconstituted unit dose of the invention as described herein for said uses, wherein said unit dose is administered by subcutaneous injection. According to some of these embodiments the subcutaneous injection is administered to the arm, preferably to the deltoid region of the arm.

In certain embodiments the invention is directed to a reconstituted unit dose of the invention as described herein for said uses, wherein the subject or subject population is seronegative to all dengue serotypes.

In certain embodiments the invention is directed to a reconstituted unit dose of the invention as described herein for said uses, wherein a single unit dose of the invention as described herein is administered.

In certain embodiments the invention is directed to a reconstituted unit dose of the invention as described herein for said uses, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose of the invention as described herein may be administered after the second administration. Such a third administration may act as a booster and may be administered between 6 to 12 months after the first administration, such as 12 months after the first administration, or later than 12 month after the first administration, such as 12 months after the second administration.

In certain embodiments the invention is directed to a reconstituted unit dose of the invention as described herein for said uses, wherein the reconstituted unit dose of the invention as described herein is administered at most in two doses or in one dose.

In certain embodiments of the invention the subject is seronegative with respect to all dengue serotypes. In certain embodiments of the invention the subject is seronegative with respect to all dengue serotypes and the reconstituted unit dose is administered to the seronegative subject by subcutaneous injection.

In certain other embodiments of the invention the subject is seropositive with respect to at least one dengue serotype.

In certain embodiments the invention is directed to the reconstituted unit dose of the invention as described herein for said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or such a subject may be vaccinated according to the invention in the context of traveling to a dengue-endemic region. In certain embodiments, the reconstituted unit dose of the invention as described herein is administered subcutaneously to a subject or subject population from a dengue endemic region or from a dengue non-endemic region.

In some embodiments the invention is directed to the unit dose of the invention as described herein for said uses, wherein the subject or subject population is of 2 to 60 years of age or 18 to 60 years of age. In certain embodiments, the subject or subject population is of 1 to 17 years of age, or less than 9 years of age, or less than 4 years of age or less than 2 years of age. According to some of these embodiments the subject or subject population is seronegative and from a dengue-endemic region.

In certain embodiments, the invention is directed to the reconstituted unit dose of the invention as described herein for said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to the reconstituted unit dose of the invention as described herein for said uses, wherein the reconstituted unit dose is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

The unit dose for use in the methods described above may be any unit dose of a dengue vaccine composition as described above under the headings "Unit dose" or "Dengue vaccine composition" and comprise any dengue virus strain as described above under the heading "Dengue virus strain".

Use for the Manufacture of a Medicament for Preventing Dengue Disease

The present invention is directed in part to the use of a unit dose of the invention as described herein for the manufacture of a medicament for preventing dengue disease (in particular virologically confirmable dengue, VCD) in a subject.

The present invention is directed in part to the use of a unit dose of the invention as described herein for the manufacture of a medicament for preventing dengue disease (in particular virologically confirmable dengue, VCD) in a subject population.

Any method described herein above under the heading "Method of preventing" is to be understood to be also disclosed as the use of a unit dose for the manufacture of a medicament for preventing dengue disease in a subject or subject population with such a method irrespective of being expressly stated below.

The present invention is in part directed to the use of a unit dose of the invention as described herein for the manufacture of a medicament for preventing dengue disease in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein for the manufacture of a medicament for preventing dengue disease in a subject, comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to said uses, wherein the reconstituted unit dose of the invention as described herein is administered by subcutaneous injection. According to some of these embodiments the subcutaneous injection is administered to the arm, preferably to the deltoid region of the arm.

In certain embodiments the invention is directed to said uses, wherein one reconstituted unit dose of the invention as described is administered, In certain embodiments the invention is directed to said uses, wherein two reconstituted unit doses of the invention as described herein are administered. In one embodiment, the two unit doses are administered within 12 months or more, or within six months, or within three months, such as at day 0 and day 90 or at day 1 and day 90. According to some of these embodiments a third unit dose of the invention as described herein may be administered after the second administration. Such a third administration may act as a booster and may be administered between 6 to 12 months after the first administration, such as 12 months after the first administration, or later than 12 month after the first administration, such as 12 months after the second administration.

In certain embodiments of the invention the subject is seronegative with respect to all dengue serotypes.

In certain other embodiments of the invention the subject is seropositive with respect to at least one dengue serotype.

In certain embodiments the invention is directed to said uses, wherein the reconstituted unit dose is administered to the seronegative subject by subcutaneous injection.

In certain embodiments the invention is directed to said uses, wherein the reconstituted unit dose is administered to a subject of unknown serostatus and/or wherein no test has been carried out to determine whether the subject is seropositive or seronegative before the unit dose is administered.

In certain embodiments the invention is directed to said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or subject may be vaccinated according to the invention in the context of traveling to a dengue endemic region. In certain embodiments, the reconstituted unit dose of the invention as described herein is administered subcutaneously to a subject or subject population from a dengue endemic region or from a dengue non-endemic region.

In certain embodiments the invention is directed to said uses, wherein the subject is of 2 to 60 years of age or 18 to 60 years of age. In certain embodiments the subject is 1 to 17 years of age, or less than 9 years of age, or less than 4 years of age or less than 2 years of age. According to some of these embodiments the subject is seronegative and from a dengue-endemic region.

In certain embodiments, the invention is directed to said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to said uses, wherein the reconstituted unit dose of the invention as described herein is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

Method of Stimulating an Immune Response and Uses

Method of Stimulating an Immune Response

In certain embodiments the invention is directed to a method for stimulating an immune response, preferably a balanced immune response, to all four dengue serotypes in a subject, comprising administering to the subject a reconstituted unit dose of the invention as described herein.

The present invention is in part directed to a method for stimulating an immune response to all four serotypes of dengue virus in a subject, comprising administering to the subject a reconstituted unit dose of the invention as described herein by subcutaneous injection.

In certain embodiments, the invention is directed to said method, wherein the immune response to all four serotypes of dengue virus is balanced.

In certain embodiments, the invention is directed to said method, wherein the reconstituted unit dose is administered by subcutaneous injection to the arm, preferably to the deltoid region of the arm.

In certain embodiments, the invention is directed to said method, wherein the subject is seronegative to all dengue serotypes.

In certain embodiments, the invention is directed to said method, wherein two reconstituted unit doses of the invention as described herein are administered. In some embodiments, the two reconstituted doses are administered within 12 months or more, or within six months, or within three months, such as at day 0 and day 90 or at day 1 and day 90. According to some of these embodiments, a third unit dose of the invention as described herein is administered between 6 and 12 months after the administration of said first unit dose, such as 12 months after the first administration, or later than 12 month after the first administration, such as 12 months after the second administration.

In certain embodiments, the invention is directed to said method, wherein the unit dose of the invention as described herein is administered to a subject from a dengue endemic region. In some of these embodiments, the subject is from Singapore, Dominican Republic, Panama, Philippines, Colombia, Puerto Rico or Thailand, in particular from Singapore, Dominican Republic, Panama, or Philippines. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said method, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said method, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said method, wherein the unit dose of the invention as described herein is administered to a subject of 2 to 60 years of age or 18 to 60 years of age. In certain embodiments the subject is 1 to 17 years of age, or less than 9 years of age, or less than 4 years of age or less than 2 years of age. According to some of these embodiments the subject is seronegative and from a dengue-endemic region.

In certain embodiments, the invention is directed to said method, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said method, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

Unit Dose for Use in a Method of Stimulating an Immune Response

The present invention is in part directed to the reconstituted unit dose of the invention as described herein for use in a method for stimulating an immune response to all four serotypes of dengue virus in a subject.

The present invention is in part directed to the reconstituted unit dose of the invention as described herein for use in a method for stimulating an immune response to all four serotypes of dengue virus in a subject, wherein a reconstituted unit dose of the invention as described herein is administered to the subject, preferably by subcutaneous injection.

In certain embodiments, the invention is directed to the reconstituted unit dose of the invention as described herein for said use, wherein the immune response to all four serotypes of dengue virus is balanced.

In certain embodiments, the invention is directed to the reconstituted unit dose of the invention as described herein for said use, wherein the reconstituted unit dose is administered by subcutaneous injection to the arm, preferably to the deltoid region of the arm.

In certain embodiments, the invention is directed the reconstituted unit dose of the invention as described herein for said use, wherein the subject is seronegative to all dengue serotypes.

In certain embodiments, the invention is directed to the unit dose of the invention as described herein for said use, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose is administered 6 to 12 months after the administration of the first reconstituted unit dose, such as 12 months after the first administration, or later than 12 month after the first administration, such as 12 months after the second administration.

In certain embodiments, the invention is directed to the unit dose of the invention as described herein for said use, wherein the subject is from a dengue endemic region. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to the unit dose of the invention as described herein for said use, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to the unit dose of the invention as described herein for said use, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to the reconstituted unit dose of the invention as described herein for said use, wherein the unit dose of the invention as described herein is administered to a subject of 2 to 60 years of age or 18 to 60 years of age. In certain embodiments the subject is 1 to 17 years of age, or less than 9 years of age, or less than 4 years of age or less than 2 years of age. According to some of these embodiments the subject is seronegative and from a dengue-endemic region.

In certain embodiments, the invention is directed to the reconstituted unit dose of the invention as described herein for said use, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to the reconstituted unit dose of the invention as described herein for said use, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

Use for the Manufacture of a Medicament for Stimulating an Immune Response

The present invention is in part directed to the use of the reconstituted unit dose of the invention as described herein for the manufacture of a medicament for stimulating an immune response to all four serotypes of dengue virus in a subject. In one embodiment a reconstituted unit dose of the invention as described herein is administered by subcutaneous injection.

In certain embodiments, the invention is directed to said use, wherein the immune response to all four serotypes of dengue virus is balanced.

In certain embodiments, the invention is directed to said use, wherein the reconstituted unit dose is administered by subcutaneous injection to the arm, preferably to the deltoid region of the arm.

In certain embodiments, the invention is directed the reconstituted unit dose of the invention as described herein for said use, wherein the subject is seronegative to all dengue serotypes.

In certain embodiments, the invention is directed to said use, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose is administered 6 to 12 months after the administration of the first reconstituted unit dose, such as 12 months after the first administration, or later than 12 month after the first administration, such as 12 months after the second administration.

In certain embodiments, the invention is directed to said use, wherein the subject is from a dengue endemic region. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said use, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said use, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said use, wherein the reconstituted unit dose of the invention as described herein is administered to a subject of 2 to 60 years of age or 18 to 60 years of age. In certain embodiments the subject is 1 to 17 years of age, or less than 9 years of age, or less than 4 years of age or less than 2 years of age. According to some of these embodiments the subject is seronegative and from a dengue-endemic region.

In certain embodiments, the invention is directed to said use, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said use, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

Method for Determining the Titer of Neutralizing Antibodies

The present invention is directed in part to a method for determining the titer of neutralizing antibodies against each of dengue serotypes 1, 2, 3 and 4 in a blood serum sample, the method comprising the steps of:
(a) seeding cells from a dengue-susceptible cell line on 96-well assay plates and culturing the cells for a culture period;
(b) preparing serial dilutions of the blood serum sample;
(c) separately mixing the serially diluted blood serum samples prepared in step (b) with dengue serotype 1, dengue serotype 2, dengue serotype 3 and dengue serotype 4 to obtain separate mixtures for each dengue serotype and incubating the separate mixtures;
(d) adding the separate mixtures prepared in (c) to the cells seeded and cultured in step (a) and incubating the cells with the separate mixtures;
(e) providing an overlay for the inoculated cells and incubating the cells for an incubation period of 40 to 75 hours;
(f) determining the number of plaques in each well and comparing the number of plaques in each well to a control to determine the level of neutralizing antibodies against each of dengue serotypes 1, 2, 3 and 4.

In one embodiment, different incubation periods are used in step (e) for the mixtures of different dengue serotypes. In some embodiments, the incubation period for mixtures of dengue serotype 4 is shorter than the incubation period for mixtures of dengue serotypes 1, 2 and 3, for example the incubation period for mixtures of dengue serotype 4 is less than 50 hours, preferably 46±2 hours. In some embodiments, the incubation period for mixtures of dengue serotype 2 is longer than the incubation period for mixtures of dengue serotypes 1, 3 and 4, for example the incubation period for mixtures of dengue serotype 2 is between 60 and 70 hours, preferably 70±2 hours.

In one embodiment, the dengue-susceptible cell line used in step (a) is selected from Vero cells, LLC-MK2 cells and BHK-21 cells. In some embodiments, the culture period of the cells is 12 to 36 hours.

In one embodiment, in step (c) the dengue serotype 1 is DENV-1 strain 16007, dengue serotype 2 is DENV-2 strain 16681, dengue serotype 3 is DENV-3 strain 16562 and dengue serotype 4 is DENV-4 strain 1036.

In one embodiment, the separate mixtures in step (c) are incubated overnight at a temperature of 2 to 8° C.

In one embodiment, the overlay in step (e) is selected from the group consisting of methylcellulose, carboxymethylcellulose and agarose. In some embodiments, the cells with the overlay are incubated at a temperature of 33° C. to 35° C.

In one embodiment, the number of plaques in each well is determined using serotype-specific anti-dengue monoclonal antibodies.

In one embodiment, the invention is directed to a method for determining the titer of neutralizing antibodies against each of dengue serotypes 1, 2, 3 and 4 in a blood serum sample, the method comprising the steps of:
(a) seeding Vero cells on 96-well assay plates and culturing the Vero cells for a period of 20 to 30 hours;
(b) preparing serial dilutions of the serum sample;
(c) separately mixing the serially diluted serum samples with dengue serotype 1, dengue serotype 2, dengue serotype 3 and dengue serotype 4 to prepare separate mixtures and incubating the separate mixtures overnight at a temperature of 2 to 8° C.;
(d) incubating the cells seeded and cultured in step (a) with the separate mixtures prepared in step (c) in separate wells for 90 to 120 minutes;
(e) providing a methylcellulose overlay for the inoculated cells and incubating the cells for an incubation period of 40 to 75 hours at 34° C.;
(f) determining the number of plaques in each well using serotype-specific anti-dengue monoclonal antibodies and comparing the number of plaques in each well to a control to determine the level of neutralizing antibodies against each of dengue serotypes 1, 2, 3 and 4.

In one embodiment, the invention is directed to the use of said method for determining the dengue serostatus of a subject before vaccination with a dengue virus vaccine or for analyzing a subjects immune response after vaccination with a dengue virus vaccine.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1

Preparation of the Dengue Virus Strains

The methods used to generate the chimeric dengue strains TDV-1, -3 and -4 were standard molecular cloning and DNA engineering methods and are described in Huang et al. (2003) J. Virology 77(21): 11436-11447. The following well-known methods were used to construct and introduce the prM-E genes of dengue serotypes 1, 3 and 4 into the TDV-2 backbone: Reverse-transcriptase PCR (RT-PCR), PCR, restriction enzyme digestion, DNA fragment ligation, bacterial transformations by electroporation, plasmid DNA preparations, in vitro transcription by T7 RNA polymerase, and transfection of Vero cells by electroporation.

After growing and purifying the different dengue serotypes separately as described in Huang et al. (2013) PLOS Neglected Dis, 7(5):e2243, they are mixed in the concentrations provided in Table 5. The mixture of dengue serotypes is present in a dengue vaccine composition and combined with a composition of pharmaceutically acceptable excipients resulting in a dengue vaccine composition comprising 15% w/v α,α trehalose dihydrate, 1% w/v poloxamer 407, 0.1% w/v human serum albumin and 100 mM sodium chloride. The dengue vaccine composition is lyophilized and represents a lyophilized unit dose of TDV. The lyophilized unit dose is reconstituted with 37 mM aqueous sodium chloride solution and the reconstituted unit dose comprises 15% w/v α,α trehalose dihydrate, 1% w/v poloxamer 407, 0.1% w/v human serum albumin and 137 mM sodium chloride.

Example 2

Microneutralization Test

Immunogenicity was measured by a microneutralization assay to each one of the four dengue serotypes with titers defined as the dilution resulting in a 50% reduction in plaque values (MNT50). Briefly, on day 1 Vero cells were seeded on 96-well assay plates in DMEM and 10% FBS at a density of $2.5\times10^5$ cells/ml and incubated at 37° C. for 24 hours. On day 2 serial dilutions of the heat-inactivated antibody-containing test and control sera samples (dilutions range 1:10 to 1:20480) were prepared and mixed with a constant concentration of dengue viruses, in particular DENV-1 strain 16007, DENV-2 strain 16681, DENV-3 strain 16562 and DENV-4 strain 1036, (target 60-80 pfu/well) in a 96 well microtiter plate and incubated overnight at 2-8° C. to enable the neutralization of the virus by the antibodies present in the sera. After the incubation the mixture of virus and antibodies was transferred onto the 96 well plates with Vero cells and the plates were incubated at 37° C. for 90-120 minutes to infect the Vero cells. A 1% methylcellulose overlay in DMEM was applied to the plate to restrict spread of progeny virus and the plate was incubated for 46-70 hours at 34° C. depending on the Dengue serotype:

DENV1—66±2 hours
DENV2—70±2 hours
DENV3—66±2 hours
DENV4—46±2 hours

After the incubation the cells were washed twice with PBS and fixed by adding cold methanol and incubating for 60 minutes at a temperature of ≤−20° C. After fixing the plates were dried and washed three times with washing buffer (1× PBS, pH 7.4 with 0.5% Tween), before 50 μl of serotype-specific anti-dengue monoclonal antibodies in blocking solution (2.5% nonfat dry milk in PBST) per well were added and incubated with the cells for 18±4 hours at 2-8° C.

The monoclonal antibodies were made as described in Gentry et al. (1982) Am. J. Trop. Med. Hyg. 31, 548-555; Henchal et al. (1985) Am. J. Trop. Med. Hyg. 34, 162-169; and Henchal et al. (1982) Am. J. Trop. Med. Hyg. 31(4): 830-6). Briefly, the anti-DENV-1 HBD was made against dengue 1 strain Hawaii, Envelope, the anti-DENV-2 was made against dengue 2 strain New Guinea C, Envelope, isotype 1, the anti-DENV-3 HBD was made against dengue 3 strain H87, Envelope, isotype 2A, and the anti-DENV-4 HBD was made against dengue 4 strain H241, Envelope, isotype 2A.

After incubation, the plates were washed three times with washing buffer and 50 μl of a secondary peroxidase labelled goat anti-mouse IgG (H+L) (KPL Cat #074-1806) in blocking solution was added and incubated for 90 to 120 minutes at 37° C. Then the plates were washed three times with washing buffer and 50 μl of precipitant substrate (2-amino-9-ethyl carbazole (AEC) tablet in 2.5 ml DMSO, 47.5 ml 50 mM acetate buffer and 250 μl hydrogen peroxide) were added and the mixture was incubated for 20 minutes at room temperature. Finally, the substrate was removed, the plates were rinsed with $dH_2O$ and dried.

Sample titers are calculated using the linear regression method and reported as MNT50 titers for each sample. Clinical data are reported as a geometric mean titer for all the individual MNT50 titers in each treatment group. Briefly, the number of infectious foci in each well was counted and the titer of neutralizing antibodies was determined by comparing the percent reduction of infectious foci centers in wells containing antibody (test samples) in comparison to wells containing virus alone. The MNT50 was calculated using the following linear regression equation:

$$MNT50=10^{[(50-c)/m]}$$ where $c=y$ intercept of regression line and $m$=slope of regression line Each test sample was tested in triplicates and the titer was calculated from the average of the triplicates. A schematic drawing of the steps performed in this test is provided in FIG. 2.

Example 3

Clinical Trial Comparing Two Different Unit Doses

A descriptive Phase II, double-blind, randomized, and controlled trial in 351 subjects aged 21 to 45 years living in Singapore was performed comparing two different formulations of a tetravalent dengue vaccine. Subjects were randomized (1:1), stratified by baseline dengue serostatus, into two treatment groups: groups 1 received one subcutaneous (SC) dose of HD-TDV and group 2 received one subcutaneous dose of TDV. The dengue vaccine formulations were prepared as described in Example 1. The concentration of the four dengue serotypes in the HD-TDV vaccine (high dose tetravalent dengue vaccine) and in the TDV vaccine (corresponding to the unit dose of the invention as described herein) is outlined in Table 5.

TABLE 5

Unit doses used in the trial.

| | |
|---|---|
| Comparative unit dose (HD-TDV) | 0.5 mL comprising TDV-1, TDV-2, TDV-3 and TDV-4 containing $3.2\times10^4$ PFU, $1.3\times10^5$ PFU, $2.5\times10^5$ PFU, and $4\times10^5$ PFU, respectively. Administered by subcutaneous injection on day 1. |
| Example 1 unit dose (TDV) | 0.5 mL comprising TDV-1, TDV-2, TDV-3 and TDV-4 containing $2.5\times10^4$ PFU, $6.3\times10^3$ PFU, $3.2\times10^4$ PFU, and $4\times10^5$ PFU, respectively. Administered by subcutaneous injection on day 1. |

Immunogenicity was evaluated at Days 15, 30, 90, 180, and 365 post-vaccination as geometric mean titers (GMTs) and seropositivity rates. Immunogenicity of the vaccines against each of the four dengue serotypes was assessed using a microneutralization assay, with titers corresponding to the dilution resulting in a 50% reduction in plaque reduction (MNT50) as described in Example 2. Primary immunogenicity endpoints were reported in terms of geometric mean titers (GMTs) of neutralizing antibodies, and seropositivity rates (which were defined as percentages of subjects with reciprocal neutralizing titers ≥10 for each of the DENV serotypes) in the overall trial population. As a secondary endpoint, GMTs and seropositivity rates were analyzed by dengue baseline seropositivity status. Seropositive at baseline was defined as being seropositive for at least one DENV serotype, whereas seronegative at baseline was defined as being seronegative for all four DENV serotypes.

Solicited and unsolicited adverse events (AEs) were assessed by severity and causality.

a) Seropositivity

Dengue seropositivity is based on the result of the microneutralization test (MNT) described in Example 2 and is defined as a reciprocal neutralizing antibody titer for one or more dengue serotype at baseline. The baseline seropositivity rate for each dengue serotype is defined as the percentage of seropositive subjects for the given dengue serotype and was derived from the neutralizing antibodies titers of the dengue serotypes as measured in the subjects before administration of the first unit dose. The seropositivity rate at day 180 or day 365 is defined as the percentage of seropositive subjects and was derived from the neutralizing antibodies titers of the dengue serotypes as measured in the subjects 180 and 365 days after administration of the first unit dose, respectively.

In total, 187 subjects (53.6%) were seropositive, based on MNT50, for at least one dengue serotype at baseline: 48.7% were seropositive for DENV-1, 49.0% for DENV-2, 45.2% for DENV-3, and 41.2% for DENV-4. The seropositive status and rate at baseline of the two different vaccination groups is shown in Table 6.

TABLE 6

Serostatus and seropositivity rate at baseline

|  | Comparative unit dose | Example 1 unit dose |
| --- | --- | --- |
| Baseline seropositivity status (count of participants) |  |  |
| Seropositive for at least one dengue serotype | 92 | 95 |
| Seronegative for all dengue serotypes | 83 | 80 |
| Baseline seropositivity rate for each serotype (percentage of participants) |  |  |
| TDV-1 | 48.6 | 48.6 |
| TDV-2 | 47.4 | 50.3 |
| TDV-3 | 44.0 | 46.3 |
| TDV-4 | 41.7 | 40.6 |

Figure 3A:
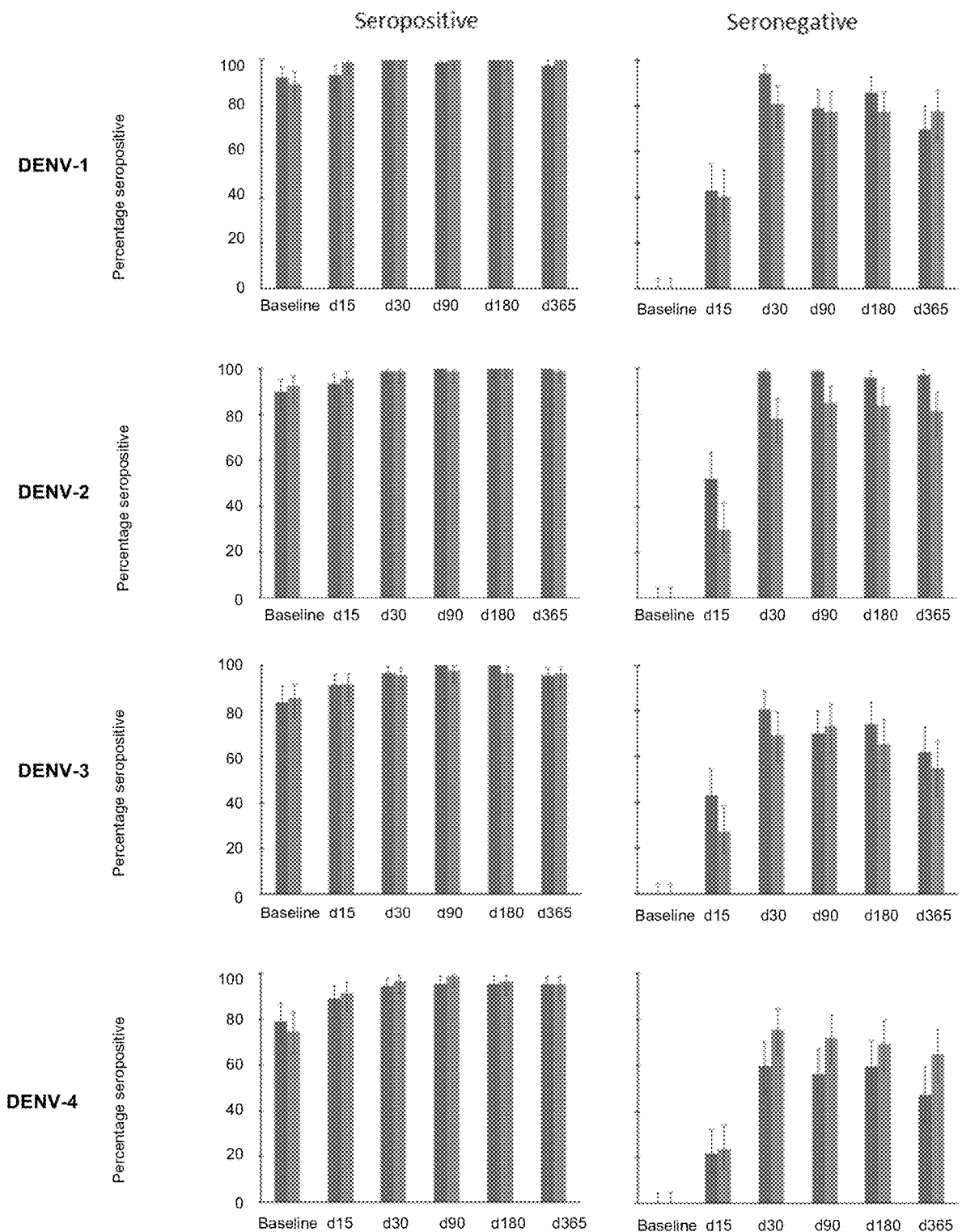
FIGS. 3A & 3B: Percentage of subjects (±95% confidence intervals) who were seropositive (reciprocal neutralizing titer≥10) for each of the dengue serotypes at different time points of the trial in the HD-TDV group (dark colored, left bar) and TDV group (light colored, right bar) throughout the trial. Time points shown are baseline, day 15 (d15), day 30 (d30), day 90 (d90), day 180 (d180) and day 365 (d365).
Figure 3B:
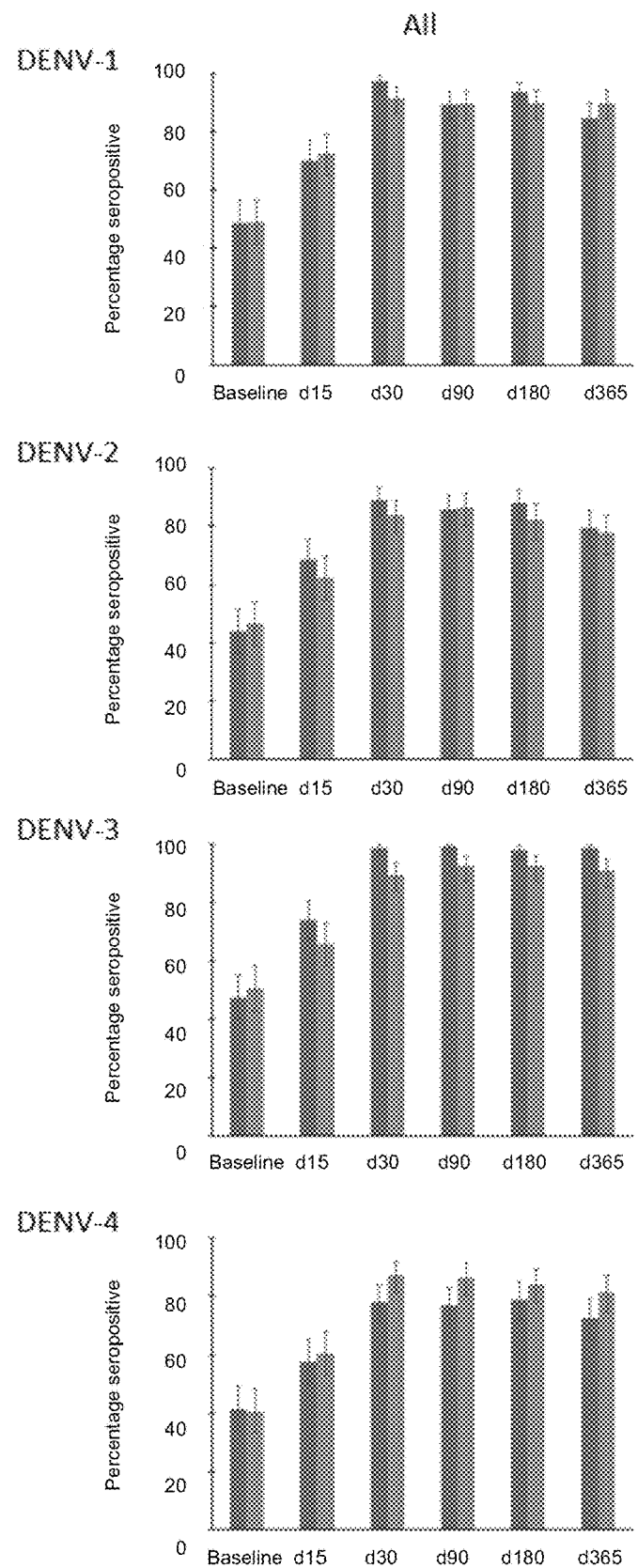

Seropositivity rates increased to Day 30 after administration of the unit doses, and remained high through to Day 365 for each of the four serotypes (FIG. 3). For the overall trial population, the percentages of subjects who were seropositive for DENV-1 and DENV-3 were similar in the HD-TDV and TDV groups, whereas higher post-baseline seropositivity rates were seen for the HD-TDV group against DENV-2, and for the TDV group against DENV-4 (FIG. 3B). In general, higher seropositivity rates were seen in subjects already seropositive at baseline than in seronegative subjects. Seropositivity rates rose to nearly 100% against all four dengue serotypes in the seropositive vaccine groups by Day 30, and remained at this level through to Day 365; no difference was seen between HD-TDV and TDV (FIG. 3A). In the seronegative group, the seropositivity rates increased more gradually to a peak at Day 30, with limited decline until Day 365. The rates were consistently higher for HD-TDV than TDV against DENV-2, but were higher for TDV than HD-TDV against DENV-4, through to Day 365 (FIG. 3A).

TABLE 7

Seropositivity rate at day 180

|  | Comparative unit dose | Example 1 unit dose |
| --- | --- | --- |
| Overall number of participants analyzed | 166 | 163 |
| Seropositivity rate at day 180 (95% Confidence Interval) |  |  |
| Day 180, TDV-1 | 93.4 (88.5 to 96.6) | 89.6 (83.8 to 93.8) |
| Day 180, TDV-2 | 98.2 (94.8 to 99.6) | 92.6 (87.5 to 96.1) |
| Day 180, TDV-3 | 88.0 (82.0 to 92.5) | 82.2 (75.5 to 87.7) |
| Day 180, TDV-4 | 78.9 (71.9 to 84.9) | 84.0 (77.5 to 89.3) |

TABLE 8

Seropositivity rate at day 365

|  | Comparative unit dose | Example 1 unit dose |
| --- | --- | --- |
| Overall number of participants analyzed | 160 | 156 |
| Seropositivity rate at day 365 (95% Confidence Interval) |  |  |
| Day 365, TDV-1 | 84.4 (77.8 to 89.6) | 89.7 (83.9 to 94.0) |
| Day 365, TDV-2 | 98.8 (95.6 to 99.8) | 91.0 (85.4 to 95.0) |
| Day 365, TDV-3 | 79.4 (72.3 to 85.4) | 77.6 (70.2 to 83.8) |
| Day 365, TDV-4 | 72.5 (64.9 to 79.3) | 81.4 (74.4 to 87.2) | b) Geometric Mean Neutralizing Antibody Titers (GMTs)

Neutralizing antibody titers (GMTs) for each dengue serotype were determined in a serum sample of a subject taken before administration of the first unit dose of the dengue vaccine composition and 180 or 365 days after administration of the first unit dose of the dengue vaccine composition using the microneutralization (MNT) assay as described in Example 2.

Figure 4A:
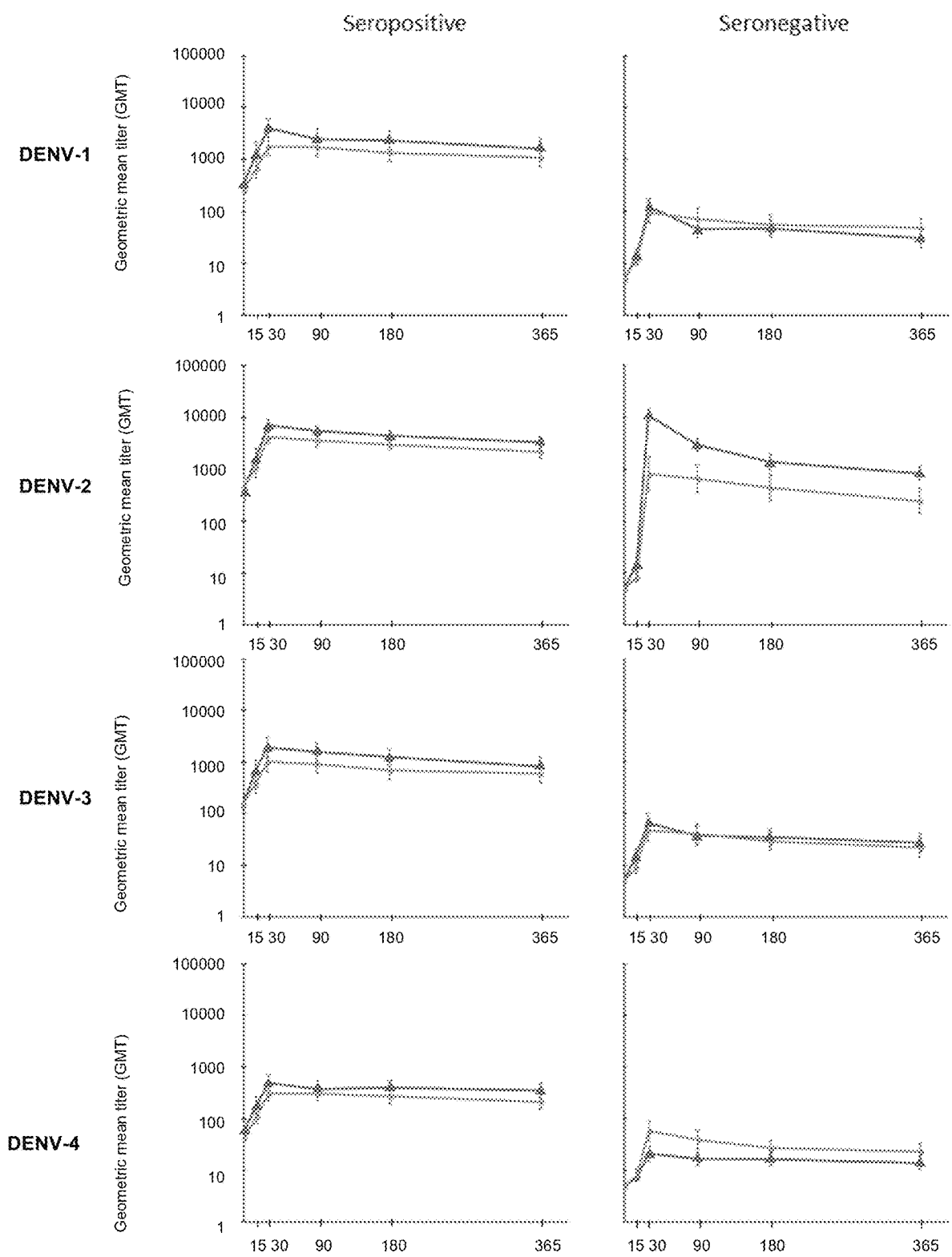
FIGS. 4A & 4B: Geometric mean titers (GMTs) (±95% confidence intervals) of neutralizing antibodies against each of the four dengue serotypes during the course of the trial for HD-TDV (dark line with triangles) and TDV (light line with circles) recipients, for the entire trial population (FIG. 4B) and for participants seropositive and seronegative at baseline (FIG. 4A), per-protocol set.
Figure 4B:
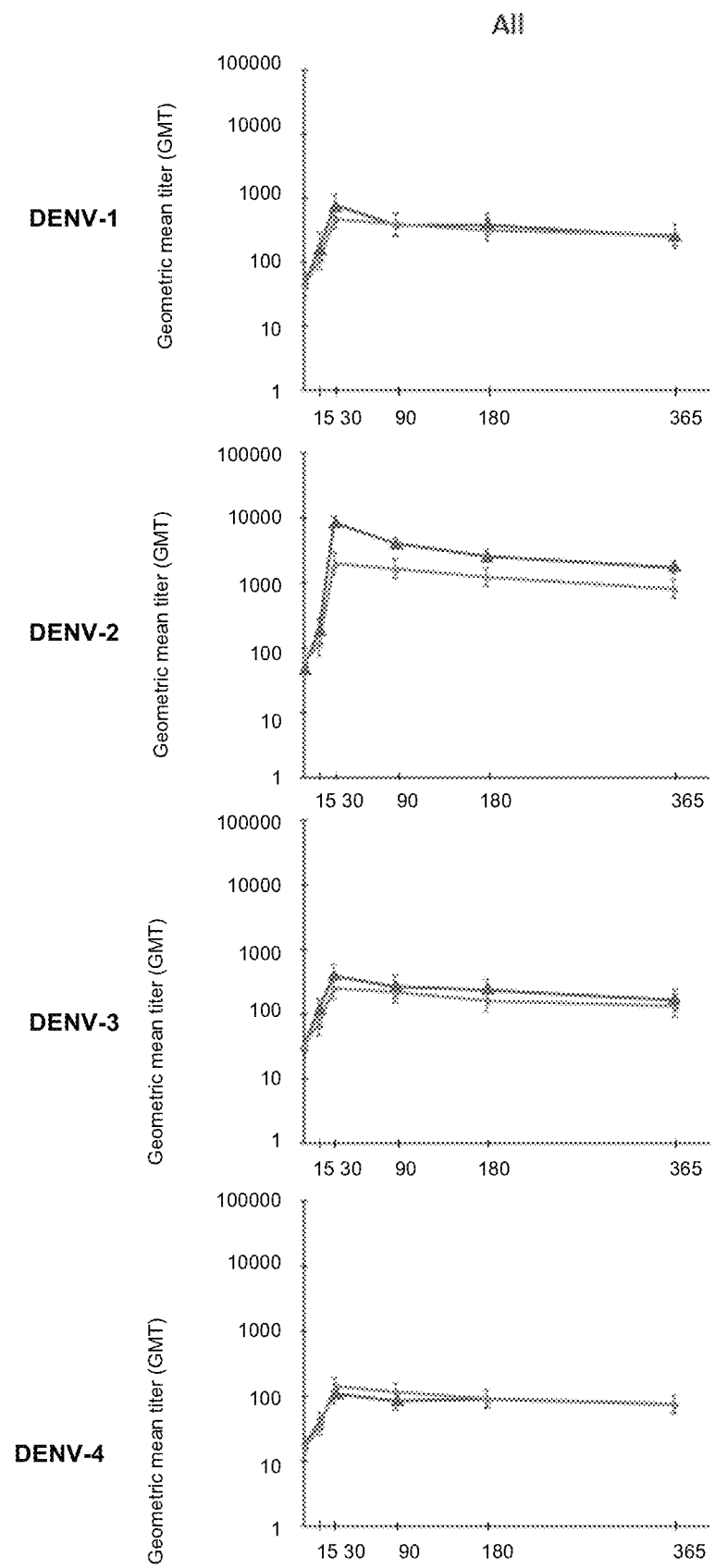

For both HD-TDV and TDV, an increase in GMTs was observed by Day 15, reaching a maximum by Day 30 (FIG. 4). Antibody titers remained above baseline levels throughout the trial for both unit doses. In the overall trial population, no substantial differences were seen in GMT titers between the two unit dose groups, except against DENV-2, where the response was higher for the HD-TDV group compared with the TDV group (8640.3 versus 1992.7 at Day 30). When assessed by baseline seropositivity status, the GMT profiles were similar as for the entire population, with a rise by Day 15, peak at Day 30, and gradual decline thereafter (FIG. 4B). In the group who were seropositive at baseline, the difference between the unit dose groups in response to DENV-2 was reduced, with GMTs of 6970.3 and 4193.3 at Day 30 for the HD-TDV and TDV groups, respectively. Responses were higher against DENV-1, DENV-3, and DENV-4 in the baseline seropositive group, compared with the baseline seronegative group, across both unit doses. Against DENV-2, a lower response was seen in baseline seronegative subjects receiving TDV, compared with HD-TDV; Day 30 GMTs were 812.9 in the TDV group, compared with 10965.9 in the HD-TDV group. The response in these subjects also differed against DENV-4, with a higher response being observed in the TDV group (Day 30 GMTs of 57.7, compared with 20.9 in the HD-TDV group); this difference persisted to Day 365 (FIG. 4A).

TABLE 9

Geometric mean neutralizing antibody titers (GMTs) at day 180

|  | Comparative unit dose | Example 1 unit dose |
| --- | --- | --- |
| Overall number of participants analyzed | 166 | 163 |
| GMTs (95% Confidence Interval) [units: Titer] | | |
| Day 180, TDV-1 | 379.4 (252.3 to 570.3) | 312.2 (212.2 to 459.2) |
| Day 180, TDV-2 | 2585.5 (2088.8 to 3200.3) | 1235.0 (890.7 to 1712.5) |
| Day 180, TDV-3 | 236.2 (162.2 to 344.0) | 161.0 (110.5 to 234.6) |
| Day 180, TDV-4 | 91.0 (65.7 to 125.9) | 92.9 (68.9 to 125.4) |

TABLE 10

Ratio of geometric mean neutralizing antibody titers (GMTs) at day 180

|  | Comparative unit dose | Example 1 unit dose |
| --- | --- | --- |
| TDV-2:TDV-1 | 7 | 4 |
| TDV-2:TDV-3 | 11 | 8 |
| TDV-2:TDV-4 | 28 | 13 |

TABLE 11

Geometric mean neutralizing antibody titers (GMTs) at day 365

|  | Comparative unit dose | Example 1 unit dose |
| --- | --- | --- |
| Overall number of participants analyzed | 160 | 156 |
| GMTs (95% Confidence Interval) [units: Titer] | | |
| Day 365, TDV-1 | 247.3 (160.9 to 380.2) | 264.1 (181.1 to 385.1) |
| Day 365, TDV-2 | 1726.0 (1392.6 to 2139.3) | 809.5 (576.6 to 1136.4) |
| Day 365, TDV-3 | 163.2 (110.0 to 242.3) | 132.6 (89.9 to 195.5) |
| Day 365, TDV-4 | 75.3 (53.8 to 105.4) | 77.0 (56.9 to 104.2) |

TABLE 12

Ratio of geometric mean neutralizing antibody titers (GMTs) at day 365

|  | Comparative unit dose | Example 1 unit dose |
| --- | --- | --- |
| TDV-2:TDV-1 | 7 | 3 |
| TDV-2:TDV-3 | 11 | 6 |
| TDV-2:TDV-4 | 23 | 11 |

TABLE 13

Geometric mean neutralizing antibody titers (GMTs) of all four dengue serotypes assessed by dengue baseline seropositivity status at day 180

|  | Comparative unit dose | Example 1 unit dose |
| --- | --- | --- |
| Seropositive | 89 Participants | 88 Participants |
| Day 180, TDV-1 (Seropositive) | 2327.2 (1550.4 to 3493.3) | 1356.2 (905.5 to 2031.2) |
| Day 180, TDV-2 (Seropositive) | 4412.0 (3586.6 to 5427.4) | 2952.0 (2358.2 to 3695.4) |

TABLE 13-continued

Geometric mean neutralizing antibody titers (GMTs) of all four dengue serotypes assessed by dengue baseline seropositivity status at day 180

|  | Comparative unit dose | Example 1 unit dose |
| --- | --- | --- |
| Day 180, TDV-3 (Seropositive) | 1248.3 (879.7 to 1771.3) | 693.6 (459.6 to 1046.6) |
| Day 180, TDV-4 (Seropositive) | 399.5 (291.3 to 547.9) | 268.3 (190.2 to 378.6) |
| Seronegative | 77 Participants | 75 Participants |
| Day 180, TDV-1 (Seronegative) | 46.6 (32.0 to 67.9) | 55.7 (35.6 to 87.1) |
| Day 180, TDV-2 (Seronegative) | 1394.1 (983.2 to 1976.6) | 444.3 (247.2 to 798.5) |
| Day 180, TDV-3 (Seronegative) | 34.5 (23.4 to 50.7) | 29.0 (19.4 to 43.3) |
| Day 180, TDV-4 (Seronegative) | 16.4 (12.3 to 22.0) | 26.8 (19.0 to 37.7) |

TABLE 14

Ratio of geometric mean neutralizing antibody titers (GMTs) assessed by dengue baseline seropositivity status at day 180 and 365

|  | Comparative unit dose | Example 1 unit dose |
| --- | --- | --- |
| Seropositive 180 Days | | |
| TDV-2:TDV-1 | 1.9 | 2.2 |
| TDV-2:TDV-3 | 3.5 | 4.3 |
| TDV-2:TDV-4 | 11.0 | 11.0 |
| Seronegative 180 Days | | |
| TDV-2:TDV-1 | 29.9 | 8.0 |
| TDV-2:TDV-3 | 40.4 | 15.3 |
| TDV-2:TDV-4 | 85.0 | 16.6 |

TABLE 15

Geometric mean neutralizing antibody titers (GMTs) of all four dengue serotypes assessed by dengue baseline seropositivity status at day 365

|  | Comparative unit dose | Example 1 unit dose |
| --- | --- | --- |
| Seropositive | 84 Participants | 85 Participants |
| Day 365, TDV-1 (Seropositive) | 1633.3 (1055.8 to 2526.7) | 1081.5 (724.0 to 1615.6) |
| Day 365, TDV-2 (Seropositive) | 3316.0 (2623.8 to 4190.9) | 2177.3 (1613.5 to 2938.1) |
| Day 365, TDV-3 (Seropositive) | 830.6 (551.2 to 1251.5) | 600.2 (402.3 to 895.3) |
| Day 365, TDV-4 (Seropositive) | 346.3 (249.2 to 481.1) | 212.6 (152.2 to 296.9) |
| Seronegative | 76 Participants | 71 Participants |
| Day 365, TDV-1 (Seronegative) | 30.7 (20.4 to 46.2) | 48.8 (32.1 to 74.2) |
| Day 365, TDV-2 (Seronegative) | 838.7 (621.9 to 1131.1) | 247.6 (143.9 to 426.1) |
| Day 365, TDV-3 (Seronegative) | 27.0 (17.8 to 41.1) | 21.7 (14.3 to 33.1) |
| Day 365, TDV-4 (Seronegative) | 13.9 (10.3 to 19.0) | 22.9 (15.8 to 33.1) |

TABLE 16

Ratio of geometric mean neutralizing antibody titers (GMTs) assessed by dengue baseline seropositivity status at day 365

|  | Comparative unit dose | Example 1 unit dose |
| --- | --- | --- |
| Seropositive 365 Days | | |
| TDV-2:TDV-1 | 2.0 | 2.0 |
| TDV-2:TDV-3 | 4.0 | 3.6 |
| TDV-2:TDV-4 | 9.6 | 10.2 |
| Seronegative 365 Days | | |
| TDV-2:TDV-1 | 27.3 | 5.1 |
| TDV-2:TDV-3 | 31.1 | 11.4 |
| TDV-2:TDV-4 | 60.3 | 10.8 | c) Safety

Overall, rates of solicited local and systemic adverse events (AEs), unsolicited AEs, and serious adverse events (SAEs) were similar across the two unit dose groups. No deaths or AEs leading to discontinuation were recorded in the trial. Three subjects in each unit dose group experienced SAEs, one of these events in the HD-TDV group was considered by the sponsor to be vaccine-related based on temporal association. The SAE was polyarthritis which began six days following receipt of the vaccine. Rates of solicited reactions were similar across unit dose groups, and seropositivity status at baseline. Overall, 47.4% and 53.7% of subjects reported local reactions, and 52.0% and 50.9% reported solicited systemic AEs, in the HD-TDV and TDV groups, respectively. Most reactions were mild or moderate. The most commonly reported local adverse reaction was injection site pain (46.3% in the HD-TDV group, 52.0% in the TDV group) and the most common systemic AE was headache (28.6% in the HD-TDV group, 34.9% in the TDV group).

d) Conclusion

Both unit doses showed an acceptable safety profile. The results show a more balanced immune response with the new TDV unit dose compared to the early HD-TDV unit dose, particularly in the subjects who were seronegative prior to vaccination: (i) in baseline seronegative subjects, response to DENV-2 was less dominant with TDV and (ii) DENV-4 seropositivity rates and GMTs were also higher with TDV in these subjects.

Example 4

Cell-Mediated Immunity Stimulated by the Dengue Vaccine

A gamma interferon (IFNγ) enzyme-linked immunosorbent spot (ELISPOT) assay was performed using peripheral blood mononuclear cells (PBMCs) from the subjects taking part in the clinical trial of Example 3 and the commercial ELISpot assay kit available from Mabtech according to the manufacturer's instructions. Briefly, cryopreserved PBMCs were thawed and left to rest overnight, then incubated with various peptide pools for 18-22 hours in plates coated with anti-IFNγ antibodies. PBMCs were then removed and spots were developed and then counted. Results were reported as mean spot forming cells (SFC) per $10^6$ PBMCs. Peptide pools matched selected DENV-derived proteins, covering the entire DENV-2 proteome with NS1, NS3, and NS5 proteins from New Guinea C (NGC) and Thailand/16681/84 strains; and C, prM+E, NS2 and NS4 proteins from Thailand/16681/84 only plus TDV-1, TDV-3 and TDV-4 prM+E inserts from DENV-1, -3 and -4 strains Thailand/16007/1964, Philippines/16562/1964 and Indonesia/1036/1976, respectively.

Figure 5:
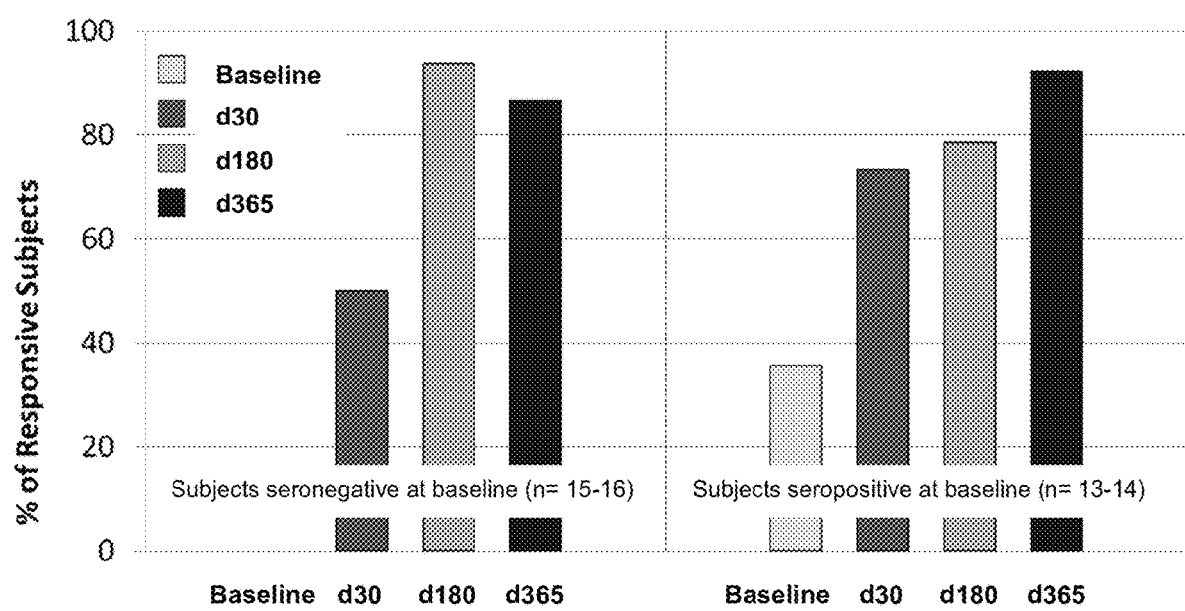
FIG. 5: IFNγ ELISpot analysis of peripheral blood mononuclear cells before vaccination (baseline) and at different time points after administration of TDV. Shown are the response frequencies to the entire DENV-2 proteome. A subject was considered responsive if response to more than one peptide pool from DENV-2 was positive (i.e. ≥4× mean of negative control and ≥50 SFC/$10^6$ PBMCs).

Response rates to DENV-2 proteome at 6 and 12 months post-single dose of TDV were >90%, and were comparable between subjects seronegative and seropositive at baseline (FIG. 5).

Figure 6A:
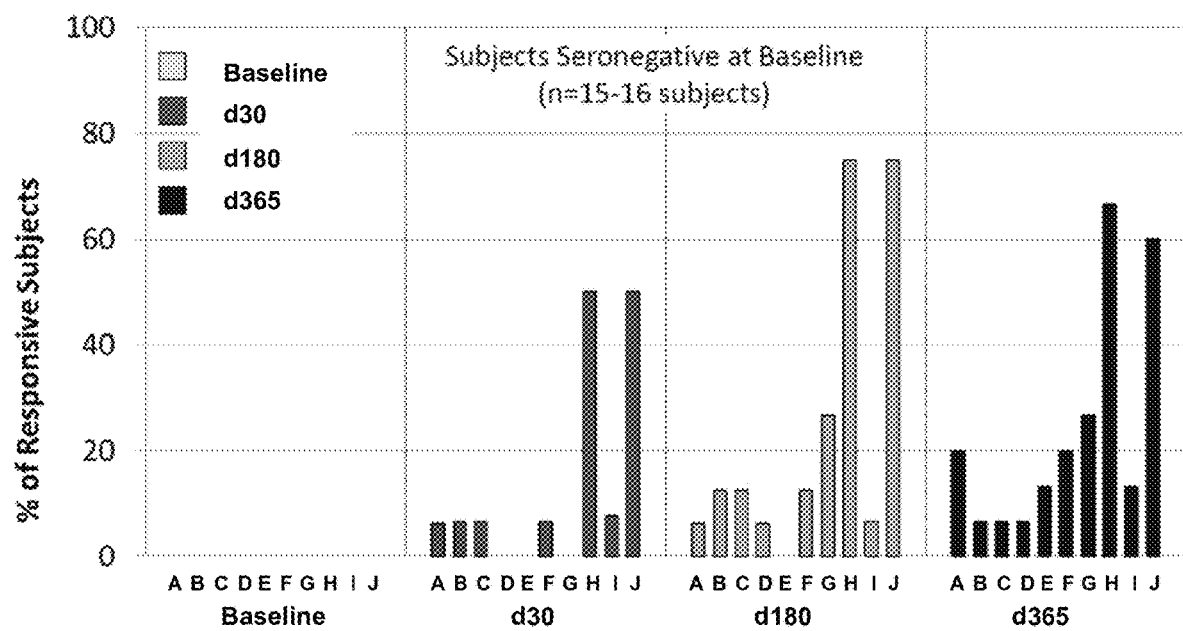
FIGS. 6A & 6B: IFNγ ELISpot analysis of peripheral blood mononuclear cells before vaccination (baseline) and at different time points after administration of TDV. Shown are the response frequencies to peptide pools matching selected DENV-derived proteins as indicated. A subject was considered responsive if response to more than one peptide pool from DENV-2 was positive (i.e. ≥4× mean of negative control and ≥50 SFC/$10^6$ PBMCs). A=DENV-2 C; B=DENV-1 prM+E; C=DENV-2 prM+E; D=DENV-3 prM+E; E=DENV-4 prM+E; F=DENV-2 NS1; G=DENV-2 NS2; H=DENV-2 NS3; I=DENV-2 NS4; J=DENV-2 NS5.
Figure 6B:
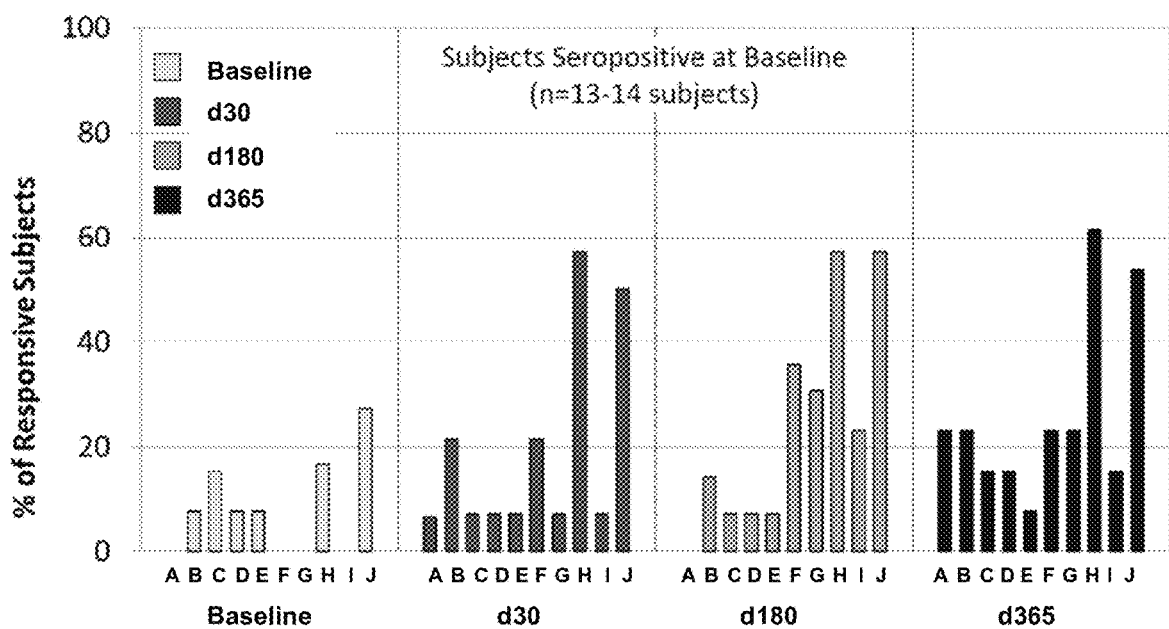

The response was primarily directed to the NS proteins, particularly in subjects seronegative at baseline (FIG. 6).

The NS3 and NS5 proteins were the most recognized antigens (by 50-75% of subjects). Immunodominance of NS3 and NS5 was independent of baseline serostatus. Durability of the response was maintained equally between NS3 and NS5 throughout the 12-month post-single vaccination follow-up.

Example 5

Antibody Responses to Non-Structural Proteins

The non-structural protein NS-1 from all four dengue serotypes can induce endothelial hyperpermeability of human pulmonary microvascular endothelial cells (HP-MEC) as measured by transendothelial electrical resistance (TEER) (Puerta-Guardo et al. (2016) PloS Pathog. 12(7): e1005738). It also interacts with endothelial cells to induce degradation of the glycocalyx via activation of sialidases and the cathepsin L/heparanase pathway (Glasner et al. (2017) PloS Pathog. 13(11): e1006673). In view of these effects, it was investigated whether the comparative unit dose induces antibodies against NS1 and inhibits NS1-mediated physiological effects.

a) Anti-NS1 Antibodies

Serum samples were collected at day 0 before vaccination and day 120 after administration of the first unit dose. Serum was collected from 6 dengue seronegative and 6 dengue seropositive subjects at both day 0 and day 120, and Ab concentrations were determined by ELISA.

The anti-NS1 antibody concentration in seronegative and seropositive subjects at day 0 and day 120 is shown in Tables 17 and 18:

TABLE 17

Anti-NS1 antibody concentration in seronegative subjects at day 0 and day 120
Dengue seronegative subjects
Anti-NS1 antibody concentration (RU/ml)

| Subj. | DENV1 | | DENV2 | | DENV3 | | DENV4 | |
|---|---|---|---|---|---|---|---|---|
| | d0 | d120 | d0 | d120 | d0 | d120 | d0 | d120 |
| 1023014 | 13.49 | 602.56 | 16.22 | 2570.40 | 10.00 | 489.78 | 28.18 | 302.00 |
| 1025011 | 66.07 | 173.78 | 35.48 | 794.33 | 67.61 | 117.49 | 42.66 | 85.11 |
| 1025013 | 5.62 | 380.19 | 24.55 | 2454.71 | 16.98 | 316.23 | 10.00 | 186.21 |
| 1035002 | 34.67 | 177.83 | 31.62 | 977.24 | 17.78 | 114.82 | 19.05 | 44.67 |
| 1035005 | 50.12 | 467.74 | 20.42 | 1659.59 | 104.71 | 309.03 | 66.07 | 288.40 |
| 1035001 | 40.74 | 186.21 | 52.48 | 489.78 | 44.67 | 169.82 | 51.29 | 177.83 |

TABLE 18

Anti-NS1 antibody concentration in seronegative subjects at day 0 and day 120
Dengue seropositive subjects
Anti-NS1 antibody concentration (RU/ml)

| Subj. | DENV1 | | DENV2 | | DENV3 | | DENV4 | |
|---|---|---|---|---|---|---|---|---|
| | d0 | d120 | d0 | d120 | d0 | d120 | d0 | d120 |
| 1052010 | 691.83 | 11481.54 | 309.03 | 12022.64 | 436.52 | 7585.78 | 245.47 | 4677.35 |
| 1052014 | 758.58 | 1445.44 | 407.38 | 891.25 | 758.58 | 1122.02 | 724.44 | 707.95 |
| 1052015 | 3890.45 | 3467.37 | 2570.40 | 2344.23 | 3235.94 | 2818.38 | 660.69 | 707.95 |
| 1071007 | 478.63 | 851.14 | 239.88 | 478.63 | 660.69 | 1202.26 | 870.96 | 1258.93 |
| 1071012 | 691.83 | 776.25 | 724.44 | 676.08 | 776.25 | 812.83 | 346.74 | 446.68 |
| 1082009 | 5888.44 | 5370.32 | 7413.10 | 6309.57 | 5248.07 | 4897.79 | 891.25 | 794.33 |

These data show that the vaccine induces antibodies against NS1 from all dengue serotypes in both seropositive and seronegative subjects.

b) Transendothelial Electrical Resistance (TEER)

The effect of recombinant NS1 proteins from dengue serotypes 1, 2, 3 and 4 and sera from vaccinated seronegative and seropositive subjects on endothelial permeability was evaluated by measuring TEER of HPMEC grown on a 24-well Transwell polycarbonate membrane system (Transwell® permeable support, 0.4 μM, 6.5 mm insert; Corning Inc.) as previously described (Beatty et al. (2015) Sci. Transl. Med. 7(304): 304ra141; Puerta-Guardo et al. (2016) PloS Pathog. 12(7):e1005738). Briefly, TEER was measured in Ohms (Ω) at sequential 2-hour time-points following the addition of test proteins using an Epithelial Volt Ohm Meter (EVOM) with "chopstick" electrodes (World Precision Instruments). Untreated endothelial cells grown on Transwell inserts were used as negative untreated controls, and inserts with medium alone were used for blank resistance measurements. Relative TEER represents a ratio of resistance values (Ω) as follows: (Ω experimental condition–Ω medium alone)/(Ω non-treated endothelial cells–Ω medium alone). After 24 hours of treatment, 50% of upper and lower chamber media was replaced by fresh endothelial cell medium. For experiments using sera, 30 μl of culture supernatant was removed from the apical chamber and replaced with 30 μl of serum samples immediately before the addition of 5 μg/ml DENV-2 NS1.

Figure 7A:
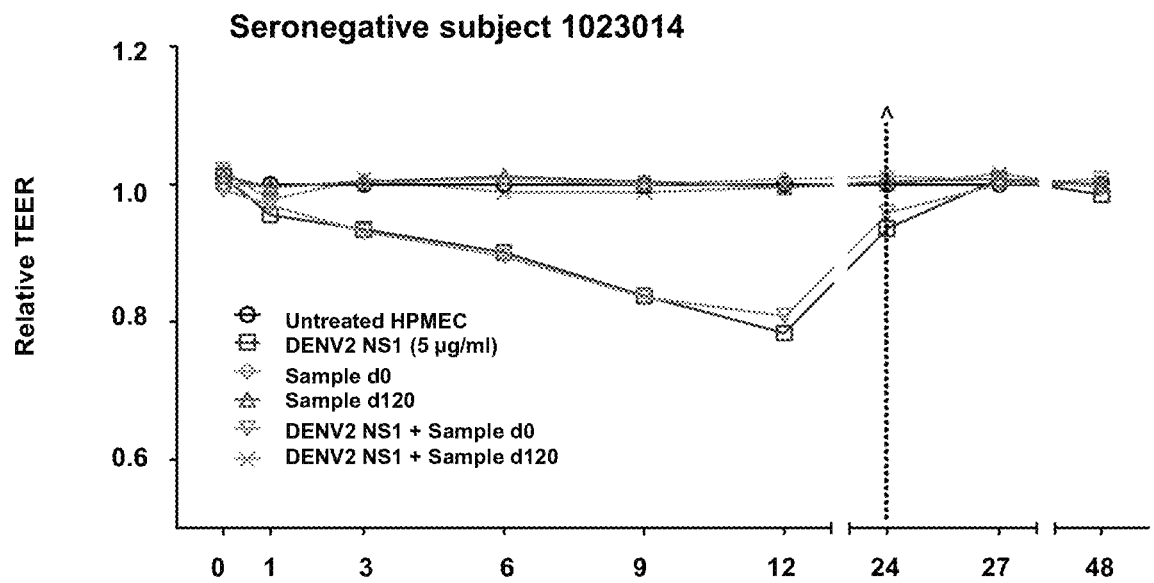
FIGS. 7A & 7B: Effect of sera from a seronegative subject (FIG. 7A) and a seropositive subject (FIG. 7B) to whom TDV was administered on DENV-2 NS1-induced hyperpermeability as determined by TEER. HPMEC were grown on Transwell semi-permeable membranes (0.4 μm pore size), and serum samples (30 μl) were added to the apical chamber in the presence or absence of DENV2 NS1 (5 μg/ml). DENV2 NS1 is depicted as squares; day 0 serum alone is depicted as diamonds; day 120 serum alone is depicted as triangles; day 0 serum+DENV2 NS1, is depicted as upside-down triangles; day 120 serum+DENV2 NS1 is depicted as X's. (ˆ) represents media change. Endothelial permeability was measured at indicated time-points over 48 hours. Relative TEER values from one independent experiment performed in duplicate are plotted. Error bars indicate standard error of the mean (SEM).
Figure 7B:
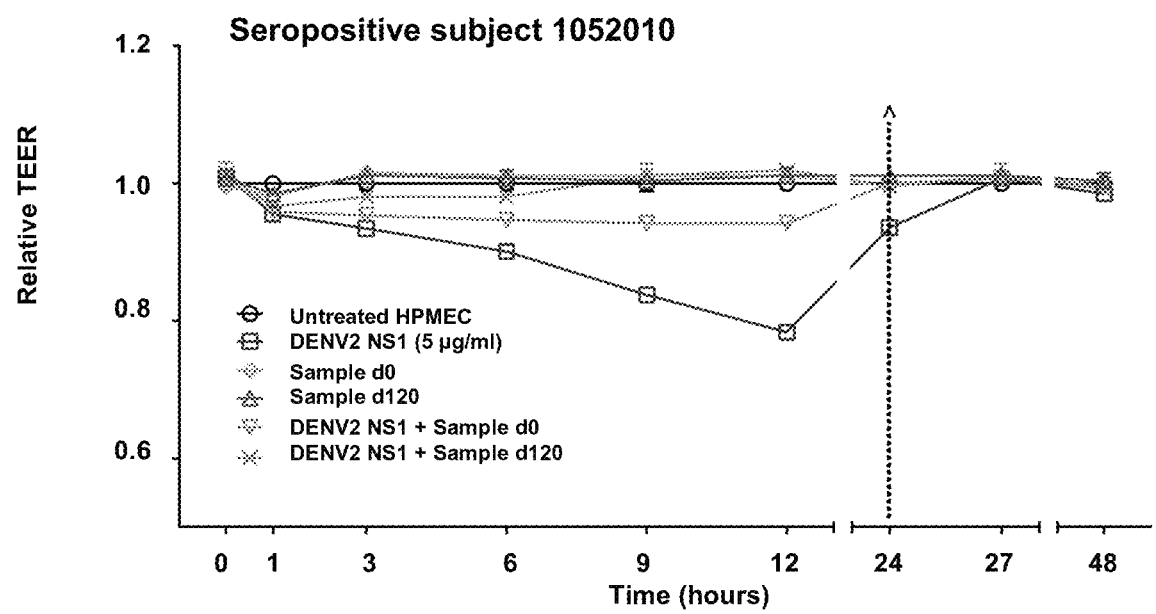

Day 0 serum samples from seronegative subjects did not protect against NS1-mediated barrier dysfunction, but day 120 samples from all seronegative subjects blocked decreases in TEER values induced by NS1 (see FIG. 7A). Day 0 samples from seropositive subjects produced varying levels of protection, and all day 120 samples from seropositive subjects completely abrogated NS1-induced hyperpermeability (see FIG. 7B).

c) Degradation of Glycocalyx-Like Layer (EGL)

Microscopy was performed as previously described (Puerta-Guardo et al. (2016) PloS Pathog. 12(7):e1005738). For imaging experiments, HPMEC were grown on coverslips coated with 0.2% gelatin (Sigma) and imaged on a Zeiss LSM 710 Axio Observer inverted fluorescence microscope equipped with a 34-channel spectral detector. Images acquired using the Zen 2010 software (Zeiss) were processed and analyzed with ImageJ software. All RGB images were converted to grayscale, then mean grayscale values and integrated density from selected areas were taken, along with adjacent background readings, and plotted as mean fluorescence intensity (MFI). To assess the effect of sera from vaccinated subjects on DENV2 NS1-induced EGL disruption, the distribution of sialic acid and heparan sulfate was examined on confluent HPMEC monolayers treated with DENV2 NS1 (5 μg/ml)+negative control serum (30 μl), NS1+positive control serum (30 μl), or NS1+serum from vaccinated subjects (30 μl) and fixed with 4% paraformaldehyde (PFA) at 6 hours post-treatment. Primary antibodies (Wheat germ agglutinin (WGA) lectin conjugated to Alexa Fluor 647 (WGA-A647, Molecular Probes) to stain N-acetyl neuraminic acid (sialic acid); Ab Heparan Sulfate, purified (clone F58-10E4, Amsbio) were incubated overnight at 4° C., and detection was performed using secondary species-specific anti-IgG or anti-IgM antibodies conjugated to Alexa fluorophores (488 and 647).

Figure 8A:
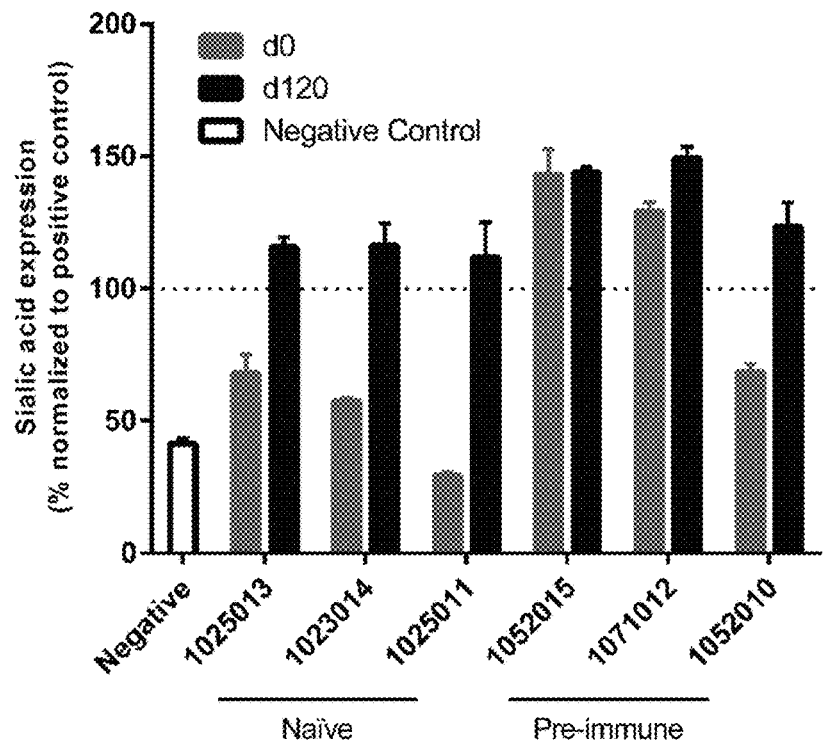
FIGS. 8A & 8B: Effect of sera from seronegative and seropositive subjects to which TDV was administered on NS1-induced sialic acid and heparan sulfate degradation. Shown is the quantification of mean fluorescence intensity (MFI) of (FIG. 8A) sialic acid and (FIG. 8B) heparan sulfate expression after staining with sialic acid- and heparan sulfate-specific fluorescent antibodies as visualized by confocal microscopy. Values are normalized to MFI from the NS1+ positive control serum group (represented by dotted line at 100%) and expressed as percentage of control. Error bars indicate SEM. The left bar for each subject shows the results at day 0 (d0), the right car for each subject shows the results at day 120 (d120).
Figure 8B:
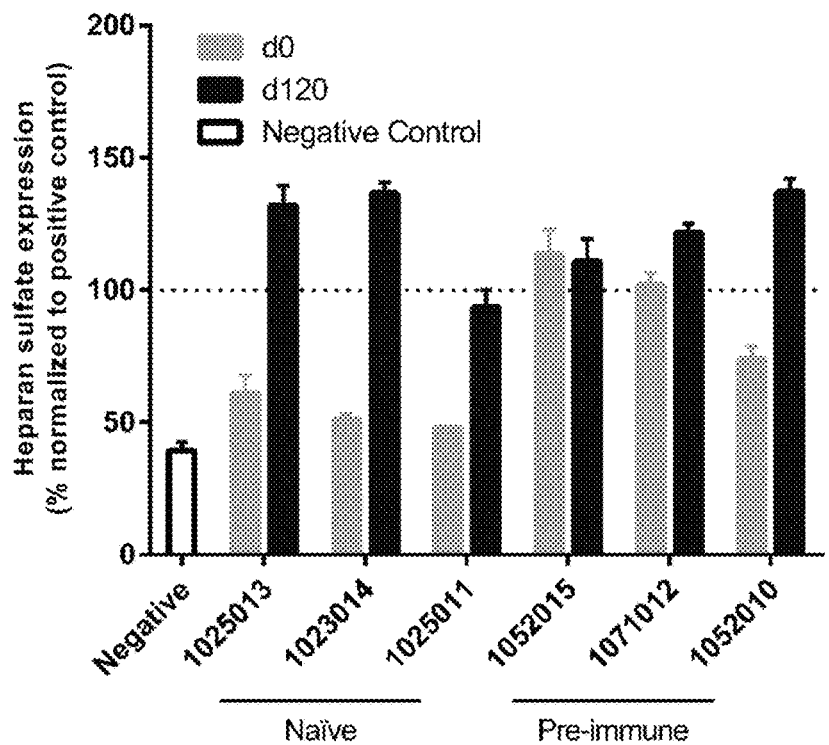

Day 0 sera from seronegative subjects had no substantial protective effect, while day 120 sera from seronegative subjects completely blocked degradation of both sialic acid and heparan sulfate. Similarly, day 0 samples from seropositive subjects exhibited varying levels of protection, and sera from seropositive subjects at day 120 were completely protective (see FIG. 8). Positive control serum was used as a baseline for protection, and negative control serum represented maximum NS1-mediated disruption. These results show that the anti-NS1 antibody response stimulated by the dengue vaccine can protect against NS1-induced hyperpermeability by preventing the degradation of key EGL components.

Taken together, these results suggest that the dengue vaccine stimulates robust and protective anti-DENV2 NS1 Ab responses following vaccination.

Example 6

Phase III Clinical Trial in Children

A Phase III, double-blind, randomized, and placebo-controlled trial in 20100 subjects aged 4 to 16 years living in Thailand, Sri Lanka, Philippines, Panama, Nicaragua, Dominican Republic, Colombia or Brazil was performed evaluating the efficacy, safety and immunogenicity of a tetravalent dengue vaccine referred to hereinafter as TDV. The trial includes 3 parts. Part 1 evaluates vaccine efficacy (VE) and lasts until both of the following 2 criteria are fulfilled: (i) 120 cases of dengue fever are confirmed and (ii) minimum duration of subject follow-up of 12 months post-second vaccination. Part 2 is for an additional 6 months to evaluate VE and for secondary efficacy analyses. Part 3 will evaluate long-term safety by following participants for side effects and will last an additional 3 years.

Part 1: Active surveillance for the primary assessment of efficacy in all subjects. During this time subjects were contacted at least weekly to ensure identification of febrile illness that could potentially be due to dengue. This part commenced on the day of vaccination and finished once both of the following 2 criteria were fulfilled: (i) 120 cases of dengue fever are confirmed and (ii) minimum duration of subject follow-up of 12 months post-second vaccination. The end of Part 1 was defined for each subject so that the duration of follow up after the second vaccination was approximately the same for all subjects. Virologically-confirmed cases in Part 1 count towards the primary efficacy objective if occurring at least 30 days post-second vaccination.

Part 2: Active surveillance for an additional 6 months for each subject following the completion of Part 1. During this time subjects were contacted at least weekly to ensure identification of febrile illness that could potentially be due to dengue. Virologically-confirmed cases in Parts 1 and 2 contribute towards the secondary efficacy objectives.

Part 3: Modified active surveillance for the assessment of safety in all subjects following the completion of Part 2 and lasting 3 years for each subject. The modified surveillance during Part 3 will maintain at least weekly contacts through Part 3 of the trial, but the intensity of investigation will be modified based on the need for hospitalization. Surveillance will identify febrile illness of any severity that could potentially be due to dengue.

Criteria for Inclusion include:
The subject was aged 4 to 16 years inclusive, at the time of randomization.
Individuals who were in good health at the time of entry into the trial as determined by medical history, physical examination (including vital signs) and clinical judgment of the Investigator.
The subject and/or the subject's parent/guardian signed and dated an assent/written informed consent form where applicable, and any required privacy authorization prior to the initiation of any trial procedures, after the nature of the trial has been explained according to local regulatory requirements.
Individuals who can comply with trial procedures and are available for the duration of follow-up.
Exclusion criteria include:
1. Febrile illness (temperature 38° C.) or moderate or severe acute illness or infection at the time of randomization.
2. History or any illness that, in the opinion of the Investigator, might interfere with the results of the trial or pose an additional risk to the subject due to participation in the trial, including but not limited to:
   a. Known hypersensitivity or allergy to any of the vaccine components.
   b. Female subjects (post-menarche) who are pregnant or breastfeeding.

c. Individuals with any serious chronic or progressive disease according to judgment of the Investigator (eg, neoplasm, insulin-dependent diabetes, cardiac, renal or hepatic disease, neurologic or seizure disorder or Guillain-Barré syndrome).
d. Known or suspected impairment/alteration of immune function, including:
  i. Chronic use of oral steroids (equivalent to 20 mg/day prednisone weeks/mg/kg body weight/day prednisone weeks) within 60 days prior to Day 1 (Month 0) (use of inhaled, intranasal, or topical corticosteroids is allowed).
  ii. Receipt of parenteral steroids (equivalent to 20 mg/day prednisone weeks/mg/kg body weight/day prednisone weeks) within 60 days prior to Day 1 (Month 0).
  iii. Administration of immunoglobulins and/or any blood products within the 3 months prior to Day 1 (Month 0) or planned administration during the trial.
  iv. Receipt of immunostimulants within 60 days prior to Day 1 (Month 0).
  v. Immunosuppressive therapy such as anti-cancer chemotherapy or radiation therapy within 6 months prior to Day 1 (Month 0).
  vi. Human Immunodeficiency Virus (HIV) infection or HIV-related disease.
  vii. Genetic immunodeficiency.
3. Receipt of any other vaccine within 14 days (for inactivated vaccines) or 28 days (for live vaccines) prior to Day 1 (Month 0) or planning to receive any vaccine within 28 days after Day 1 (Month 0).
4. Participation in any clinical trial with another investigational product 30 days prior to Day 1 (Month 0) or intent to participate in another clinical trial at any time during the conduct of this trial.
5. Previous participation in any clinical trial of a dengue candidate vaccine, or previous receipt of a dengue vaccine.
6. First degree relatives of individuals involved in trial conduct.
7. Females of childbearing potential who are sexually active, and who have not used any of the acceptable contraceptive method for at least 2 months prior to Day 1 (Month 0).
8. Females of childbearing potential who are sexually active, and who refuse to use an acceptable contraceptive method up to 6 weeks post-second vaccination.
9. Deprived of freedom by administrative or court order, or in an emergency setting, or hospitalized involuntarily.
10. Current alcohol abuse or drug addiction that may interfere with the subject's ability to comply with trial procedures.
11. Identified as an employee of the Investigator or trial center, with direct involvement in the proposed trial or other trials under the direction of that Investigator or trial center.

Eligible subjects were randomized (2:1) into two treatment groups: groups 1 received one subcutaneous (SC) dose of TDV in the upper arm on Day 1 and on Day 90, and group 2 received one subcutaneous dose of placebo in the upper arm on Day 1 and on Day 90. Randomization was stratified by region (Asia Pacific and Latin America) and age range (children aged 4-5 years, 6-11 years, and 12-16 years) to ensure each age range has the appropriate ratio of TDV to placebo in each region. After randomization dropouts were not replaced. Study Day 1 is defined to be the date of the first dose administration of TDV or placebo. The TDV was prepared as described in Example 1. Each subcutaneous dose of TDV was 0.5 mL and the concentration of the four dengue serotypes in the TDV vaccine in each dose was 3.6 $\log_{10}$ PFU/dose, 4.0 $\log_{10}$ PFU/dose, 4.6 $\log_{10}$ PFU/dose and 5.1 $\log_{10}$ PFU/dose of TDV-1, TDV-2, TDV-3 and TDV-4, respectively.

Primary Outcome Measures included the vaccine efficacy (VE) of two doses of TDV in preventing virologically-confirmed dengue (VCD) fever induced by any dengue serotype [time frame: 30 days post-second vaccination (Day 120) until the end of Part 1]. VE is defined as $1-(\lambda v/\lambda c)$, wherein $\lambda v$ and $\lambda c$ denote the hazard rates for the TDV and placebo groups, respectively. A virologically-confirmed dengue case is defined as febrile illness (defined as temperature $\geq 38°$ C. on any 2 of 3 consecutive days) or illness clinically suspected to be dengue by the Investigator with a positive serotype-specific reverse transcriptase polymerase chain reaction (RT-PCR). A febrile illness will require an interval of at least 14 days from a previous febrile illness to avoid overlap of acute and convalescent visits from one episode with those from a second episode.

Secondary Outcome Measures include:
1) VE of two doses of TDV in preventing virologically-confirmed dengue fever induced by each dengue serotype [time frame: from 30 days post-second vaccination (Day 120) until the end of Part 2].
2) VE of two doses of TDV in preventing virologically-confirmed dengue fever induced by any dengue serotype in participants dengue seronegative at baseline [time frame: from 30 days post-second vaccination (Day 120) until the end of Part 2 (up to 21 months)].
3) VE of two doses of TDV in preventing virologically-confirmed dengue fever induced by any dengue serotype in participants dengue seropositive at baseline [ time frame: from 30 days post-second vaccination (Day 120) until the end of Part 2].
4) VE of two doses of TDV in preventing hospitalization due to virologically-confirmed dengue fever induced by any dengue serotype [time frame: from 30 days post-second vaccination (Day 120) until the end of Part 2].
5) VE of two doses of TDV in preventing virologically-confirmed severe dengue fever induced by any dengue serotype [time frame: from 30 days post-second vaccination (Day 120) until the end of Part 2].
6) Percentage of participants with solicited local injection site adverse events (AEs) in the safety subset [time frame: Days 1 through 7 after each vaccination] and severity of solicited local injection AEs. Solicited local AEs at injection site are defined as pain, erythema and swelling that occurred within 7 days after each vaccination.
7) Percentage of participants with solicited systemic adverse events (AEs) in the safety subset [time frame: Days 1 through 14 after each vaccination] and severity of solicited systemic AEs. Solicited systemic AEs in children (<6 years) are defined as fever, irritability/fussiness, drowsiness and loss of appetite that occurred within 14 days after each vaccination. Solicited systemic AEs in children 6 years) are defined as fever, headache, asthenia, malaise and myalgia that occurred within 14 days after each vaccination.
8) Percentage of participants with any unsolicited adverse events (AEs) in the safety subset [time frame: Days 1 through 28 after each vaccination]. Unsolicited AEs are any AEs that are not solicited local or systemic AEs, as defined above.

9) Percentage of participants with serious adverse events (SAEs) during Parts 1 and 2 [time frame: from Day 1 until the end of Parts 1 and 2]. A serious adverse event (SAE) is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

10) Percentage of participants with fatal SAEs and SAEs related to study drug during the first and second half of Part 3 [time frame: for 3 years (18 month halves) beginning at the end of Part 2 (approximately 21 months after the first vaccination)].

11) Percentage of participants with a seropositive response for each of the four dengue serotypes in the immunogenicity subset [time frame: Day 1 and months 1, 3, 4, 9, 15 and then annually (up to 3 years)]. Seropositive response is defined as a reciprocal neutralizing titer ≥10. The four DENV serotypes are DEN-1, DEN-2, DEN-3 and DEN-4.

12) Percentage of participants with a seropositive response for multiple dengue serotypes in the immunogenicity subset [time frame: Day 1 and months 1, 3, 4, 9, 15 and then annually (up to 3 years)].

13) Geometric Mean Titers (GMTs) of neutralizing antibodies for each of the four dengue serotypes in the immunogenicity subset [time frame: Day 1 and months 1, 3, 4, 9, 15 and then annually (up to 3 years)]. GMTs of neutralizing antibodies will be measured via microneutralization test (MNT) as described in Example 2.

a) Study Population

Figure 9:
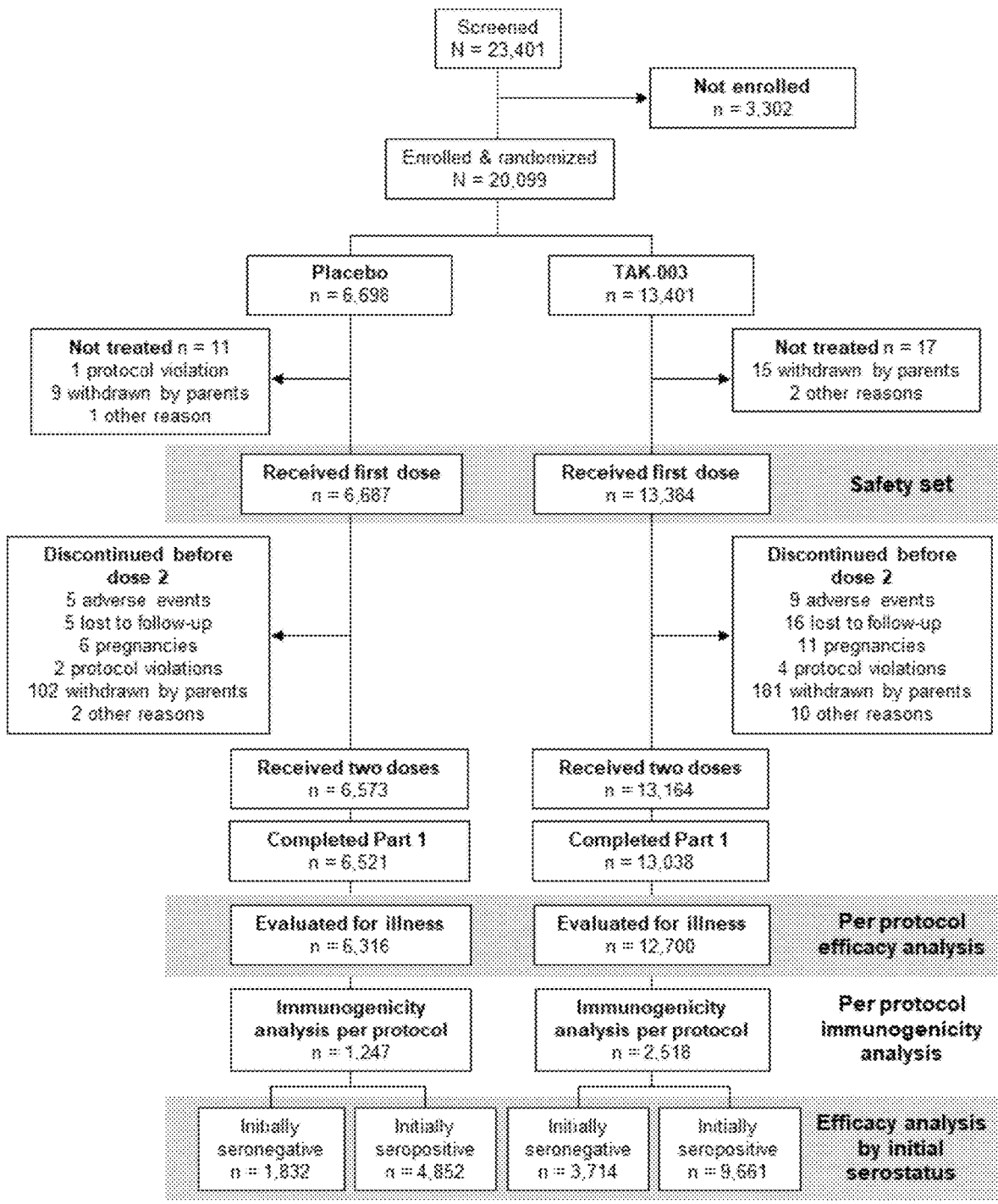
FIG. 9: Flow diagram of the clinical trial of Example 6.

After screening, 20,099 participants were randomized, and 20,071 received at least one injection. In total, 97.4% of placebo participants (n/N: 6,521/6,698) and 97.3% of vaccinees (n/N: 13,038/13,401) completed Part 1 of the study (FIG. 9). Reasons for study withdrawals included AEs, participants lost to follow-up, pregnancy, protocol violations, and withdrawal by participants (or parents/guardians). Baseline characteristics were similar across both treatment groups (Table 19). Mean age of study participants was 9.6 years, with baseline seronegativity of 27.7%, and enrollment was broadly balanced across regions (46.5% in Asia, 53.5% in Latin America). The highest seronegative rate was in Panama (62.2%), followed by Sri Lanka (38.5%), Thailand (34.4%), Brazil (28.8%), Nicaragua (22.3%), Colombia (15.4%), the Philippines (12.4%), and the Dominican Republic (2.8%).

TABLE 19

Baseline characteristics of study population (number, %)

| | TDV | Placebo | Total |
|---|---|---|---|
| Per Protocol Set | | | |
| Number of Participants | 12,704 | 6,317 | 19,021 |
| Mean Age (Years, SD) | 9.6 (3.35) | 9.6 (3.34) | 9.6 (3.35) |
| Baseline Seronegative[a] | 3,533 (27.8) | 1,726 (27.3) | 5,259 (27.7) |

TABLE 19-continued

Baseline characteristics of study population (number, %)

| | TDV | Placebo | Total |
|---|---|---|---|
| Female | 6,314 (49.7) | 3,098 (49.0) | 9,412 (49.5) |
| Male | 6,390 (50.3) | 3,219 (51.0) | 9,609 (50.5) |
| Asia Pacific | 5,896 (46.4) | 2,942 (46.6) | 8,838 (46.5) |
| Baseline Seronegative[a] | 1,503 (25.5) | 773 (26.3) | 2,276 (25.8) |
| Latin America | 6,808 (53.6) | 3,375 (53.4) | 10,183 (53.5) |
| Baseline Seronegative[a] | 2,030 (29.8) | 953 (28.2) | 2,983 (29.3) |
| Safety Set[b] | | | |
| Number of Participants | 13,380 | 6,687 | 20,071 |
| Mean Age (Years, SD) | 9.6 (3.36) | 9.6 (3.34) | 9.6 (3.35) |
| Baseline Seronegative[a] | 3,714 (27.8) | 1,832 (27.4) | 5,547 (27.6) |
| Female | 6,651 (49.7) | 3,276 (49.0) | 9,929 (49.5) |
| Male | 6,729 (50.3) | 3,411 (51.0) | 10,142 (50.5) |
| Safety Set of Subset[b] | | | |
| Number of Participants | 2,663 | 1,329 | 3,993 |
| Baseline Seronegative[a] | 740 (27.8) | 369 (27.8) | 1,109 (27.8) |

[a]Seronegative for all serotypes; seropositive defined as reciprocal neutralizing antibody titer ≥10; SD, standard deviation.
[b]numbers of participants in TVD plus placebo groups are not equal to total numbers shown because misallocated participants (i.e. those who received both TVD and placebo due to an administrative error) are not included in the TDV and placebo group data.

b) Febrile Illnesses and VCD

During Part 1, 5,754 and 4,663 episodes of febrile illness were reported in Asian and Latin American sites, respectively. Acute samples were obtained in 99.5% and 96.6% of these cases, with 98.3% and 85.1% of samples taken within five days, in Asia and Latin America, respectively. There were 278 VCD cases (76 hospitalized) in the safety set during the entire Part 1 period, of which 210 (58 hospitalized) were 30 days post-second vaccination in the PPS (Table 20; Table 22) and were included in primary endpoint analysis.

c) Distribution of VCD Included in Primary Endpoint Analysis

DENV-1 was reported in all countries with VCD and included all the 21 cases in Panama. In Sri Lanka, 54 of 60 VCD were DENV-2, and 87 of 109 VCD in the Philippines were DENV-3. All seven DENV-4 VCD were reported in the Philippines. No VCD were reported in Nicaragua or the Dominican Republic. Of the associated 58 hospitalized VCD, 43 were reported in Sri Lanka. A total of two severe dengue (both DENV-3) and five dengue hemorrhagic fever (DHF; three DENV-2; two DENV-3) cases were reported (Table 21). These seven were also the only such cases in the entire part 1 safety set.

d) Vaccine Efficacy

Figure 10A:
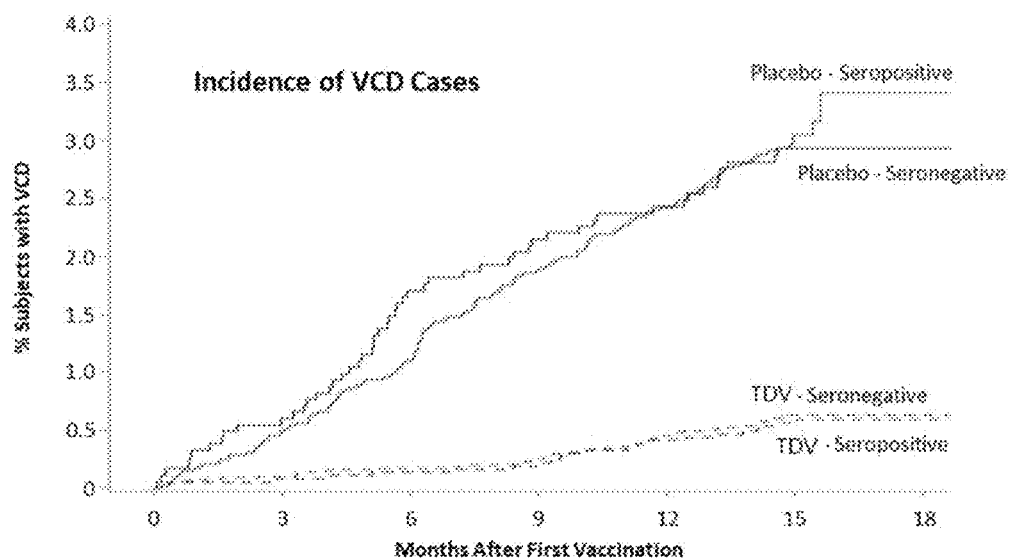
FIGS. 10A & 10B: Cumulative incidence of FIG. 10A) virologically-confirmed dengue cases and FIG. 10B) hospitalized virologically-confirmed dengue cases over time during Part 1 study period by baseline serostatus (safety set data; data presented truncated at Month 18). Tables show numbers of participants under follow-up at various time points to end of Part 1 study period.
Figure 10B:
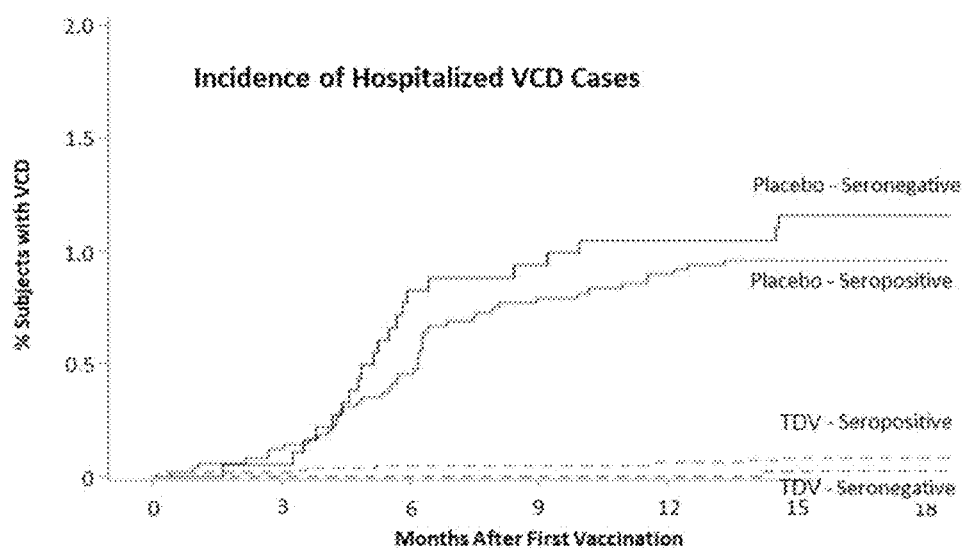

VE against VCD of any serotype was 80.2% (95% CI: 73.3-85.3; P<0.001). A similar efficacy of 81% (95% CI: 64.1-90.0) between the doses and from first dose onwards in the safety set (Table 20) suggests that the vaccine was efficacious after the first dose. Exploratory analysis of the secondary efficacy endpoints showed a trend of differential efficacy by serotype, with the highest efficacy against DENV-2 (97.7%), followed by DENV-1 (73.7%), DENV-4 (63.2% with CI containing zero), and DENV-3 (62.6%; Table 3). Overall, efficacy was similar in baseline seronegatives (74.9%) and seropositives (82.2%; FIG. 10A); however, this varied by serotype. Efficacy against DENV-2 was not impacted by serostatus; efficacy against DENV-1 was slightly higher in baseline seropositives (79.8%; 95% CI: 51.3-91.6) than baseline seronegatives (67.2%; 95% CI: 23.2-86.0). No efficacy was observed against DENV-3 in baseline seronegatives (−38.7%; 95% CI: −335.7-55.8) compared to baseline seropositives (71.3%; 95% CI: 54.2-82.0). Efficacy by serostatus could not be calculated for DENV-4 because no cases were observed in baseline seronegatives. In the primary endpoint timeframe of the PPS, only five VCD requiring hospitalization were reported in the vaccine group compared with 53 cases in the placebo group, with a VE of 95.4% (95% CI: 88.4-98.2; 97.2% for baseline seronegatives and 94.4% for baseline seropositives; Table 21; FIG. 10B), consistent with a VE of 93.3% (95% CI: 86.7-96.7) in the safety set from first dose onwards.

The primary vaccine efficacy (VE) of two doses of TDV in preventing virologically-confirmed dengue (VCD) fever induced by any dengue serotype is shown in Table 20.

TABLE 20

Vaccine efficacy of TDV in preventing virologically confirmed dengue (VCD) fever against any serotype from 30 days post-second vaccination until end of part 1 Per Protocol Set (PPS). Safety set analysis from first dose to end of Part 1 study period

|  | Placebo n = 6317 | TDV (PPS) n = 12,704 |
|---|---|---|
| number of subject evaluated | 6,316 | 12,700 |
| number of subjects with febrile illness | 1,712 | 3,195 |
| number of febrile illness cases | 2,591 | 4,692 |
| virologically confirmed dengue fever (n [%]) | 149 [2.4] | 61 [0.5] |
| Person-years at risk | 5,670.1 | 11,578.7 |
| incident density | 2.6 | 0.5 |
| relative risk | 0.20 | |
| 95% CI of relative risk | (0.15, 0.27) | |
| vaccine efficacy (%) | 80.2 | |
| 95% CI of vaccine efficacy | (73.3, 85.3) | |
| p-value for vaccine efficacy | <0.001 | |

|  | Placebo | TDV (Safety Set)* |
|---|---|---|
| number of subject evaluated | 6,687 | 13,380 |
| virologically confirmed dengue fever (n [%]) | 199 [3.0] | 78 [0.6] |
| Person-years at risk | 8,072.0 | 16,351.5 |
| incident density | 2.5 | 0.5 |
| vaccine efficacy (%) | 80.9 | |
| 95% CI of vaccine efficacy | (75.2, 85.3) | |

Note 1:
Percentage of virologically confirmed dengue (VCD) fever are based on number of subjects evaluated.
Note 2:
Person-years at risks is defined as cumulative time in years until start of VCD fever or until end of Part 1 study period or discontinuation date, whichever comes first. Incident density is defined as the number of cases per 100 person-years at risk. Percentages are based on total number (denominator) of analysis set participants evaluated and may not be equal to the total number of participants in the per protocol analysis set.
*One participant had two instances of VCD during Part 1, only the first VCD was included in efficacy calculation
Note 3:
Vaccine efficacy (VE) and 2-sided 95% CIs are estimated from a Cox proportional hazard model with TDV as a factor, adjusted for age and stratified by region.
Note 4:
Statistical significance will be concluded if the lower bound of the 95% CI for VE is above 25%. Since the hypotheses will be tested in a confirmatory manner at a 2-sided significance level of 5%, the calculated p-value should be compared with 0.025.
Note 5:
Relative risk is calculated as the number of events divided by the number of subjects evaluated in the TDV group, over the number of events divided by the number of subjects evaluated in the placebo group.

For the efficacy evaluation shown in Table 20, a case of VCD was defined as febrile illness (defined as fever 38° C. on any 2 of 3 consecutive days) with a positive serotype-specific RT-PCR (i.e., positive dengue detection RT-PCR) and occurring at any time starting from 30 days post-second vaccination (Day 120 [Month 4]) through the end of Part 1. The analysis was performed on the Per-Protocol Set (PPS) and Safety Set.

As used herein, the "Per-Protocol Set (PPS)" consist of all subjects in the Full Analysis Set (FAS) consisting of all randomized subjects who received at least one dose of TDV or placebo who had no major protocol violations. Major protocol violations are not receiving both doses of TDV or placebo administration, not receiving both doses in the correct interval, not having the correct administration of TDV or placebo, use of prohibited medications/vaccines by the subject, the subject meets any of the exclusion criteria of 2d, 3, 4 or 5 defined above or product preparation error.

The p-value is obtained by solving the critical value Z in the following equation:

Upper bound of 1-sided (1−$p$ %) $CI$ of HR=0.75, wherein HR is the hazard ratio and defined as HR=$\lambda V/\lambda C$.

$e^{[\hat{\beta}+Z*\hat{S}\hat{E}]}=0.75$, wherein $\hat{\beta}$ defines the treatment and $\hat{S}\hat{E}$ the related standard error.

The 1-sided p-value is 1−(area to the left of the critical value Z from a standard normal distribution). Since the hypotheses will be tested in a confirmatory manner 2-sided at a significance level of 5%, the calculated 1-sided p-value should be compared with 0.025.

In summary in Part 1 of this study, a high vaccine efficacy of 80.2% against virologically-confirmed dengue of any serotype in children 4-16 years of age was found. It included an efficacy of 74.9% in baseline seronegatives and a robust 95.4% reduction in hospitalizations. Onset of protection could be seen after the first dose with 81% efficacy between doses. Overall, these results suggest a potential benefit for each vaccine recipient regardless of prior dengue exposure or age. This finding is significant because vaccine development against dengue has been challenging, especially for dengue naïve individuals, and dengue remains one of the WHO's top ten threats to global health in 2019.19 Furthermore, the onset of protection after the first dose has potential utility in the context of outbreak control or travel vaccination, offering a reduction in the risk of dengue after only one dose.

Severe forms of dengue were assessed as follows: Dengue Hemorrhagic Fever (DHF) as defined by the 1997 WHO definition. Severe Dengue through the Dengue Case Adjudication Committee. The Dengue Case Adjudication Committee (DCAC) consisted of four members: a voting chairperson, two voting members, and an independent non-voting statistician. The three DCAC voting members are all physicians and clinical dengue experts. DCAC members are not study investigators and do not have any conflict of interest that would bias their review of the trial data. All non-hospitalized cases were considered non-severe. The DCAC severe dengue case criteria applied in a blinded manner to virologically-confirmed hospitalized dengue cases are as follows: 1) bleeding abnormality, for a case to be considered severe there needs to be a significant intervention required in response to the bleeding episode such as blood transfusion, nasal packing, hormonal therapy, or, bleeding occurred into critical organs such as the brain; 2) plasma leakage, for a case to be considered severe there needs to be evidence of both plasma leakage and functional impairment (plasma leakage includes clinical evidence, radiological evidence, or hematocrit elevated >20% above normal levels or baseline; functional impairment defined as shock or respiratory distress); 3) liver, for a case to be considered severe there needs to be evidence of both hepatitis and functional impairment (hepatitis defined as an aspartate aminotransferase [AST] or alanine aminotransferase [ALT]>10 upper limit of normal range [ULN]; functional impairment defined as prothrombin [PT]>1.5 ULN or hypoalbuminemia); 4) renal, serum creatinine >2.5 times ULN or requiring dialysis; 5) cardiac, abnormalities intrinsic to the heart (i.e. not resulting from intravascular volume depletion) and with evidence of functional impairment (examples of intrinsic abnormality: myocarditis, pericarditis, and myopericarditis; example of functional impairment: new conduction abnormality resulting in irregular heart rhythm [i.e. not transient first-degree heart block]); 6) central nervous system, any abnormality with the exception of a simple febrile convulsion or a brief delirium; 7) shock, all shock cases considered severe. At least 1 functional impairment (of criterion 3,4,5,6), needs to be present but the totality of data were considered by the members in their assessment.

TABLE 21

Distribution of cases contributing to primary endpoint by per protocol set subgroup

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Baseline Seropositive[a] | 41/9,165 (0.4%) | 0.5 | 110/4,587 (2.4%) | 2.7 | 82.2% (74.5%-87.6%) |
| Baseline Seronegative[a] | 20/3,531 (0.6%) | 0.6 | 39/1,726 (2.3%) | 2.5 | 74.9% (57.0%-85.4%) |
| DENV-1 | 16/12,700 (0.1%) | 0.1 | 30/6,316 (0.5%) | 0.5 | 73.7% (51.7%-85.7%) |
| DENV-2 | 3/12,700 (<0.1%) | <0.1 | 64/6,316 (1.0%) | 1.1 | 97.7% (92.7%-99.3%) |
| DENV-3 | 39/12,700 (0.3%) | 0.3 | 51/6,316 (0.8%) | 0.9 | 62.6% (43.3%-75.4%) |
| DENV-4[d] | 3/12,700 (<0.1%) | <0.1 | 4/6,316 (<0.1%) | <0.1 | 63.2% (−64.6%-91.8%) |
| 4-5 Years Old | 13/1,619 (0.8%) | 0.9 | 23/801 (2.9%) | 3.2 | 72.8% (46.2%-86.2%) |
| 6-11 Years Old | 34/7,009 (0.5%) | 0.5 | 85/3,491 (2.4%) | 2.7 | 80.7% (71.3%-87.0%) |
| 12-16 Years Old | 14/4,072 (0.3%) | 0.4 | 41/2,024 (2.0%) | 2.2 | 83.3% (69.3%-90.9%) |
| Asia | 54/5,894 (0.9%) | 1.0 | 127/2,942 (4.3%) | 4.9 | 79.5% (71.8%-85.1%) |
| Latin America | 7/6,806 (0.1%) | 0.1 | 22/3,374 (0.7%) | 0.7 | 84.3% (63.1%-93.3%) |
| Hospitalized VCD cases | | | | | |
| Baseline Seropositive[a] | 4/9,165 (<0.1%) | <0.1 | 35/4,587 (0.8%) | 0.8 | 94.4% (84.3%-98.0%) |
| Baseline Seronegative[a] | 1/3,531 (<0.1%) | <0.1 | 18/1,726 (1.0%) | 1.2 | 97.2% (79.1%-99.6%) |
| Cases of DHF[b] | | | | | |
| All participants | 1/12,700 (<0.1%) | <0.1 | 4/6,316 (<0.1%) | <0.1 | 87.3% (−13.5%-98.6%) |
| Severe VCD Cases[c] | | | | | |
| All participants | 1/12,700 (<0.1%) | <0.1 | 1/6,316 (<0.1%) | <0.1 | 50.8% (−686.9%-96.9%) |

VCD, virologically-confirmed dengue;
DHF, dengue hemorrhagic fever
[a]Seronegative for all serotypes; baseline seropositive defined as reciprocal neutralizing antibody titer ≥10 to one or more serotypes.
[b]VCD cases meeting WHO 1997 DHF criteria; incidence density defined as the number of cases per 100 person-years at risk; percentages are based on total number (denominator) of per protocol set participants evaluated.
[c]two severe VCD were not classified as DHF.
[d]The number of cases identified was sufficient to provide reasonably precise estimates of vaccine efficacy against all individual serotypes, except DENV-4.

Clinical signs and symptoms of virologically-confirmed dengue cases during Part 1 study period in safety set data are shown in Table 22.

TABLE 22

Clinical signs and symptoms of virologically-confirmed dengue cases during Part 1 study period (safety set data)

| | TDV (N = 13,380) | Placebo (N = 6,687) | Relative Risk |
|---|---|---|---|
| Number of VCD Cases | 78 | 200 | — |
| Median Duration of Febrile Illness (days; 95% CI)[a] | 6.0 (5.7-7.4) | 6.0 (5.9-6.8) | — |
| Median Duration of Fever (days; 95% CI) | 4.0 (3.9-4.6) | 5.0 (4.5-5.0) | — |
| Number of Hospitalized VCD Cases | 9 | 67 | — |
| Median Duration of Hospitalization (days; 95% CI) | 5.0 (2.8-5.4) | 5.0 (4.6-5.4) | — |
| Evidence of Bleeding (%, n/N) | 3.8% (3/78) | 3.5% (7/200) | 1.10 |
| Plasma Leakage (%, n/N) | 2.6% (2/78) | 6.5% (13/200) | 0.39 |
| Plasma Leakage - Pleural Effusion (%, n/N) | 1.3% (1/78) | 1.5% (3/200) | — |
| Plasma Leakage - Ascites (%, n/N) | 1.3% (1/78) | 3.0% (6/200) | — |
| Plasma Leakage - Radiological Signs (%, n/N) | 40.0% (2/5) | 19.6% (10/51) | — |
| Plasma Leakage - Hematocrit Increase ≥20% (%, n/N)[b] | 3.8% (2/53) | 9.5% (13/137) | — |

TABLE 22-continued

Clinical signs and symptoms of virologically-confirmed dengue cases during Part 1 study period (safety set data)

| | TDV (N = 13,380) | Placebo (N = 6,687) | Relative Risk |
|---|---|---|---|
| Platelet Count ≤100 × 10$^9$ (%, n/N)$^c$ | 6.4% (5/78) | 22.0% (44/200) | 0.29 |
| Platelet Count ≤50 × 10$^9$ (%, n/N)$^c$ | 3.8% (3/78) | 11.0% (22/200) | 0.35 |
| ALT or AST ≥1000 U/L (%, n/N)$^c$ | 0% (0/78) | 0% (0/200) | — |

VCD, virologically-confirmed dengue;
ALT, alanine aminotransferase;
AST, aspartate aminotransferase $^a$Duration of febrile illness defined as start date of earliest symptom to end date of latest symptom plus one day (symptoms considered include fever and any general symptoms).
$^b$Hematocrit increase defined as maximum hematocrit between Day 3 and Day 7 inclusive, from onset of fever ≥20% increase over minimum hematocrit before Day 3 or after Day 7 from onset of fever.
$^c$For platelet, ALT, and AST data, assessments within 14 days of onset of febrile illness have been considered.
N refers to number of VCD cases with available data for the specific parameter e) Immunogenicity

The highest geometric mean titers (GMTs) were observed against DENV-2 regardless of baseline serostatus (Table 24). A very high tetravalent seropositivity rate (99.5%) in baseline seronegatives one month after the second dose (Tables 23 and 24) was observed.

Seropositivity rate (% of seropositive subjects) for each of the four dengue serotypes is determined at prevaccination on Day 1 (Month 0), post-first vaccination on Day 30 (Month 1), prevaccination on Day 90 (Month 3), post-second vaccination on Day 120 (Month 4), Day 270 (Month 9), Day 450 (Month 15), and then annually. Seropositivity rates (% participants, 95% CI) by dengue serotype per protocol set for immunogenicity data for Day 0, Day 30, Day 90, Day 120, and Day 270 are shown in Table 23.

Seropositivity rates (% participants, 95% CI) by dengue serotype against three or more serotypes (trivalent) and against all four serotypes (tetravalent) per protocol set for immunogenicity data for Day 0, Day 30, Day 90, Day 120, and Day 270 are shown in Table 23. The tetravalent seropositivity rates were high (>91%) in baseline seronegatives six months after second dose.

TABLE 23

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| DENV-1 | | | |
| 89.1 (87.6-90.5) | 90.6 (88.5-92.4) | 0 (0-0.5) | 0 (0-1.1) |
| 99.5 (99.1-99.8) | 88.6 (86.3-90.7) | 94.1 (92.0-95.8) | 4.9 (2.8-7.8) |
| 99.3 (98.8-99.6) | 90.2 (88.1-92.1) | 91.6 (89.3-93.5) | 6.1 (3.8-9.2) |
| >99.9 (99.7-100) | 90.3 (88.1-92.3) | 99.5 (98.6-99.9) | 8.3 (5.5-11.9) |
| 99.6 (99.1-99.8) | 89.8 (87.5-91.8) | 95.1 (93.0-96.6) | 9.0 (6.0-12.8) |
| DENV-2 | | | |
| 96.5 (95.6-97.3) | 97.2 (95.9-98.2) | 0 (0-0.5) | 0 (0-1.1) |
| 99.9 (99.6-100) | 93.3 (91.4-94.9) | 98.6 (97.4-99.4) | 10.7 (7.5-14.5) |
| >99.9 (99.7-100) | 94.0 (92.2-95.5) | 99.0 (98.0-99.6) | 12.2 (8.9-16.1) |
| 99.9 (99.6-100) | 93.6 (91.7-95.2) | 100 (99.4-100) | 14.7 (11.0-19.1) |
| 100 (99.8-100) | 94.6 (92.8-96.1) | 100 (99.4-100) | 18.3 (14.1-23.2) |
| DENV-3 | | | |
| 88.1 (86.5-89.6) | 88.0 (85.7-90.1) | 0 (0-0.5) | 0 (0-1.1) |
| 99.8 (99.4-99.9) | 87.6 (85.1-89.7) | 96.1 (94.3-97.4) | 4.0 (2.1-6.7) |
| 99.5 (99.1-99.8) | 87.3 (84.9-89.4) | 94.4 (92.5-96.0) | 2.0 (0.8-4.1) |
| 99.8 (99.5-100) | 87.9 (85.5-90.1) | 100 (99.4-100) | 5.1 (2.9-8.2) |
| 99.7 (99.4-99.9) | 87.1 (84.6-89.4) | 96.4 (94.6-97.7) | 7.7 (4.9-11.3) |
| DENV-4 | | | |
| 88.1 (86.5-89.6) | 87.4 (85.0-89.5) | 0 (0-0.5) | 0 (0-1.1) |
| 99.6 (99.2-99.9) | 86.4 (84.1-88.8) | 90.5 (88.0-92.6) | 1.8 (0.7-3.9) |
| 99.3 (98.8-99.7) | 86.9 (84.5-89.0) | 92.0 (89.8-93.9) | 2.9 (1.4-5.3) |
| >99.9 (99.7-100) | 88.3 (85.9-90.4) | 99.8 (99.1-100) | 4.8 (2.7-7.8) |
| 99.7 (99.3-99.9) | 87.6 (85.1-89.9) | 97.0 (95.4-98.2) | 6.3 (3.9-9.7) |
| Three or More Serotypes | | | |
| 87.5 (85.9-89.0) | 87.3 (84.9-89.4) | 0 (0-0.5) | 0 (0-1.1) |
| 99.8 (99.5-100) | 87.2 (84.7-89.4) | 96.5 (94.8-97.8) | 1.2 (0.3-3.1) |
| 99.7 (99.3-99.9) | 87.7 (85.3-89.7) | 94.9 (93.0-96.4) | 1.7 (0.6-3.7) |

TABLE 23-continued

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| 99.9 (99.6-100) | 88.4 (86.0-90.5) | 99.8 (99.1-100) | 4.2 (2.2-7.0) |
| 99.7 (99.4-99.9) | 87.3 (84.7-89.5) | 97.5 (96.0-98.6) | 5.7 (3.3-8.9) |
| All Four Serotypes | | | |
| 83.5 (81.7-85.2) | 83.5 (80.9-85.8) | 0 (0-0.5) | 0 (0-1.1) |
| 99.1 (98.5-99.5) | 82.9 (80.2-85.4) | 85.3 (82.4-87.9) | 0.9 (0.2-2.6) |
| 98.6 (97.9-99.1) | 83.6 (81.0-86.0) | 84.3 (81.4-86.9) | 1.4 (0.5-3.3) |
| 99.8 (99.5-100) | 85.2 (82.6-87.6) | 99.5 (98.6-99.9) | 3.5 (1.8-6.2) |
| 99.2 (98.7-99.6) | 84.6 (81.9-87.0) | 91.3 (88.7-93.4) | 5.3 (3.1-8.5) |

Seropositivity rates (% participants, 95% CI) by dengue serotype (per protocol set for immunogenicity data; seropositive defined as a reciprocal neutralizing antibody titer ≥10; baseline seronegative defined as seronegative to all serotype; baseline seropositive defined as seropositive to one or more serotypes; N refers to number of participants in the analysis set; number of participants evaluated at each timepoint may vary)

Geometric mean titers (GMTs) of neutralizing antibodies (microneutralization test [MNT]) for each dengue serotype are determined at pre-vaccination on Day 1 (Month 0), post-first vaccination on Day 30 (Month 1), pre-vaccination on Day 90 (Month 3), post-second vaccination on Day 120 (Month 4), Day 270 (Month 9), Day 450 (Month 15), and then annually. Geometric mean titers (95% CI) by dengue serotype per protocol set for immunogenicity data for Day 0, Day 30, Day 90, Day 120, and Day 270 are shown in Table 24.

Vaccine viremia is assessed by three PCRs: dengue detection RT-PCR, vaccine screening PCR and TDV sequencing in subjects with febrile illness within 30 days after each vaccination.

f) Safety

Rates of serious adverse events (SAEs) were similar in the vaccine and placebo groups (3.1% and 3.8% of participants, respectively; Table 25). One vaccine and four placebo recipients experienced SAEs considered to be related to receiving blinded investigational product by the investigator (two experienced hypersensitivity, two were diagnosed with

TABLE 24

Geometric mean titers (95% CI) by dengue serotype (per protocol set for immunogenicity data)

| | BASELINE SEROPOSITIVE | | BASELINE SERONEGATIVE | |
|---|---|---|---|---|
| | TDV N = 1,816 | Placebo N-902 | TDV N = 702 | Placebo N = 345 |
| DENV-1 | | | | |
| Day 1 | 410 (365-461) | 445 (377-524) | 5.0 (5.0-5.0) | 5.0 (5.0-5.0) |
| Day 30 | 2,404 (2,204-2,622) | 430 (361-512) | 118 (106-131) | 5.8 (5.3-6.3) |
| Day 90 | 1,945 (1,791-2,112) | 410 (349-481) | 91 (82-102) | 5.9 (5.4-6.3) |
| Day 120 | 2,115 (1,957-2,286) | 451 (381-534) | 184 (169-201) | 6.3 (5.7-7.0) |
| Day 270 | 1,447 (1,329-1,574) | 415 (350-492) | 87 (79-97) | 6.3 (5.7-6.9) |
| DENV-2 | | | | |
| Day 1 | 745 (674-825) | 802 (697-924) | 5.0 (5.0-5.0) | 5.0 (5.0-5.0) |
| Day 30 | 6,697 (6,301-7,117) | 744 (635-870) | 6,277 (5,648-6,977) | 6.6 (6.0-7.3) |
| Day 90 | 4,826 (4,571-5,096) | 729 (629-845) | 1,682 (1,544-1,834) | 7.0 (6.3-7.9) |
| Day 120 | 4,897 (4,646-5,163) | 766 (655-896) | 1,730 (1,614-1,855) | 7.7 (6.7-8.8) |
| Day 270 | 3,692 (3,496-3,898) | 776 (665-906) | 929 (856-1,010) | 8.7 (7.4-10.2) |
| DENV-3 | | | | |
| Day 1 | 357 (321-398) | 356 (305-415) | 5.0 (5.0-5.0) | 5.0 (5.0-5.0) |
| Day 30 | 2,255 (2,094-2,428) | 349 (298-409) | 194 (173-218) | 5.5 (5.2-5.9) |
| Day 90 | 1,563 (1,453-1,682) | 321 (277-374) | 94 (85-104) | 5.5 (5.1-5.9) |
| Day 120 | 1,761 (1,646-1,885) | 353 (301-414) | 228 (212-246) | 6.0 (5.4-6.6) |
| Day 270 | 1,089 (1,009-1,175) | 307 (261-360) | 72 (66-78) | 6.3 (5.7-7.0) |
| DENV-4 | | | | |
| Day 1 | 218 (198-241) | 234 (203-270) | 5.0 (5.0-5.0) | 5.0 (5.0-5.0) |
| Day 30 | 1,303 (1,221-1,391) | 222 (191-258) | 111 (98-125) | 5.4 (5.0-5.7) |
| Day 90 | 1,002 (940-1,069) | 215 (187-248) | 63 (57-70) | 5.5 (5.1-5.9) |
| Day 120 | 1,129 (1,066-1,196) | 241 (208-280) | 144 (134-155) | 5.8 (5.3-6.4) |
| Day 270 | 778 (730-830) | 229 (197-266) | 64 (59-70) | 6.2 (5.6-6.9) | dengue, and one with DHF). There were five deaths during Part 1, and all were considered unrelated to the investigational product or study procedures. Total rates of unsolicited AEs were similar between the vaccine and placebo groups. The most commonly (≥1% of vaccine-recipients) reported unsolicited AEs within four weeks of any dose by preferred term were pyrexia (vaccine group 1.5%; placebo 1.4%), nasopharyngitis (vaccine 2.7%; placebo 3.0%), upper respiratory tract infection (vaccine 2.6%; placebo 2.9%), and viral infection (vaccine 1.1%; placebo 0.9%). Solicited local reactions were reported more frequently in the vaccine group.

TABLE 25

Overview of safety data. Subjects with at least one adverse event after any vaccine dose. Data presented as number of events (percentage of subjects; number [n] of subjects/total [N] subjects) unless otherwise stated (safety set data)

| | TDV | Placebo |
|---|---|---|
| Safety Set | N = 13,380 | N = 6,687 |
| SAEs | 3.1% (409/13,380) | 3.8% (255/6,687) |
| Non-IP-Related[a] SAEs | 3.0% (408/13,380) | 3.8% (251/6,687) |
| IP-Related[a] SAEs | <0.1% (1/13,380) | <0.1% (4/6,687) |
| SAEs Leading to IP Withdrawal and/or Trial Discontinuation | 0.1% (18/13,380) | 0.1% (8/6,687) |
| Deaths | <0.1% (4/13,380) | <0.1% (1/6,687) |
| IP-Related Deaths | 0% (0/13,380) | 0% (0/6,687) |
| Safety Subset | N = 2,663 | N = 1,329 |
| Unsolicited AEs Occurring Within 4 Weeks of Any Dose | 18.4% (490/2,663) | 18.8% (250/1,329) |
| IP-Related[a] Unsolicited AEs Occurring Within 4 Weeks of Any Dose | 1.0% (27/2,663) | 1.6% (21/1,329) |
| Solicited Systemic AEs Occurring Within 2 Weeks of Any Dose[b] | 42.0% (1,107/2,635) | 38.0% (501/1,317) |
| IP-Related[a] Solicited Systemic AEs Occurring Within 2 Weeks of Any Dose | 31.2% (821/2,635) | 28.2% (371/1,317) |
| Solicited Local Reactions Occurring Within 1 Week of Any Dose[c] | 36.7% (967/2,633) | 25.7% (338/1,317) |

AE, adverse event;
SAE, serious adverse event;
IP, investigational product/TDV
[a]IP-related, defined as related to the investigational product as assessed by investigator
[b]only participants with diary data available were evaluated
[c]all injection site (solicited local) reactions considered to be IP-related

LIST OF ITEMS OF THE INVENTION

1. A unit dose of a dengue vaccine composition comprising: a tetravalent dengue virus composition including four live, attenuated dengue virus strains wherein the unit dose is lyophilized and upon reconstitution with 0.5 mL of a pharmaceutically acceptable diluent comprises:
   (i) a chimeric dengue serotype 2/1 strain in a concentration of at least 3.3 log 10 pfu/0.5 mL,
   (ii) a dengue serotype 2 strain in a concentration of at least 2.7 log 10 pfu/0.5 mL,
   (iii) a chimeric dengue serotype 2/3 strain in a concentration of at least 4.0 log 10 pfu/0.5 mL, and
   (iv) a chimeric dengue serotype 2/4 strain in a concentration of at least 4.5 log 10 pfu/0.5 mL.
2. The unit dose of item 1, wherein upon reconstitution with 0.5 mL of a pharmaceutically acceptable diluent
   (i) has a concentration of 3.3 log 10 pfu/0.5 mL to 5.0 log 10 pfu/0.5 mL,
   (ii) has a concentration of 2.7 log 10 pfu/0.5 mL to 4.9 log 10 pfu/0.5 mL,
   (iii) has a concentration of 4.0 log 10 pfu/0.5 mL to 5.7 log 10 pfu/0.5 mL, and
   (iv) has a concentration of 4.5 log 10 pfu/0.5 mL to 6.2 log 10 pfu/0.5 mL.
3. The unit dose of item 1, wherein upon reconstitution with 0.5 mL of a pharmaceutically acceptable diluent:
   (i) has a concentration of 3.3 log 10 pfu/0.5 mL to 5.0 log 10 pfu/0.5 mL,
   (ii) has a concentration of 2.7 log 10 pfu/0.5 mL to 4.9 log 10 pfu/0.5 mL,
   (iii) has a concentration of 4.0 log 10 pfu/0.5 mL to 5.7 log 10 pfu/0.5 mL, and
   (iv) has a concentration of 4.5 log 10 pfu/0.5 mL to 5.5 log 10 pfu/0.5 mL.
4. The unit dose of any one of items 1 to 3, wherein upon reconstitution with 0.5 mL of a pharmaceutically acceptable diluent
   (i) has a concentration of 3.3 log 10 pfu/0.5 mL to 3.6 log 10 pfu/0.5 mL,
   (ii) has a concentration of 2.7 log 10 pfu/0.5 mL to 4.0 log 10 pfu/0.5 mL,
   (iii) has a concentration of 4.0 log 10 pfu/0.5 mL to 4.6 log 10 pfu/0.5 mL, and
   (iv) has a concentration of 4.5 log 10 pfu/0.5 mL to 5.1 log 10 pfu/0.5 mL.
5. The unit dose of any one of items 1 to 4, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10% or less than 8%, and the concentration of (iv) in pfu/0.5 mL is at least 50%.
6. The unit dose of item 5, wherein upon reconstitution with a pharmaceutically acceptable diluent (i), (ii), (iii), and (iv) provide a total concentration of pfu/0.5 mL and based on said total concentration the concentration of (i) in pfu/0.5 mL is at least 1%, and the concentration of (iii) in pfu/0.5 mL is at least 7% or at least 8%.
7. The unit dose of any one of items 1 to 6, wherein upon reconstitution with a pharmaceutically acceptable diluent (i), (ii), (iii), and (iv) provide a total concentration of pfu/0.5 mL and based on said total concentration the concentration of (i) in pfu/0.5 mL is 1% to 7% of the total concentration, (ii) in pfu/0.5 mL is less than 8% of the total concentration, such as in the range of 1% to 8% of the total concentration, (iii) in pfu/0.5 mL is at least 10% of the total concentration, and (iv) in pfu/0.5 mL is at least 65% of the total concentration, such as in the range of 65% to 80%.

8. The unit dose of any one of items 1 to 7, wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

9. The unit dose of any one of items 1 to 8, wherein reconstitution with a pharmaceutically acceptable diluent is made with 0.5 ml of the pharmaceutically acceptable diluent.

10. The unit dose of any one of items 1 to 9, wherein the lyophilized unit dose is prepared from a solution further comprising a non-reducing sugar, a surfactant, a protein and an inorganic salt.

11. The unit dose of item 10, wherein the non-reducing sugar is trehalose, the surfactant is poloxamer 407, the protein is human serum albumin and the inorganic salt is sodium chloride.

12. The unit dose of item 10 or 11, wherein the solution comprises:
from about 10% (w/v) to about 20% (w/v) α,α-trehalose dihydrate or an equimolar amount of other forms of α,α-trehalose,
from about 0.5% (w/v) to about 1.5% (w/v) poloxamer 407,
from about 0.05% (w/v) to about 2% (w/v) human serum albumin, and
from about 70 mM to about 140 mM sodium chloride.

13. The unit dose of any one of items 1 to 12, wherein the lyophilized unit dose is prepared from a solution comprising:
about 15% (w/v) α,α-trehalose dihydrate,
about 1% (w/v) poloxamer 407,
about 0.1% (w/v) human serum albumin, and
and about 100 mM sodium chloride.

14. The unit dose of any one of items 1 to 13, wherein each one of the four live attenuated dengue virus strains has attenuating mutations in the 5'-noncoding region (NCR) at nucleotide 57 from cytosine to thymidine, in the NS1 gene at nucleotide 2579 from guanine to adenine resulting in an amino acid change at position 828 from glycine to asparagine, and in the NS3 gene at nucleotide 5270 from adenine to thymine resulting in an amino acid change at position 1725 from glutamine to valine, preferably further comprising one or more of the mutations selected from the list comprising:
a) a mutation in the NS2A gene at nucleotide 4018 from cytosine to thymidine resulting in an amino acid at position 1308 from leucine to phenylalanine,
b) a silent mutation in the NS3 gene at nucleotide 5547 from thymidine to cytosine, and
c) a mutation in the NS4A gene at nucleotide 6599 from guanine to cytosine resulting in an amino acid change at position 2168 from glycine to alanine.

15. The unit dose of item 14, wherein (i) further comprises one or more of the mutations selected from the list comprising:

a mutation in the NS2A gene at nucleotide 3823 from adenine to cytosine resulting in an amino acid change at position 1243 from isoleucine to leucine,
a mutation in the NS2B gene at nucleotide 4407 from adenine to thymidine resulting in an amino acid change at position 1437 from glutamine to asparagine, and
a silent mutation in the NS4B gene at nucleotide 7311 from adenine to guanine.

16. The unit dose of item 14 or 15, wherein (ii) further comprises one or more of the mutations selected from the list comprising:
a mutation in the prM gene at nucleotide 592 from adenine to guanine resulting in an amino acid change at position 166 from lysine to glutamine, and
a mutation in the NS5 gene at nucleotide 8803 from adenine to guanine resulting in an amino acid change at position 2903 from isoleucine to valine.

17. The unit dose of any one of items 14 to 16, wherein (iii) further comprises one or more of the mutations selected from the list comprising:
a mutation in the E gene at nucleotide 1603 from adenine to thymidine resulting in an amino acid change at position 503 from threonine to serine, and
a silent mutation in the NS5 gene at nucleotide 7620 from adenine to guanine.

18. The unit dose of any one of items 14 to 17, wherein (iv) further comprises one or more of the mutations selected from the list comprising
a silent mutation in the C gene at nucleotide 225 from adenine to thymidine,
a mutation in the NS2A gene at nucleotide 3674 from adenine to guanine resulting in an amino acid change at position 1193 from asparagine to glycine,
a mutation in the NS2A gene at nucleotide 3773 from adenine to an adenine/guanine mix resulting in an amino acid change at position 1226 from lysine to a lysine/asparagine mix,
a silent mutation in the NS3 gene at nucleotide 5391 from cytosine to thymidine,
a mutation in the NS4A gene at nucleotide 6437 from cytosine to thymidine resulting in an amino acid change at position 2114 from alanine to valine,
a silent mutation in the NS4B gene at nucleotide 7026 from thymidine to a thymidine/cytosine mix, and
a silent mutation in the NS5 gene at nucleotide 9750 from adenine to cytosine.

19. The unit dose of any one of items 1 to 18, wherein
(i) has the amino acid sequence of SEQ ID NO. 2,
(ii) has the amino acid sequence of SEQ ID NO. 4,
(iii) has the amino acid sequence of SEQ ID NO. 6, and
(iv) has the amino acid sequence of SEQ ID NO. 8.

20. The unit dose of any one of items 1 to 19 reconstituted with 0.3 to 0.8 mL of liquid for reconstitution.

21. The unit dose of item 20 reconstituted with 0.5 mL of liquid for reconstitution.

22. The unit dose of item 20 or 21, wherein the liquid for reconstitution is 37 mM aqueous sodium chloride solution.

23. A kit for preparing a reconstituted unit dose comprising the following components:
a) a unit dose of any one of items 1 to 19, and
b) a pharmaceutically acceptable diluent for reconstitution.

24. The kit of item 23, wherein the pharmaceutically acceptable diluent for reconstitution is 37 mM sodium chloride.

25. Container, such as a vial, comprising one to ten unit doses of any one of items 1 to 22.

26. A method of preventing dengue disease in a subject population comprising administering to the subject population a reconstituted unit dose of any one of items 20 to 22.
27. A method of preventing virologically confirmable dengue disease in a subject population comprising administering to the subject population a reconstituted unit dose of a tetravalent dengue virus composition including four live, attenuated dengue virus strains.
28. A method of preventing virologically confirmable dengue disease with hospitalization in a subject population comprising administering to the subject population a reconstituted unit dose of a tetravalent dengue virus composition including four live, attenuated dengue virus strains.
29. The method of items 26 to 28, wherein the geometric mean neutralizing antibody titers (GMTs) of the subject population when tested in at least 40, or at least 50, or at least 60 subjects at day 180 or day 365 after at least a first administration of said unit dose, and optionally a second administration of said unit dose 90 days after said first administration, provide a ratio of not more than 50, or not more than 40, or nor more than 30, or not more than 20 for the GMT of dengue serotype 2 to the GMT of dengue serotype 4.
30. The method of item 29, wherein said GMTs of the subject population further provide a ratio of not more than 20 for the GMT of dengue serotype 2 to the GMT of dengue serotype 1, and/or a ratio of not more than 20 for the GMT of dengue serotype 2 to the GMT of dengue serotype 3.
31. A method of preventing dengue disease in a subject comprising administering to the subject a reconstituted unit dose of any one of items 20 to 22.
32. A method of preventing virologically confirmable dengue disease in a subject comprising administering to the subject a reconstituted unit dose of a tetravalent dengue virus composition including four live, attenuated dengue virus strains.
33. A method of preventing virologically confirmable dengue disease with hospitalization in a subject comprising administering to the subject a reconstituted unit dose of a tetravalent dengue virus composition including four live, attenuated dengue virus strains.
34. The method of items 31 to 33, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4.
35. The method of item 34, wherein said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.
36. The method of any one of items 26 to 35, wherein the method is for preventing dengue hemorrhagic fever (DHF) or dengue shock syndrome (DSS).
37. The method of any one of items 26 to 36, wherein the reconstituted unit dose is administered by subcutaneous injection, preferably to the deltoid region of the arm.
38. The method of any one of items 26 to 37, wherein two reconstituted unit doses of any one of items 20 to 22 are administered within 12 months or more.
39. The method of any one of items 26 to 37, wherein two reconstituted unit doses of any one of items 20 to 22 are administered within six months, preferably within three months.
40. The method of item 39, wherein the two reconstituted unit doses are administered at day 0 and day 90 or at day 1 and day 90.
41. The method of item 38 to 40, wherein a third unit dose is administered after administration of the second unit dose, preferably within 12 months after administration of the first unit dose.
42. The method of item 38 to 40, wherein a third unit dose is administered after administration of the second unit dose, preferably within 12 months after administration of the second unit dose.
43. The method of any one of items 26 to 42, wherein the subject or subject population is seronegative with respect to all dengue serotypes.
44. The method of any one of items 26 to 42, wherein the subject population or subject is seropositive with respect to at least one dengue serotype.
45. The method of any one of items 26 to 44, wherein the subject or subject population is of 2 to 60 years of age.
46. The method of any one of items 26 to 44, wherein the subject or subject population is of 2 to 17 years of age.
47. The method of any one of items 26 to 44, wherein the subject or subject population is under 9 years of age, under 4 years of age, or under 2 years of age or from 2 to 9 years of age, or from 2 to 5 years of age, or from 4 to 9 years of age or from 6 to 9 years of age, and optionally wherein the subject is seronegative with respect to all dengue serotypes.
48. The method of any one of items 26 to 44, wherein the subject or subject population is of 4 to 16 years of age.
49. The method of item 48, wherein the subject or subject population is of 4 to 5 years of age
50. The method of item 48, wherein the subject or subject population is of 6 to 11 years of age.
51. The method of item 48, wherein the subject or subject population is of 12 to 16 years of age.
52. The method of any one of items 26 to 51, wherein the subject or subject population is from a dengue endemic region.
53. The method of any one of items 26 to 51, wherein the subject or subject population is from a dengue non-endemic region.
54. The method of any one of items 52 or 53, wherein the subject or subject population is from Asia Pacific or Latin America.
55. The method of any one of items 26 to 54, wherein the subject or subject population has been subject to prior vaccination against Yellow Fever, wherein prior vaccination against Yellow Fever refers to a vaccination prior to the second administration or prior to the first administration.
56. The method of any one of items 26 to 54, wherein the subject or subject population is has been subject to prior vaccination against Japanese Encephalitis, wherein prior vaccination against Japanese Encephalitis refers to a vaccination prior to the second administration or prior to the first administration.
57. The method of any one of items 26 to 54, wherein the subject or subject population is has not been subject to prior vaccination against Yellow Fever.

58. The method of any one of items 26 to 54, wherein the subject or subject population is has not been subject to prior vaccination against Japanese Encephalitis.
59. The method of any one of items 26 to 58 having a combined vaccine efficacy against all four serotypes with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule.
60. The method of item 59, wherein the lower bound is more than 30%, is more than 40%, is more than 50%, is more than 55%, is more than 60%, is more than 65%, is more than 70% or is more than 72%.
61. The method of any one of items 26 to 60 having a combined vaccine efficacy against all four serotypes of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.
62. The method of item 61, wherein the combined vaccine efficacy against all four serotypes is more than 40%, is more than 50%, is more than 55%, is more than 60%, is more than 65%, is more than 70%, is more than 75% is more than 78%, is more than 79% or is about 80%.
63. The method of any one of items 26 to 62 having a combined relative risk against all four serotypes with a 2-sided 95% confidence interval, wherein the upper bound is less than 0.75, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.
64. The method of item 63, wherein the upper bound is less than 0.70, is less than 0.65, is less than 0.60, is less than 0.55, is less than 0.50, is less than 0.45, is less than 0.40, is less than 0.35, is less than 0.30 or is less than 0.28.
65. The method of any one of items 26 to 64, wherein the combined relative risk against all four serotypes is less than 0.70, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.
66. The method of item 65, wherein the combined relative risk against all four serotypes is less than 0.65, is less than 0.60, is less than 0.55, is less than 0.50, is less than 0.45, is less than 0.40, is less than 0.35, is less than 0.30, is less than 0.25 or is less than 0.23.
67. The method of any one of items 26 to 58 having a combined vaccine efficacy against all four serotypes with a 2-sided 95% confidence interval, wherein the lower bound is more than 61.0%, or more than 65.0% or more than 70.0% or more than 72.0% when measured against placebo in a subject population of at least 5,000 healthy subjects, or at least 10,000 healthy subjects, or at least 15,000 healthy subjects from endemic irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 or 13 months after the last administration of the administration schedule.
68. The method of any one of items 26 to 58 having a combined vaccine efficacy against all four serotypes of more than 66%, or of more than 70%, or of more than 75%, or of more than 77%, or of more than 80%, when measured against placebo in a subject population of at least 5,000 healthy subjects, or at least 10,000 healthy subjects, or at least 15,000 healthy subjects from endemic areas irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 months or 13 month after the last administration of the administration schedule.
69. The method of item 67 or 68, wherein the combined vaccine efficacy against all four serotypes is measured about 30 days after the last administration of the administration schedule until 12 or 13 months after the last administration of the administration schedule.
70. The method of item 67 or 68, wherein said unit dose or said placebo is administered twice within three months, in particular at about day 1 and about day 90, and wherein the combined vaccine efficacy against all four serotypes is measured 30 days after the second administration until 12 or 13 months after the second administration of the administration schedule.
71. The method of any one of items 26 to 70 being effective and safe.
72. The method of any one of items 26 to 71 having a relative risk for virologically confirmed dengue with hospitalization which is 1 or less, or 0.8 or less, or 0.6 or less, when measured against placebo in a subject population of at least 5,000 healthy subjects, or at least 10,000 healthy subjects, or at least 15,000 healthy subjects.
73. The method of any one of items 59 to 72, wherein the healthy subjects of the subject population are of 4 to 16 years of age at the time of randomization.
74. The method of any one of items 59 to 72, wherein the healthy subjects of the subject population are of 4 to 5 years of age at the time of randomization
75. The method of any one of items 59 to 72, wherein the healthy subjects of the subject population are of 6 to 11 years of age at the time of randomization.
76. The method of any one of items 59 to 72, wherein the healthy subjects of the subject population are of 12 to 16 years of age at the time of randomization.
77. The method of any one of items 59 to 72, wherein the healthy subjects of the subject population are from Asia Pacific or Latin America.
78. The method of any one of items 59 to 77, wherein the healthy subjects of the subject population are seropositive with respect to at least one serotype at baseline.

79. The method of any one of items 59 to 77, wherein the healthy subjects of the subject population are seronegative with respect to all serotypes at baseline.
80. The method of any one of items 59 to 79, wherein the healthy subjects of the subject population have been subject to prior vaccination against Yellow Fever.
81. The method of any one of items 59 to 79, wherein the healthy subjects of the subject population have been subject to prior vaccination against Japanese Encephalitis.
82. The method of any one of items 59 to 79, wherein the healthy subjects of the subject population have not been subject to prior vaccination against Yellow Fever.
83. The method of any one of items 59 to 79, wherein the healthy subjects of the subject population have not been subject to prior vaccination against Japanese Encephalitis.
84. A method for stimulating an immune response to all four serotypes of dengue virus in a subject, comprising administering to the subject a reconstituted unit dose of items 20 to 22.
85. The method of item 84, wherein the immune response to all four serotypes of dengue virus is balanced.
86. The method of item 84 or 85, wherein the reconstituted unit dose is administered by subcutaneous injection, preferably to the deltoid region of the arm.
87. The method of any one of items 84 to 86, wherein two unit doses of any one of items 20 to 22 are administered within 12 months or more.
88. The method of any one of items 84 to 87, wherein two reconstituted unit doses of any one of items 20 to 22 are administered within six months, preferably within three months.
89. The method of item 88, wherein the two reconstituted unit doses are administered at day 0 and day 90 or at day 1 and day 90.
90. The method of item 87 to 89, wherein a third unit dose is administered after the administration of the second unit dose, preferably within 12 month of administration of the first unit dose.
91. The method of item 87 to 89, wherein a third unit dose is administered after the administration of the second unit dose, preferably within 12 month of administration of the second unit dose.
92. The method of any one of items 84 to 91, wherein the subject is from a dengue endemic region.
93. The method of any one of items 84 to 91, wherein the subject is from a dengue non-endemic region.
94. The method of any one of items 84 to 93, wherein the subject is seronegative with respect to all dengue serotypes.
95. The method of any one of items 84 to 93, wherein the subject is seropositive with respect to at least one dengue serotype.
96. The method of any one of items 84 to 95, wherein the neutralizing antibody titers of the subject when tested at day 180 or day 365 after at least a first administration of said reconstituted unit dose, and optionally a second administration of said reconstituted unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4.
97. The method of item 96, wherein said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.
98. The method of any one of items 84 to 97, wherein the subject is of 2 and 60 years of age.
99. The method of any one of items 84 to 97, wherein the subject is under 9 years of age, under 4 years of age, or under 2 years of age.
100. The method of any one of items 26 to 99, wherein the reconstituted unit dose is obtained from the kit according to item 23 or 24.
101. The reconstituted unit dose of any one of item 20 to 22 for use in a method of items 26 to 100.
102. Use of a reconstituted unit dose of any one of items 20 to 22 for the manufacture of a medicament for a method according to items 26 to 100.
103. A method for determining the titer of neutralizing antibodies against each of dengue serotypes 1, 2, 3 and 4 in a blood serum sample, the method comprising the steps of:
    (a) seeding cells from a dengue-susceptible cell line on 96-well assay plates and culturing the cells for a culture period;
    (b) preparing serial dilutions of the blood serum sample;
    (c) separately mixing the serially diluted blood serum samples prepared in step (b) with dengue serotype 1, dengue serotype 2, dengue serotype 3 and dengue serotype 4 to obtain separate mixtures for each dengue serotype and incubating the separate mixtures;
    (d) adding the separate mixtures prepared in (c) to the cells seeded and cultured in step (a) and incubating the cells with the separate mixtures;
    (e) providing an overlay for the inoculated cells and incubating the cells for an incubation period of 40 to 75 hours;
    (f) determining the number of plaques in each well and comparing the number of plaques in each well to a control to determine the level of neutralizing antibodies against each of dengue serotypes 1, 2, 3 and 4.
104. Method according to item 103, wherein in step (e) different incubation periods are used for the mixtures of different dengue serotypes.
105. Method according to item 103 or 104 wherein in step (e) the incubation period for mixtures of dengue serotype 4 is shorter than the incubation period for mixtures of dengue serotypes 1, 2 and 3.
106. Method according to item 105, wherein the incubation period for mixtures of dengue serotype 4 is 46±2 hours.
107. Method according to any one of the items 103 to 106, wherein in step (e) the incubation period for mixtures of dengue serotype 2 is longer than the incubation period for mixtures of dengue serotypes 1, 3 and 4.
108. Method according to item 107, wherein the incubation period for mixtures of dengue serotype 2 is 70±2 hours.
109. Method according to any one of items 103 to 108, wherein the dengue-susceptible cell line is selected from Vero cells, LLC-MK2 cells and BHK-21 cells.
110. Method according to any one of items 103 to 109, wherein the culture period in step (a) is 12 to 36 hours.
111. Method according to any one of items 103 to 110 wherein in step (c) the dengue serotype 1 is DENV-1 strain 16007, dengue serotype 2 is DENV-2 strain 16681, dengue serotype 3 is DENV-3 strain 16562 and dengue serotype 4 is DENV-4 strain 1036.
112. Method according to any one of items 103 to 111, wherein the separate mixtures in step (c) are incubated overnight at a temperature of 2° C. to 8° C.

113. Method according to any one of items 103 to 112, wherein the overlay in step (e) is selected from the group consisting of methylcellulose, carboxymethylcellulose and agarose.

114. Method according to any one of items 103 to 113, wherein in step (e) the cells are incubated at a temperature of 33° C. to 35° C.

115. Method according to any one of items 103 to 114, wherein the number of plaques in each well is determined using serotype-specific anti-dengue monoclonal antibodies.

116. A method for determining the titer of neutralizing antibodies against each of dengue serotypes 1, 2, 3 and 4 in a blood serum sample, the method comprising the steps of:
(a) seeding Vero cells on 96-well assay plates and culturing the Vero cells for a period of 20 to 30 hours;
(b) preparing serial dilutions of the serum sample;
(c) separately mixing the serially diluted serum samples with dengue serotype 1, dengue serotype 2, dengue serotype 3 and dengue serotype 4 to prepare separate mixtures and incubating the separate mixtures overnight at a temperature of 2° C. to 8° C.;
(d) incubating the cells seeded and cultured in step (a) with the separate mixtures prepared in step (c) in separate wells for 90 to 120 minutes;
(e) providing a methylcellulose overlay for the inoculated cells and incubating the cells for an incubation period of 40 to 75 hours at 34° C.;
(f) determining the number of plaques in each well using serotype-specific anti-dengue monoclonal antibodies and comparing the number of plaques in each well to a control to determine the level of neutralizing antibodies against each of dengue serotypes 1, 2, 3 and 4.

117. Use of the method according to any one of items 103 to 116 for determining the dengue serostatus of a subject before vaccination with a dengue virus vaccine or for analyzing a subjects immune response after vaccination with a dengue virus vaccine.

LIST OF FURTHER ITEMS OF THE INVENTION

1. A dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL.

2. The composition for use of item 1, wherein the method does not comprise a determination of a previous dengue infection in the subject before the administration of the first unit dose of the tetravalent dengue virus composition and wherein the method is safe and effective.

3. The composition for use of item 1 or 2, wherein the dengue serotype 3 is at least about 10% of the total concentration in pfu/0.5 mL and/or wherein the dengue serotype 4 is at least about 70% of the total concentration in pfu/0.5 mL.

4. The composition for use of any one of items 1 to 3, wherein the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

5. The composition for use of any one of items 1 to 4, wherein the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain.

6. The composition for use of any one of items 1 to 5, wherein the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

7. The composition for use of any one of items 1 to 6, wherein the unit dose upon reconstitution with 0.5 mL of a pharmaceutically acceptable diluent
(i) dengue serotype 1 has a concentration of 3.3 log 10 pfu/0.5 mL to 5.0 log 10 pfu/0.5 mL,
(ii) dengue serotype 2 has a concentration of 2.7 log 10 pfu/0.5 mL to 4.9 log 10 pfu/0.5 mL,
(iii) dengue serotype 3 has a concentration of 4.0 log 10 pfu/0.5 mL to 5.7 log 10 pfu/0.5 mL, and
(iv) dengue serotype 4 has a concentration of 4.5 log 10 pfu/0.5 mL to 6.2 log 10 pfu/0.5 mL.

8. The composition for use of any one of items 1 to 7, wherein the composition further comprises about 15 (w/v) α,α-trehalose dihydrate, about 1% (w/v) poloxamer 407, about 0.1% (w/v) human serum albumin, and about 100 mM sodium chloride when measured in 0.5 ml.

9. The composition for use of any one of items 1 to 8, wherein the unit doses are administered to the deltoid region of the arm.

10. The composition for use of any one of items 1 to 9, wherein the subject is seronegative to all dengue serotypes at baseline and/or is under 9 years of age.

11. The composition for use of any one of items 1 to 10, wherein the subject is 4 to 5 years of age or 6 to 11 years of age or 12 to 16 years of age.

12. The composition for use of any one of items 1 to 11, wherein the method is for preventing dengue hemorrhagic fever (DHF) or dengue shock syndrome (DSS).

13. The composition for use of any one of items 1 to 12, wherein the subject is from a dengue endemic region.

14. The composition for use of any one of items 1 to 12, wherein the subject is from a dengue non-endemic region.

15. The composition for use of any one of items 1 or 14, wherein the subject is from Asia Pacific or Latin America.

16. The composition for use of any one items of 1 to 15, wherein the composition provides a seropositivity rate when it is administered to a subject population of at least 50 subjects in two unit doses subcutaneously at day 1 and at day 90, wherein the subjects of the subject population are seronegative to all dengue serotypes at baseline.

17. The composition for use of item 16, wherein at least one month after administration of the first unit dose, such as at day 30, at least 80% of the subject population are seropositive for all four dengue serotypes.

18. The composition for use of item 16 or 17, wherein before or at the time of the administration of the second unit dose, such as at day 90, at least 80% of the subject population are seropositive for all four dengue serotypes.

19. The composition for use of any one of items 16 to 18, wherein after the administration of the second unit dose, such as at day 120, at least 80%, or at least 85%, or at least 90% or at least 95% of the subject population are seropositive for all four dengue serotypes.

20. The composition for use of any one of items 11 to 14, wherein after the administration of the second unit dose, such as at day 270, at least 80%, or at least 85%, or at least 90% of the subject population are seropositive for all four dengue serotypes.

21. The composition for use of any one of items 16 to 20, wherein the composition provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

22. A method of inoculating a subject against virologically confirmable dengue disease in a subject comprising administering to the subject a tetravalent dengue virus composition including four dengue virus strains representing serotype 1, serotype 2, serotype 3 and serotype 4.

23. A method of inoculating a subject against virologically confirmable dengue disease consisting of administering to the subject a tetravalent dengue virus composition including four dengue virus strains representing serotype 1, serotype 2, serotype 3 and serotype 4.

24. The method of item 22 or 23, wherein the method does not comprise a determination of a previous dengue infection in the subject before the administration of the tetravalent dengue virus composition.

25. The method of any one of items 22 to 24, wherein the inoculation is safe irrespective of whether there is a determination that the subject had a previous dengue infection before the administration of the tetravalent dengue virus composition.

26. The method of any one of items 22 to 25 which is safe.

27. The method of any one of items 22 to 26 which is effective.

28. The method of any one of items 22 to 27, wherein the virus strains are live, attenuated dengue virus strains.

29. The method of any one of items 22 to 28, wherein the composition includes at least one chimeric dengue virus and optionally at least one non-chimeric dengue virus.

30. The method of any one of items 22 to 29, wherein the composition includes a chimeric dengue serotype 2/1 strain and a dengue serotype 2 strain and a chimeric dengue serotype 2/3 strain and a chimeric dengue serotype 2/4 strain.

31. The method of any one of items 22 to 30, wherein the subject is seronegative to all dengue serotypes at base line and/or under 9 years of age, 4 to 5 years of age, 6 to 11 years of age or 12 to 16 years of age.

32. The method of any one of items 22 to 31, wherein the composition is administered by subcutaneous injection.

33. The method of any one of items 22 to 32 including consecutively administering at least a first and a second unit dose of the dengue vaccine composition to the subject, wherein said first and second unit dose are administered subcutaneously within 3 months and at least four 4 apart, optionally at about day 1 and at about day 90.

34. The method of any one of items 22 to 33, wherein the dengue serotypes 1 and 2 are present in similar amounts and/or make up less than about 10% of the total viral concentration.

35. The method of any one of items 22 to 34, wherein the dengue serotype 3 makes up at least about 10% of the total viral concentration.

36. The method of any one of items 22 to 35, wherein the dengue serotype 4 makes up at least about 70% of the total viral concentration.

37. The method of any one of items 22 to 36 wherein the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

38. The method of any one of items 22 to 37, wherein the method is for preventing dengue hemorrhagic fever (DHF) or dengue shock syndrome (DSS).

39. The method of any one of items 22 to 38 wherein the subject or subject population is from a dengue endemic region.

40. The method of any one of items 22 to 38, wherein the subject or subject population is from a dengue non-endemic region.

41. The method of any one of items 22 to 40, wherein the subject or subject population is from Asia Pacific or Latin America.

42. The method of any one of items 22 to 41 having a combined vaccine efficacy against all four dengue serotypes with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, and optionally at least 4 weeks apart, about 30 days after the second administration of the administration schedule until at least 12 months after the second administration of the administration schedule.

43. The method of item 42, wherein the lower bound is more than 30%, is more than 40%, is more than 50%, is more than 55%, is more than 60%, is more than 65%, is more than 70% or is more than 72%. 44. The method of any one of items 22 to 43 having a combined vaccine efficacy against all four dengue serotypes of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, and optionally at least 4 weeks apart, 30 days after the second administration until at least 12 months after the second administration.
45. The method of item 44, wherein the combined vaccine efficacy against all four dengue serotypes is more than 40%, is more than 50%, is more than 55%, is more than 60%, is more than 65%, is more than 70%, is more than 75% is more than 78%, is more than 79% or is about 80%.
46. The method of any one of items 22 to 45 having a combined vaccine efficacy against all four dengue serotypes in seronegative subjects with a 2-sided 95% confidence interval, wherein the lower bound is more than 25%, when measured against placebo in a subject population of at least 2,000 healthy subjects being seronegative against all serotypes at baseline, wherein said unit dose or said placebo is administered at least twice within less than 6 months, such as within 3 months, about 30 days after the second administration of the administration schedule until at least 12 months after the second administration of the administration schedule.
47. The method of item 46, wherein the lower bound is more than 30%, is more than 40%, is more than 50%, or is more than 55%.
48. The method of any one of items 22 to 47 having a combined vaccine efficacy against all four dengue serotypes in seronegative subjects of more than 30%, when measured against placebo in a subject population of at least 2,000 healthy subjects being seronegative against all serotypes at baseline, wherein said unit dose or said placebo is administered at least twice within less than 6 months, such as within 3 months, 30 days after the second administration until at least 12 months after the second administration.
49. The method of item 48, wherein the combined vaccine efficacy against all four dengue serotypes in seronegative subjects is more than 40%, is more than 50%, is more than 60%, is more than 65%, or is more than 70%.
50. The method of any one of items 22 to 49 having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule.
51. The method of item 50, wherein the lower bound is more than 30%, is more than 40%, is more than 45%.
52. The method of any one of items 22 to 51 having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose or said placebo is administered at least twice within less than 6 months, such as within 3 months, 30 days after the second administration until at least 12 months after the second administration.
53. The method of item 52, wherein the combined vaccine efficacy against all four dengue serotypes is more than 40%, is more than 50%, is more than 60%, is more than 65%, or is more than 70%.
54. The method of any one of items 22 to 53 having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule.
55. The method of item 54, wherein the lower bound is more than 30%, is more than 40%, is more than 50%, is more than 60%, or is more than 70%.
56. The method of any one of items 22 to 55 having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose or said placebo is administered at least twice within less than 6 months, such as within 3 months, 30 days after the second administration until at least 12 months after the second administration.
57. The method of item 56, wherein the combined vaccine efficacy against all four dengue serotypes is more than 40%, is more than 50%, is more than 60%, is more than 70%, is more than 75%, or is more than 80%.
58. The method of any one of items 26 to 57 having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose or said placebo is administered at least twice within less than 6 months, such as within 3 months, about 30 days after the second administration of the administration schedule until at least 12 months after the second administration of the administration schedule.
59. The method of item 58, wherein the lower bound is more than 30%, is more than 40%, is more than 50%, is more than 60%, is more than 65%, or is more than 68%.
60. The method of any one of items 26 to 59 having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose or said placebo is administered at least twice within less than 6 months, such as within 3 months, 30 days after the second administration until at least 12 months after the second administration.
61. The method of item 60, wherein the combined vaccine efficacy against all four dengue serotypes is more than 40%, is more than 50%, is more than 60%, is more than 70%, is more than 75%, or is more than 80%.

62. The method of any one of items 22 to 61 having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule.

63. The method of item 62, wherein the lower bound is more than 30%, is more than 40%, or is more than 50%.

64. The method of any one of items 22 to 63 having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.

65. The method of item 64, wherein the vaccine efficacy against dengue serotype 1 is more than 40%, is more than 50%, is more than 60%, is more than 65%, or is more than 70%.

66. The method of any one of items 22 to 65 having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule.

67. The method of item 66, wherein the lower bound is more than 30%, is more than 40%, is more than 50, is more than 60, is more than 70, is more than 80, or is more than 90%.

68. The method of any one of items 22 to 67 having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.

69. The method of item 68, wherein the vaccine efficacy against dengue serotype 2 is more than 40%, is more than 50%, is more than 60%, is more than 70%, is more than 80, or is more than 90%.

70. The method of any one of items 22 to 69 having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, about 30 days after the second administration of the administration schedule until at least 12 months after the second administration of the administration schedule.

71. The method of item 70, wherein the lower bound is more than 30%, is more than 40%.

72. The method of any one of items 22 to 71 having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.

73. The method of item 72, wherein the vaccine efficacy against dengue serotype 3 is more than 40%, is more than 50%, is more than 55%, or is more than 60%.

74. The method of any one of items 22 to 73 having a combined vaccine efficacy against virologically-confirmed dengue with hospitalization against all four serotypes with a 2-sided 95% confidence interval, wherein the lower bound is more than 25%, when measured against placebo in a subject population of at least 2,000 healthy subjects being seronegative against all serotypes at baseline, wherein said unit dose or said placebo is administered at least twice within less than 6 months, such as within 3 months, about 30 days after the second administration of the administration schedule until at least 12 months after the second administration of the administration schedule.

75. The method of item 74, wherein the lower bound is more than 30%, is more than 40%, is more than 50%, is more than 60%, is more than 70%, or is more than 75%.

76. The method of any one of items 22 to 75 having a combined vaccine efficacy against virologically-confirmed dengue with hospitalization against all four serotypes of more than 30%, when measured against placebo in a subject population of at least 2,000 healthy subjects, healthy subjects being seronegative against all serotypes at baseline, wherein said unit dose or said placebo is administered at least twice within less than 6 months, such as within 3 months, 30 days after the second administration until at least 12 months after the second administration.

77. The method of item 76, wherein the combined vaccine efficacy against virologically-confirmed dengue with hospitalization against all four serotypes is more than 40%, is more than 50%, is more than 60%, is more than 70%, is more than 80%, or is more than 90%.

78. The method of any one of items 21 to 77 having a combined vaccine efficacy against virologically-confirmed dengue with hospitalization against all four serotypes with a 2-sided 95% confidence interval, wherein the lower bound is more than 25%, when measured against placebo in a subject population of at least 2,000 healthy subjects being seropositive at baseline, wherein said unit dose or said placebo is administered at least twice within less than 6 months, such as within 3 months, about 30 days after the second administration of the administration schedule until at least 12 months after the second administration of the administration schedule.

79. The method of item 78, wherein the lower bound is more than 30%, is more than 40%, is more than 50%, is more than 60%, is more than 70%, or is more than 80%.

80. The method of any one of items 22 to 79 having a combined vaccine efficacy against virologically-confirmed dengue with hospitalization against all four serotypes of more than 30%, when measured against placebo in a subject population of at least 2,000 healthy subjects, healthy subjects being seropositive at baseline, wherein said unit dose or said placebo is administered at least twice within less than 6 months, such as within 3 months, 30 days after the second administration until at least 12 months after the second administration.
81. The method of item 80, combined vaccine efficacy against virologically-confirmed dengue with hospitalization against all four serotypes is more than 40%, is more than 50%, is more than 60%, is more than 70%, is more than 80%, or is more than 90%.
82. The method of any one of items 22 to 81 having a combined relative risk against all four dengue serotypes with a 2-sided 95% confidence interval, wherein the upper bound is less than 0.75, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.
83. The method of item 82, wherein the upper bound is less than 0.70, is less than 0.65, is less than 0.60, is less than 0.55, is less than 0.50, is less than 0.45, is less than 0.40, is less than 0.35, is less than 0.30 or is less than 0.28.
84. The method of any one of items 22 to 83, wherein the combined relative risk against all four dengue serotypes is less than 0.70, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, such as within 3 months, 30 days after the second administration until at least 12 months after the second administration.
85. The method of item 84, wherein the combined relative risk against all four serotypes is less than 0.65, is less than 0.60, is less than 0.55, is less than 0.50, is less than 0.45, is less than 0.40, is less than 0.35, is less than 0.30, is less than 0.25 or is less than 0.23.
86. The method of any one of items 22 to 85 having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects, or at least 10,000 healthy subjects, or at least 15,000 healthy subjects from endemic regions irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 or 13 months after the last administration of the administration schedule.
87. The method of any one of items 22 to 86 having a combined vaccine efficacy against all four serotypes of more than 66%, or of more than 70%, or of more than 75%, or of more than 77%, or of more than 80.0%, when measured against placebo in a subject population of at least 5,000 healthy subjects, or at least 10,000 healthy subjects, or at least 15,000 healthy subjects from endemic regions irrespective of serostatus at baseline and being selected from the group consisting of 4 to 16 year old subjects at the time of randomization, wherein said unit dose or said placebo is administered at least twice within 6 months or less, about 30 days after the last administration of the administration schedule until at least 12 months or 13 month after the last administration of the administration schedule.
88. The method of any one of items 22 to 87, wherein said unit dose or said placebo is administered at day 1 and day 90.
89. The method of any one of items 22 to 88 having a relative risk for virologically confirmed dengue with hospitalization which is 1 or less, or 0.8 or less, or 0.6 or less, when measured against placebo in a subject population of at least 1,000 healthy subjects, or at least 5,000 healthy subjects, or at least 10,000 healthy subjects irrespective of serostatus at baseline and in age groups from 4 to 16 years, in particular in subjects 4 to 5 years of age at the time of randomization.
90. The method of any one of items 22 to 89, wherein the occurrence of vaccine related serious adverse events is less than 0.1%.
91. The method of any one of items 22 to 90, wherein the occurrence of vaccine related unsolicited adverse events occurring within 4 weeks of administration is less than 2%.
92. The method of any one of items 22 to 91, wherein the occurrence of vaccine related solicited adverse events occurring within 2 weeks of administration is less than 35%.
93. The method of any one of items 22 to 92, wherein the occurrence of solicited local reactions occurring within 1 weeks of administration is less than 40%.
94. The method of any one of items 22 to 93, wherein the unit dose upon reconstitution with 0.5 mL of a pharmaceutically acceptable diluent
  (i) dengue serotype 1 has a concentration of 3.3 log 10 pfu/0.5 mL to 5.0 log 10 pfu/0.5 mL,
  (ii) dengue serotype 2 has a concentration of 2.7 log 10 pfu/0.5 mL to 4.9 log 10 pfu/0.5 mL,
  (iii) dengue serotype 3 has a concentration of 4.0 log 10 pfu/0.5 mL to 5.7 log 10 pfu/0.5 mL, and
  (iv) dengue serotype 4 has a concentration of 4.5 log 10 pfu/0.5 mL to 6.2 log 10 pfu/0.5 mL,
  and optionally comprises about 15% (w/v) α,α-trehalose dihydrate, about 1% (w/v) poloxamer 407, about 0.1% (w/v) human serum albumin, and about 100 mM sodium chloride when measured in 0.5 mL.
95. A reconstituted unit dose of a dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent
  (i) dengue serotype 1 has a concentration of at least 3.3 log 10 pfu/0.5 mL,
  (ii) dengue serotype 2 has a concentration of at least 2.7 log 10 pfu/0.5 mL,
  (iii) dengue serotype 3 has a concentration of at least 4.0 log 10 pfu/0.5 mL, and (iv) dengue serotype 4 has a concentration of at least 4.5 log 10 pfu/0.5 mL.
96. The unit dose for use of item 95, wherein the subject is under 9 years of age and/or when the serostatus of the subject is unknown or seronegative.
97. The unit dose for use of item 95 or 96, which is effective.
98. The unit dose for use of any one of items 95 to 97, which is effective against all four dengue serotypes.
99. The unit dose for use of any one of items 95 to 98, which is safe.
100. The unit dose for use of any one of items 95 to 99, wherein the unit dose includes at least one chimeric dengue virus.
101. The unit dose for use of any one of items 95 to 100, wherein the unit dose includes at least one non-chimeric dengue virus and at least one chimeric dengue virus.
102. The unit dose for use of any one of items 95 to 101, wherein the subject is seronegative to all dengue serotypes at baseline and/or is under 9 years of age.
103. The unit dose for use of any one of items 95 to 102, wherein the subject is 4 to 5 years of age or 6 to 11 years of age or 12 to 16 years of age.
104. The unit dose for use of any one of items 95 to 103, wherein the method does not comprise a determination of a previous dengue infection in the subject before the administration of the first unit dose of the tetravalent dengue virus composition.
105. The unit dose for use of any one of items 95 to 104, wherein the dengue serotype 4 represents the highest concentration in the composition of all four serotypes, optionally with at least about 70% of the total concentration in pfu/0.5 mL, dengue serotype 3 represents the second highest concentration in the composition of all four serotypes with at least about 10% of the total concentration in pfu/0.5 mL, and dengue serotype 1 and dengue serotype 2 each represent lower concentrations than the concentration of serotype 3 and together represent less than about 10% of the total concentration in pfu/0.5 mL and/or which are within 5%-points of each other.
106. The unit dose for use of any one of items 95 to 105, wherein the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain.
107. The unit dose for use of any one of items 95 to 106, wherein the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.
108. The unit dose for use of any one of items 95 to 107, wherein the unit dose further comprises from about 10 w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and from about 70 mM to 140 mM sodium chloride when measured in 0.5 mL.
109. The unit dose for use of any one of items 95 to 108, wherein the unit dose further comprises about 15 (w/v) α,α-trehalose dihydrate, about 1% (w/v) poloxamer 407, about 0.1% (w/v) human serum albumin, and about 100 mM sodium chloride when measured in 0.5 mL.
110. The unit dose for use of any one of items 95 to 109, wherein the method is for preventing dengue hemorrhagic fever (DHF) or dengue shock syndrome (DSS).
111. The unit dose for use of any one of items 95 to 110, wherein the subject is from a dengue endemic region.
112. The unit dose for use of any one of items 95 to 111, wherein the subject is from a dengue non-endemic region.
113. The unit dose for use of any one of items 95 to 112, wherein the subject is from Asia Pacific or Latin America.
114. The unit dose for use of any one items of 95 to 113, wherein the unit dose provides a seropositivity rate when it is administered to a subject population of at least 50 subjects in two unit doses subcutaneously at day 1 and at day 90, wherein the subjects of the subject population are seronegative to all dengue serotypes at baseline.
115. The unit dose for use of item 114, wherein at least one month after administration of the first unit dose, such as at day 30, at least 80% of the subject population are seropositive for all four dengue serotypes.
116. The unit dose for use of item 114 or 115, wherein before or at the time of the administration of the second unit dose, such as at day 90, at least 80% of the subject population are seropositive for all four dengue serotypes.
117. The unit dose for use of any one of items 114 to 116, wherein after the administration of the second unit dose, such as at day 120, at least 80%, or at least 85%, or at least 90% or at least 95% of the subject population are seropositive for all four dengue serotypes.
118. The unit dose for use of any one of items 114 to 117, wherein after the administration of the second unit dose, such as at day 270, at least 80%, or at least 85%, or at least 90% of the subject population are seropositive for all four dengue serotypes.
119. The unit dose for use of any one of items 114 to 118, wherein the unit dose provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.
120. The unit dose for use of any one of items 95 to 119, wherein upon reconstitution with 0.5 mL of a pharmaceutically acceptable diluent
    (i) dengue serotype 1 has a concentration of 3.3 log 10 pfu/0.5 mL to 5.0 log 10 pfu/0.5 mL,
    (ii) dengue serotype 2 has a concentration of 2.7 log 10 pfu/0.5 mL to 4.9 log 10 pfu/0.5 mL,
    (iii) dengue serotype 3 has a concentration of 4.0 log 10 pfu/0.5 mL to 5.7 log 10 pfu/0.5 mL, and
    (iv) dengue serotype 4 has a concentration of 4.5 log 10 pfu/0.5 mL to 6.2 log 10 pfu/0.5 mL.
121. The unit dose for use of any one of items 95 to 120, wherein upon reconstitution with 0.5 mL of a pharmaceutically acceptable diluent:

(i) dengue serotype 1 has a concentration of 3.3 log 10 pfu/0.5 mL to 5.0 log 10 pfu/0.5 mL,
(ii) dengue serotype 2 has a concentration of 2.7 log 10 pfu/0.5 mL to 4.9 log 10 pfu/0.5 mL,
(iii) dengue serotype 3 has a concentration of 4.0 log 10 pfu/0.5 mL to 5.7 log 10 pfu/0.5 mL, and
(iv) dengue serotype 4 has a concentration of 4.5 log 10 pfu/0.5 mL to 5.5 log 10 pfu/0.5 mL.

The invention claimed is:

1. A method of vaccinating against virologically confirmable dengue disease in subjects aged 4 to 60 years of age, the method providing a combined vaccine efficacy of at least 60% which is represented by at least 60% reduction in dengue disease occurrence in vaccinated subjects compared to unvaccinated subjects, in each of seropositive subjects and seronegative subjects, for at least 12 months after a second unit dose administration, by administering to a subject population of seropositive subjects, seronegative subjects, or a combination thereof, a tetravalent dengue virus composition including four dengue virus strains representing serotype 1, serotype 2, serotype 3 and serotype 4, represented by a chimeric dengue serotype 2/1 strain, a dengue serotype 2 strain, a chimeric dengue serotype 2/3 strain, and a chimeric dengue serotype 2/4 strain, the dengue serotype 2 strain being derived from the wild type virus strain DEN-2 16681 and differing in at least three nucleotides from the wild type as follows:
 a) 5'-noncoding region (NCR)-57 (nt-57 C-to-T)
 b) NS1-53 Gly-to-Asp (nt-2579 G-to-A)
 c) NS3-250 Glu-to-Val (nt-5270 A-to-T); and
 the three chimeric dengue strains being derived from the serotype 2 strain by replacing the structural proteins prM and E from serotype 2 strain with the corresponding structural proteins from the other dengue serotypes, resulting in the following chimeric dengue strains:
  a DENV-2/1 chimera,
  a DENV-2/3 chimera and
  a DENV-2/4 chimera,
the method consisting of:
 selecting a subject without determining whether the subject had a previous dengue infection,
 subcutaneously administering a first unit dose of said tetravalent dengue vaccine composition to said subject, the first unit dose corresponding to a dose of 0.5 ml comprising
  (i) the dengue serotype 1 with a concentration of at least 3.3 log 10 pfu/0.5 mL,
  (ii) the dengue serotype 2 with a concentration of at least 2.7 log 10 pfu/0.5 mL,
  (iii) the dengue serotype 3 with a concentration of at least 4.0 log 10 pfu/0.5 mL, and
  (iv) the dengue serotype 4 with a concentration of at least 4.5 log 10 pfu/0.5 mL,
 subcutaneously administering to said subject a second unit dose of said tetravalent dengue vaccine composition within 3 months after the first unit dose, the second unit dose corresponding to a dose of 0.5 ml comprising
  (i) the dengue serotype 1 with a concentration of at least 3.3 log 10 pfu/0.5 mL,
  (ii) the dengue serotype 2 with a concentration of at least 2.7 log 10 pfu/0.5 mL,
  (iii) the dengue serotype 3 with a concentration of at least 4.0 log 10 pfu/0.5 mL, and
  (iv) the dengue serotype 4 with a concentration of at least 4.5 log 10 pfu/0.5 mL,
and optionally administering a booster dose of said tetravalent dengue vaccine composition to said subject at least 12 months after administration of the second unit dose.

2. The method of claim 1, which is safe.

3. The method of claim 1, wherein the subject is under 9 years of age, 4 to 5 years of age, 6 to 11 years of age or 12 to 16 years of age.

4. The method of claim 1, wherein the subject or subject population is from a dengue endemic region.

5. The method of claim 1, wherein the subject or subject population is from a dengue non-endemic region.

6. The method of claim 1, wherein the occurrence of vaccine related serious adverse events is less than 0.1%.

7. The method of claim 1, wherein the combined vaccine efficacy against all four dengue serotypes is measured using a 2-sided 95% confidence interval, wherein the lower bound is more than 60%, when measured against placebo in a subject population of at least 5,000 healthy subjects, or at least 10,000 healthy subjects, or at least 15,000 healthy subjects irrespective of serostatus at baseline.

8. The method of claim 1, wherein the combined vaccine efficacy against dengue serotype 2 is measured using a 2-sided 95% confidence interval, wherein the lower bound is more than 70%, when measured against placebo in a subject population of at least 5,000 healthy subjects, or at least 10,000 healthy subjects, or at least 15,000 healthy subjects irrespective of serostatus at baseline.

9. The method of claim 1, wherein the dengue disease occurrence includes occurrences of virologically-confirmed dengue disease with hospitalization, wherein the combined vaccine efficacy against virologically-confirmed dengue disease with hospitalization against all four serotypes, is measured using a 2-sided 95% confidence interval, wherein the lower bound is more than 70%, when measured against placebo in a subject population of at least 2,000 healthy subjects being seronegative against all serotypes at baseline.

10. The method of claim 1, wherein the combined vaccine efficacy against all four dengue serotypes is measured using a 2-sided 95% confidence interval, wherein the lower bound is more than 70%, when measured against placebo in a subject population of at least 5,000 healthy subjects, or at least 10,000 healthy subjects, or at least 15,000 healthy subjects irrespective of serostatus at baseline, wherein said unit dose or said placebo is administered at least twice within less than 6 months, and optionally at least 4 weeks apart, about 30 days after the second administration of the administration schedule until at least 12 months after the second administration of the administration schedule.

11. The method of claim 1, having a combined relative risk against all four dengue serotypes with a 2-sided 95% confidence interval, wherein the upper bound is less than 0.50, when measured against placebo in a subject population of at least 5,000 healthy subjects, or at least 10,000 healthy subjects, or at least 15,000 healthy subjects irrespective of serostatus at baseline.

12. The method of claim 1, having a relative risk for dengue disease with hospitalization which is 1 or less, or 0.8 or less, or 0.6 or less, when measured against placebo in a subject population of at least 1,000 healthy subjects, or at least 5,000 healthy subjects, or at least 10,000 healthy subjects irrespective of serostatus at baseline and in age groups from 4 to 16 years.

13. The method of claim 1, wherein the unit dose upon reconstitution with 0.5 mL of a pharmaceutically acceptable diluent comprises:
 (i) dengue serotype 1 with a concentration of 3.3 log 10 pfu/0.5 mL to 5.0 log 10 pfu/0.5 mL,
 (ii) dengue serotype 2 with a concentration of 2.7 log 10 pfu/0.5 mL to 4.9 log 10 pfu/0.5 mL,
 (iii) dengue serotype 3 with a concentration of 4.0 log 10 pfu/0.5 mL to 5.7 log 10 pfu/0.5 mL, and
 (iv) dengue serotype 4 with a concentration of 4.5 log 10 pfu/0.5 mL to 6.2 log 10 pfu/0.5 mL,
 and optionally comprises about 15% (w/v) α,α-trehalose dihydrate, about 1% (w/v) poloxamer 407, about 0.1% (w/v) human serum albumin, and about 100 mM sodium chloride when measured in 0.5 mL.

14. The method of claim 1, wherein the first unit dose and second unit dose each are reconstituted from a lyophilized composition.

15. A method of vaccinating against virologically confirmable dengue disease with hospitalization in subjects aged 4 to 60 years of age, the method providing a combined vaccine efficacy against virologically confirmable dengue disease with hospitalization of at least 70% which is represented by a reduction of at least 70% dengue disease with hospitalization occurrence in vaccinated subjects aged 4 to 60 years compared to unvaccinated subjects, in each of seropositive subjects and seronegative subjects, for at least 12 months after a second unit dose administration, by administering to a subject population of seropositive subjects, seronegative subjects, or a combination thereof a tetravalent dengue virus composition including four dengue virus strains representing serotype 1, serotype 2, serotype 3 and serotype 4, represented by a chimeric dengue serotype 2/1 strain, a dengue serotype 2 strain, a chimeric dengue serotype 2/3 strain, and a chimeric dengue serotype 2/4 strain, the dengue serotype 2 strain being derived from the wild type virus strain DEN-2 16681 and differing in at least three nucleotides from the wild type as follows:
a) 5'-noncoding region (NCR)-57 (nt-57 C-to-T)
b) NS1-53 Gly-to-Asp (nt-2579 G-to-A)

c) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera, the method consisting of:

selecting a subject without determining whether the subject had a previous dengue infection, subcutaneously administering a first unit dose of said tetravalent dengue vaccine composition to said subject, the first unit dose corresponding to a dose of 0.5 ml comprising (i) the dengue serotype 1 with a concentration of at least 3.3 log 10 pfu/0.5 mL, (ii) the dengue serotype 2 with a concentration of at least 2.7 log 10 pfu/0.5 mL, (iii) the dengue serotype 3 with a concentration of at least 4.0 log 10 pfu/0.5 mL, and (iv) the dengue serotype 4 with a concentration of at least 4.5 log 10 pfu/0.5 mL, subcutaneously administering to said subject a second unit dose of said tetravalent dengue vaccine composition within 3 months after the first unit dose, the second unit dose corresponding to a dose of 0.5 ml comprising (i) the dengue serotype 1 with a concentration of at least 3.3 log 10 pfu/0.5 mL, (ii) the dengue serotype 2 with a concentration of at least 2.7 log 10 pfu/0.5 mL, (iii) the dengue serotype 3 with a concentration of at least 4.0 log 10 pfu/0.5 mL, and (iv) the dengue serotype 4 with a concentration of at least 4.5 log 10 pfu/0.5 mL, and optionally administering a booster dose of said tetravalent dengue vaccine composition to said subject at least 12 months after administration of the second unit dose.

16. The method of claim 1, wherein the combined vaccine efficacy is 70% or more.

17. The method of claim 15, wherein the combined vaccine efficacy is more than 75%.

18. The method of claim 1, wherein the subject is from 4 years old to 16 years old.

19. The method of claim 15, wherein the subject is from 4 years old to 16 years old.

* * * * *

SEQUENCE LISTING

<160> NUMBER OF SEQ ID NOS: 8

<210> SEQ ID NO 1
<211> LENGTH: 10723
<212> TYPE: DNA
<213> ORGANISM: chimeric dengue seroytpe 2/1 (MVS)

<400> SEQUENCE: 1

```
agttgttagt ctacgtggac cgacaaagac agattctttg agggagctaa gctcaatgta      60
gttctaacag ttttttaatt agagagcaga tctctgatga ataaccaacg gaaaaaggcg     120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag gaaagagatt     360
ggaaggatgc tgaacatctt gaataggaga cgcagatctg caggcatgat cattatgctg     420
attccaacag tgatggcgtt ccatttaacc acgcgtgggg gagagccgca tatgatagtt     480
agcaagcagg aaagaggaaa gtcacttttg ttcaagacct ctgcaggtgt caacatgtgc     540
accctcattg cgatggattt gggagagttg tgtgaggaca cgatgaccta caaatgcccc     600
cggatcactg aggcggaacc agatgacgtt gactgttggt gcaatgccac ggacacatgg     660
gtgacctatg aacgtgctc tcaaactggc gaacaccgac gagacaaacg ttccgtcgca     720
ttggccccac acgtggggct tggcctagaa acaagagccg aaacgtggat gtcctctgaa     780
ggtgcttgga acagataca aaaagtagag acttgggctc tgagacatcc aggattcacg     840
gtgatagccc tttttctagc acatgccata ggaacatcca tcacccagaa agggatcatt     900
ttcattttgc tgatgctggt aacaccatct atggccatgc gatgcgtggg aataggcaac     960
agagacttcg tggaaggact gtcaggagca catgggtgg atgtggtact ggagcatgga    1020
agttgcgtca ccaccatggc aaaaaacaaa ccaacactgg acattgaact cttgaagacg    1080
gaggtcacaa accctgcagt tctgcgtaaa ttgtgcattg aagctaaaat atcaaacacc    1140
accacgattc gagatgtcc aacacaagga gaagccacac tggtggaaga caagacgcg    1200 aactttgtgt gccgacgaac gttcgtggac agaggctggg gcaatggctg tgggctattc    1260
ggaaaaggta gtctaataac gtgtgccaag tttaagtgtg tgacaaaact agaaggaaag    1320
atagttcaat atgaaaacct aaaatattca gtgatagtca ccgtccacac tggagatcag    1380
caccaggtgg gaaatgagac tacagaacat ggaacaactg caaccataac acctcaagct    1440
cctacgtcgg aaatacagct gaccgactac ggaacccta cattagattg ttcacctagg    1500
acagggctag attttaacga gatggtgttg ctgcaatga agaaagatc atggcttgtc    1560 cacaaacaat ggttcctaga cttaccactg ccttggacct ctgggcttc aacatcccaa    1620 gagacttgga acagacaaga tttactggtc acatttaaga cagctcatgc aaagaagcag    1680
gaagtagtcg tactaggatc acaagaagga gcaatgcaca ctgcgctgac tggagcgaca    1740
gaaatccaaa cgtcaggaac gacaacaatt ttcgcaggac acctaaaatg cagactaaaa    1800
atggacaaac taacttaaa agggatgtca tatgtgatgt gcacaggctc attcaagtta    1860
gagaaagaag tggctgagac ccagcatgga actgttctgg tgcaggttaa atatgaagga    1920
```

| | |
|---|---|
| acagacgcac catgcaagat tcccttttcg acccaagatg agaaaggagc aacccagaat | 1980 |
| gggagattaa taacagccaa ccccatagtc actgacaaag aaaaaccagt caatattgag | 2040 |
| gcagaaccac cctttggtga gagctacatc gtggtaggag caggtgaaaa agctttgaaa | 2100 |
| ctaagctggt tcaagaaagg aagcagcata gggaaaatgt ttgaagcaac tgcccgagga | 2160 |
| gcacgaagga tggccattct gggagacacc gcatgggact tcggttctat aggaggagtg | 2220 |
| ttcacgtcta tgggaaaact ggtacaccag gttttttggaa ctgcatatgg agttttgttt | 2280 |
| agcggagttt cttggaccat gaaaatagga atagggattc tgctgacatg gctaggatta | 2340 |
| aattcaagga acacgtccct ttcgatgatg tgcatcgcag ccggcattgt gacactgtat | 2400 |
| ttgggagtca tggtgcaggc cgatagtggt tgcgttgtga gctggaaaaa caagaactg | 2460 |
| aaatgtggca gtgggatttt catcacagac aacgtgcaca catggacaga acaatacaag | 2520 |
| ttccaaccag aatccccttc aaaactagct tcagctatcc agaaagccca tgaagaggac | 2580 |
| atttgtggaa tccgctcagt aacaagactg gagaatctga tgtggaaaca aataacacca | 2640 |
| gaattgaatc acattctatc agaaaatgag gtgaagttaa ctattatgac aggagacatc | 2700 |
| aaaggaatca tgcaggcagg aaaacgatct ctgcggcctc agcccactga gctgaagtat | 2760 |
| tcatggaaaa catggggcaa agcaaaaatg ctctctacag agtctcataa ccagaccttt | 2820 |
| ctcattgatg gccccgaaac agcagaatgc cccaacacaa atagagcttg gaattcgttg | 2880 |
| gaagttgaag actatggctt tggagtattc accaccaata tatggctaaa attgaaagaa | 2940 |
| aaacaggatg tattctgcga ctcaaaactc atgtcagcgg ccataaaaga caacagagcc | 3000 |
| gtccatgccg atatgggtta ttggatagaa agtgcactca atgacacatg gaagatagag | 3060 |
| aaagcctctt tcattgaagt taaaaactgc cactggccaa aatcacacac cctctggagc | 3120 |
| aatggagtgc tagaaagtga gatgataatt ccaagaatc tcgctggacc agtgtctcaa | 3180 |
| cacaactata gaccaggcta ccatacacaa ataacaggac catggcatct aggtaagctt | 3240 |
| gagatggact ttgatttctg tgatggaaca acagtggtag tgactgagga ctgcggaaat | 3300 |
| agaggaccct ctttgagaac aaccactgcc tctggaaaac tcataacaga atggtgctgc | 3360 |
| cgatcttgca cattaccacc gctaagatac agaggtgagg atgggtgctg gtacgggatg | 3420 |
| gaaatcagac cattgaagga gaagaagag aatttggtca actccttggt cacagctgga | 3480 |
| catgggcagg tcgacaactt ttcactagga gtcttgggaa tggcattgtt cctggaggaa | 3540 |
| atgcttagga cccgagtagg aacgaaacat gcaatactac tagttgcagt ttcttttgtg | 3600 |
| acattgatca cagggaacat gtcctttaga gacctgggaa gagtgatggt tatggtaggc | 3660 |
| gccactatga cggatgacat aggtatgggc gtgacttatc ttgccctact agcagccttc | 3720 |
| aaagtcagac caactttttgc agctggacta ctcttgagaa agctgacctc caaggaattg | 3780 |
| atgatgacta ctataggaat tgtactcctc tcccagagca ccctaccaga gaccattctt | 3840 |
| gagttgactg atgcgttagc cttaggcatg atggtcctca aaatggtgag aaatatggaa | 3900 |
| aagtatcaat tggcagtgac tatcatggct atcttgtgcg tcccaaacgc agtgatatta | 3960 |
| caaaacgcat ggaaagtgag ttgcacaata ttggcagtgg tgtccgtttc cccactgttc | 4020 |
| ttaacatcct cacagcaaaa aacagattgg ataccattag cattgacgat caaaggtctc | 4080 |
| aatccaacag ctatttttct aacaaccctc tcaagaacca gcaagaaaag gagctggcca | 4140 |
| ttaaatgagg ctatcatggc agtcgggatg gtgagcattt agccagttc tctcctaaaa | 4200 |
| aatgatattc ccatgacagg accattagtg gctggagggc tcctcactgt gtgctacgtg | 4260 |

```
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagatcaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag     4740
aaagacctaa tatcatatgg aggaggctgg aagttagaag agaatggaa ggaaggagaa     4800
gaagtccagg tattggcact ggagcctgga aaaaatccaa gagccgtcca aacgaaacct    4860
ggtctttcca aaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag atcgaagaa tgacattttc cgaaagagaa gactgaccat catggaccct    5100
cacccaggag cggaaaagac gaagagatac cttccggcca tagtcagaga agctataaaa    5160
cggggtttga gaacattaat cttggccccc actagagttg tggcagctga atggaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggatttt    5460
atgacagcca ctccccgggg aagcagagac ccatttcctc agagcaatgc accaatcata    5520
gatgaagaaa gagaaatccc tgaacgctcg tggaattccg acatgaatg ggtcacggat    5580
tttaaaggga gactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata daccccagac gctgcatgaa accagtcata    5820
ctaacagatg gtgaagagcg ggtgattctg gcaggaccta tgccagtgac ccactctagt    5880
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aagaagggg aaaggaagaa attgaaaccc    6300
agatggttgg atgctaggat ctattctgac ccactggcgc taaagaatt taaggaattt    6360
gcagccggaa gaaagtctct gaccctgaac ctaatcacag aaatgggtag ctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct tttattctt gatgagcgca    6600
agggcatag gaagatgac cctgggaatg tgctgcataa tcacggctag catcctccta    6660
```

```
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc gaagtttgaa   7320
aagcagttgg acaagtaat gctcctagtc tctgcgtga ctcaagtatt gatgatgagg     7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaagtga attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt ttttaaagag   8640
aaagtggaca cgagaaccca agaaccgaaa gaaggcacga gaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
```

-continued

```
tggcttggag cacgcttctt agagtttgaa gccctaggat tcttaaatga agatcactgg    9060
ttctccagag agaactccct gagtggagtg aaggagaag gctgcacaa gctaggttac     9120 attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca taacaatg gaaccttca    9660 agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aagagaaga ccaatggtgc ggctcattga ttgggttaac aagcagggcc     10140
acctgggcaa gaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga acaaggcta gaagtcaggt cggattaagc     10320
catagtacgg aaaaaactat gctacctgtg agccccgtcc aaggacgtta aaagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat gggggcccaa ggcgagatga   10560
agctgtagtc tcgctggaag gactagaggt tagaggagac ccccgaaa caaaaaacag    10620 catattgacg ctgggaaaga ccagagatcc tgctgtctcc tcagcatcat ccaggcaca    10680 gaacgccaga aatggaatg gtgctgttga atcaacaggt tct                      10723
```

<210> SEQ ID NO 2
<211> LENGTH: 3391
<212> TYPE: PRT
<213> ORGANISM: chimeric dengue serotype 2/1 (MVS)

<400> SEQUENCE: 2

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val

```
            65                  70                  75                  80
Leu Arg Gly Phe Arg Lys Glu Ile Gly Arg Met Leu Asn Ile Leu Asn
                    85                  90                  95

Arg Arg Arg Ser Ala Gly Met Ile Ile Met Leu Ile Pro Thr Val
            100                 105                 110

Met Ala Phe His Leu Thr Thr Arg Gly Gly Pro His Met Ile Val
            115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
            195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
            275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
            355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
            435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495
```

```
Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Leu Gly Ser Gln Glu Gly Ala Met His Thr Ala Leu
    530                 535                 540

Thr Gly Ala Thr Glu Ile Gln Thr Ser Gly Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910
```

Pro Glu Thr Ala Glu Cys Pro Asn Thr Asn Arg Ala Trp Asn Ser Leu
915                 920                 925

Glu Val Glu Asp Tyr Gly Phe Gly Val Phe Thr Thr Asn Ile Trp Leu
930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
            995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Thr Leu Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu

```
         1310                1315                1320
Thr Ile Lys Gly Leu Asn Pro Thr Ala Ile Phe Leu Thr Thr Leu
         1325                1330                1335
Ser Arg Thr Ser Lys Lys Arg Ser Trp Pro Leu Asn Glu Ala Ile
         1340                1345                1350
Met Ala Val Gly Met Val Ser Ile Leu Ala Ser Ser Leu Leu Lys
         1355                1360                1365
Asn Asp Ile Pro Met Thr Gly Pro Leu Val Ala Gly Gly Leu Leu
         1370                1375                1380
Thr Val Cys Tyr Val Leu Thr Gly Arg Ser Ala Asp Leu Glu Leu
         1385                1390                1395
Glu Arg Ala Ala Asp Val Lys Trp Glu Asp Gln Ala Glu Ile Ser
         1400                1405                1410
Gly Ser Ser Pro Ile Leu Ser Ile Thr Ile Ser Glu Asp Gly Ser
         1415                1420                1425
Met Ser Ile Lys Asn Glu Glu Glu Asp Gln Thr Leu Thr Ile Leu
         1430                1435                1440
Ile Arg Thr Gly Leu Leu Val Ile Ser Gly Leu Phe Pro Val Ser
         1445                1450                1455
Ile Pro Ile Thr Ala Ala Ala Trp Tyr Leu Trp Glu Val Lys Lys
         1460                1465                1470
Gln Arg Ala Gly Val Leu Trp Asp Val Pro Ser Pro Pro Pro Met
         1475                1480                1485
Gly Lys Ala Glu Leu Glu Asp Gly Ala Tyr Arg Ile Lys Gln Lys
         1490                1495                1500
Gly Ile Leu Gly Tyr Ser Gln Ile Gly Ala Gly Val Tyr Lys Glu
         1505                1510                1515
Gly Thr Phe His Thr Met Trp His Val Thr Arg Gly Ala Val Leu
         1520                1525                1530
Met His Lys Gly Lys Arg Ile Glu Pro Ser Trp Ala Asp Val Lys
         1535                1540                1545
Lys Asp Leu Ile Ser Tyr Gly Gly Gly Trp Lys Leu Glu Gly Glu
         1550                1555                1560
Trp Lys Glu Gly Glu Glu Val Gln Val Leu Ala Leu Glu Pro Gly
         1565                1570                1575
Lys Asn Pro Arg Ala Val Gln Thr Lys Pro Gly Leu Phe Lys Thr
         1580                1585                1590
Asn Ala Gly Thr Ile Gly Ala Val Ser Leu Asp Phe Ser Pro Gly
         1595                1600                1605
Thr Ser Gly Ser Pro Ile Ile Asp Lys Lys Gly Lys Val Val Gly
         1610                1615                1620
Leu Tyr Gly Asn Gly Val Val Thr Arg Ser Gly Ala Tyr Val Ser
         1625                1630                1635
Ala Ile Ala Gln Thr Glu Lys Ser Ile Glu Asp Asn Pro Glu Ile
         1640                1645                1650
Glu Asp Asp Ile Phe Arg Lys Arg Arg Leu Thr Ile Met Asp Leu
         1655                1660                1665
His Pro Gly Ala Gly Lys Thr Lys Arg Tyr Leu Pro Ala Ile Val
         1670                1675                1680
Arg Glu Ala Ile Lys Arg Gly Leu Arg Thr Leu Ile Leu Ala Pro
         1685                1690                1695
Thr Arg Val Val Ala Ala Glu Met Glu Glu Ala Leu Arg Gly Leu
         1700                1705                1710
```

-continued

Pro Ile Arg Tyr Gln Thr Pro Ala Ile Arg Ala Val His Thr Gly
1715                1720                1725

Arg Glu Ile Val Asp Leu Met Cys His Ala Thr Phe Thr Met Arg
1730                1735                1740

Leu Leu Ser Pro Val Arg Val Pro Asn Tyr Asn Leu Ile Ile Met
1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Ala Gly Ile Phe
1775                1780                1785

Met Thr Ala Thr Pro Pro Gly Ser Arg Asp Pro Phe Pro Gln Ser
1790                1795                1800

Asn Ala Pro Ile Ile Asp Glu Glu Arg Glu Ile Pro Glu Arg Ser
1805                1810                1815

Trp Asn Ser Gly His Glu Trp Val Thr Asp Phe Lys Gly Lys Thr
1820                1825                1830

Val Trp Phe Val Pro Ser Ile Lys Ala Gly Asn Asp Ile Ala Ala
1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile
1895                1900                1905

Leu Thr Asp Gly Glu Glu Arg Val Ile Leu Ala Gly Pro Met Pro
1910                1915                1920

Val Thr His Ser Ser Ala Ala Gln Arg Arg Gly Arg Ile Gly Arg
1925                1930                1935

Asn Pro Lys Asn Glu Asn Asp Gln Tyr Ile Tyr Met Gly Glu Pro
1940                1945                1950

Leu Glu Asn Asp Glu Asp Cys Ala His Trp Lys Glu Ala Lys Met
1955                1960                1965

Leu Leu Asp Asn Ile Asn Thr Pro Glu Gly Ile Ile Pro Ser Met
1970                1975                1980

Phe Glu Pro Glu Arg Glu Lys Val Asp Ala Ile Asp Gly Glu Tyr
1985                1990                1995

Arg Leu Arg Gly Glu Ala Arg Lys Thr Phe Val Asp Leu Met Arg
2000                2005                2010

Arg Gly Asp Leu Pro Val Trp Leu Ala Tyr Arg Val Ala Ala Glu
2015                2020                2025

Gly Ile Asn Tyr Ala Asp Arg Arg Trp Cys Phe Asp Gly Val Lys
2030                2035                2040

Asn Asn Gln Ile Leu Glu Glu Asn Val Glu Val Glu Ile Trp Thr
2045                2050                2055

Lys Glu Gly Glu Arg Lys Lys Leu Lys Pro Arg Trp Leu Asp Ala
2060                2065                2070

Arg Ile Tyr Ser Asp Pro Leu Ala Leu Lys Glu Phe Lys Glu Phe
2075                2080                2085

Ala Ala Gly Arg Lys Ser Leu Thr Leu Asn Leu Ile Thr Glu Met
2090                2095                2100

```
Gly Arg Leu Pro Thr Phe Met Thr Gln Lys Ala Arg Asp Ala Leu
2105                2110                2115

Asp Asn Leu Ala Val Leu His Thr Ala Glu Ala Gly Gly Arg Ala
2120                2125                2130

Tyr Asn His Ala Leu Ser Glu Leu Pro Glu Thr Leu Glu Thr Leu
2135                2140                2145

Leu Leu Leu Thr Leu Leu Ala Thr Val Thr Gly Gly Ile Phe Leu
2150                2155                2160

Phe Leu Met Ser Ala Arg Gly Ile Gly Lys Met Thr Leu Gly Met
2165                2170                2175

Cys Cys Ile Ile Thr Ala Ser Ile Leu Leu Trp Tyr Ala Gln Ile
2180                2185                2190

Gln Pro His Trp Ile Ala Ala Ser Ile Ile Leu Glu Phe Phe Leu
2195                2200                2205

Ile Val Leu Leu Ile Pro Glu Pro Glu Lys Gln Arg Thr Pro Gln
2210                2215                2220

Asp Asn Gln Leu Thr Tyr Val Val Ile Ala Ile Leu Thr Val Val
2225                2230                2235

Ala Ala Thr Met Ala Asn Glu Met Gly Phe Leu Glu Lys Thr Lys
2240                2245                2250

Lys Asp Leu Gly Leu Gly Ser Ile Ala Thr Gln Gln Pro Glu Ser
2255                2260                2265

Asn Ile Leu Asp Ile Asp Leu Arg Pro Ala Ser Ala Trp Thr Leu
2270                2275                2280

Tyr Ala Val Ala Thr Thr Phe Val Thr Pro Met Leu Arg His Ser
2285                2290                2295

Ile Glu Asn Ser Ser Val Asn Val Ser Leu Thr Ala Ile Ala Asn
2300                2305                2310

Gln Ala Thr Val Leu Met Gly Leu Gly Lys Gly Trp Pro Leu Ser
2315                2320                2325

Lys Met Asp Ile Gly Val Pro Leu Leu Ala Ile Gly Cys Tyr Ser
2330                2335                2340

Gln Val Asn Pro Ile Thr Leu Thr Ala Ala Leu Phe Leu Leu Val
2345                2350                2355

Ala His Tyr Ala Ile Ile Gly Pro Gly Leu Gln Ala Lys Ala Thr
2360                2365                2370

Arg Glu Ala Gln Lys Arg Ala Ala Ala Gly Ile Met Lys Asn Pro
2375                2380                2385

Thr Val Asp Gly Ile Thr Val Ile Asp Leu Asp Pro Ile Pro Tyr
2390                2395                2400

Asp Pro Lys Phe Glu Lys Gln Leu Gly Gln Val Met Leu Leu Val
2405                2410                2415

Leu Cys Val Thr Gln Val Leu Met Met Arg Thr Thr Trp Ala Leu
2420                2425                2430

Cys Glu Ala Leu Thr Leu Ala Thr Gly Pro Ile Ser Thr Leu Trp
2435                2440                2445

Glu Gly Asn Pro Gly Arg Phe Trp Asn Thr Thr Ile Ala Val Ser
2450                2455                2460

Met Ala Asn Ile Phe Arg Gly Ser Tyr Leu Ala Gly Ala Gly Leu
2465                2470                2475

Leu Phe Ser Ile Met Lys Asn Thr Thr Asn Thr Arg Arg Gly Thr
2480                2485                2490

Gly Asn Ile Gly Glu Thr Leu Gly Glu Lys Trp Lys Ser Arg Leu
```

-continued

```
               2495                2500                2505

Asn Ala Leu Gly Lys Ser Glu Phe Gln Ile Tyr Lys Lys Ser Gly
        2510                2515                2520

Ile Gln Glu Val Asp Arg Thr Leu Ala Lys Glu Gly Ile Lys Arg
        2525                2530                2535

Gly Glu Thr Asp His His Ala Val Ser Arg Gly Ser Ala Lys Leu
        2540                2545                2550

Arg Trp Phe Val Glu Arg Asn Met Val Thr Pro Glu Gly Lys Val
        2555                2560                2565

Val Asp Leu Gly Cys Gly Arg Gly Gly Trp Ser Tyr Tyr Cys Gly
        2570                2575                2580

Gly Leu Lys Asn Val Arg Glu Val Lys Gly Leu Thr Lys Gly Gly
        2585                2590                2595

Pro Gly His Glu Glu Pro Ile Pro Met Ser Thr Tyr Gly Trp Asn
        2600                2605                2610

Leu Val Arg Leu Gln Ser Gly Val Asp Val Phe Phe Ile Pro Pro
        2615                2620                2625

Glu Lys Cys Asp Thr Leu Leu Cys Asp Ile Gly Glu Ser Ser Pro
        2630                2635                2640

Asn Pro Thr Val Glu Ala Gly Arg Thr Leu Arg Val Leu Asn Leu
        2645                2650                2655

Val Glu Asn Trp Leu Asn Asn Asn Thr Gln Phe Cys Ile Lys Val
        2660                2665                2670

Leu Asn Pro Tyr Met Pro Ser Val Ile Glu Lys Met Glu Ala Leu
        2675                2680                2685

Gln Arg Lys Tyr Gly Gly Ala Leu Val Arg Asn Pro Leu Ser Arg
        2690                2695                2700

Asn Ser Thr His Glu Met Tyr Trp Val Ser Asn Ala Ser Gly Asn
        2705                2710                2715

Ile Val Ser Ser Val Asn Met Ile Ser Arg Met Leu Ile Asn Arg
        2720                2725                2730

Phe Thr Met Arg Tyr Lys Lys Ala Thr Tyr Glu Pro Asp Val Asp
        2735                2740                2745

Leu Gly Ser Gly Thr Arg Asn Ile Gly Ile Glu Ser Glu Ile Pro
        2750                2755                2760

Asn Leu Asp Ile Ile Gly Lys Arg Ile Glu Lys Ile Lys Gln Glu
        2765                2770                2775

His Glu Thr Ser Trp His Tyr Asp Gln Asp His Pro Tyr Lys Thr
        2780                2785                2790

Trp Ala Tyr His Gly Ser Tyr Glu Thr Lys Gln Thr Gly Ser Ala
        2795                2800                2805

Ser Ser Met Val Asn Gly Val Val Arg Leu Leu Thr Lys Pro Trp
        2810                2815                2820

Asp Val Val Pro Met Val Thr Gln Met Ala Met Thr Asp Thr Thr
        2825                2830                2835

Pro Phe Gly Gln Gln Arg Val Phe Lys Glu Lys Val Asp Thr Arg
        2840                2845                2850

Thr Gln Glu Pro Lys Glu Gly Thr Lys Lys Leu Met Lys Ile Thr
        2855                2860                2865

Ala Glu Trp Leu Trp Lys Glu Leu Gly Lys Lys Lys Thr Pro Arg
        2870                2875                2880

Met Cys Thr Arg Glu Glu Phe Thr Arg Lys Val Arg Ser Asn Ala
        2885                2890                2895
```

Ala Leu Gly Ala Ile Phe Thr Asp Glu Asn Lys Trp Lys Ser Ala
2900              2905                    2910

Arg Glu Ala Val Glu Asp Ser Arg Phe Trp Glu Leu Val Asp Lys
2915              2920                    2925

Glu Arg Asn Leu His Leu Glu Gly Lys Cys Glu Thr Cys Val Tyr
2930              2935                    2940

Asn Met Met Gly Lys Arg Glu Lys Lys Leu Gly Glu Phe Gly Lys
2945              2950                    2955

Ala Lys Gly Ser Arg Ala Ile Trp Tyr Met Trp Leu Gly Ala Arg
2960              2965                    2970

Phe Leu Glu Phe Glu Ala Leu Gly Phe Leu Asn Glu Asp His Trp
2975              2980                    2985

Phe Ser Arg Glu Asn Ser Leu Ser Gly Val Glu Gly Glu Gly Leu
2990              2995                    3000

His Lys Leu Gly Tyr Ile Leu Arg Asp Val Ser Lys Lys Glu Gly
3005              3010                    3015

Gly Ala Met Tyr Ala Asp Asp Thr Ala Gly Trp Asp Thr Arg Ile
3020              3025                    3030

Thr Leu Glu Asp Leu Lys Asn Glu Glu Met Val Thr Asn His Met
3035              3040                    3045

Glu Gly Glu His Lys Lys Leu Ala Glu Ala Ile Phe Lys Leu Thr
3050              3055                    3060

Tyr Gln Asn Lys Val Val Arg Val Gln Arg Pro Thr Pro Arg Gly
3065              3070                    3075

Thr Val Met Asp Ile Ile Ser Arg Arg Asp Gln Arg Gly Ser Gly
3080              3085                    3090

Gln Val Gly Thr Tyr Gly Leu Asn Thr Phe Thr Asn Met Glu Ala
3095              3100                    3105

Gln Leu Ile Arg Gln Met Glu Gly Glu Gly Val Phe Lys Ser Ile
3110              3115                    3120

Gln His Leu Thr Ile Thr Glu Glu Ile Ala Val Gln Asn Trp Leu
3125              3130                    3135

Ala Arg Val Gly Arg Glu Arg Leu Ser Arg Met Ala Ile Ser Gly
3140              3145                    3150

Asp Asp Cys Val Val Lys Pro Leu Asp Asp Arg Phe Ala Ser Ala
3155              3160                    3165

Leu Thr Ala Leu Asn Asp Met Gly Lys Ile Arg Lys Asp Ile Gln
3170              3175                    3180

Gln Trp Glu Pro Ser Arg Gly Trp Asn Asp Trp Thr Gln Val Pro
3185              3190                    3195

Phe Cys Ser His His Phe His Glu Leu Ile Met Lys Asp Gly Arg
3200              3205                    3210

Val Leu Val Val Pro Cys Arg Asn Gln Asp Glu Leu Ile Gly Arg
3215              3220                    3225

Ala Arg Ile Ser Gln Gly Ala Gly Trp Ser Leu Arg Glu Thr Ala
3230              3235                    3240

Cys Leu Gly Lys Ser Tyr Ala Gln Met Trp Ser Leu Met Tyr Phe
3245              3250                    3255

His Arg Arg Asp Leu Arg Leu Ala Ala Asn Ala Ile Cys Ser Ala
3260              3265                    3270

Val Pro Ser His Trp Val Pro Thr Ser Arg Thr Thr Trp Ser Ile
3275              3280                    3285

-continued

```
His Ala Lys His Glu Trp Met Thr Thr Glu Asp Met Leu Thr Val
    3290            3295                3300
Trp Asn Arg Val Trp Ile Gln Glu Asn Pro Trp Met Glu Asp Lys
    3305            3310                3315
Thr Pro Val Glu Ser Trp Glu Ile Pro Tyr Leu Gly Lys Arg
    3320            3325                3330
Glu Asp Gln Trp Cys Gly Ser Leu Ile Gly Leu Thr Ser Arg Ala
    3335            3340                3345
Thr Trp Ala Lys Asn Ile Gln Ala Ala Ile Asn Gln Val Arg Ser
    3350            3355                3360
Leu Ile Gly Asn Glu Glu Tyr Thr Asp Tyr Met Pro Ser Met Lys
    3365            3370                3375
Arg Phe Arg Arg Glu Glu Glu Ala Gly Val Leu Trp
    3380            3385                3390
```

<210> SEQ ID NO 3
<211> LENGTH: 10723
<212> TYPE: DNA
<213> ORGANISM: dengue serotype 2 (MVS)

<400> SEQUENCE: 3

```
agttgttagt ctacgtggac cgacaaagac agattctttg agggagctaa gctcaatgta      60
gttctaacag tttttaatt agagagcaga tctctgatga ataaccaacg aaaaaggcg       120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg agaaccaca catgatcgtc      480
agcagacaag agaaagggaa agtcttctg tttaaaacag aggttggcgt gaacatgtgt      540
accctcatgg ccatggacct tggtgaattg tgtgaagaca caatcacgta cgagtgtccc    600
cttctcaggc agaatgagcc agaagacata gactgttggt gcaactctac gtccacgtgg    660
gtaacttatg gacgtgtac caccatggga aacatagaa agaaaaaag atcagtggca      720
ctcgttccac atgtgggaat gggactggag acacgaactg aaacatggat gtcatcagaa    780
ggggcctgga acatgtcca gagaattgaa acttggatct tgagacatcc aggcttcacc    840
atgatggcag caatcctggc atacaccata ggaacgacac atttccaaag agccctgatc    900
ttcatcttac tgacagctgt cactccttca atgacaatgc gttgcatagg aatgtcaaat    960
agagactttg tggaagggt ttcaggagga agctgggttg acatagtctt agaacatgga    1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaagaacat ggaaggaaaa    1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
```

```
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460 aaaatgtggca gtgggatttt catcacagac aacgtgcaca catggacaga acaatacaag    2520
ttccaaccag aatcccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagacctt    2820 ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct cttgagaac aaccactgcc tctggaaaac tcataacaga tggtgctgc    3360 cgatcttgca cattaccacc gctaagatac agaggtgagg atgggtgctg gtacgggatg    3420
gaaatcagac cattgaagga aaagaagag aatttggtca actccttggt cacagctgga    3480
catgggcagg tcgacaactt ttcactagga gtcttggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caactttgc agctggacta ctcttgagaa agctgacctc caaggaattg    3780
atgatgacta ctataggaat tgtactcctc tcccagcagc cataccaga gaccattctt    3840 gagttgactg atgcgttagc cttaggcatg atggtcctca aaatggtgag aaatatggaa    3900
```

```
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttcct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg agagagcag  ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactgaaga  tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaagttg  tgggtcttta tggtaatggt    4980
gttgttacaa ggagtggagc atatgtgagt gctatagccc agactgaaaa aagcattgaa    5040
gacaacccag atcgaagaa  tgacattttc cgaaagagaa gactgaccat catggaccte    5100 cacccaggag cgggaaagac gaagagatac cttccggcca tagtcagaga gctataaaa    5160 cggggtttga gaacattaat cttggccccc actagagttg tggcagctga atggaggaa     5220 gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggatttt     5460 atgacagcca ctcccccggg aagcagagac ccatttcctc agagcaatgc accaatcata    5520
gatgaagaaa gagaaatccc tgaacgctcg tggaattccg acatgaatg  ggtcacggat    5580 tttaagggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg tgaagagcg  ggtgattctg gcaggaccta tgccagtgac ccactctagt    5880
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag  gaaaaccttt    6120 gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
```

```
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctctttttcta ttatgaagaa cacaaccaac    7560
acaagaaggg gaactggcaa cataggagag acgcttggag agaaatggaa agccgattg    7620 aacgcattgg gaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttaacaa caacactcaa    8100 ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt cgtcccatg    8580 gtgacacaga tggcaatgac agacacgact ccatttggac aacagcgcgt ttttaaagag    8640
```

-continued

```
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccgtattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg gaaggagaag ggctgcacaa gctaggttac    9120
attctaagag acgtgagcaa aaagagggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatgac ttgtgttgtg aaacctttag atgacaggtt cgcaagcgct    9600
ttaacagctc taaatgacat gggaaagatt aggaaagaca tacaacaatg gaaccttca     9660 agaggatgga tgattggac acaagtgccc ttctgttcac accatttcca tgagttaatc     9720
atgaaagacg gtcgcgtact cgttgttcca tgtagaaacc aagatgaact gattggcaga     9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg    10020
attcaagaaa acccatggat ggaagacaaa actccagtgg aatcatggga ggaaatccca    10080
tacttgggga aaagagaaga ccaatggtgc ggctcattga ttgggttaac aagcagggcc    10140
acctgggcaa agaacatcca agcagcaata aatcaagtta gatcccttat aggcaatgaa    10200
gaatacacag attacatgcc atccatgaaa agattcagaa gagaagagga agaagcagga    10260
gttctgtggt agaaagcaaa actaacatga aacaaggcta gaagtcaggt cggattaagc    10320
catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gacccctccc ttacaaatcg cagcaacaat ggggggccaa ggcgagatga    10560
agctgtagtc tcgctggaag gactagaggt tagaggagac cccccgaaa caaaaaacag     10620 catattgacg ctgggaaaga ccagagatcc tgctgtctcc tcagcatcat tccaggcaca    10680
gaacgccaga aaatggaatg gtgctgttga atcaacaggt tct                      10723
```

<210> SEQ ID NO 4
<211> LENGTH: 3391
<212> TYPE: PRT
<213> ORGANISM: dengue seroytpe 2 (MVS)

<400> SEQUENCE: 4

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Ser Thr Ser Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
```

```
              420             425             430
Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
            835                 840                 845
```

-continued

```
Glu Leu Asn His Ile Leu Ser Glu Asn Glu Val Lys Leu Thr Ile Met
    850                 855                 860
Thr Gly Asp Ile Lys Gly Ile Met Gln Ala Gly Lys Arg Ser Leu Arg
865                 870                 875                 880
Pro Gln Pro Thr Glu Leu Lys Tyr Ser Trp Lys Thr Trp Gly Lys Ala
                885                 890                 895
Lys Met Leu Ser Thr Glu Ser His Asn Gln Thr Phe Leu Ile Asp Gly
                900                 905                 910
Pro Glu Thr Ala Glu Cys Pro Asn Thr Asn Arg Ala Trp Asn Ser Leu
            915                 920                 925
Glu Val Glu Asp Tyr Gly Phe Gly Val Phe Thr Thr Asn Ile Trp Leu
    930                 935                 940
Lys Leu Lys Glu Lys Gln Asp Val Phe Cys Asp Ser Lys Leu Met Ser
945                 950                 955                 960
Ala Ala Ile Lys Asp Asn Arg Ala Val His Ala Asp Met Gly Tyr Trp
                965                 970                 975
Ile Glu Ser Ala Leu Asn Asp Thr Trp Lys Ile Glu Lys Ala Ser Phe
                980                 985                 990
Ile Glu Val Lys Asn Cys His Trp Pro Lys Ser His Thr Leu Trp Ser
            995                1000                1005
Asn Gly Val Leu Glu Ser Glu Met Ile Ile Pro Lys Asn Leu Ala
    1010                1015                1020
Gly Pro Val Ser Gln His Asn Tyr Arg Pro Gly Tyr His Thr Gln
    1025                1030                1035
Ile Thr Gly Pro Trp His Leu Gly Lys Leu Glu Met Asp Phe Asp
    1040                1045                1050
Phe Cys Asp Gly Thr Thr Val Val Val Thr Glu Asp Cys Gly Asn
    1055                1060                1065
Arg Gly Pro Ser Leu Arg Thr Thr Ala Ser Gly Lys Leu Ile
    1070                1075                1080
Thr Glu Trp Cys Cys Arg Ser Cys Thr Leu Pro Pro Leu Arg Tyr
    1085                1090                1095
Arg Gly Glu Asp Gly Cys Trp Tyr Gly Met Glu Ile Arg Pro Leu
    1100                1105                1110
Lys Glu Lys Glu Glu Asn Leu Val Asn Ser Leu Val Thr Ala Gly
    1115                1120                1125
His Gly Gln Val Asp Asn Phe Ser Leu Gly Val Leu Gly Met Ala
    1130                1135                1140
Leu Phe Leu Glu Glu Met Leu Arg Thr Arg Val Gly Thr Lys His
    1145                1150                1155
Ala Ile Leu Leu Val Ala Val Ser Phe Val Thr Leu Ile Thr Gly
    1160                1165                1170
Asn Met Ser Phe Arg Asp Leu Gly Arg Val Met Val Met Val Gly
    1175                1180                1185
Ala Thr Met Thr Asp Asp Ile Gly Met Gly Val Thr Tyr Leu Ala
    1190                1195                1200
Leu Leu Ala Ala Phe Lys Val Arg Pro Thr Phe Ala Ala Gly Leu
    1205                1210                1215
Leu Leu Arg Lys Leu Thr Ser Lys Glu Leu Met Met Thr Thr Ile
    1220                1225                1230
Gly Ile Val Leu Leu Ser Gln Ser Thr Ile Pro Glu Thr Ile Leu
    1235                1240                1245
```

-continued

| | | | | | | | | | | | | |
|---|---|---|---|---|---|---|---|---|---|---|---|---|
| Glu | Leu 1250 | Thr | Asp | Ala | Leu 1255 | Ala | Leu | Gly | Met | Met 1260 | Val | Leu | Lys | Met |
| Val | Arg 1265 | Asn | Met | Glu | Lys 1270 | Tyr | Gln | Leu | Ala | Val 1275 | Thr | Ile | Met | Ala |
| Ile | Leu 1280 | Cys | Val | Pro | Asn 1285 | Ala | Val | Ile | Leu | Gln 1290 | Asn | Ala | Trp | Lys |
| Val | Ser 1295 | Cys | Thr | Ile | Leu 1300 | Ala | Val | Val | Ser | Val 1305 | Ser | Pro | Leu | Phe |
| Leu | Thr 1310 | Ser | Ser | Gln | Gln 1315 | Lys | Thr | Asp | Trp | Ile 1320 | Pro | Leu | Ala | Leu |
| Thr | Ile 1325 | Lys | Gly | Leu | Asn 1330 | Pro | Thr | Ala | Ile | Phe 1335 | Leu | Thr | Thr | Leu |
| Ser | Arg 1340 | Thr | Ser | Lys | Lys 1345 | Arg | Ser | Trp | Pro | Leu 1350 | Asn | Glu | Ala | Ile |
| Met | Ala 1355 | Val | Gly | Met | Val 1360 | Ser | Ile | Leu | Ala | Ser 1365 | Ser | Leu | Leu | Lys |
| Asn | Asp 1370 | Ile | Pro | Met | Thr 1375 | Gly | Pro | Leu | Val | Ala 1380 | Gly | Gly | Leu | Leu |
| Thr | Val 1385 | Cys | Tyr | Val | Leu 1390 | Thr | Gly | Arg | Ser | Ala 1395 | Asp | Leu | Glu | Leu |
| Glu | Arg 1400 | Ala | Ala | Asp | Val 1405 | Lys | Trp | Glu | Asp | Gln 1410 | Ala | Glu | Ile | Ser |
| Gly | Ser 1415 | Ser | Pro | Ile | Leu 1420 | Ser | Ile | Thr | Ile | Ser 1425 | Glu | Asp | Gly | Ser |
| Met | Ser 1430 | Ile | Lys | Asn | Glu 1435 | Glu | Glu | Glu | Gln | Thr 1440 | Leu | Thr | Ile | Leu |
| Ile | Arg 1445 | Thr | Gly | Leu | Leu 1450 | Val | Ile | Ser | Gly | Leu 1455 | Phe | Pro | Val | Ser |
| Ile | Pro 1460 | Ile | Thr | Ala | Ala 1465 | Ala | Trp | Tyr | Leu | Trp 1470 | Glu | Val | Lys | Lys |
| Gln | Arg 1475 | Ala | Gly | Val | Leu 1480 | Trp | Asp | Val | Pro | Ser 1485 | Pro | Pro | Pro | Met |
| Gly | Lys 1490 | Ala | Glu | Leu | Glu 1495 | Asp | Gly | Ala | Tyr | Arg 1500 | Ile | Lys | Gln | Lys |
| Gly | Ile 1505 | Leu | Gly | Tyr | Ser 1510 | Gln | Ile | Gly | Ala | Gly 1515 | Val | Tyr | Lys | Glu |
| Gly | Thr 1520 | Phe | His | Thr | Met 1525 | Trp | His | Val | Thr | Arg 1530 | Gly | Ala | Val | Leu |
| Met | His 1535 | Lys | Gly | Lys | Arg 1540 | Ile | Glu | Pro | Ser | Trp 1545 | Ala | Asp | Val | Lys |
| Lys | Asp 1550 | Leu | Ile | Ser | Tyr 1555 | Gly | Gly | Gly | Trp | Lys 1560 | Leu | Glu | Gly | Glu |
| Trp | Lys 1565 | Glu | Gly | Glu | Glu 1570 | Val | Gln | Val | Leu | Ala 1575 | Leu | Glu | Pro | Gly |
| Lys | Asn 1580 | Pro | Arg | Ala | Val 1585 | Gln | Thr | Lys | Pro | Gly 1590 | Leu | Phe | Lys | Thr |
| Asn | Ala 1595 | Gly | Thr | Ile | Gly 1600 | Ala | Val | Ser | Leu | Asp 1605 | Phe | Ser | Pro | Gly |
| Thr | Ser 1610 | Gly | Ser | Pro | Ile 1615 | Ile | Asp | Lys | Lys | Gly 1620 | Lys | Val | Val | Gly |
| Leu | Tyr 1625 | Gly | Asn | Gly | Val 1630 | Val | Thr | Arg | Ser | Gly 1635 | Ala | Tyr | Val | Ser |
| Ala | Ile | Ala | Gln | Thr | Glu | Lys | Ser | Ile | Glu | Asp | Asn | Pro | Glu | Ile |

-continued

```
            1640                1645                1650
Glu Asp Asp Ile Phe Arg Lys Arg Arg Leu Thr Ile Met Asp Leu
            1655                1660                1665
His Pro Gly Ala Gly Lys Thr Lys Arg Tyr Leu Pro Ala Ile Val
            1670                1675                1680
Arg Glu Ala Ile Lys Arg Gly Leu Arg Thr Leu Ile Leu Ala Pro
            1685                1690                1695
Thr Arg Val Val Ala Ala Glu Met Glu Glu Ala Leu Arg Gly Leu
            1700                1705                1710
Pro Ile Arg Tyr Gln Thr Pro Ala Ile Arg Ala Val His Thr Gly
            1715                1720                1725
Arg Glu Ile Val Asp Leu Met Cys His Ala Thr Phe Thr Met Arg
            1730                1735                1740
Leu Leu Ser Pro Val Arg Val Pro Asn Tyr Asn Leu Ile Ile Met
            1745                1750                1755
Asp Glu Ala His Phe Thr Asp Pro Ala Ser Ile Ala Ala Arg Gly
            1760                1765                1770
Tyr Ile Ser Thr Arg Val Glu Met Gly Glu Ala Ala Gly Ile Phe
            1775                1780                1785
Met Thr Ala Thr Pro Pro Gly Ser Arg Asp Pro Phe Pro Gln Ser
            1790                1795                1800
Asn Ala Pro Ile Ile Asp Glu Glu Arg Glu Ile Pro Glu Arg Ser
            1805                1810                1815
Trp Asn Ser Gly His Glu Trp Val Thr Asp Phe Lys Gly Lys Thr
            1820                1825                1830
Val Trp Phe Val Pro Ser Ile Lys Ala Gly Asn Asp Ile Ala Ala
            1835                1840                1845
Cys Leu Arg Lys Asn Gly Lys Lys Val Ile Gln Leu Ser Arg Lys
            1850                1855                1860
Thr Phe Asp Ser Glu Tyr Val Lys Thr Arg Thr Asn Asp Trp Asp
            1865                1870                1875
Phe Val Val Thr Thr Asp Ile Ser Glu Met Gly Ala Asn Phe Lys
            1880                1885                1890
Ala Glu Arg Val Ile Asp Pro Arg Arg Cys Met Lys Pro Val Ile
            1895                1900                1905
Leu Thr Asp Gly Glu Glu Arg Val Ile Leu Ala Gly Pro Met Pro
            1910                1915                1920
Val Thr His Ser Ser Ala Ala Gln Arg Arg Gly Arg Ile Gly Arg
            1925                1930                1935
Asn Pro Lys Asn Glu Asn Asp Gln Tyr Ile Tyr Met Gly Glu Pro
            1940                1945                1950
Leu Glu Asn Asp Glu Asp Cys Ala His Trp Lys Glu Ala Lys Met
            1955                1960                1965
Leu Leu Asp Asn Ile Asn Thr Pro Glu Gly Ile Ile Pro Ser Met
            1970                1975                1980
Phe Glu Pro Glu Arg Glu Lys Val Asp Ala Ile Asp Gly Glu Tyr
            1985                1990                1995
Arg Leu Arg Gly Glu Ala Arg Lys Thr Phe Val Asp Leu Met Arg
            2000                2005                2010
Arg Gly Asp Leu Pro Val Trp Leu Ala Tyr Arg Val Ala Ala Glu
            2015                2020                2025
Gly Ile Asn Tyr Ala Asp Arg Arg Trp Cys Phe Asp Gly Val Lys
            2030                2035                2040
```

-continued

Asn Asn Gln Ile Leu Glu Glu Asn Val Glu Val Glu Ile Trp Thr
2045                2050                2055

Lys Glu Gly Glu Arg Lys Lys Leu Lys Pro Arg Trp Leu Asp Ala
2060                2065                2070

Arg Ile Tyr Ser Asp Pro Leu Ala Leu Lys Glu Phe Lys Glu Phe
2075                2080                2085

Ala Ala Gly Arg Lys Ser Leu Thr Leu Asn Leu Ile Thr Glu Met
2090                2095                2100

Gly Arg Leu Pro Thr Phe Met Thr Gln Lys Ala Arg Asp Ala Leu
2105                2110                2115

Asp Asn Leu Ala Val Leu His Thr Ala Glu Ala Gly Gly Arg Ala
2120                2125                2130

Tyr Asn His Ala Leu Ser Glu Leu Pro Glu Thr Leu Glu Thr Leu
2135                2140                2145

Leu Leu Leu Thr Leu Leu Ala Thr Val Thr Gly Gly Ile Phe Leu
2150                2155                2160

Phe Leu Met Ser Ala Arg Gly Ile Gly Lys Met Thr Leu Gly Met
2165                2170                2175

Cys Cys Ile Ile Thr Ala Ser Ile Leu Leu Trp Tyr Ala Gln Ile
2180                2185                2190

Gln Pro His Trp Ile Ala Ala Ser Ile Ile Leu Glu Phe Phe Leu
2195                2200                2205

Ile Val Leu Leu Ile Pro Glu Pro Glu Lys Gln Arg Thr Pro Gln
2210                2215                2220

Asp Asn Gln Leu Thr Tyr Val Val Ile Ala Ile Leu Thr Val Val
2225                2230                2235

Ala Ala Thr Met Ala Asn Glu Met Gly Phe Leu Glu Lys Thr Lys
2240                2245                2250

Lys Asp Leu Gly Leu Gly Ser Ile Ala Thr Gln Gln Pro Glu Ser
2255                2260                2265

Asn Ile Leu Asp Ile Asp Leu Arg Pro Ala Ser Ala Trp Thr Leu
2270                2275                2280

Tyr Ala Val Ala Thr Thr Phe Val Thr Pro Met Leu Arg His Ser
2285                2290                2295

Ile Glu Asn Ser Ser Val Asn Val Ser Leu Thr Ala Ile Ala Asn
2300                2305                2310

Gln Ala Thr Val Leu Met Gly Leu Gly Lys Gly Trp Pro Leu Ser
2315                2320                2325

Lys Met Asp Ile Gly Val Pro Leu Leu Ala Ile Gly Cys Tyr Ser
2330                2335                2340

Gln Val Asn Pro Ile Thr Leu Thr Ala Ala Leu Phe Leu Leu Val
2345                2350                2355

Ala His Tyr Ala Ile Ile Gly Pro Gly Leu Gln Ala Lys Ala Thr
2360                2365                2370

Arg Glu Ala Gln Lys Arg Ala Ala Ala Gly Ile Met Lys Asn Pro
2375                2380                2385

Thr Val Asp Gly Ile Thr Val Ile Asp Leu Asp Pro Ile Pro Tyr
2390                2395                2400

Asp Pro Lys Phe Glu Lys Gln Leu Gly Gln Val Met Leu Leu Val
2405                2410                2415

Leu Cys Val Thr Gln Val Leu Met Met Arg Thr Thr Trp Ala Leu
2420                2425                2430

```
Cys Glu Ala Leu Thr Leu Ala Thr Gly Pro Ile Ser Thr Leu Trp
2435                2440                2445

Glu Gly Asn Pro Gly Arg Phe Trp Asn Thr Thr Ile Ala Val Ser
2450                2455                2460

Met Ala Asn Ile Phe Arg Gly Ser Tyr Leu Ala Gly Ala Gly Leu
2465                2470                2475

Leu Phe Ser Ile Met Lys Asn Thr Thr Asn Thr Arg Arg Gly Thr
2480                2485                2490

Gly Asn Ile Gly Glu Thr Leu Gly Glu Lys Trp Lys Ser Arg Leu
2495                2500                2505

Asn Ala Leu Gly Lys Ser Glu Phe Gln Ile Tyr Lys Lys Ser Gly
2510                2515                2520

Ile Gln Glu Val Asp Arg Thr Leu Ala Lys Glu Gly Ile Lys Arg
2525                2530                2535

Gly Glu Thr Asp His His Ala Val Ser Arg Gly Ser Ala Lys Leu
2540                2545                2550

Arg Trp Phe Val Glu Arg Asn Met Val Thr Pro Glu Gly Lys Val
2555                2560                2565

Val Asp Leu Gly Cys Gly Arg Gly Gly Trp Ser Tyr Tyr Cys Gly
2570                2575                2580

Gly Leu Lys Asn Val Arg Glu Val Lys Gly Leu Thr Lys Gly Gly
2585                2590                2595

Pro Gly His Glu Glu Pro Ile Pro Met Ser Thr Tyr Gly Trp Asn
2600                2605                2610

Leu Val Arg Leu Gln Ser Gly Val Asp Val Phe Phe Ile Pro Pro
2615                2620                2625

Glu Lys Cys Asp Thr Leu Leu Cys Asp Ile Gly Glu Ser Ser Pro
2630                2635                2640

Asn Pro Thr Val Glu Ala Gly Arg Thr Leu Arg Val Leu Asn Leu
2645                2650                2655

Val Glu Asn Trp Leu Asn Asn Asn Thr Gln Phe Cys Ile Lys Val
2660                2665                2670

Leu Asn Pro Tyr Met Pro Ser Val Ile Glu Lys Met Glu Ala Leu
2675                2680                2685

Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg Tyr Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu
2765                2770                2775

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

Asp Val Val Pro Met Val Thr Gln Met Ala Met Thr Asp Thr Thr
```

```
                    2825                2830                2835
Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Phe Thr Arg Lys Val Arg Ser Asn Ala
    2885                2890                2895

Ala Leu Gly Ala Val Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225
```

| | | | | | | | | | |
|---|---|---|---|---|---|---|---|---|---|
| Ala | Arg | Ile | Ser | Gln | Gly | Ala | Gly | Trp | Ser | Leu | Arg | Glu | Thr | Ala |
| | 3230 | | | | 3235 | | | | 3240 |

Ala Arg Ile Ser Gln Gly Ala Gly Trp Ser Leu Arg Glu Thr Ala
    3230              3235                3240

Cys Leu Gly Lys Ser Tyr Ala Gln Met Trp Ser Leu Met Tyr Phe
    3245              3250                3255

His Arg Arg Asp Leu Arg Leu Ala Ala Asn Ala Ile Cys Ser Ala
    3260              3265                3270

Val Pro Ser His Trp Val Pro Thr Ser Arg Thr Thr Trp Ser Ile
    3275              3280                3285

His Ala Lys His Glu Trp Met Thr Thr Glu Asp Met Leu Thr Val
    3290              3295                3300

Trp Asn Arg Val Trp Ile Gln Glu Asn Pro Trp Met Glu Asp Lys
    3305              3310                3315

Thr Pro Val Glu Ser Trp Glu Ile Pro Tyr Leu Gly Lys Arg
    3320              3325                3330

Glu Asp Gln Trp Cys Gly Ser Leu Ile Gly Leu Thr Ser Arg Ala
    3335              3340                3345

Thr Trp Ala Lys Asn Ile Gln Ala Ala Ile Asn Gln Val Arg Ser
    3350              3355                3360

Leu Ile Gly Asn Glu Glu Tyr Thr Asp Tyr Met Pro Ser Met Lys
    3365              3370                3375

Arg Phe Arg Arg Glu Glu Glu Ala Gly Val Leu Trp
    3380              3385                3390

<210> SEQ ID NO 5
<211> LENGTH: 10717
<212> TYPE: DNA
<213> ORGANISM: chimeric dengue serotype 2/3 (MVS)

<400> SEQUENCE: 5

```
agttgttagt ctacgtggac cgacaaagac agattctttg agggagctaa gctcaatgta      60
gttctaacag ttttttaatt agagagcaga tctctgatga ataaccaacg aaaaaggcg      120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag aaagagaatt     360
ggaaggatgc tgaacatctt gaataggaga cgcagatctg caggcatgat cattatgctg     420
attccaacag tgatggcgtt ccatttaacc acgcgtgatg gagagccgcg catgattgtg     480
gggaagaatg aaagaggaaa atccctactt ttcaagacag cctctggaat caacatgtgc     540
acactcatag ctatggatct gggagagatg tgtgatgaca cggtcactta caaatgcccc     600
cacattaccg aagtggagcc tgaagacatt gactgctggt gcaaccttac atcgacatgg     660
gtgacttatg aacatgcaa tcaagctgga gagcatagac gcgataagag atcagtggcg     720
ttagctcccc atgttggcat gggactggac acacgcactc aaacctggat gtcggctgaa     780
ggagcttgga gacaagtcga gaaggtagag acatgggccc ttaggcaccc agggtttacc     840
atactagccc tatttcttgc ccattacata ggcacttcct tgacccagaa agtggttatt     900
tttatactat taatgctggt taccccatcc atgacaatga gatgtgtagg agtaggaaac     960
agagattttg tggaaggcct atcgggagct acgtgggttg acgtggtgct cgagcacggt    1020
gggtgtgtga ctaccatggc taagaacaag cccacgctgg acatagagct tcagaagacc    1080
gaggccaccc aactggcgac cctaaggaag ctatgcattg agggaaaaat taccaacata    1140
```

```
acaaccgact caagatgtcc cacccaaggg gaagcgattt tacctgagga gcaggaccag    1200
aactacgtgt gtaagcatac atacgtggac agaggctggg gaaacggttg tggtttgttt    1260
ggcaagggaa gcttggtgac atgcgcgaaa tttcaatgtt tagaatcaat agagggaaaa    1320
gtggtgcaac atgagaacct caaatacacc gtcatcatca cagtgcacac aggagaccaa    1380
caccaggtgg gaaatgaaac gcagggagtc acggctgaga taacacccca ggcatcaacc    1440
gctgaagcca ttttacctga atatggaacc ctcgggctag aatgctcacc acggacaggt    1500
ttggatttca atgaaatgat ctcattgaca atgaagaaca agcatggat ggtacataga     1560 caatggttct ttgacttacc cctaccatgg acatcaggag cttcagcaga acaccaact     1620 tggaacagga aagagcttct tgtgacattt aaaaatgcac atgcaaaaaa gcaagaagta    1680
gttgttcttg gatcacaaga gggagcaatg catacagcac tgacaggagc tacagagatc    1740
caaacctcag gaggcacaag tatctttgcg gggcacttaa aatgtagact caagatggac    1800
aaattggaac tcaaggggat gagctatgca atgtgcttga gtagctttgt gttgaagaaa    1860
gaagtctccg aaacgcagca tgggacaata ctcattaagg ttgagtacaa aggggaagat    1920
gcaccctgca agattccttt ctccacggag gatggacaag gaaaagctct caatggcaga    1980
ctgatcacag ccaatccagt ggtgaccaag aaggaggagc ctgtcaacat tgaggctgaa    2040
cctccttttg agaaagtaa catagtaatt ggaattggag acaaagccct gaaaatcaac     2100
tggtacaaga agggaagctc gattgggaag atgttcgagg ccactgccag aggtgcaagg    2160
cgcatggcca tcttgggaga cacagcctgg gactttggat cagtgggtgg tgttttgaat    2220
tcattaggga aaatggtcca ccaaatattt gggagtgctt acacagccct atttggtgga    2280
gtctcctgga tgatgaaaat tggaataggt gtcctcttaa cctggatagg gttgaactca    2340
aaaaatactt ctatgtcatt ttcatgcatc gcggccggca ttgtgacact gtatttggga    2400
gtcatggtgc aggccgatag tggttgcgtt gtgagctgga aaaacaaaga actgaaatgt    2460
ggcagtggga ttttcatcac agacaacgtg cacacatgga cagaacaata caagttccaa    2520
ccagaatccc cttcaaaact agcttcagct atccagaaag cccatgaaga ggacatttgt    2580
ggaatccgct cagtaacaag actggagaat ctgatgtgga acaaataac accagaattg     2640 aatcacattc tatcagaaaa tgaggtgaag ttaactatta tgacaggaga catcaaagga    2700
atcatgcagg caggaaaacg atctctgcgg cctcagccca ctgagctgaa gtattcatgg    2760
aaaacatggg gcaaagcaaa aatgctctct acagagtctc ataaccagac ctttctcatt    2820
gatggccccg aaacagcaga atgccccaac acaaatagag cttggaattc gttggaagtt    2880
gaagactatg ctttggagt attcaccacc aatatatggc taaaattgaa agaaaaacag     2940
gatgtattct gcgactcaaa actcatgtca gcggccataa aagacaacag agccgtccat    3000
gccgatatgg gttattggat agaaagtgca ctcaatgaca catggaagat agagaaagcc    3060
tctttcattg aagttaaaaa ctgccactgg ccaaaatcac acaccctctg gagcaatgga    3120
gtgctagaaa gtgagatgat aattccaaag aatctcgctg gaccagtgtc tcaacacaac    3180
tatagaccag gctaccatac acaaataaca ggaccatggc atctaggtaa gcttgagatg    3240
gactttgatt tctgtgatgg aacaacagtg gtagtgactg aggactgcgg aaatagagga    3300
ccctctttga acaaccac tgcctctgga aaactcataa cagaatggtg ctgccgatct      3360
tgcacattac caccgctaag atacagaggt gaggatgggt gctggtacgg gatggaaatc    3420
agaccattga aggagaaaga agagaatttg gtcaactcct ggtcacagc tggacatggg    3480
```

```
caggtcgaca acttttcact aggagtcttg ggaatggcat tgttcctgga ggaaatgctt    3540
aggacccgag taggaacgaa acatgcaata ctactagttg cagtttcttt tgtgacattg    3600
atcacaggga acatgtcctt tagagacctg ggaagagtga tggttatggt aggcgccact    3660
atgacggatg acataggtat gggcgtgact tatcttgccc tactagcagc cttcaaagtc    3720
agaccaactt ttgcagctgg actactcttg agaaagctga cctccaagga attgatgatg    3780
actactatag gaattgtact cctctcccag agcaccatac cagagaccat tcttgagttg    3840
actgatgcgt tagccttagg catgatggtc ctcaaaatgg tgagaaatat ggaaaagtat    3900
caattggcag tgactatcat ggctatcttg tgcgtcccaa acgcagtgat attacaaaac    3960
gcatggaaag tgagttgcac aatattggca gtggtgtccg tttccccact gttcttaaca    4020
tcctcacagc aaaaaacaga ttggatacca ttagcattga cgatcaaagg tctcaatcca    4080
acagctattt ttctaacaac cctctcaaga accagcaaga aaaggagctg ccattaaat    4140
gaggctatca tggcagtcgg gatggtgagc attttagcca gttctctcct aaaaaatgat    4200
attcccatga caggaccatt agtggctgga gggctcctca ctgtgtgcta cgtgctcact    4260
ggacgatcgg ccgatttgga actggagaga gcagccgatg tcaaatggga agaccaggca    4320
gagatatcag gaagcagtcc aatcctgtca ataacaatat cagaagatgg tagcatgtcg    4380
ataaaaaatg aagaggaaga acaaacactg accatactca ttagaacagg attgctggtg    4440
atctcaggac tttttcctgt atcaatacca atcacggcag cagcatggta cctgtgggaa    4500
gtgaagaaac aacgggccgg agtattgtgg gatgttcctt acccccacc catgggaaag    4560
gctgaactgg aagatggagc ctatagaatt aagcaaaaag ggattcttgg atattcccag    4620
atcggagccg gagtttacaa agaaggaaca ttccatacaa tgtggcatgt cacacgtggc    4680
gctgttctaa tgcataaagg aaagaggatt gaaccatcat gggcggacgt caagaaagac    4740
ctaatatcat atggaggagg ctggaagtta gaaggagaat ggaaggaagg agaagaagtc    4800
caggtattgg cactggagcc tggaaaaaat ccaagagccg tccaaacgaa acctggtctt    4860
ttcaaaacca acgccggaac aataggtgct gtatctctgg acttttctcc tggaacgtca    4920
ggatctccaa ttatcgacaa aaaaggaaaa gttgtgggtc tttatggtaa tggtgttgtt    4980
acaaggagtg gagcatatgt gagtgctata gcccagactg aaaaaagcat tgaagacaac    5040
ccagagatcg aagatgacat tttccgaaag agaagactga ccatcatgga cctccaccca    5100
ggagcgggaa agacgaagag ataccttccg gccatagtca gagaagctat aaaacggggt    5160
ttgagaacat taatcttggc ccccactaga gttgtggcag ctgaaatgga ggaagccctt    5220
agaggacttc caataagata ccagaccccca gccatcagag ctgtgcacac cgggcgggag    5280
attgtggacc taatgtgtca tgccacattt accatgagc tgctatcacc agttagagtg    5340
ccaaactaca acctgattat catggacgaa gcccatttca cagacccagc aagtatagca    5400
gctagaggat acatctcaac tcgagtggag atgggtgagg cagctggat ttttatgaca    5460
gccactcccc cgggaagcag agacccattt cctcagagca atgcaccaat catagatgaa    5520
gaaagagaaa tccctgaacg ctcgtggaat tccggacatg aatgggtcac ggattttaaa    5580
gggaagactg tttggttcgt tccaagtata aaagcaggaa atgatatagc agcttgcctg    5640
aggaaaaatg gaaagaaagt gatacaactc agtaggaaga cctttgattc tgagtatgtc    5700
aagactagaa ccaatgattg ggacttcgtg gttacaactg acatttcaga aatgggtgcc    5760
aatttcaagg ctgagagggt tatagacccc agacgctgca tgaaaccagt catactaaca    5820
gatggtgaag agcgggtgat tctggcagga cctatgccag tgacccactc tagtgcagca    5880
```

```
caaagaagag ggagaatagg aagaaatcca aaaaatgaga atgaccagta catatacatg   5940 gggggaacctc tggaaaatga tgaagactgt gcacactgga aagaagctaa aatgctccta   6000
gataacatca acacgccaga aggaatcatt cctagcatgt tcgaaccaga gcgtgaaaag   6060
gtggatgcca ttgatggcga ataccgcttg agaggagaag caaggaaaac ctttgtagac   6120
ttaatgagaa gaggagacct accagtctgg ttggcctaca gagtggcagc tgaaggcatc   6180
aactacgcag acagaaggtg gtgttttgat ggagtcaaga caaccaaat cctagaagaa    6240 aacgtggaag ttgaaatctg gacaaaagaa ggggaaagga agaaattgaa acccagatgg   6300
ttggatgcta ggatctattc tgacccactg gcgctaaaag aatttaagga atttgcagcc   6360
ggaagaaagt ctctgaccct gaacctaatc acagaaatgg gtaggctccc aaccttcatg   6420
actcagaagg caagagacgc actggacaac ttagcagtgc tgcacacggc tgaggcaggt   6480
ggaagggcgt acaaccatgc tctcagtgaa ctgccggaga ccctggagac attgctttta   6540
ctgacacttc tggctacagt cacgggaggg atcttttat tcttgatgag cgcaaggggc   6600 ataggggaaga tgaccctggg aatgtgctgc ataatcacgg ctagcatcct cctatggtac   6660
gcacaaatac agccacactg gatagcagct tcaataatac tggagttttt tctcatagtt   6720
ttgcttattc cagaacctga aaacagaga acaccccaag acaaccaact gacctacgtt    6780
gtcatagcca tcctcacagt ggtggccgca accatggcaa acgagatggg tttcctagaa   6840
aaaacgaaga aagatctcgg attgggaagc attgcaaccc agcaacccga gagcaacatc   6900
ctggacatag atctacgtcc tgcatcagca tggacgctgt atgccgtggc cacaacattt   6960
gttacaccaa tgttgagaca tagcattgaa aattcctcag tgaatgtgtc cctaacagct   7020
atagccaacc aagccacagt gttaatgggt ctcgggaaag gatggccatt gtcaaagatg   7080
gacatcggag ttccccttct cgccattgga tgctactcac aagtcaaccc cataactctc   7140
acagcagctc ttttcttatt ggtagcacat tatgccatca tagggccagg actccaagca   7200
aaagcaacca gagaagctca gaaaagagca gcggcgggca tcatgaaaaa cccaactgtc   7260 gatgaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca ctccacatt gtgggaagga   7440 aatccaggga ggttttggaa cactaccatt gcggtgtcaa tggctaacat ttttagaggg   7500
agttacttgg ccggagctgg acttctcttt tctattatga agaacacaac caacacaaga   7560
aggggaactg gcaacatagg agagacgctt ggagagaaat ggaaaagccg attgaacgcg   7620
ttgggaaaaa gtgaattcca gatctacaag aaaagtggaa tccaggaagt ggatagaacc   7680
ttagcaaaag aaggcattaa agaggagaaa acggaccatc acgctgtgtc gcgaggctca   7740
gcaaaactga gatggttcgt tgagagaaac atggtcacac cagaagggaa agtagtggac   7800
ctcggttgtg gcagaggagg ctggtcatac tattgtggag gactaaagaa tgtaagagaa   7860
gtcaaaggcc taacaaaagg aggaccagga cacgaagaac ccatccccat gtcaacatat   7920
gggtggaatc tagtgcgtct tcaaagtgga gttgacgttt tcttcatccc gccagaaaag   7980
tgtgacacat tattgtgtga catagggggag tcatcaccaa atcccacagt ggaagcagga   8040
cgaacactca gagtccttaa cttagtagaa aattggttga acaacaacac tcaattttgc   8100
ataaaggttc tcaacccata tatgcccctca gtcatagaaa aatgaagc actacaaagg    8160 aaatatggag gagccttagt gaggaatcca ctctcacgaa actccacaca tgagatgtac   8220
```

```
tgggtatcca atgcttccgg gaacatagtg tcatcagtga acatgatttc aaggatgttg    8280
atcaacagat ttacaatgag atacaagaaa gccacttacg agccggatgt tgacctcgga    8340
agcggaaccc gtaacatcgg gattgaaagt gagataccaa acctagatat aattgggaaa    8400
agaatagaaa aaataaagca agagcatgaa acatcatggc actatgacca agaccaccca    8460
tacaaaacgt gggcatacca tggtagctat gaaacaaaac agactggatc agcatcatcc    8520
atggtcaacg gagtggtcag gctgctgaca aaaccttggg acgtcgtccc catggtgaca    8580
cagatggcaa tgacagacac gactccattt ggacaacagc gcgttttaa agagaaagtg     8640 gacacgagaa cccaagaacc gaagaaggc acgaagaaac taatgaaaat aacagcagag      8700
tggctttgga aagaattagg gaagaaaaag acacccagga tgtgcaccag agaagaattc    8760
acaagaaagg tgagaagcaa tgcagccttg ggggccatat tcactgatga gaacaagtgg    8820
aagtcggcac gtgaggctgt tgaagatagt aggttttggg agctggttga caaggaaagg    8880
aatctccatc ttgaaggaaa gtgtgaaaca tgtgtgtaca acatgatggg aaaaagagag    8940
aagaagctag gggaattcgg caaggcaaaa ggcagcagag ccatatggta catgtggctt    9000
ggagcacgct tcttagagtt tgaagcccta ggattcttaa atgaagatca ctggttctcc    9060
agagagaact ccctgagtgg agtggaagga aagggctgc acaagctagg ttacattcta     9120
agagacgtga gcaagaaaga gggaggagca atgtatgccg atgacaccgc aggatgggat    9180
acaagaatca cactagaaga cctaaaaaat gaagaaatgg taacaaacca catggaagga    9240
gaacacaaga actagccga ggccattttc aaactaacgt accaaaacaa ggtggtgcgt      9300
gtgcaaagac caacaccaag aggcacagta atggacatca tcgagaag agaccaaaga      9360 ggtagtggac aagttggcac ctatggactc aatacttca ccaatatgga agcccaacta      9420
atcagacaga tggagggaga aggagtcttt aaaagcattc agcacctaac aatcacagaa    9480
gaaatcgctg tgcaaaactg gttagcaaga gtggggcgcg aaaggttatc aagaatggcc    9540
atcagtggag atgattgtgt tgtgaaacct ttagatgaca ggttcgcaag cgcttaaca     9600 gctctaaatg acatgggaaa gattaggaaa gacatacaac aatgggaacc ttcaagagga    9660
tggaatgatt ggacacaagt gcccttctgt tcacaccatt tccatgagtt aatcatgaaa    9720
gacggtcgcg tactcgttgt tccatgtaga accaagatg aactgattgg cagagcccga     9780
atctcccaag gagcagggtg gtcttttgcg gagacggcct gtttggggaa gtcttacgcc    9840
caaatgtgga gcttgatgta cttccacaga cgcgacctca ggctggcggc aaatgctatt    9900
tgctcggcag taccatcaca ttgggttcca acaagtcgaa caacctggtc catacatgct    9960
aaacatgaat ggatgacaac ggaagacatg ctgacagtct ggaacagggt gtggattcaa   10020
gaaaacccat ggatggaaga caaaactcca gtggaatcat gggaggaaat ccccatacttg  10080 gggaaaagag aagaccaatg gtgcggctca ttgattgggt taacaagcag gccacctgg    10140 gcaaagaaca tccaagcagc aataaatcaa gttagatccc ttataggcaa tgaagaatac   10200
acagattaca tgccatccat gaaaagattc agaagagaag aggaagaagc aggagttctg   10260
tggtagaaag caaaactaac atgaaacaag gctagaagtc aggtcggatt aagccatagt   10320
acggaaaaaa ctatgctacc tgtgagcccc gtccaaggac gttaaaagaa gtcaggccat   10380
cataaatgcc atagcttgag taaactatgc agcctgtagc tccacctgag aaggtgtaaa   10440
aaatccggga ggccacaaac catggaagct gtacgcatgg cgtagtggac tagcggttag   10500
aggagacccc tcccttacaa atcgcagcaa caatgggggc ccaaggcgag atgaagctgt   10560
agtctcgctg gaaggactag aggttagagg agaccccccc gaaacaaaaa acagcatatt   10620
```

-continued

```
gacgctggga aagaccagag atcctgctgt ctcctcagca tcattccagg cacagaacgc    10680
cagaaaatgg aatggtgctg ttgaatcaac aggttct                              10717
```

<210> SEQ ID NO 6
<211> LENGTH: 3389
<212> TYPE: PRT
<213> ORGANISM: chimeric dengue serotype 2/3 (MVS)

<400> SEQUENCE: 6

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350
```

```
Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Gln His Glu Asn Leu Lys
                405                 410                 415

Tyr Thr Val Ile Ile Thr Val His Thr Gly Asp Gln His Gln Val Gly
                420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
```

```
                770                 775                 780
Glu Leu Lys Cys Gly Ser Gly Ile Phe Ile Thr Asp Asn Val His Thr
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
                820                 825                 830

Val Thr Arg Leu Glu Asn Leu Met Trp Lys Gln Ile Thr Pro Glu Leu
                835                 840                 845

Asn His Ile Leu Ser Glu Asn Glu Val Lys Leu Thr Ile Met Thr Gly
                850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
                900                 905                 910

Thr Ala Glu Cys Pro Asn Thr Asn Arg Ala Trp Asn Ser Leu Glu Val
                915                 920                 925

Glu Asp Tyr Gly Phe Gly Val Phe Thr Thr Asn Ile Trp Leu Lys Leu
930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
                965                 970                 975

Ser Ala Leu Asn Asp Thr Trp Lys Ile Glu Lys Ala Ser Phe Ile Glu
                980                 985                 990

Val Lys Asn Cys His Trp Pro Lys Ser His Thr Leu Trp Ser Asn Gly
                995                 1000                1005

Val Leu Glu Ser Glu Met Ile Ile Pro Lys Asn Leu Ala Gly Pro
1010                1015                1020

Val Ser Gln His Asn Tyr Arg Pro Gly Tyr His Thr Gln Ile Thr
1025                1030                1035

Gly Pro Trp His Leu Gly Lys Leu Glu Met Asp Phe Asp Phe Cys
1040                1045                1050

Asp Gly Thr Thr Val Val Thr Glu Asp Cys Gly Asn Arg Gly
1055                1060                1065

Pro Ser Leu Arg Thr Thr Thr Ala Ser Gly Lys Leu Ile Thr Glu
1070                1075                1080

Trp Cys Cys Arg Ser Cys Thr Leu Pro Pro Leu Arg Tyr Arg Gly
1085                1090                1095

Glu Asp Gly Cys Trp Tyr Gly Met Glu Ile Arg Pro Leu Lys Glu
1100                1105                1110

Lys Glu Glu Asn Leu Val Asn Ser Leu Val Thr Ala Gly His Gly
1115                1120                1125

Gln Val Asp Asn Phe Ser Leu Gly Val Leu Gly Met Ala Leu Phe
1130                1135                1140

Leu Glu Glu Met Leu Arg Thr Arg Val Gly Thr Lys His Ala Ile
1145                1150                1155

Leu Leu Val Ala Val Ser Phe Val Thr Leu Ile Thr Gly Asn Met
1160                1165                1170

Ser Phe Arg Asp Leu Gly Arg Val Met Val Met Val Gly Ala Thr
1175                1180                1185
```

-continued

```
Met Thr Asp Asp Ile Gly Met Gly Val Thr Tyr Leu Ala Leu Leu
    1190            1195                1200

Ala Ala Phe Lys Val Arg Pro Thr Phe Ala Ala Gly Leu Leu Leu
    1205            1210                1215

Arg Lys Leu Thr Ser Lys Glu Leu Met Met Thr Thr Ile Gly Ile
    1220            1225                1230

Val Leu Leu Ser Gln Ser Thr Ile Pro Glu Thr Ile Leu Glu Leu
    1235            1240                1245

Thr Asp Ala Leu Ala Leu Gly Met Met Val Leu Lys Met Val Arg
    1250            1255                1260

Asn Met Glu Lys Tyr Gln Leu Ala Val Thr Ile Met Ala Ile Leu
    1265            1270                1275

Cys Val Pro Asn Ala Val Ile Leu Gln Asn Ala Trp Lys Val Ser
    1280            1285                1290

Cys Thr Ile Leu Ala Val Val Ser Val Ser Pro Leu Phe Leu Thr
    1295            1300                1305

Ser Ser Gln Gln Lys Thr Asp Trp Ile Pro Leu Ala Leu Thr Ile
    1310            1315                1320

Lys Gly Leu Asn Pro Thr Ala Ile Phe Leu Thr Thr Leu Ser Arg
    1325            1330                1335

Thr Ser Lys Lys Arg Ser Trp Pro Leu Asn Glu Ala Ile Met Ala
    1340            1345                1350

Val Gly Met Val Ser Ile Leu Ala Ser Ser Leu Leu Lys Asn Asp
    1355            1360                1365

Ile Pro Met Thr Gly Pro Leu Val Ala Gly Gly Leu Leu Thr Val
    1370            1375                1380

Cys Tyr Val Leu Thr Gly Arg Ser Ala Asp Leu Glu Leu Glu Arg
    1385            1390                1395

Ala Ala Asp Val Lys Trp Glu Asp Gln Ala Glu Ile Ser Gly Ser
    1400            1405                1410

Ser Pro Ile Leu Ser Ile Thr Ile Ser Glu Asp Gly Ser Met Ser
    1415            1420                1425

Ile Lys Asn Glu Glu Glu Gln Thr Leu Thr Ile Leu Ile Arg
    1430            1435                1440

Thr Gly Leu Leu Val Ile Ser Gly Leu Phe Pro Val Ser Ile Pro
    1445            1450                1455

Ile Thr Ala Ala Ala Trp Tyr Leu Trp Glu Val Lys Lys Gln Arg
    1460            1465                1470

Ala Gly Val Leu Trp Asp Val Pro Ser Pro Pro Met Gly Lys
    1475            1480                1485

Ala Glu Leu Glu Asp Gly Ala Tyr Arg Ile Lys Gln Lys Gly Ile
    1490            1495                1500

Leu Gly Tyr Ser Gln Ile Gly Ala Gly Val Tyr Lys Glu Gly Thr
    1505            1510                1515

Phe His Thr Met Trp His Val Thr Arg Gly Ala Val Leu Met His
    1520            1525                1530

Lys Gly Lys Arg Ile Glu Pro Ser Trp Ala Asp Val Lys Lys Asp
    1535            1540                1545

Leu Ile Ser Tyr Gly Gly Gly Trp Lys Leu Glu Gly Glu Trp Lys
    1550            1555                1560

Glu Gly Glu Glu Val Gln Val Leu Ala Leu Glu Pro Gly Lys Asn
    1565            1570                1575
```

Pro Arg Ala Val Gln Thr Lys Pro Gly Leu Phe Lys Thr Asn Ala
1580            1585            1590

Gly Thr Ile Gly Ala Val Ser Leu Asp Phe Ser Pro Gly Thr Ser
1595            1600            1605

Gly Ser Pro Ile Ile Asp Lys Lys Gly Lys Val Val Gly Leu Tyr
1610            1615            1620

Gly Asn Gly Val Val Thr Arg Ser Gly Ala Tyr Val Ser Ala Ile
1625            1630            1635

Ala Gln Thr Glu Lys Ser Ile Glu Asp Asn Pro Glu Ile Glu Asp
1640            1645            1650

Asp Ile Phe Arg Lys Arg Arg Leu Thr Ile Met Asp Leu His Pro
1655            1660            1665

Gly Ala Gly Lys Thr Lys Arg Tyr Leu Pro Ala Ile Val Arg Glu
1670            1675            1680

Ala Ile Lys Arg Gly Leu Arg Thr Leu Ile Leu Ala Pro Thr Arg
1685            1690            1695

Val Val Ala Ala Glu Met Glu Glu Ala Leu Arg Gly Leu Pro Ile
1700            1705            1710

Arg Tyr Gln Thr Pro Ala Ile Arg Ala Val His Thr Gly Arg Glu
1715            1720            1725

Ile Val Asp Leu Met Cys His Ala Thr Phe Thr Met Arg Leu Leu
1730            1735            1740

Ser Pro Val Arg Val Pro Asn Tyr Asn Leu Ile Ile Met Asp Glu
1745            1750            1755

Ala His Phe Thr Asp Pro Ala Ser Ile Ala Ala Arg Gly Tyr Ile
1760            1765            1770

Ser Thr Arg Val Glu Met Gly Glu Ala Ala Gly Ile Phe Met Thr
1775            1780            1785

Ala Thr Pro Pro Gly Ser Arg Asp Pro Phe Pro Gln Ser Asn Ala
1790            1795            1800

Pro Ile Ile Asp Glu Glu Arg Glu Ile Pro Glu Arg Ser Trp Asn
1805            1810            1815

Ser Gly His Glu Trp Val Thr Asp Phe Lys Gly Lys Thr Val Trp
1820            1825            1830

Phe Val Pro Ser Ile Lys Ala Gly Asn Asp Ile Ala Ala Cys Leu
1835            1840            1845

Arg Lys Asn Gly Lys Lys Val Ile Gln Leu Ser Arg Lys Thr Phe
1850            1855            1860

Asp Ser Glu Tyr Val Lys Thr Arg Thr Asn Asp Trp Asp Phe Val
1865            1870            1875

Val Thr Thr Asp Ile Ser Glu Met Gly Ala Asn Phe Lys Ala Glu
1880            1885            1890

Arg Val Ile Asp Pro Arg Arg Cys Met Lys Pro Val Ile Leu Thr
1895            1900            1905

Asp Gly Glu Glu Arg Val Ile Leu Ala Gly Pro Met Pro Val Thr
1910            1915            1920

His Ser Ser Ala Ala Gln Arg Arg Gly Arg Ile Gly Arg Asn Pro
1925            1930            1935

Lys Asn Glu Asn Asp Gln Tyr Ile Tyr Met Gly Glu Pro Leu Glu
1940            1945            1950

Asn Asp Glu Asp Cys Ala His Trp Lys Glu Ala Lys Met Leu Leu
1955            1960            1965

Asp Asn Ile Asn Thr Pro Glu Gly Ile Ile Pro Ser Met Phe Glu

-continued

```
            1970                1975              1980
Pro Glu Arg Glu Lys Val Asp Ala Ile Asp Gly Glu Tyr Arg Leu
        1985                1990              1995
Arg Gly Glu Ala Arg Lys Thr Phe Val Asp Leu Met Arg Arg Gly
        2000                2005              2010
Asp Leu Pro Val Trp Leu Ala Tyr Arg Val Ala Ala Glu Gly Ile
        2015                2020              2025
Asn Tyr Ala Asp Arg Arg Trp Cys Phe Asp Gly Val Lys Asn Asn
        2030                2035              2040
Gln Ile Leu Glu Glu Asn Val Glu Val Glu Ile Trp Thr Lys Glu
        2045                2050              2055
Gly Glu Arg Lys Lys Leu Lys Pro Arg Trp Leu Asp Ala Arg Ile
        2060                2065              2070
Tyr Ser Asp Pro Leu Ala Leu Lys Glu Phe Lys Glu Phe Ala Ala
        2075                2080              2085
Gly Arg Lys Ser Leu Thr Leu Asn Leu Ile Thr Glu Met Gly Arg
        2090                2095              2100
Leu Pro Thr Phe Met Thr Gln Lys Ala Arg Asp Ala Leu Asp Asn
        2105                2110              2115
Leu Ala Val Leu His Thr Ala Glu Ala Gly Gly Arg Ala Tyr Asn
        2120                2125              2130
His Ala Leu Ser Glu Leu Pro Glu Thr Leu Glu Thr Leu Leu Leu
        2135                2140              2145
Leu Thr Leu Leu Ala Thr Val Thr Gly Gly Ile Phe Leu Phe Leu
        2150                2155              2160
Met Ser Ala Arg Gly Ile Gly Lys Met Thr Leu Gly Met Cys Cys
        2165                2170              2175
Ile Ile Thr Ala Ser Ile Leu Leu Trp Tyr Ala Gln Ile Gln Pro
        2180                2185              2190
His Trp Ile Ala Ala Ser Ile Ile Leu Glu Phe Phe Leu Ile Val
        2195                2200              2205
Leu Leu Ile Pro Glu Pro Glu Lys Gln Arg Thr Pro Gln Asp Asn
        2210                2215              2220
Gln Leu Thr Tyr Val Val Ile Ala Ile Leu Thr Val Val Ala Ala
        2225                2230              2235
Thr Met Ala Asn Glu Met Gly Phe Leu Glu Lys Thr Lys Lys Asp
        2240                2245              2250
Leu Gly Leu Gly Ser Ile Ala Thr Gln Gln Pro Glu Ser Asn Ile
        2255                2260              2265
Leu Asp Ile Asp Leu Arg Pro Ala Ser Ala Trp Thr Leu Tyr Ala
        2270                2275              2280
Val Ala Thr Thr Phe Val Thr Pro Met Leu Arg His Ser Ile Glu
        2285                2290              2295
Asn Ser Ser Val Asn Val Ser Leu Thr Ala Ile Ala Asn Gln Ala
        2300                2305              2310
Thr Val Leu Met Gly Leu Gly Lys Gly Trp Pro Leu Ser Lys Met
        2315                2320              2325
Asp Ile Gly Val Pro Leu Leu Ala Ile Gly Cys Tyr Ser Gln Val
        2330                2335              2340
Asn Pro Ile Thr Leu Thr Ala Ala Leu Phe Leu Leu Val Ala His
        2345                2350              2355
Tyr Ala Ile Ile Gly Pro Gly Leu Gln Ala Lys Ala Thr Arg Glu
        2360                2365              2370
```

-continued

```
Ala Gln Lys Arg Ala Ala Ala Gly Ile Met Lys Asn Pro Thr Val
    2375            2380                2385

Asp Gly Ile Thr Val Ile Asp Leu Asp Pro Ile Pro Tyr Asp Pro
    2390            2395                2400

Lys Phe Glu Lys Gln Leu Gly Gln Val Met Leu Leu Val Leu Cys
    2405            2410                2415

Val Thr Gln Val Leu Met Met Arg Thr Thr Trp Ala Leu Cys Glu
    2420            2425                2430

Ala Leu Thr Leu Ala Thr Gly Pro Ile Ser Thr Leu Trp Glu Gly
    2435            2440                2445

Asn Pro Gly Arg Phe Trp Asn Thr Thr Ile Ala Val Ser Met Ala
    2450            2455                2460

Asn Ile Phe Arg Gly Ser Tyr Leu Ala Gly Ala Gly Leu Leu Phe
    2465            2470                2475

Ser Ile Met Lys Asn Thr Thr Asn Thr Arg Arg Gly Thr Gly Asn
    2480            2485                2490

Ile Gly Glu Thr Leu Gly Glu Lys Trp Lys Ser Arg Leu Asn Ala
    2495            2500                2505

Leu Gly Lys Ser Glu Phe Gln Ile Tyr Lys Lys Ser Gly Ile Gln
    2510            2515                2520

Glu Val Asp Arg Thr Leu Ala Lys Glu Gly Ile Lys Arg Gly Glu
    2525            2530                2535

Thr Asp His His Ala Val Ser Arg Gly Ser Ala Lys Leu Arg Trp
    2540            2545                2550

Phe Val Glu Arg Asn Met Val Thr Pro Glu Gly Lys Val Val Asp
    2555            2560                2565

Leu Gly Cys Gly Arg Gly Gly Trp Ser Tyr Tyr Cys Gly Gly Leu
    2570            2575                2580

Lys Asn Val Arg Glu Val Lys Gly Leu Thr Lys Gly Gly Pro Gly
    2585            2590                2595

His Glu Glu Pro Ile Pro Met Ser Thr Tyr Gly Trp Asn Leu Val
    2600            2605                2610

Arg Leu Gln Ser Gly Val Asp Val Phe Phe Ile Pro Pro Glu Lys
    2615            2620                2625

Cys Asp Thr Leu Leu Cys Asp Ile Gly Glu Ser Ser Pro Asn Pro
    2630            2635                2640

Thr Val Glu Ala Gly Arg Thr Leu Arg Val Leu Asn Leu Val Glu
    2645            2650                2655

Asn Trp Leu Asn Asn Asn Thr Gln Phe Cys Ile Lys Val Leu Asn
    2660            2665                2670

Pro Tyr Met Pro Ser Val Ile Glu Lys Met Glu Ala Leu Gln Arg
    2675            2680                2685

Lys Tyr Gly Gly Ala Leu Val Arg Asn Pro Leu Ser Arg Asn Ser
    2690            2695                2700

Thr His Glu Met Tyr Trp Val Ser Asn Ala Ser Gly Asn Ile Val
    2705            2710                2715

Ser Ser Val Asn Met Ile Ser Arg Met Leu Ile Asn Arg Phe Thr
    2720            2725                2730

Met Arg Tyr Lys Lys Ala Thr Tyr Glu Pro Asp Val Asp Leu Gly
    2735            2740                2745

Ser Gly Thr Arg Asn Ile Gly Ile Glu Ser Glu Ile Pro Asn Leu
    2750            2755                2760
```

```
Asp Ile Ile Gly Lys Arg Ile Glu Lys Ile Lys Gln Glu His Glu
    2765                2770                2775

Thr Ser Trp His Tyr Asp Gln Asp His Pro Tyr Lys Thr Trp Ala
    2780                2785                2790

Tyr His Gly Ser Tyr Glu Thr Lys Gln Thr Gly Ser Ala Ser Ser
    2795                2800                2805

Met Val Asn Gly Val Val Arg Leu Leu Thr Lys Pro Trp Asp Val
    2810                2815                2820

Val Pro Met Val Thr Gln Met Ala Met Thr Asp Thr Thr Pro Phe
    2825                2830                2835

Gly Gln Gln Arg Val Phe Lys Glu Lys Val Asp Thr Arg Thr Gln
    2840                2845                2850

Glu Pro Lys Glu Gly Thr Lys Lys Leu Met Lys Ile Thr Ala Glu
    2855                2860                2865

Trp Leu Trp Lys Glu Leu Gly Lys Lys Lys Thr Pro Arg Met Cys
    2870                2875                2880

Thr Arg Glu Glu Phe Thr Arg Lys Val Arg Ser Asn Ala Ala Leu
    2885                2890                2895

Gly Ala Ile Phe Thr Asp Glu Asn Lys Trp Lys Ser Ala Arg Glu
    2900                2905                2910

Ala Val Glu Asp Ser Arg Phe Trp Glu Leu Val Asp Lys Glu Arg
    2915                2920                2925

Asn Leu His Leu Glu Gly Lys Cys Glu Thr Cys Val Tyr Asn Met
    2930                2935                2940

Met Gly Lys Arg Glu Lys Lys Leu Gly Glu Phe Gly Lys Ala Lys
    2945                2950                2955

Gly Ser Arg Ala Ile Trp Tyr Met Trp Leu Gly Ala Arg Phe Leu
    2960                2965                2970

Glu Phe Glu Ala Leu Gly Phe Leu Asn Glu Asp His Trp Phe Ser
    2975                2980                2985

Arg Glu Asn Ser Leu Ser Gly Val Glu Gly Glu Gly Leu His Lys
    2990                2995                3000

Leu Gly Tyr Ile Leu Arg Asp Val Ser Lys Lys Glu Gly Gly Ala
    3005                3010                3015

Met Tyr Ala Asp Asp Thr Ala Gly Trp Asp Thr Arg Ile Thr Leu
    3020                3025                3030

Glu Asp Leu Lys Asn Glu Glu Met Val Thr Asn His Met Glu Gly
    3035                3040                3045

Glu His Lys Lys Leu Ala Glu Ala Ile Phe Lys Leu Thr Tyr Gln
    3050                3055                3060

Asn Lys Val Val Arg Val Gln Arg Pro Thr Pro Arg Gly Thr Val
    3065                3070                3075

Met Asp Ile Ile Ser Arg Arg Asp Gln Arg Gly Ser Gly Gln Val
    3080                3085                3090

Gly Thr Tyr Gly Leu Asn Thr Phe Thr Asn Met Glu Ala Gln Leu
    3095                3100                3105

Ile Arg Gln Met Glu Gly Glu Gly Val Phe Lys Ser Ile Gln His
    3110                3115                3120

Leu Thr Ile Thr Glu Glu Ile Ala Val Gln Asn Trp Leu Ala Arg
    3125                3130                3135

Val Gly Arg Glu Arg Leu Ser Arg Met Ala Ile Ser Gly Asp Asp
    3140                3145                3150

Cys Val Val Lys Pro Leu Asp Asp Arg Phe Ala Ser Ala Leu Thr
```

```
    3155                3160                3165

Ala Leu  Asn Asp Met Gly Lys  Ile Arg Lys Asp Ile  Gln Gln Trp
    3170                3175                3180

Glu Pro  Ser Arg Gly Trp Asn  Asp Trp Thr Gln Val  Pro Phe Cys
    3185                3190                3195

Ser His  His Phe His Glu Leu  Ile Met Lys Asp Gly  Arg Val Leu
    3200                3205                3210

Val Val  Pro Cys Arg Asn Gln  Asp Glu Leu Ile Gly  Arg Ala Arg
    3215                3220                3225

Ile Ser  Gln Gly Ala Gly Trp  Ser Leu Arg Glu Thr  Ala Cys Leu
    3230                3235                3240

Gly Lys  Ser Tyr Ala Gln Met  Trp Ser Leu Met Tyr  Phe His Arg
    3245                3250                3255

Arg Asp  Leu Arg Leu Ala Ala  Asn Ala Ile Cys Ser  Ala Val Pro
    3260                3265                3270

Ser His  Trp Val Pro Thr Ser  Arg Thr Thr Trp Ser  Ile His Ala
    3275                3280                3285

Lys His  Glu Trp Met Thr Thr  Glu Asp Met Leu Thr  Val Trp Asn
    3290                3295                3300

Arg Val  Trp Ile Gln Glu Asn  Pro Trp Met Glu Asp  Lys Thr Pro
    3305                3310                3315

Val Glu  Ser Trp Glu Glu Ile  Pro Tyr Leu Gly Lys  Arg Glu Asp
    3320                3325                3330

Gln Trp  Cys Gly Ser Leu Ile  Gly Leu Thr Ser Arg  Ala Thr Trp
    3335                3340                3345

Ala Lys  Asn Ile Gln Ala Ala  Ile Asn Gln Val Arg  Ser Leu Ile
    3350                3355                3360

Gly Asn  Glu Glu Tyr Thr Asp  Tyr Met Pro Ser Met  Lys Arg Phe
    3365                3370                3375

Arg Arg  Glu Glu Glu Glu Ala  Gly Val Leu Trp
    3380                3385

<210> SEQ ID NO 7
<211> LENGTH: 10723
<212> TYPE: DNA
<213> ORGANISM: chimeric dengue seroytpe 2/4 (MVS)
<220> FEATURE:
<221> NAME/KEY: r
<222> LOCATION: (3773)..(3773)
<223> OTHER INFORMATION: a or g
<220> FEATURE:
<221> NAME/KEY: y
<222> LOCATION: (7026)..(7026)
<223> OTHER INFORMATION: t or c

<400> SEQUENCE: 7
agttgttagt ctacgtggac cgacaaagac agattctttg agggagctaa gctcaatgta     60
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gacctttaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
```

-continued

```
gcaaaacatg aaaggggag acctctcttg tttaagacaa cagaggggat caacaaatgc      540
actctcattg ccatggactt gggtgaaatg tgtgaggaca ctgtcacgta taaatgcccc      600
ttactggtca ataccgaacc tgaagacatt gattgctggt gcaatctcac gtctacctgg      660
gtcatgtatg ggacatgcac ccagagcgga aacggagac gagagaagcg ctcagtagct       720
ttaacaccac attcaggaat gggattggaa acaagagctg agacatggat gtcatcggaa      780
ggggcttgga agcatgctca gagagtagag agctggatac tcagaaaccc aggattcgcg      840
ctcttggcag gatttatggc ttatatgatt gggcaaacag gaatccagcg aactgtcttc      900
tttgtcctaa tgatgctggt cgccccatcc tacggaatgc gatgcgtagg agtaggaaac      960
agagactttg tggaaggagt ctcaggtgga gcatgggtcg atctggtgct agaacatgga     1020
ggatgcgtca caaccatggc ccagggaaaa ccaaccttgg attttgaact gactaagaca     1080
acagccaagg aagtggctct gttaagaacc tattgcattg aagcctcaat atcaaacata     1140
accacggcaa caagatgtcc aacgcaagga gagccttatc taaaagagga caagaccaa      1200 cagtacattt gccggagaga tgtggtagac agagggtggg gcaatggctg tggcttgttt     1260
ggaaaaggag gagttgtgac atgtgcgaag ttttcatgtt cggggaagat aacaggcaat     1320
ttggtccaaa ttgagaacct tgaatacaca gtggttgtaa cagtccacaa tggagacacc     1380
catgcagtag gaaatgacac gtccaatcat ggagttacag ccacgataac tcccaggtca     1440
ccatcggtgg aagtcaaatt gccggactat ggagaactaa cactcgattg tgaacccagg     1500
tctggaattg actttaatga gatgattctg atgaaaatga aaagaaaac atggcttgtg     1560 cataagcaat ggttttgga tctacctcta ccatggacag caggagcaga cacatcagag     1620
gttcactgga attacaaaga gagaatggtg acatttaagg ttcctcatgc caagagacag     1680
gatgtgcaca gtgctgggatc tcaggaagga gccatgcatt ctgccctcgc tggagccaca     1740
gaagtggact ccggtgatgg aaatcacatg tttgcaggac atctcaagtg caaagtccgt     1800
atggagaaat tgaagaatcaa gggaatgtca tacacgatgt gttcaggaaa gttctcaatt     1860
gacaaagaga tggcagaaac acagcatggg acaacagtgg tgaaagtcaa gtatgaaggt     1920
gctggagctc cgtgtaaagt ccccatagag ataagagatg tgaacaagga aaagtggtt      1980 gggcgtatca tctcatccac ccctttggct gagaatacca acagtgtaac caacatagag     2040 ttagaaccc cctttgggga cagctacata gtgataggtg ttggaaacag tgcattaaca     2100
ctccattggt tcaggaaagg gagttccatt ggcaagatgt ttgagtccac atacagaggt     2160
gcaaaacgaa tggccattct aggtgaaaca gcttgggatt ttggttccgt tggtggactg     2220
ttcacatcat tgggaaaggc tgtgcaccag ttttttggaa gtgtgtatac aaccctgttt     2280
ggaggagtct catggatgat tagaatccta attgggttcc tagtgttgtg gattggcacg     2340
aactcaagga acacttcaat ggctatgacg tgcatagctg ccggcattgt gacactgtat     2400 ttggggggtca tggtgcaggc cgatagtggt tgcgttgtga gctggaaaaa caaagaactg     2460
aaatgtggca gtgggatttt catcacagac aacgtgcaca catggacaga acaatacaag     2520
ttccaaccag aatccccttc aaaactagct tcagctatcc agaaagccca tgaagaggac     2580
atttgtggaa tccgctcagt aacaagactg gagaatctga tgtggaaaca ataacacca     2640 gaattgaatc acattctatc agaaaatgag gtgaagttaa ctattatgac aggagacatc     2700
aaaggaatca tgcaggcagg aaaacgatct ctgcggcctc agcccactga gctgaagtat     2760
tcatggaaaa catgggcaa agcaaaaatg ctctctacag agtctcataa ccagacctt      2820 ctcattgatg gcccccgaaac agcagaatgc cccaacacaa atagagcttg gaattcgttg     2880
```

```
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cgggtgacat aggtatgggc gtgacttatc ttgccctact agcagccttc    3720
aaagtcagac caacttttgc agctggacta ctcttgagaa agctgaccte carggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaacctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatggg ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggaccte    5100
cacccaggag cgggaaagac gaagagatac cttccggcca tagtcagaga agctataaaa    5160
cggggtttga gaacattaat cttggccccc actagagttg tggcagctga aatggaggaa    5220
```

```
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga tccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaagggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt    6120 gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggtaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagcyatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
```

```
aacgcattgg gaaaaagtga attccagatc tacaagaaaa gtggaatcca ggaagtggat    7680
agaaccttag caaaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460 caccccataca aaacgtgggc ataccatggt agctatgaaa caaaacagac tggatcagca    8520
tcatccatgg tcaacggagt ggtcaggctg ctgacaaaac cttgggacgt cgtcccatg    8580 gtgacacaga tggcaatgac agacacgact ccatttggac aacagcgcgt ttttaaagag    8640
aaagtggaca cgagaacccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctaggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180 tgggataacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttccacca tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatgaa ttgtgttgtg aaaccttag atgacaggtt cgcaagcgct    9600
ttaacagctc taaatgacat gggaaagatt aggaaagaca tacaacaatg gaaccttca    9660 agaggatgga atgattggac acaagtgccc ttctgttcac accatttcca tgagttaatc    9720
atgaaagacg tcgcgtact cgttgttccc tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
```

-continued

```
catgctaaac atgaatggat gacaacggaa gacatgctga cagtctggaa cagggtgtgg    10020
attcaagaaa acccatggat ggaagacaaa actccagtgg aatcatggga ggaaatccca    10080
tacttgggga aaagagaaga ccaatggtgc ggctcattga ttgggttaac aagcagggcc    10140
acctgggcaa agaacatcca agcagcaata aatcaagtta gatcccttat aggcaatgaa    10200
gaatacacag attacatgcc atccatgaaa agattcagaa gagaagagga agaagcagga    10260
gttctgtggt agaaagcaaa actaacatga acaaggcta gaagtcaggt cggattaagc    10320
catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gacccctccc ttacaaatcg cagcaacaat ggggccaa ggcgagatga    10560 agctgtagtc tcgctggaag gactagaggt tagaggagac cccccgaaa caaaaaacag    10620 catattgacg ctgggaaaga ccagagatcc tgctgtctcc tcagcatcat tccaggcaca    10680
gaacgccaga aatggaatg gtgctgttga atcaacaggt tct                      10723
```

<210> SEQ ID NO 8
<211> LENGTH: 3391
<212> TYPE: PRT
<213> ORGANISM: chimeric dengue serotype 2/4 (MVS)
<220> FEATURE:
<221> NAME/KEY: Xaa
<222> LOCATION: (1226)..(1226)
<223> OTHER INFORMATION: Arg or Lys

<400> SEQUENCE: 8

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

```
Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
            245                 250                 255

Met Ile Gly Gln Thr Gly Ile Gln Arg Thr Val Phe Phe Val Leu Met
        260                 265                 270

Met Leu Val Ala Pro Ser Tyr Gly Met Arg Cys Val Gly Val Gly Asn
    275                 280                 285

Arg Asp Phe Val Glu Gly Val Ser Gly Gly Ala Trp Val Asp Leu Val
290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640
```

```
Thr Asn Ser Val Thr Asn Ile Glu Leu Glu Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
            675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
                740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
                820                 825                 830

Arg Ser Val Thr Arg Leu Glu Asn Leu Met Trp Lys Gln Ile Thr Pro
    835                 840                 845

Glu Leu Asn His Ile Leu Ser Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
                900                 905                 910

Pro Glu Thr Ala Glu Cys Pro Asn Thr Asn Arg Ala Trp Asn Ser Leu
    915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Asn Cys His Trp Pro Lys Ser His Thr Leu Trp Ser
            995                1000                1005

Asn Gly Val Leu Glu Ser Glu Met Ile Ile Pro Lys Asn Leu Ala
        1010                1015                1020

Gly Pro Val Ser Gln His Asn Tyr Arg Pro Gly Tyr His Thr Gln
        1025                1030                1035

Ile Thr Gly Pro Trp His Leu Gly Lys Leu Glu Met Asp Phe Asp
        1040                1045                1050

Phe Cys Asp Gly Thr Thr Val Val Val Thr Glu Asp Cys Gly Asn
```

```
                    1055                1060                1065
Arg Gly Pro Ser Leu Arg Thr Thr Thr Ala Ser Gly Lys Leu Ile
    1070                1075                1080
Thr Glu Trp Cys Cys Arg Ser Cys Thr Leu Pro Pro Leu Arg Tyr
    1085                1090                1095
Arg Gly Glu Asp Gly Cys Trp Tyr Gly Met Glu Ile Arg Pro Leu
    1100                1105                1110
Lys Glu Lys Glu Glu Asn Leu Val Asn Ser Leu Val Thr Ala Gly
    1115                1120                1125
His Gly Gln Val Asp Asn Phe Ser Leu Gly Val Leu Gly Met Ala
    1130                1135                1140
Leu Phe Leu Glu Glu Met Leu Arg Thr Arg Val Gly Thr Lys His
    1145                1150                1155
Ala Ile Leu Leu Val Ala Val Ser Phe Val Thr Leu Ile Thr Gly
    1160                1165                1170
Asn Met Ser Phe Arg Asp Leu Gly Arg Val Met Val Met Val Gly
    1175                1180                1185
Ala Thr Met Thr Gly Asp Ile Gly Met Gly Val Thr Tyr Leu Ala
    1190                1195                1200
Leu Leu Ala Ala Phe Lys Val Arg Pro Thr Phe Ala Ala Gly Leu
    1205                1210                1215
Leu Leu Arg Lys Leu Thr Ser Xaa Glu Leu Met Met Thr Thr Ile
    1220                1225                1230
Gly Ile Val Leu Leu Ser Gln Ser Thr Ile Pro Glu Thr Ile Leu
    1235                1240                1245
Glu Leu Thr Asp Ala Leu Ala Leu Gly Met Met Val Leu Lys Met
    1250                1255                1260
Val Arg Asn Met Glu Lys Tyr Gln Leu Ala Val Thr Ile Met Ala
    1265                1270                1275
Ile Leu Cys Val Pro Asn Ala Val Ile Leu Gln Asn Ala Trp Lys
    1280                1285                1290
Val Ser Cys Thr Ile Leu Ala Val Val Ser Val Ser Pro Leu Phe
    1295                1300                1305
Leu Thr Ser Ser Gln Gln Lys Thr Asp Trp Ile Pro Leu Ala Leu
    1310                1315                1320
Thr Ile Lys Gly Leu Asn Pro Thr Ala Ile Phe Leu Thr Thr Leu
    1325                1330                1335
Ser Arg Thr Ser Lys Lys Arg Ser Trp Pro Leu Asn Glu Ala Ile
    1340                1345                1350
Met Ala Val Gly Met Val Ser Ile Leu Ala Ser Leu Leu Lys
    1355                1360                1365
Asn Asp Ile Pro Met Thr Gly Pro Leu Val Ala Gly Gly Leu Leu
    1370                1375                1380
Thr Val Cys Tyr Val Leu Thr Gly Arg Ser Ala Asp Leu Glu Leu
    1385                1390                1395
Glu Arg Ala Ala Asp Val Lys Trp Glu Asp Gln Ala Glu Ile Ser
    1400                1405                1410
Gly Ser Ser Pro Ile Leu Ser Ile Thr Ile Ser Glu Asp Gly Ser
    1415                1420                1425
Met Ser Ile Lys Asn Glu Glu Glu Glu Gln Thr Leu Thr Ile Leu
    1430                1435                1440
Ile Arg Thr Gly Leu Leu Val Ile Ser Gly Leu Phe Pro Val Ser
    1445                1450                1455
```

-continued

```
Ile Pro Ile Thr Ala Ala Ala Trp Tyr Leu Trp Glu Val Lys Lys
    1460            1465                1470
Gln Arg Ala Gly Val Leu Trp Asp Val Pro Ser Pro Pro Pro Met
    1475            1480                1485
Gly Lys Ala Glu Leu Glu Asp Gly Ala Tyr Arg Ile Lys Gln Lys
    1490            1495                1500
Gly Ile Leu Gly Tyr Ser Gln Ile Gly Ala Gly Val Tyr Lys Glu
    1505            1510                1515
Gly Thr Phe His Thr Met Trp His Val Thr Arg Gly Ala Val Leu
    1520            1525                1530
Met His Lys Gly Lys Arg Ile Glu Pro Ser Trp Ala Asp Val Lys
    1535            1540                1545
Lys Asp Leu Ile Ser Tyr Gly Gly Gly Trp Lys Leu Glu Gly Glu
    1550            1555                1560
Trp Lys Glu Gly Glu Glu Val Gln Val Leu Ala Leu Glu Pro Gly
    1565            1570                1575
Lys Asn Pro Arg Ala Val Gln Thr Lys Pro Gly Leu Phe Lys Thr
    1580            1585                1590
Asn Ala Gly Thr Ile Gly Ala Val Ser Leu Asp Phe Ser Pro Gly
    1595            1600                1605
Thr Ser Gly Ser Pro Ile Ile Asp Lys Lys Gly Lys Val Val Gly
    1610            1615                1620
Leu Tyr Gly Asn Gly Val Val Thr Arg Ser Gly Ala Tyr Val Ser
    1625            1630                1635
Ala Ile Ala Gln Thr Glu Lys Ser Ile Glu Asp Asn Pro Glu Ile
    1640            1645                1650
Glu Asp Asp Ile Phe Arg Lys Arg Arg Leu Thr Ile Met Asp Leu
    1655            1660                1665
His Pro Gly Ala Gly Lys Thr Lys Arg Tyr Leu Pro Ala Ile Val
    1670            1675                1680
Arg Glu Ala Ile Lys Arg Gly Leu Arg Thr Leu Ile Leu Ala Pro
    1685            1690                1695
Thr Arg Val Val Ala Ala Glu Met Glu Glu Ala Leu Arg Gly Leu
    1700            1705                1710
Pro Ile Arg Tyr Gln Thr Pro Ala Ile Arg Ala Val His Thr Gly
    1715            1720                1725
Arg Glu Ile Val Asp Leu Met Cys His Ala Thr Phe Thr Met Arg
    1730            1735                1740
Leu Leu Ser Pro Val Arg Val Pro Asn Tyr Asn Leu Ile Ile Met
    1745            1750                1755
Asp Glu Ala His Phe Thr Asp Pro Ala Ser Ile Ala Ala Arg Gly
    1760            1765                1770
Tyr Ile Ser Thr Arg Val Glu Met Gly Glu Ala Ala Gly Ile Phe
    1775            1780                1785
Met Thr Ala Thr Pro Pro Gly Ser Arg Asp Pro Phe Pro Gln Ser
    1790            1795                1800
Asn Ala Pro Ile Ile Asp Glu Glu Arg Glu Ile Pro Glu Arg Ser
    1805            1810                1815
Trp Asn Ser Gly His Glu Trp Val Thr Asp Phe Lys Gly Lys Thr
    1820            1825                1830
Val Trp Phe Val Pro Ser Ile Lys Ala Gly Asn Asp Ile Ala Ala
    1835            1840                1845
```

-continued

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Val Arg Asp Ala Leu
    2105                2110                2115

Asp Asn Leu Ala Val Leu His Thr Ala Glu Ala Gly Gly Arg Ala
    2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
    2150                2155                2160

Phe Leu Met Ser Ala Arg Gly Ile Gly Lys Met Thr Leu Gly Met
    2165                2170                2175

Cys Cys Ile Ile Thr Ala Ser Ile Leu Leu Trp Tyr Ala Gln Ile
    2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
    2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys

```
                    2240                2245                2250

Lys Asp Leu Gly Leu Gly Ser Ile Ala Thr Gln Gln Pro Glu Ser
        2255                2260                2265

Asn Ile Leu Asp Ile Asp Leu Arg Pro Ala Ser Ala Trp Thr Leu
        2270                2275                2280

Tyr Ala Val Ala Thr Thr Phe Val Thr Pro Met Leu Arg His Ser
        2285                2290                2295

Ile Glu Asn Ser Ser Val Asn Val Ser Leu Thr Ala Ile Ala Asn
        2300                2305                2310

Gln Ala Thr Val Leu Met Gly Leu Gly Lys Gly Trp Pro Leu Ser
        2315                2320                2325

Lys Met Asp Ile Gly Val Pro Leu Leu Ala Ile Gly Cys Tyr Ser
        2330                2335                2340

Gln Val Asn Pro Ile Thr Leu Thr Ala Ala Leu Phe Leu Leu Val
        2345                2350                2355

Ala His Tyr Ala Ile Ile Gly Pro Gly Leu Gln Ala Lys Ala Thr
        2360                2365                2370

Arg Glu Ala Gln Lys Arg Ala Ala Gly Ile Met Lys Asn Pro
        2375                2380                2385

Thr Val Asp Gly Ile Thr Val Ile Asp Leu Asp Pro Ile Pro Tyr
        2390                2395                2400

Asp Pro Lys Phe Glu Lys Gln Leu Gly Gln Val Met Leu Leu Val
        2405                2410                2415

Leu Cys Val Thr Gln Val Leu Met Met Arg Thr Thr Trp Ala Leu
        2420                2425                2430

Cys Glu Ala Leu Thr Leu Ala Thr Gly Pro Ile Ser Thr Leu Trp
        2435                2440                2445

Glu Gly Asn Pro Gly Arg Phe Trp Asn Thr Thr Ile Ala Val Ser
        2450                2455                2460

Met Ala Asn Ile Phe Arg Gly Ser Tyr Leu Ala Gly Ala Gly Leu
        2465                2470                2475

Leu Phe Ser Ile Met Lys Asn Thr Thr Asn Thr Arg Arg Gly Thr
        2480                2485                2490

Gly Asn Ile Gly Glu Thr Leu Gly Glu Lys Trp Lys Ser Arg Leu
        2495                2500                2505

Asn Ala Leu Gly Lys Ser Glu Phe Gln Ile Tyr Lys Lys Ser Gly
        2510                2515                2520

Ile Gln Glu Val Asp Arg Thr Leu Ala Lys Glu Gly Ile Lys Arg
        2525                2530                2535

Gly Glu Thr Asp His His Ala Val Ser Arg Gly Ser Ala Lys Leu
        2540                2545                2550

Arg Trp Phe Val Glu Arg Asn Met Val Thr Pro Glu Gly Lys Val
        2555                2560                2565

Val Asp Leu Gly Cys Gly Arg Gly Gly Trp Ser Tyr Tyr Cys Gly
        2570                2575                2580

Gly Leu Lys Asn Val Arg Glu Val Lys Gly Leu Thr Lys Gly Gly
        2585                2590                2595

Pro Gly His Glu Glu Pro Ile Pro Met Ser Thr Tyr Gly Trp Asn
        2600                2605                2610

Leu Val Arg Leu Gln Ser Gly Val Asp Val Phe Phe Ile Pro Pro
        2615                2620                2625

Glu Lys Cys Asp Thr Leu Leu Cys Asp Ile Gly Glu Ser Ser Pro
        2630                2635                2640
```

```
Asn Pro Thr Val Glu Ala Gly Arg Thr Leu Arg Val Leu Asn Leu
2645                2650                2655

Val Glu Asn Trp Leu Asn Asn Thr Gln Phe Cys Ile Lys Val
2660            2665                2670

Leu Asn Pro Tyr Met Pro Ser Val Ile Glu Lys Met Glu Ala Leu
2675                2680                2685

Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg Tyr Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu
2765                2770                2775

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

Asp Val Val Pro Met Val Thr Gln Met Ala Met Thr Asp Thr Thr
2825                2830                2835

Pro Phe Gly Gln Gln Arg Val Phe Lys Glu Lys Val Asp Thr Arg
2840                2845                2850

Thr Gln Glu Pro Lys Glu Gly Thr Lys Lys Leu Met Lys Ile Thr
2855                2860                2865

Ala Glu Trp Leu Trp Lys Glu Leu Gly Lys Lys Lys Thr Pro Arg
2870                2875                2880

Met Cys Thr Arg Glu Glu Phe Thr Arg Lys Val Arg Ser Asn Ala
2885                2890                2895

Ala Leu Gly Ala Ile Phe Thr Asp Glu Asn Lys Trp Lys Ser Ala
2900                2905                2910

Arg Glu Ala Val Glu Asp Ser Arg Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970

Phe Leu Glu Phe Glu Ala Leu Gly Phe Leu Asn Glu Asp His Trp
2975                2980                2985

Phe Ser Arg Glu Asn Ser Leu Ser Gly Val Glu Gly Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030
```

```
Thr Leu Glu Asp Leu Lys Asn Glu Glu Met Val Thr Asn His Met
    3035            3040            3045

Glu Gly Glu His Lys Lys Leu Ala Glu Ala Ile Phe Lys Leu Thr
    3050            3055            3060

Tyr Gln Asn Lys Val Val Arg Val Gln Arg Pro Thr Pro Arg Gly
    3065            3070            3075

Thr Val Met Asp Ile Ile Ser Arg Arg Asp Gln Arg Gly Ser Gly
    3080            3085            3090

Gln Val Gly Thr Tyr Gly Leu Asn Thr Phe Thr Asn Met Glu Ala
    3095            3100            3105

Gln Leu Ile Arg Gln Met Glu Gly Glu Gly Val Phe Lys Ser Ile
    3110            3115            3120

Gln His Leu Thr Ile Thr Glu Glu Ile Ala Val Gln Asn Trp Leu
    3125            3130            3135

Ala Arg Val Gly Arg Glu Arg Leu Ser Arg Met Ala Ile Ser Gly
    3140            3145            3150

Asp Asp Cys Val Val Lys Pro Leu Asp Asp Arg Phe Ala Ser Ala
    3155            3160            3165

Leu Thr Ala Leu Asn Asp Met Gly Lys Ile Arg Lys Asp Ile Gln
    3170            3175            3180

Gln Trp Glu Pro Ser Arg Gly Trp Asn Asp Trp Thr Gln Val Pro
    3185            3190            3195

Phe Cys Ser His His Phe His Glu Leu Ile Met Lys Asp Gly Arg
    3200            3205            3210

Val Leu Val Val Pro Cys Arg Asn Gln Asp Glu Leu Ile Gly Arg
    3215            3220            3225

Ala Arg Ile Ser Gln Gly Ala Gly Trp Ser Leu Arg Glu Thr Ala
    3230            3235            3240

Cys Leu Gly Lys Ser Tyr Ala Gln Met Trp Ser Leu Met Tyr Phe
    3245            3250            3255

His Arg Arg Asp Leu Arg Leu Ala Ala Asn Ala Ile Cys Ser Ala
    3260            3265            3270

Val Pro Ser His Trp Val Pro Thr Ser Arg Thr Thr Trp Ser Ile
    3275            3280            3285

His Ala Lys His Glu Trp Met Thr Thr Glu Asp Met Leu Thr Val
    3290            3295            3300

Trp Asn Arg Val Trp Ile Gln Glu Asn Pro Trp Met Glu Asp Lys
    3305            3310            3315

Thr Pro Val Glu Ser Trp Glu Glu Ile Pro Tyr Leu Gly Lys Arg
    3320            3325            3330

Glu Asp Gln Trp Cys Gly Ser Leu Ile Gly Leu Thr Ser Arg Ala
    3335            3340            3345

Thr Trp Ala Lys Asn Ile Gln Ala Ala Ile Asn Gln Val Arg Ser
    3350            3355            3360

Leu Ile Gly Asn Glu Glu Tyr Thr Asp Tyr Met Pro Ser Met Lys
    3365            3370            3375

Arg Phe Arg Arg Glu Glu Glu Glu Ala Gly Val Leu Trp
    3380            3385            3390
```